United States Patent
Kamei et al.

(10) Patent No.: US 10,131,653 B2
(45) Date of Patent: Nov. 20, 2018

(54) HETEROCYCLIC COMPOUND

(71) Applicant: TAKEDA PHARMACEUTICAL COMPANY LIMITED, Osaka (JP)

(72) Inventors: Taku Kamei, Fujisawa (JP); Yasuyoshi Arikawa, Fujisawa (JP); Tomohiro Ohashi, Fujisawa (JP); Toshihiro Imaeda, Fujisawa (JP); Ikuo Fujimori, Fujisawa (JP); Takashi Miki, Fujisawa (JP); Jinichi Yonemori, Fujisawa (JP); Yuya Oguro, Fujisawa (JP); Takahiro Sugimoto, Fujisawa (JP); Masaki Seto, Fujisawa (JP); Goushi Nishida, Fujisawa (JP); Makoto Kamata, Fujisawa (JP); Hiroshi Imoto, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/568,644

(22) PCT Filed: Apr. 22, 2016

(86) PCT No.: PCT/JP2016/062750
§ 371 (c)(1),
(2) Date: Oct. 23, 2017

(87) PCT Pub. No.: WO2016/171248
PCT Pub. Date: Oct. 27, 2016

(65) Prior Publication Data
US 2018/0155333 A1 Jun. 7, 2018

(30) Foreign Application Priority Data
Apr. 24, 2015 (JP) .................. 2015-089714

(51) Int. Cl.
*C07D 413/14* (2006.01)
*C07D 409/14* (2006.01)
*C07D 413/04* (2006.01)
*C07D 417/14* (2006.01)
*A61P 25/20* (2006.01)
*A61P 25/28* (2006.01)
*A61P 25/30* (2006.01)
*A61P 25/22* (2006.01)
*A61P 25/18* (2006.01)
*A61P 25/24* (2006.01)
*A61K 31/553* (2006.01)

(52) U.S. Cl.
CPC .......... *C07D 413/14* (2013.01); *A61K 31/553* (2013.01); *A61P 25/18* (2018.01); *A61P 25/20* (2018.01); *A61P 25/22* (2018.01); *A61P 25/24* (2018.01); *A61P 25/28* (2018.01); *A61P 25/30* (2018.01); *C07D 409/14* (2013.01); *C07D 413/04* (2013.01); *C07D 417/14* (2013.01)

(58) Field of Classification Search
CPC .. C07D 413/04; C07D 413/14; C07D 409/14; C07D 417/14; A61P 25/20; A61P 25/28; A61P 25/30; A61P 25/22; A61P 25/18; A61P 25/24; A61P 31/553
See application file for complete search history.

(56) References Cited

FOREIGN PATENT DOCUMENTS

| | | |
|---|---|---|
| JP | 2016000700 A | 7/2016 |
| WO | 2007126935 A2 | 11/2007 |
| WO | 2008008518 A1 | 1/2008 |
| WO | 2008069997 A1 | 6/2008 |
| WO | 2008143856 A1 | 11/2008 |
| WO | 2009058238 A1 | 5/2009 |
| WO | 2012145581 A1 | 10/2012 |
| WO | 2013050938 A1 | 4/2013 |
| WO | 2015095111 A1 | 6/2015 |

OTHER PUBLICATIONS

International Search Report dated Jun. 16, 2016 corresponding to application No. PCT/JP2016/062750.
Oida, Sadao, et al."Synthesis of 4,5-Epiminotetrahydro-1,2-oxazine". Chemical & Pharmaceutical Bulletin; Central Research Laboratories, Sankyo Co., Ltd.; No. 3; Aug. 21, 1968.
Sakuri, Takeshi, et al."Orexins and Orexin Receptors: A Family of Hypothalamic Neuropeptides and G Protein-Coupled Receptors that Regulate Feeding Behavior".Cell, vol. 92, 573-585, 1998.
Lin, Ling, et al."The Sleep Disorder Canine Narcolepsy is Caused by Mutation in the Hypocretin (Orexin) Receptor 2 Gene".Cell, vol. 98, 365-376, 1999.
Mieda, Michihiro, et al."Orexin Peptides Prevent Cataplexy and Improve Wakefulness in an Orexin Neuron-ablated Model of Narcolepsy in Mice".Proc. Natl. Acad. Sci. USA, vol. 101, 4649-4654, 2004.

(Continued)

*Primary Examiner* — Timothy R Rozof
(74) *Attorney, Agent, or Firm* — Nath, Goldberg & Meyer; Joshua B. Goldberg

(57) ABSTRACT

The present invention provide a compound having an orexin receptor antagonistic activity, which is expected to be useful as medicaments such as agents for the prophylaxis or treatment of sleep disorder, depression, anxiety disorder, panic disorder, schizophrenia, drug dependence, Alzheimer's disease and the like.
The present invention relates to a compound represented by the formula (I):

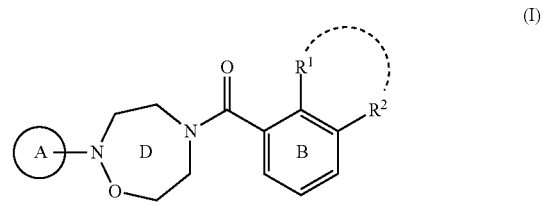

(I)

wherein each symbol is as defined in the specification, or a salt thereof.

12 Claims, 2 Drawing Sheets

(56) References Cited

OTHER PUBLICATIONS

Brisbare-Roch, Catherine, et al."Promotion of Sleep by Targeting the Orexin System in Rats, Dogs and Humans". Nature Medicine, vol. 13, 150-155, 2007.
Cox, Christopher D., et al."Discovery of the Dual Orexin Receptor Antagonist [(7R)-4-(5-Chloro-1,3-benzoxazol-2-yl)-7-methyl-1,4-diazepan-1-yl][5-methyl-2-(2H,1,2,3-triazol-2-yl)phenyl]methanone (MK-4305) for the Treatment of Insomnia". Journal of Medicinal Chemistry, vol. 53, 5320-5332, 2010.
Bingham, Matilda J., et al."Eating, Sleeping and Rewarding: Orexin Receptors and their Antagonists". Current Opinion in Drug Discovery & Development; 2006.
Coleman, Paul J., et al."Orexin Receptor Antagonists: A Review of Promising Compounds Patented Since 2006". Expert Opinion on Therapeutic Patents; 2010.
Coleman, Paul J., et al."Discovery of Dual Orexin Receptor Antagonists (DORAs) for the Treatment of Insomnia". Current Topics in Medicinal Chemistry; 2011.

HETEROCYCLIC COMPOUND

This is a National Phase Application filed under 35 U.S.C. 371 as a national stage of PCT/JP2016/062750, filed Apr. 22, 2016, an application claiming the benefit of Japanese Application No. 089714/2015, filed Apr. 24, 2015, the content of each of which is hereby incorporated by reference in its entirety.

TECHNICAL FIELD

The present invention relates to a heterocyclic compound having an orexin receptor antagonistic activity, which is expected to be useful as medicaments such as agents for the prophylaxis or treatment of sleep disorder, depression, anxiety disorder, panic disorder, schizophrenia, drug dependence, Alzheimer's disease and the like.

BACKGROUND OF THE INVENTION

Orexin is a neuropeptide locally produced in the lateral hypothalamus, and orexin A and orexin B which consist of 33 or 28 amino acids, respectively, are now identified. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin is localized in feeding center, and intraventricular administration thereof results in an increase in food intake, orexin initially attracted attention as a neuropeptide having a feeding behavioral regulation. Thereafter, however, it was reported that the cause of dog narcolepsy is genetic mutation of orexin type 2 receptor (non-patent document 2), and the role of orexin in sleep-wake controlling has been also attracted.

From the studies using a double transgenic mouse obtained by crossing orexin neuron-deficient transgenic mouse with orexin overexpressing transgenic mouse, it is considered that monoaminergic nerve and cholinergic nerve are activated by orexin during wakefulness, and thereby the balance between sleep and wakefulness is shifted toward wakefulness phase to maintain wakefulness state, and on the other hand, orexin nerve is suppressed during sleep, and thereby sleep phase is maintained (non-patent document 3). In addition, it was reported that administration of a compound having same level antagonistic activities against orexin type 1 and orexin type 2 receptors decreases activity, shortens sleep latency, and increases total sleep (non-patent document 4 and non-patent document 5).

Therefore, a compound having an orexin receptor antagonistic activity is expected to exhibit sleep-promoting action, and to be useful as an novel agent for the prophylaxis or treatment of sleep disorder. As a compound having an orexin receptor antagonistic activity, for example, compounds having various structures, which are described as a review article in non-patent documents 6-8, are known. In addition, patent documents 1 to 6 describe homopiperazine derivatives and the like. However, these documents do not describe the 1,2,5-oxadiazepane ring compound described in the present specification.

Patent Document 1 describes the following compound, which has an orexin receptor antagonistic activity, and is useful for the prophylaxis or treatment of sleep disorder, insomnia and the like.

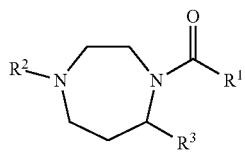

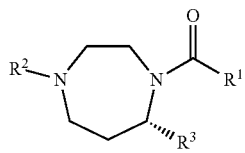

wherein each symbol is as defined in the document.

Patent Document 2 describes the following compound, which has an orexin receptor antagonistic activity, and is useful for the prophylaxis or treatment of sleep disorder, depression, anxiety, cognitive disorder, appetite disorder, addiction disorder and the like.

Formula (I)

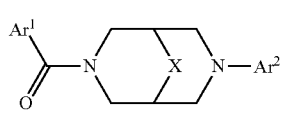

wherein each symbol is as defined in the document.

Patent Document 3 describes the following compound, which has an orexin receptor antagonistic activity, and is useful for the treatment of insomnia, jet-lag, depression, schizophrenia, obesity and the like.

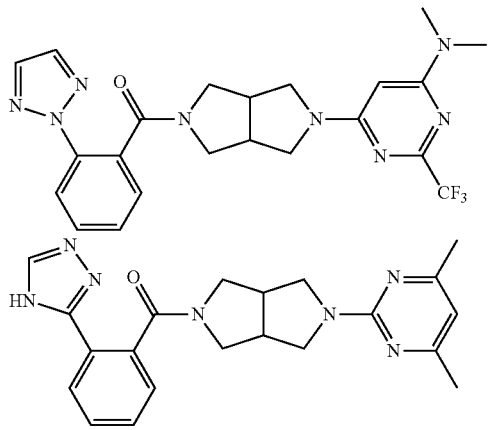

Patent Document 4 describes the following compound, which has an orexin receptor antagonistic activity, and is useful for the treatment of sleep disorder, insomnia and the like.

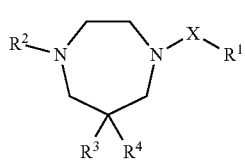

wherein each symbol is as defined in the document.

Patent Document 5 describes the following compound, which has an orexin receptor antagonistic activity, and is useful for the treatment of sleep disorder, insomnia and the like.

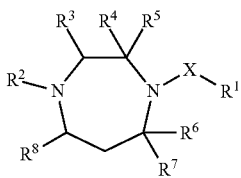

wherein each symbol is as defined in the document.

Patent Document 6 describes the following compound, which has an orexin receptor antagonistic activity, and is useful for the treatment of sleep disorder, insomnia and the like.

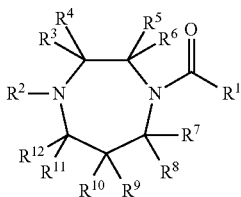

wherein each symbol is as defined in the document.

DOCUMENT LIST

Patent Document

Patent Document 1: WO 2008/069997
Patent Document 2: WO 2013/050938
Patent Document 3: WO 2012/145581
Patent Document 4: WO 2007/126935
Patent Document 5: WO 2008/008518
Patent Document 6: WO 2009/058238

Non-Patent Document

Non-Patent Document 1: Cell, Vol. 92, 573-585, 1998
Non-Patent Document 2: Cell, Vol. 98, 365-376, 1999
Non-Patent Document 3: Proceedings of the National Academy of Sciences of the United States of America, Vol. 101, 4649-4654, 2004
Non-Patent Document 4: Nature Madicine, Vol. 13, 150-155, 2007
Non-Patent Document 5: Journal of Medicinal Chemistry, Vol. 53, 5320-5332, 2010
Non-Patent Document 6: Current Opinion in Drug Discovery & Development, Vol. 9, 551-559, 2006
Non-Patent Document 7: Expert Opinion on Therapeutic Patents, Vol. 20, 307-324, 2010
Non-Patent Document 8: Current Topics in Medicinal Chemistry, Vol. 11, 696-725, 2011

SUMMARY OF THE INVENTION

Problems to be Solved by the Invention

Development of a compound having an orexin receptor antagonistic activity, which is useful as an agent for the prophylaxis or treatment of sleep disorder, depression, anxiety disorder, panic disorder, schizophrenia, drug dependence, Alzheimer's disease and the like, is desired.

Means of Solving the Problems

The present inventors have conducted intensive studies in an attempt to solve the above-mentioned problems and found that a compound represented by the following formula (I) may have an orexin receptor antagonistic activity, which resulted in the completion of the present invention.

Accordingly, the present invention provides the following.

[1] A compound represented by the formula (I):

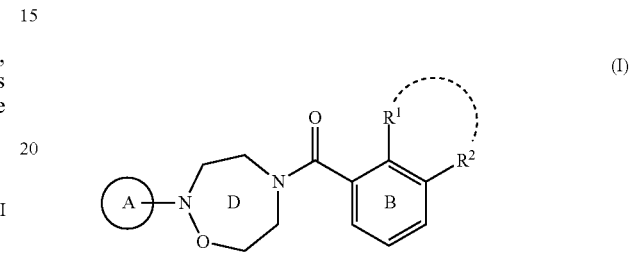

wherein
$R^1$ and $R^2$ are each independently a hydrogen atom or a substituent, or $R^1$ and $R^2$ are optionally bonded to each other to form, together with the adjacent carbon atoms, an optionally substituted ring,
Ring A is an optionally substituted aromatic ring,
Ring B is an optionally further substituted benzene ring, and
Ring D is an optionally further substituted 1,2,5-oxadiazepane ring,
or a salt thereof (in the present specification, sometimes to be referred to as compound (I)).

[2] The compound or salt of the above mentioned [1], wherein Ring A is a pyrimidine ring optionally substituted by 1 to 3 substituents selected from
(a) a halogen atom,
(b) a hydroxy group,
(c) a cyano group,
(d) a $C_{1-6}$ alkyl group optionally substituted by 1 to 3 halogen atoms,
(e) a $C_{1-6}$ alkoxy group,
(f) a $C_{3-10}$ cycloalkyl group optionally substituted by 1 to 3 $C_{1-6}$ alkyl groups, and
(g) a $C_{6-14}$ aryl group optionally substituted by 1 to 3 halogen atoms.

[3] The compound or salt of the above mentioned [1], wherein Ring B is a benzene ring optionally further substituted by 1 to 3 substituents, in addition to $R^1$ and $R^2$, selected from
(a) a halogen atom,
(b) a cyano group,
(c) a $C_{1-6}$ alkyl group optionally substituted by 1 to 3 halogen atoms,
(d) a $C_{1-6}$ alkoxy group,
(e) a $C_{3-10}$ cycloalkyl group, and
(f) a 5- to 14-membered aromatic heterocyclic group.

[4] The compound or salt of the above mentioned [1], wherein $R^1$ is
(1) a hydrogen atom,
(2) a halogen atom,
(3) a cyano group,
(4) a $C_{1-6}$ alkyl group optionally substituted by 1 to 3 halogen atoms, (5) a $C_{1-6}$ alkoxy group,
(6) a $C_{1-6}$ alkoxy-carbonyl group,
(7) a $C_{3-10}$ cycloalkyl group,
(8) a $C_{6-14}$ aryl group, or
(9) a 5- to 14-membered aromatic heterocyclic group optionally substituted by 1 to 3 substituents selected from
  (i) a halogen atom, and
  (ii) a $C_{1-6}$ alkyl group;
$R^2$ is
(1) a hydrogen atom,
(2) a halogen atom,
(3) a cyano group,
(4) a $C_{1-6}$ alkyl group optionally substituted by 1 to 3 halogen atoms,
(5) a $C_{1-6}$ alkoxy group,
(6) a $C_{6-14}$ aryl group, or
(7) a $C_{3-10}$ cycloalkyl group; or
$R^1$ and $R^2$ are optionally bonded to each other to form, together with the adjacent carbon atoms, benzene, a $C_{5-6}$ cycloalkene, a 5- or 6-membered monocyclic aromatic heterocycle, or a 5- or 6-membered monocyclic non-aromatic heterocycle, each of which is optionally substituted by 1 to 3 substituents selected from
  (a) a $C_{1-6}$ alkyl group, and
  (b) an oxo group;
Ring A is a benzene ring, a 5- or 6-membered monocyclic aromatic heterocycle or a 8- to 14-membered fused polycyclic aromatic heterocycle, each of which is optionally substituted by 1 to 3 substituents selected from
  (a) a halogen atom,
  (b) a hydroxy group,
  (c) a cyano group,
  (d) a $C_{1-6}$ alkyl group optionally substituted by 1 to 3 substituents selected from
    (i) a halogen atom, and
    (ii) a hydroxy group,
  (e) a $C_{1-6}$ alkoxy group,
  (f) a $C_{1-6}$ alkoxy-carbonyl group,
  (g) a $C_{3-10}$ cycloalkyl group optionally substituted by 1 to 3 $C_{1-6}$ alkyl groups,
  (h) a $C_{6-14}$ aryl group optionally substituted by 1 to 3 halogen atoms, and
  (i) a 5- to 14-membered aromatic heterocyclic group;
Ring B is a benzene ring optionally further substituted by 1 to 3 substituents, in addition to $R^1$ and $R^2$, selected from
  (a) a halogen atom,
  (b) a cyano group,
  (c) a $C_{1-6}$ alkyl group optionally substituted by 1 to 3 halogen atoms,
  (d) a $C_{1-6}$ alkoxy group,
  (e) a $C_{3-10}$ cycloalkyl group, and
  (f) a 5- to 14-membered aromatic heterocyclic group; and
Ring D is a 1,2,5-oxadiazepane ring optionally further substituted by 1 to 3 substituents selected from a $C_{1-6}$ alkyl group optionally substituted by 1 to $C_{1-6}$ alkoxy groups.

[5] The compound or salt of the above mentioned [1], wherein $R^1$ is
(1) a triazolyl group,
(2) a thiazolyl group, or
(3) a pyrimidinyl group;
$R^2$ is a hydrogen atom;
Ring A is a pyrimidine ring substituted by 1 to 3 substituents selected from
  (1) a $C_{1-6}$ alkyl group optionally substituted by 1 to 3 halogen atoms;
Ring B is a benzene ring optionally further substituted by 1 to 3 substituents, in addition to $R^1$ and $R^2$, selected from
  (a) a halogen atom, and
  (b) a $C_{1-6}$ alkyl group optionally substituted by 1 to 3 halogen atoms; and
Ring D is a 1,2,5-oxadiazepane ring optionally further substituted by 1 to 3 $C_{1-6}$ alkyl groups.

[6] The compound or salt of the above mentioned [1], wherein $R^1$ is
(1) a triazolyl group, or
(2) a pyrimidinyl group;
$R^2$ is a hydrogen atom;
Ring A is a pyrimidine ring substituted by two $C_{1-6}$ alkyl groups;
Ring B is a benzene ring optionally further substituted by 1 or 2 substituents, in addition to $R^1$ and $R^2$, selected from
  (a) a halogen atom, and
  (b) a $C_{1-6}$ alkyl group; and
Ring D is a 1,2,5-oxadiazepane ring optionally further substituted by one $C_{1-6}$ alkyl group.

[7] ((7S)-2-(2,6-Dimethylpyrimidin-4-yl)-7-methyl-1,2,5-oxadiazepan-5-yl)(5-fluoro-2-(2H-1,2,3-triazol-2-yl)phenyl)methanone, or a salt thereof.

[8] ((7S)-2-(2,6-Dimethylpyrimidin-4-yl)-7-methyl-1,2,5-oxadiazepan-5-yl)(2-(2H-1,2,3-triazol-2-yl)phenyl)methanone, or a salt thereof.

[9] (5-Chloro-2-(2H-1,2,3-triazol-2-yl)phenyl)((7S)-2-(2,6-dimethylpyrimidin-4-yl)-7-methyl-1,2,5-oxadiazepan-5-yl)methanone, or a salt thereof.

[10] A medicament comprising the compound or salt of the above mentioned [1].

[11] The medicament of the above mentioned [10], which is an orexin receptor antagonist.

[12] The medicament of the above mentioned [10], which is an agent for the prophylaxis or treatment of sleep disorder, depression, anxiety disorder, panic disorder, schizophrenia, drug dependence or Alzheimer's disease.

[13] The compound or salt of the above mentioned [1] for use in the prophylaxis or treatment of sleep disorder, depression, anxiety disorder, panic disorder, schizophrenia, drug dependence or Alzheimer's disease.

[14] A method of antagonizing an orexin receptor in a mammal, which comprises administering an effective amount of the compound or salt of the above mentioned [1] to the mammal.

[15] A method for the prophylaxis or treatment of sleep disorder, depression, anxiety disorder, panic disorder, schizophrenia, drug dependence or Alzheimer's disease in a mammal, which comprises administering an effective amount of the compound or salt of the above mentioned [1] to the mammal.

[16] Use of the compound or salt of the above mentioned [1] for the production of an agent for the prophylaxis or treatment of sleep disorder, depression, anxiety disorder, panic disorder, schizophrenia, drug dependence or Alzheimer's disease.

Effect of the Invention

Since the compound of the present invention may have an orexin receptor antagonistic activity, it is expected to be useful, for example, as an agent for the prophylaxis or treatment of sleep disorder, depression, anxiety disorder, panic disorder, schizophrenia, drug dependence, Alzheimer's disease and the like.

DETAILED DESCRIPTION OF THE INVENTION

Figure 1:
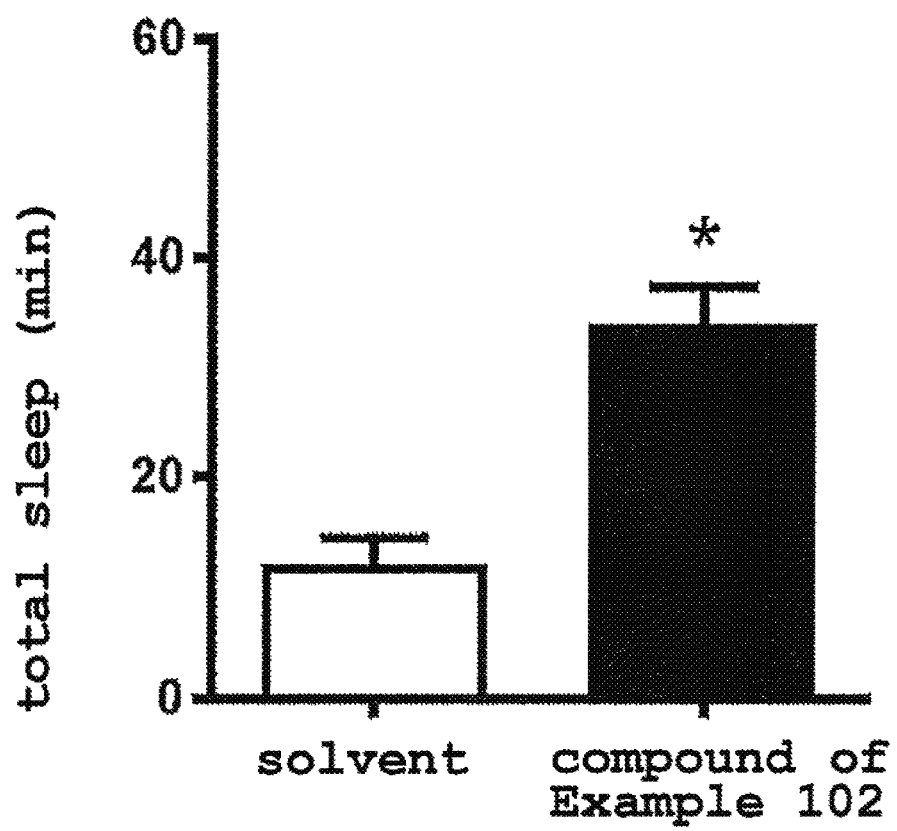
FIG. 1 shows an effect of compound of Example 102 on sleep in rat in Experimental Example 2.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethyl-phosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{6-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, the expression "1 to 3" means "1, 2 or 3".

The definition of each symbol in the formula (I) is explained in the following.

$R^1$ and $R^2$ are each independently a hydrogen atom or a substituent, or $R^1$ and $R^2$ are optionally bonded to each other to form, together with the adjacent carbon atoms, an optionally substituted ring.

Examples of the "ring" of the "optionally substituted ring" formed by $R^1$ and $R^2$ bonded to each other together with the adjacent carbon atoms include a hydrocarbon ring and a heterocycle.

The "ring" of the "optionally substituted ring" formed by $R^1$ and $R^2$ bonded to each other together with the adjacent carbon atoms optionally has 1 to 5 (preferably 1 to 3) substituents at substitutable position(s). Examples of the substituent include the above-mentioned Substituent Group A. When the number of the substituents is 2 or more, the respective substituents may be the same or different.

Preferably, $R^1$ and $R^2$ are each independently a hydrogen atom or a substituent.

$R^1$ is preferably
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{3-10}$ cycloalkyl group (e.g., cyclobutyl),
(7) a $C_{6-14}$ aryl group (e.g., phenyl), or
(8) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl).

$R^1$ is more preferably
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{3-10}$ cycloalkyl group (e.g., cyclobutyl),
(7) a phenyl group,
(8) a triazolyl group,
(9) a pyrrolyl group,
(10) a furyl group,
(11) a thienyl group,
(12) an imidazolyl group,
(13) a pyrazolyl group,
(14) a tetrazolyl group,
(15) a thiazolyl group optionally substituted by 1 to 3 substituents selected from
  (i) a halogen atom (e.g., a fluorine atom), and
  (ii) a $C_{1-6}$ alkyl group (e.g., methyl),
(16) an oxadiazolyl group optionally substituted by 1 to 3 $C_{1-6}$ alkyl groups (e.g., methyl),
(17) a pyridyl group, or
(18) a pyrimidinyl group.

In another embodiment, $R^1$ is preferably
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a $C_{6-14}$ aryl group (e.g., phenyl), or
(9) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl).

In this embodiment, $R^1$ is more preferably
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
  (i) a halogen atom (e.g., a fluorine atom), and
  (ii) a $C_{1-6}$ alkyl group (e.g., methyl),
(17) an oxadiazolyl group optionally substituted by 1 to 3 $C_{1-6}$ alkyl groups (e.g., methyl),
(18) a pyridyl group, or
(19) a pyrimidinyl group optionally substituted by 1 to 3 halogen atoms (e.g., a fluorine atom).

In this embodiment, $R^1$ is further more preferably
(1) a triazolyl group,
(2) a thiazolyl group, or
(3) a pyrimidinyl group.

In this embodiment, $R^1$ is still more preferably
(1) a triazolyl group, or
(2) a pyrimidinyl group.

$R^2$ is preferably
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl).

R² is more preferably
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a phenyl group, or
(7) a $C_{3-10}$ cycloalkyl group (e.g., cyclobutyl).

In another embodiment, R² is preferably
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl).

In this embodiment, R² is more preferably
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a phenyl group, or
(7) a $C_{3-10}$ cycloalkyl group (e.g., cyclobutyl).

In this embodiment, R² is further more preferably
(1) a hydrogen atom,
(2) a halogen atom (e.g., a fluorine atom, a chlorine atom),
(3) a cyano group,
(4) a $C_{1-6}$ alkoxy group (e.g., methoxy), or
(5) a phenyl group.

In this embodiment, R² is still more preferably a hydrogen atom.

Alternatively, preferably, R¹ and R² are bonded to each other to form, together with the adjacent carbon atoms, a 5- or 6-membered ring (e.g., benzene, a $C_{5-6}$ cycloalkene (preferably cyclopentene), a 5- or 6-membered monocyclic aromatic heterocycle (preferably pyridine, pyrimidine, pyrrole, pyrazole, oxazole, thiadiazole) or a 5- or 6-membered monocyclic non-aromatic heterocycle (preferably dihydrofuran, pyrroline)) optionally substituted by 1 to 3 substituents selected from
  (a) a $C_{1-6}$ alkyl group (e.g., methyl), and
  (b) an oxo group.

More preferably, R¹ and R² are bonded to each other to form, together with the adjacent carbon atoms,
(1) a benzene ring,
(2) a $C_{5-6}$ cycloalkene ring (preferably cyclopentene),
(3) a 5- or a 6-membered monocyclic aromatic heterocycle (preferably pyridine, pyrimidine, pyrrole, pyrazole, oxazole, thiadiazole) optionally substituted by 1 to 3 $C_{1-6}$ alkyl groups (e.g., methyl), or
(4) a 5- or 6-membered monocyclic non-aromatic heterocycle (preferably dihydrofuran, pyrroline) optionally substituted by 1 to 3 substituents selected from
  (a) a $C_{1-6}$ alkyl group (e.g., methyl), and
  (b) an oxo group.

Further more preferably, R¹ and R² are bonded to each other to form, together with the adjacent carbon atoms,
(1) a benzene ring,
(2) a cyclopentene ring,
(3) a pyridine ring,
(4) a pyrimidine ring optionally substituted by 1 to 3 $C_{1-6}$ alkyl groups (e.g., methyl),
(5) a pyrrole ring optionally substituted by 1 to 3 $C_{1-6}$ alkyl groups (e.g., methyl),
(6) a pyrazole ring optionally substituted by 1 to 3 $C_{1-6}$ alkyl groups (e.g., methyl),
(7) an oxazole ring optionally substituted by 1 to 3 $C_{1-6}$ alkyl groups (e.g., methyl),
(8) a thiadiazole ring,
(9) a dihydrofuran ring optionally substituted by 1 to 3 $C_{1-6}$ alkyl groups (e.g., methyl), or
(10) a pyrroline ring optionally substituted by 1 to 3 substituents selected from
  (a) a $C_{1-6}$ alkyl group (e.g., methyl), and
  (b) an oxo group.

Ring A is an optionally substituted aromatic ring.

Examples of the "aromatic ring" of the "optionally substituted aromatic ring" represented by Ring A include a $C_{6-14}$ aromatic hydrocarbon ring and an aromatic heterocycle.

Specific examples thereof include a benzene ring, a 5- or 6-membered monocyclic aromatic heterocycle (preferably thiazole, pyridine, pyrimidine, pyridazine, triazine), and a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine).

The "aromatic ring" of the "optionally substituted aromatic ring" represented by Ring A optionally has 1 to 5 (preferably 1 to 3) substituents at substitutable position(s). Examples of the substituent include the above-mentioned Substituent Group A. When the number of the substituents is 2 or more, the respective substituents may be the same or different.

Ring A is preferably a benzene ring, a 5- or 6-membered monocyclic aromatic heterocycle (preferably thiazole, pyridine, pyrimidine, pyridazine, triazine) or a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine), each of which is optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl),
  (g) a $C_{6-14}$ aryl group (e.g., phenyl) optionally substituted by 1 to 3 halogen atoms (e.g., a fluorine atom), and
  (h) a 5- to 14-membered aromatic heterocyclic group (preferably a 5- or 6-membered monocyclic aromatic heterocyclic group (e.g., pyrazolyl)).

Ring A is more preferably
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a 5- or a 6-membered monocyclic aromatic heterocycle (preferably thiazole, pyridine, pyrimidine, pyridazine, triazine) optionally substituted by 1 to 3 substituents selected from (a) a halogen atom (e.g., a fluorine atom, a chlorine atom),
(b) a hydroxy group,
(c) a cyano group,
(d) a $C_{1-6}$ alkyl group (e.g., methyl, ethyl, tert-butyl) optionally substituted by 1 to 3 substituents selected from
  (i) a halogen atom (e.g., a fluorine atom), and
  (ii) a hydroxy group,
(e) a $C_{1-6}$ alkoxy group (e.g., methoxy),
(f) a $C_{3-10}$ cycloalkyl group (e.g., cyclopropyl) optionally substituted by 1 to 3 $C_{1-6}$ alkyl groups (e.g., methyl),
(g) a $C_{6-14}$ aryl group (e.g., phenyl) optionally substituted by 1 to 3 halogen atoms (e.g., a fluorine atom), and
(h) a 5- to 14-membered aromatic heterocyclic group (preferably a 5- or 6-membered monocyclic aromatic heterocyclic group (e.g., pyrazolyl)), or
(3) a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine) optionally substituted by 1 to 3 substituents selected from
  (a) a halogen atom (e.g., a chlorine atom), and
  (b) a $C_{1-6}$ alkyl group (e.g., methyl).

Ring A is further more preferably
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
  (a) a halogen atom (e.g., a fluorine atom, a chlorine atom),
  (b) a cyano group,
  (c) a $C_{1-6}$ alkyl group (e.g., methyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy), and
  (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 halogen atoms (e.g., a fluorine atom),
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl), and
  (g) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring.

In another embodiment, Ring A is preferably a benzene ring, a 5- or 6-membered monocyclic aromatic heterocycle (preferably thiazole, pyridine, pyrimidine, pyridazine, triazine) or a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine), each of which is optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{1-6}$ alkoxy-carbonyl group (e.g., methoxycarbonyl, ethoxycarbonyl),
  (g) a $C_{3-10}$ cycloalkyl group (e.g., cyclopropyl) optionally substituted by 1 to 3 $C_{1-6}$ alkyl groups (e.g., methyl),
  (h) a $C_{6-14}$ aryl group (e.g., phenyl) optionally substituted by 1 to 3 halogen atoms (e.g., a fluorine atom), and
  (i) a 5- to 14-membered aromatic heterocyclic group (preferably a 5- or 6-membered monocyclic aromatic heterocyclic group (e.g., pyrazolyl)).

In this embodiment, Ring A is more preferably
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a 5- or a 6-membered monocyclic aromatic heterocycle (preferably thiazole, pyridine, pyrimidine, pyridazine, triazine) optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{1-6}$ alkoxy-carbonyl group (e.g., methoxycarbonyl, ethoxycarbonyl),
  (g) a $C_{3-10}$ cycloalkyl group (e.g., cyclopropyl) optionally substituted by 1 to 3 $C_{1-6}$ alkyl groups (e.g., methyl),
  (h) a $C_{6-14}$ aryl group (e.g., phenyl) optionally substituted by 1 to 3 halogen atoms (e.g., a fluorine atom), and
  (i) a 5- to 14-membered aromatic heterocyclic group (preferably a 5- or 6-membered monocyclic aromatic heterocyclic group (e.g., pyrazolyl)), or
(3) a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine) optionally substituted by 1 to 3 substituents selected from
  (a) a halogen atom (e.g., a chlorine atom), and
  (b) a $C_{1-6}$ alkyl group (e.g., methyl).

In this embodiment, Ring A is further more preferably
(1) a benzene ring optionally substituted by 1 to 3 substituents selected from (a) a halogen atom (e.g., a fluorine atom, a chlorine atom),
(b) a cyano group, and
(c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
  (a) a halogen atom (e.g., a fluorine atom, a chlorine atom),
  (b) a cyano group,
  (c) a $C_{1-6}$ alkyl group (e.g., methyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy), and
  (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 halogen atoms (e.g., a fluorine atom),
  (e) a $C_{1-6}$ alkoxy group (e.g., methoxy),
  (f) a $C_{1-6}$ alkoxy-carbonyl group (e.g., methoxycarbonyl, ethoxycarbonyl),
  (g) a $C_{3-10}$ cycloalkyl group (e.g., cyclopropyl) optionally substituted by 1 to 3 $C_{1-6}$ alkyl groups (e.g., methyl), and
  (h) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring.

In this embodiment, Ring A is still more preferably a pyrimidine ring optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 halogen atoms (e.g., a fluorine atom),
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl), and
  (g) a $C_{6-14}$ aryl group (e.g., phenyl) optionally substituted by 1 to 3 halogen atoms (e.g., a fluorine atom).

In this embodiment, Ring A is even more preferably a pyrimidine ring substituted by 1 to 3 (preferably 2) substituents selected from a $C_{1-6}$ alkyl group (e.g., methyl) optionally substituted by 1 to 3 halogen atoms (e.g., a fluorine atom).

In this embodiment, Ring A is particularly preferably a pyrimidine ring substituted by two $C_{1-6}$ alkyl groups (e.g., methyl).

Ring B is an optionally further substituted benzene ring, in addition to $R^1$ and $R^2$.

The "benzene ring" of the "optionally substituted benzene ring" represented by Ring B optionally has 1 to 3 (preferably 1 or 2) substituents at substitutable position(s). Examples of the substituent include the above-mentioned Substituent Group A. When the number of the substituents is 2 or more, the respective substituents may be the same or different.

Ring B is preferably a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl),
  (d) a $C_{1-6}$ alkoxy group (e.g., methoxy),
  (e) a $C_{3-10}$ cycloalkyl group (e.g., cyclobutyl), and
  (f) a 5- to 14-membered aromatic heterocyclic group (preferably a 5- or 6-membered monocyclic aromatic heterocyclic group (e.g., triazolyl, pyrazolyl, thiazolyl, pyrimidinyl)).

Ring B is more preferably a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl),
  (d) a $C_{1-6}$ alkoxy group (e.g., methoxy),
  (e) a $C_{3-10}$ cycloalkyl group (e.g., cyclobutyl),
  (f) a triazolyl group,
  (g) a pyrazolyl group,
  (h) a thiazolyl group, and
  (i) a pyrimidinyl group.

In another embodiment, Ring B is preferably a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom),
  (d) a $C_{1-6}$ alkoxy group (e.g., methoxy),
  (e) a $C_{3-10}$ cycloalkyl group (e.g., cyclobutyl), and
  (f) a 5- to 14-membered aromatic heterocyclic group (preferably a 5- or 6-membered monocyclic aromatic heterocyclic group (e.g., triazolyl, pyrazolyl, thiazolyl, pyrimidinyl)).

In this embodiment, Ring B is more preferably a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom),
  (d) a $C_{1-6}$ alkoxy group (e.g., methoxy),
  (e) a $C_{3-10}$ cycloalkyl group (e.g., cyclobutyl),
  (f) a triazolyl group,
  (g) a pyrazolyl group,
  (h) a thiazolyl group, and
  (i) a pyrimidinyl group.

In this embodiment, Ring B is further more preferably a benzene ring optionally further substituted by 1 to 3 substituents, in addition to $R^1$ and $R^2$, selected from
(a) a halogen atom (e.g., a fluorine atom, a chlorine atom, a bromine atom),
(b) a cyano group,
(c) a $C_{1-6}$ alkyl group (e.g., methyl, ethyl) optionally substituted by 1 to 3 halogen atoms (e.g., a fluorine atom),
(d) a $C_{1-6}$ alkoxy group (e.g., methoxy), and
(e) a $C_{3-10}$ cycloalkyl group (e.g., cyclobutyl).

In this embodiment, Ring B is still more preferably a benzene ring optionally further substituted by 1 to 3 (preferably 1 or 2) substituents, in addition to $R^1$ and $R^2$, selected from
(a) a halogen atom (e.g., a fluorine atom, a chlorine atom), and
(b) a $C_{1-6}$ alkyl group (e.g., methyl, ethyl) optionally substituted by 1 to 3 halogen atoms (e.g., a fluorine atom).

In this embodiment, Ring B is particularly preferably a benzene ring optionally further substituted by 1 or 2 substituents, in addition to $R^1$ and $R^2$, selected from
(a) a halogen atom (e.g., a fluorine atom, a chlorine atom), and
(b) a $C_{1-6}$ alkyl group (e.g., methyl).

Ring D is an optionally further substituted 1,2,5-oxadiazepane ring.

The "1,2,5-oxadiazepane ring" of the "optionally further substituted 1,2,5-oxadiazepane ring" represented by Ring D optionally has 1 to 5 (preferably 1 to 3) substituents at substitutable position(s). Examples of the substituent include the above-mentioned Substituent Group A. When the number of the substituents is 2 or more, the respective substituents may be the same or different.

Ring D is preferably a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).

Ring D is more preferably a 1,2,5-oxadiazepane ring optionally further substituted by 1 to 3 (preferably 1 or 2) $C_{1-6}$ alkyl groups (e.g., methyl).

Ring D is further more preferably a 1,2,5-oxadiazepane ring optionally further substituted by one $C_{1-6}$ alkyl group (e.g., methyl).

Compound (I) is preferably a compound represented by the formula (Ia):

(Ia)

wherein
$R^a$, $R^b$, $R^c$ and $R^d$ are each independently a hydrogen atom or a substituent, the carbon atom marked with * is an asymmetric carbon atom, and the other symbols are as defined above, or a salt thereof (in the present specification, sometimes to be referred to as "compound (Ia)").

When $R^a$ is a hydrogen atom, the steric configuration of the partial structure represented by the formula:

is preferably more preferably provided that a partial structure wherein Rb, Rc and Rd are each independently a hydrogen atom is included.

$R^a$ and $R^b$ are preferably each independently
(1) a hydrogen atom, or
(2) a $C_{1-6}$ alkyl group (e.g., methyl, ethyl) optionally substituted by 1 to 3 $C_{1-6}$ alkoxy groups (e.g., methoxy).

More preferably, $R^a$ is a hydrogen atom, and $R^b$ is
(1) a hydrogen atom, or
(2) a $C_{1-6}$ alkyl group (e.g., methyl, ethyl) optionally substituted by 1 to 3 $C_{1-6}$ alkoxy groups (e.g., methoxy).

Further more preferably, $R^a$ is a hydrogen atom, and $R^b$ is
(1) a hydrogen atom, or
(2) a $C_{1-6}$ alkyl group (e.g., methyl).

$R^c$ is preferably
(1) a hydrogen atom, or
(2) a $C_{1-6}$ alkyl group (e.g., methyl, ethyl).

$R^d$ is preferably
(1) a hydrogen atom, or
(2) a $C_{1-6}$ alkyl group (e.g., methyl).

$R^d$ is more preferably a hydrogen atom.

Preferable examples of compound (I) include the following compounds.

[Compound A-1]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom), (5) a $C_{1-6}$ alkoxy group (e.g., methoxy, ethoxy),
(6) a $C_{3-10}$ cycloalkyl group (e.g., cyclobutyl),
(7) a $C_{6-14}$ aryl group (e.g., phenyl), or
(8) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl);
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl); or
$R^1$ and $R^2$ are optionally bonded to each other to form, together with the adjacent carbon atoms, a 5- or 6-membered ring (e.g., benzene, a $C_{5-6}$ cycloalkene (preferably cyclopentene), a 5- or 6-membered monocyclic aromatic heterocycle (preferably pyridine, pyrimidine, pyrrole, pyrazole, oxazole, thiadiazole) or a 5- or 6-membered monocyclic non-aromatic heterocycle (preferably dihydrofuran, pyrroline)) optionally substituted by 1 to 3 substituents selected from
  (a) a $C_{1-6}$ alkyl group (e.g., methyl), and
  (b) an oxo group;
Ring A is a benzene ring, a 5- or 6-membered monocyclic aromatic heterocycle (preferably thiazole, pyridine, pyrimidine, pyridazine, triazine) or a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine), each of which is optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl),
  (g) a $C_{6-14}$ aryl group (e.g., phenyl) optionally substituted by 1 to 3 halogen atoms (e.g., a fluorine atom), and
  (h) a 5- to 14-membered aromatic heterocyclic group (preferably a 5- or 6-membered monocyclic aromatic heterocyclic group (e.g., pyrazolyl));
Ring B is a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl),
  (d) a $C_{1-6}$ alkoxy group (e.g., methoxy),
  (e) a $C_{3-10}$ cycloalkyl group (e.g., cyclobutyl), and
  (f) a 5- to 14-membered aromatic heterocyclic group (preferably a 5- or 6-membered monocyclic aromatic heterocyclic group (e.g., triazolyl, pyrazolyl, thiazolyl, pyrimidinyl)); and Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).

[Compound B-1]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{3-10}$ cycloalkyl group (e.g., cyclobutyl),
(7) a $C_{6-14}$ aryl group (e.g., phenyl), or
(8) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl);
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl); or
$R^1$ and $R^2$ are optionally bonded to each other to form, together with the adjacent carbon atoms,
(1) a benzene ring,
(2) a $C_{5-6}$ cycloalkene ring (preferably cyclopentene),
(3) a 5- or a 6-membered monocyclic aromatic heterocycle (preferably pyridine, pyrimidine, pyrrole, pyrazole, oxazole, thiadiazole) optionally substituted by 1 to 3 $C_{1-6}$ alkyl groups (e.g., methyl), or
(4) a 5- or 6-membered monocyclic non-aromatic heterocycle (preferably dihydrofuran, pyrroline) optionally substituted by 1 to 3 substituents selected from
  (a) a $C_{1-6}$ alkyl group (e.g., methyl), and
  (b) an oxo group;
Ring A is
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a 5- or 6-membered monocyclic aromatic heterocycle (preferably thiazole, pyridine, pyrimidine, pyridazine, triazine) optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{3-10}$ cycloalkyl group (e.g., cyclopropyl) optionally substituted by 1 to 2 $C_{1-6}$ alkyl groups (e.g., methyl), (g) a $C_{6-14}$ aryl group (e.g., phenyl) optionally substituted by 1 to 3 halogen atoms (e.g., a fluorine atom), and (h) a 5- to 14-membered aromatic heterocyclic group (preferably a 5- or 6-membered monocyclic aromatic heterocyclic group (e.g., pyrazolyl)), or (3) a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine) optionally substituted by 1 to 3 substituents selected from (a) a halogen atom (e.g., a chlorine atom), and (b) a $C_{1-6}$ alkyl group (e.g., methyl);

Ring B is a benzene ring optionally further substituted by 1 to 3 substituents, in addition to $R^1$ and $R^2$, selected from (a) a halogen atom (e.g., a fluorine atom, a chlorine atom, a bromine atom), (b) a cyano group, (c) a $C_{1-6}$ alkyl group (e.g., methyl), (d) a $C_{1-6}$ alkoxy group (e.g., methoxy), (e) a $C_{3-10}$ cycloalkyl group (e.g., cyclobutyl), and (f) a 5- to 14-membered aromatic heterocyclic group (preferably a 5- or 6-membered monocyclic aromatic heterocyclic group (e.g., triazolyl, pyrazolyl, thiazolyl, pyrimidinyl)); and Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).

[Compound C-1]

Compound (I) wherein $R^1$ is (1) a hydrogen atom, (2) a halogen atom (e.g., a fluorine atom, a chlorine atom), (3) a cyano group, (4) a $C_{1-6}$ alkyl group (e.g., methyl) optionally substituted by 1 to 3 halogen atoms (e.g., a fluorine atom), (5) a $C_{1-6}$ alkoxy group (e.g., methoxy, ethoxy), (6) a $C_{3-10}$ cycloalkyl group (e.g., cyclobutyl), (7) a phenyl group, (8) a triazolyl group, (9) a pyrrolyl group,

(10) a furyl group,

(11) a thienyl group,

(12) an imidazolyl group,

(13) a pyrazolyl group,

(14) a tetrazolyl group,

(15) a thiazolyl group optionally substituted by 1 to 3 substituents selected from (i) a halogen atom (e.g., a fluorine atom), and (ii) a $C_{1-6}$ alkyl group (e.g., methyl),

(16) an oxadiazolyl group optionally substituted by 1 to 3 $C_{1-6}$ alkyl groups (e.g., methyl),

(17) a pyridyl group, or

(18) a pyrimidinyl group;

$R^2$ is (1) a hydrogen atom, (2) a halogen atom (e.g., a fluorine atom, a chlorine atom, a bromine atom), (3) a cyano group, (4) a $C_{1-6}$ alkyl group (e.g., methyl), (5) a $C_{1-6}$ alkoxy group (e.g., methoxy), (6) a phenyl group, or (7) a $C_{3-10}$ cycloalkyl group (e.g., cyclobutyl); or $R^1$ and $R^2$ are optionally bonded to each other to form, together with the adjacent carbon atoms, (1) a benzene ring, (2) a cyclopentene ring, (3) a pyridine ring, (4) a pyrimidine ring optionally substituted by 1 to 3 $C_{1-6}$ alkyl groups (e.g., methyl), (5) a pyrrole ring optionally substituted by 1 to 3 $C_{1-6}$ alkyl groups (e.g., methyl), (6) a pyrazole ring optionally substituted by 1 to 3 $C_{1-6}$ alkyl groups (e.g., methyl), (7) an oxazole ring optionally substituted by 1 to 3 $C_{1-6}$ alkyl groups (e.g., methyl), (8) a thiadiazole ring, (9) a dihydrofuran ring optionally substituted by 1 to 3 $C_{1-6}$ alkyl groups (e.g., methyl), or

(10) a pyrroline ring optionally substituted by 1 to 3 substituents selected from (a) a $C_{1-6}$ alkyl group (e.g., methyl), and (b) an oxo group;

Ring A is (1) a benzene ring optionally substituted by 1 to 3 substituents selected from (a) a halogen atom (e.g., a fluorine atom, a chlorine atom), (b) a cyano group, and (c) a $C_{1-6}$ alkoxy group (e.g., methoxy), (2) a thiazole ring optionally substituted by 1 to 3 $C_{1-6}$ alkyl groups (e.g., methyl), (3) a pyridine ring optionally substituted by 1 to 3 substituents selected from (a) a halogen atom (e.g., a fluorine atom, a chlorine atom), (b) a cyano group, (c) a $C_{1-6}$ alkyl group (e.g., methyl) optionally substituted by 1 to 3 substituents selected from (i) a halogen atom (e.g., a fluorine atom), and (ii) a hydroxy group, (d) a $C_{1-6}$ alkoxy group (e.g., methoxy), and (e) a 5- to 14-membered aromatic heterocyclic group (preferably a 5- or 6-membered monocyclic aromatic heterocyclic group (e.g., pyrazolyl)), (4) a pyrimidine ring optionally substituted by 1 to 3 substituents selected from (a) a halogen atom (e.g., a fluorine atom, a chlorine atom), (b) a hydroxy group, (c) a cyano group, (d) a $C_{1-6}$ alkyl group (e.g., methyl, ethyl, tert-butyl) optionally substituted by 1 to 3 halogen atoms (e.g., a fluorine atom), (e) a $C_{1-6}$ alkoxy group (e.g., methoxy), (f) a $C_{3-10}$ cycloalkyl group (e.g., cyclopropyl) optionally substituted by 1 to 3 $C_{1-6}$ alkyl groups (e.g., methyl), and (g) a $C_{6-14}$ aryl group (e.g., phenyl) optionally substituted by 1 to 3 halogen atoms (e.g., a fluorine atom), (5) a pyridazine ring optionally substituted by 1 to 3 $C_{1-6}$ alkyl groups (e.g., methyl), (6) a triazine ring optionally substituted by 1 to 3 $C_{1-6}$ alkoxy groups (e.g., methoxy), (7) a quinazoline ring, (8) a thienopyrimidine ring, (9) a benzoxazole ring optionally substituted by 1 to 3 halogen atoms (e.g., a chlorine atom),

(10) an imidazopyridine ring,

(11) a pyrrolopyrimidine ring optionally substituted by 1 to 3 $C_{1-6}$ alkyl groups (e.g., methyl), or

(12) a pyrazolopyrimidine ring;

Ring B is a benzene ring optionally further substituted by 1 to 3 substituents, in addition to $R^1$ and $R^2$, selected from (a) a halogen atom (e.g., a fluorine atom, a chlorine atom, a bromine atom), (b) a cyano group, (c) a $C_{1-6}$ alkyl group (e.g., methyl),
(d) a $C_{1-6}$ alkoxy group (e.g., methoxy),
(e) a $C_{3-10}$ cycloalkyl group (e.g., cyclobutyl),
(f) a triazolyl group,
(g) a pyrazolyl group,
(h) a thiazolyl group, and
(i) a pyrimidinyl group; and
Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).

[Compound D-1]
Compound (Ia) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{3-10}$ cycloalkyl group (e.g., cyclobutyl),
(7) a phenyl group,
(8) a triazolyl group,
(9) a pyrrolyl group,
(10) a furyl group,
(11) a thienyl group,
(12) an imidazolyl group,
(13) a pyrazolyl group,
(14) a tetrazolyl group,
(15) a thiazolyl group optionally substituted by 1 to 3 substituents selected from
  (i) a halogen atom (e.g., a fluorine atom), and
  (ii) a $C_{1-6}$ alkyl group (e.g., methyl),
(16) an oxadiazolyl group optionally substituted by 1 to 3 $C_{1-6}$ alkyl groups (e.g., methyl),
(17) a pyridyl group, or
(18) a pyrimidinyl group;
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a phenyl group, or
(7) a $C_{3-10}$ cycloalkyl group (e.g., cyclobutyl); or
$R^1$ and $R^2$ are optionally bonded to each other to form, together with the adjacent carbon atoms,
(1) a benzene ring,
(2) a cyclopentene ring,
(3) a pyridine ring,
(4) a pyrimidine ring optionally substituted by 1 to 3 $C_{1-6}$ alkyl groups (e.g., methyl),
(5) a pyrrole ring optionally substituted by 1 to 3 $C_{1-6}$ alkyl groups (e.g., methyl),
(6) a pyrazole ring optionally substituted by 1 to 3 $C_{1-6}$ alkyl groups (e.g., methyl),
(7) an oxazole ring optionally substituted by 1 to 3 $C_{1-6}$ alkyl groups (e.g., methyl),
(8) a thiadiazole ring,
(9) a dihydrofuran ring optionally substituted by 1 to 3 $C_{1-6}$ alkyl groups (e.g., methyl), or
(10) a pyrroline ring optionally substituted by 1 to 3 substituents selected from
  (a) a $C_{1-6}$ alkyl group (e.g., methyl), and
  (b) an oxo group;

Ring A is
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
  (a) a halogen atom (e.g., a fluorine atom, a chlorine atom),
  (b) a cyano group,
  (c) a $C_{1-6}$ alkyl group (e.g., methyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy), and
  (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 halogen atoms (e.g., a fluorine atom),
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl), and
  (g) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring;
Ring B is a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl),
  (d) a $C_{1-6}$ alkoxy group (e.g., methoxy),
  (e) a $C_{3-10}$ cycloalkyl group (e.g., cyclobutyl),
  (f) a triazolyl group,
  (g) a pyrazolyl group,
  (h) a thiazolyl group, and
  (i) a pyrimidinyl group;
$R^a$ and $R^b$ are each independently
(1) a hydrogen atom, or
(2) a $C_{1-6}$ alkyl group (e.g., methyl, ethyl) optionally substituted by 1 to 3 $C_{1-6}$ alkoxy groups (e.g., methoxy);
$R^c$ is
(1) a hydrogen atom, or
(2) a $C_{1-6}$ alkyl group (e.g., methyl, ethyl); and
$R^d$ is
(1) a hydrogen atom, or
(2) a $C_{1-6}$ alkyl group (e.g., methyl).

[Compound E-1]
Compound (Ia) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{3-10}$ cycloalkyl group (e.g., cyclobutyl),
(7) a phenyl group,
(8) a triazolyl group,
(9) a pyrrolyl group,
(10) a furyl group,
(11) a thienyl group,
(12) an imidazolyl group,
(13) a pyrazolyl group,
(14) a tetrazolyl group,
(15) a thiazolyl group optionally substituted by 1 to 3 substituents selected from
  (i) a halogen atom (e.g., a fluorine atom), and
  (ii) a $C_{1-6}$ alkyl group (e.g., methyl),
(16) an oxadiazolyl group optionally substituted by 1 to 3 $C_{1-6}$ alkyl groups (e.g., methyl),
(17) a pyridyl group, or
(18) a pyrimidinyl group;
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl),
(5) a $C_{1-6}$ alkoxy group (e.g., methoxy),
(6) a phenyl group, or
(7) a $C_{3-10}$ cycloalkyl group (e.g., cyclobutyl); or
$R^1$ and $R^2$ are optionally bonded to each other to form, together with the adjacent carbon atoms,
(1) a benzene ring,
(2) a cyclopentene ring,
(3) a pyridine ring,
(4) a pyrimidine ring optionally substituted by 1 to 3 $C_{1-6}$ alkyl groups (e.g., methyl),
(5) a pyrrole ring optionally substituted by 1 to 3 $C_{1-6}$ alkyl groups (e.g., methyl),
(6) a pyrazole ring optionally substituted by 1 to 3 $C_{1-6}$ alkyl groups (e.g., methyl),
(7) an oxazole ring optionally substituted by 1 to 3 $C_{1-6}$ alkyl groups (e.g., methyl),
(8) a thiadiazole ring,
(9) a dihydrofuran ring optionally substituted by 1 to 3 $C_{1-6}$ alkyl groups (e.g., methyl), or
(10) a pyrroline ring optionally substituted by 1 to 3 substituents selected from
  (a) a $C_{1-6}$ alkyl group (e.g., methyl), and
  (b) an oxo group;
Ring A is
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
  (a) a halogen atom (e.g., a fluorine atom, a chlorine atom),
  (b) a cyano group,
  (c) a $C_{1-6}$ alkyl group (e.g., methyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy), and
  (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 halogen atoms (e.g., a fluorine atom),
  (e) a $C_{1-6}$ alkoxy group (e.g., methoxy),
  (f) a $C_{3-10}$ cycloalkyl group (e.g., cyclopropyl) optionally substituted by 1 to 3 $C_{1-6}$ alkyl groups (e.g., methyl), and
  (g) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring;
Ring B is a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl),
  (d) a $C_{1-6}$ alkoxy group (e.g., methoxy),
  (e) a $C_{3-10}$ cycloalkyl group (e.g., cyclobutyl),
  (f) a triazolyl group,
  (g) a pyrazolyl group,
  (h) a thiazolyl group, and
  (i) a pyrimidinyl group;
$R^a$ is a hydrogen atom;
$R^b$ is
(1) a hydrogen atom, or
(2) a $C_{1-6}$ alkyl group (e.g., methyl, ethyl) optionally substituted by 1 to 3 $C_{1-6}$ alkoxy groups (e.g., methoxy);
$R^c$ is
(1) a hydrogen atom, or
(2) a $C_{1-6}$ alkyl group (e.g., methyl, ethyl); and
$R^d$ is
(1) a hydrogen atom, or
(2) a $C_{1-6}$ alkyl group (e.g., methyl).
[Compound A-2]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl), (7) a $C_{3-10}$ cycloalkyl group (e.g., cyclobutyl),
(8) a $C_{6-14}$ aryl group (e.g., phenyl), or
(9) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl);

$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a $C_{1-14}$ aryl group (e.g., phenyl), or
(7) a $C_{3-10}$ cycloalkyl group (e.g., cyclobutyl); or $R^1$ and $R^2$ are optionally bonded to each other to form, together with the adjacent carbon atoms, benzene, a $C_{5-6}$ cycloalkene (preferably cyclopentene), a 5- or 6-membered monocyclic aromatic heterocycle (preferably pyridine, pyrimidine, pyrrole, pyrazole, oxazole, thiadiazole) or a 5- or 6-membered monocyclic non-aromatic heterocycle (preferably dihydrofuran, pyrroline), each of which is optionally substituted by 1 to 3 substituents selected from
  (a) a $C_{1-6}$ alkyl group (e.g., methyl), and
  (b) an oxo group
[preferably
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a $C_{6-14}$ aryl group (e.g., phenyl), or
(9) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl); and $R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl)];

Ring A is a benzene ring, a 5- or 6-membered monocyclic aromatic heterocycle (preferably thiazole, pyridine, pyrimidine, pyridazine, triazine) or a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine), each of which is optionally substituted by 1 to 3 substituents selected from
(a) a halogen atom (e.g., a fluorine atom, a chlorine atom),
(b) a hydroxy group,
(c) a cyano group,
(d) a $C_{1-6}$ alkyl group (e.g., methyl, ethyl, tert-butyl) optionally substituted by 1 to 3 substituents selected from
  (i) a halogen atom (e.g., a fluorine atom), and
  (ii) a hydroxy group,
(e) a $C_{1-6}$ alkoxy group (e.g., methoxy),
(f) a $C_{1-6}$ alkoxy-carbonyl group (e.g., methoxycarbonyl, ethoxycarbonyl),
(g) a $C_{3-10}$ cycloalkyl group (e.g., cyclopropyl) optionally substituted by 1 to 3 $C_{1-6}$ alkyl groups (e.g., methyl),
(h) a $C_{6-14}$ aryl group (e.g., phenyl) optionally substituted by 1 to 3 halogen atoms (e.g., a fluorine atom), and
(i) a 5- to 14-membered aromatic heterocyclic group (preferably a 5- or 6-membered monocyclic aromatic heterocyclic group (e.g., pyrazolyl));

Ring B is a benzene ring optionally further substituted by 1 to 3 substituents, in addition to $R^1$ and $R^2$, selected from
(a) a halogen atom (e.g., a fluorine atom, a chlorine atom, a bromine atom),
(b) a cyano group,
(c) a $C_{1-6}$ alkyl group (e.g., methyl, ethyl) optionally substituted by 1 to 3 halogen atoms (e.g., a fluorine atom),
(d) a $C_{1-6}$ alkoxy group (e.g., methoxy),
(e) a $C_{3-10}$ cycloalkyl group (e.g., cyclobutyl), and
(f) a 5- to 14-membered aromatic heterocyclic group (preferably a 5- or 6-membered monocyclic aromatic heterocyclic group (e.g., triazolyl, pyrazolyl, thiazolyl, pyrimidinyl)); and Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).

[Compound B-2]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a $C_{6-14}$ aryl group (e.g., phenyl), or
(9) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl);

$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), (6) a $C_{6-14}$ aryl group (e.g., phenyl), or
(7) a $C_{3-10}$ cycloalkyl group (e.g., cyclobutyl); or
$R^1$ and $R^2$ are optionally bonded to each other to form, together with the adjacent carbon atoms,
(1) a benzene ring,
(2) a $C_{5-6}$ cycloalkene ring (preferably cyclopentene),
(3) a 5- or a 6-membered monocyclic aromatic heterocycle (preferably pyridine, pyrimidine, pyrrole, pyrazole, oxazole, thiadiazole) optionally substituted by 1 to 3 $C_{1-6}$ alkyl groups (e.g., methyl), or
(4) a 5- or 6-membered monocyclic non-aromatic heterocycle (preferably dihydrofuran, pyrroline) optionally substituted by 1 to 3 substituents selected from
  (a) a $C_{1-6}$ alkyl group (e.g., methyl), and
  (b) an oxo group
[preferably
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a $C_{6-14}$ aryl group (e.g., phenyl), or
(9) a 5- to 14-membered aromatic heterocyclic group (preferably a 5- or 6-membered monocyclic aromatic heterocyclic group (e.g., triazolyl, pyrrolyl, furyl, thienyl, imidazolyl, pyrazolyl, tetrazolyl, thiazolyl, oxadiazolyl, pyridyl, pyrimidinyl)) optionally substituted by 1 to 3 substituents selected from
  (i) a halogen atom (e.g., a fluorine atom), and
  (ii) a $C_{1-6}$ alkyl group (e.g., methyl); and
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a $C_{6-14}$ aryl group (e.g., phenyl), or
(7) a $C_{3-10}$ cycloalkyl group (e.g., cyclobutyl)];
Ring A is
(1) a benzene ring optionally substituted by 1 to 3 substituents selected from
  (a) a halogen atom (e.g., a fluorine atom, a chlorine atom),
  (b) a cyano group, and
  (c) a $C_{1-6}$ alkoxy group (e.g., methoxy),
(2) a 5- or a 6-membered monocyclic aromatic heterocycle (preferably thiazole, pyridine, pyrimidine, pyridazine, triazine) optionally substituted by 1 to 3 substituents selected from
  (a) a halogen atom (e.g., a fluorine atom, a chlorine atom),
  (b) a hydroxy group,
  (c) a cyano group,
  (d) a $C_{1-6}$ alkyl group (e.g., methyl, ethyl, tert-butyl) optionally substituted by 1 to 3 substituents selected from
    (i) a halogen atom (e.g., a fluorine atom), and
    (ii) a hydroxy group,
  (e) a $C_{1-6}$ alkoxy group (e.g., methoxy),
  (f) a $C_{1-6}$ alkoxy-carbonyl group (e.g., methoxycarbonyl, ethoxycarbonyl),
  (g) a $C_{3-10}$ cycloalkyl group (e.g., cyclopropyl) optionally substituted by 1 to 3 $C_{1-6}$ alkyl groups (e.g., methyl),
  (h) a $C_{6-14}$ aryl group (e.g., phenyl) optionally substituted by 1 to 3 halogen atoms (e.g., a fluorine atom), and
  (i) a 5- to 14-membered aromatic heterocyclic group (preferably a 5- or 6-membered monocyclic aromatic heterocyclic group (e.g., pyrazolyl)), or
(3) a 8- to 14-membered fused polycyclic (preferably bicyclic or tricyclic) aromatic heterocycle (preferably quinazoline, thienopyrimidine, benzoxazole, imidazopyridine, pyrrolopyrimidine, pyrazolopyrimidine) optionally substituted by 1 to 3 substituents selected from
  (a) a halogen atom (e.g., a chlorine atom), and
  (b) a $C_{1-6}$ alkyl group (e.g., methyl);
Ring B is a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom),
  (d) a $C_{1-6}$ alkoxy group (e.g., methoxy),
  (e) a $C_{3-10}$ cycloalkyl group (e.g., cyclobutyl), and
  (f) a 5- to 14-membered aromatic heterocyclic group (preferably a 5- or 6-membered monocyclic aromatic heterocyclic group (e.g., triazolyl, pyrazolyl, thiazolyl, pyrimidinyl)); and
Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).
[Compound C-2]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
  (i) a halogen atom (e.g., a fluorine atom), and
  (ii) a $C_{1-6}$ alkyl group (e.g., methyl),
(17) an oxadiazolyl group optionally substituted by 1 to 3 $C_{1-6}$ alkyl groups (e.g., methyl),
(18) a pyridyl group, or
(19) a pyrimidinyl group optionally substituted by 1 to 3 halogen atoms (e.g., a fluorine atom);
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), (6) a phenyl group, or
(7) a $C_{3-10}$ cycloalkyl group (e.g., cyclobutyl); or
$R^1$ and $R^2$ are optionally bonded to each other to form, together with the adjacent carbon atoms,
(1) a benzene ring,
(2) a cyclopentene ring,
(3) a pyridine ring,
(4) a pyrimidine ring optionally substituted by 1 to 3 $C_{1-6}$ alkyl groups (e.g., methyl),
(5) a pyrrole ring optionally substituted by 1 to 3 $C_{1-6}$ alkyl groups (e.g., methyl),
(6) a pyrazole ring optionally substituted by 1 to 3 $C_{1-6}$ alkyl groups (e.g., methyl),
(7) an oxazole ring optionally substituted by 1 to 3 $C_{1-6}$ alkyl groups (e.g., methyl),
(8) a thiadiazole ring,
(9) a dihydrofuran ring optionally substituted by 1 to 3 $C_{1-6}$ alkyl groups (e.g., methyl), or
(10) a pyrroline ring optionally substituted by 1 to 3 substituents selected from
    (a) a $C_{1-6}$ alkyl group (e.g., methyl), and
    (b) an oxo group
[preferably
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
    (i) a halogen atom (e.g., a fluorine atom), and
    (ii) a $C_{1-6}$ alkyl group (e.g., methyl),
(17) an oxadiazolyl group optionally substituted by 1 to 3 $C_{1-6}$ alkyl groups (e.g., methyl),
(18) a pyridyl group, or
(19) a pyrimidinyl group optionally substituted by 1 to 3 halogen atoms (e.g., a fluorine atom); and
$R^2$ is
(1) a hydrogen atom,
(2) a halogen atom (e.g., a fluorine atom, a chlorine atom, a bromine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy),
(6) a phenyl group, or
(7) a $C_{3-10}$ cycloalkyl group (e.g., cyclobutyl)];
Ring A is
(1) a benzene ring optionally substituted by 1 to 3 substituents selected from
    (a) a halogen atom (e.g., a fluorine atom, a chlorine atom),
    (b) a cyano group, and
    (c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
    (a) a halogen atom (e.g., a fluorine atom, a chlorine atom),
    (b) a cyano group,
    (c) a $C_{1-6}$ alkyl group (e.g., methyl) optionally substituted by 1 to 3 substituents selected from
        (i) a halogen atom (e.g., a fluorine atom), and
        (ii) a hydroxy group,
    (d) a $C_{1-6}$ alkoxy group (e.g., methoxy), and
    (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
    (a) a halogen atom (e.g., a fluorine atom, a chlorine atom),
    (b) a hydroxy group,
    (c) a cyano group,
    (d) a $C_{1-6}$ alkyl group (e.g., methyl, ethyl, tert-butyl) optionally substituted by 1 to 3 halogen atoms (e.g., a fluorine atom),
    (e) a $C_{1-6}$ alkoxy group (e.g., methoxy),
    (f) a $C_{1-6}$ alkoxy-carbonyl group (e.g., methoxycarbonyl, ethoxycarbonyl),
    (g) a $C_{3-10}$ cycloalkyl group (e.g., cyclopropyl) optionally substituted by 1 to 3 $C_{1-6}$ alkyl groups (e.g., methyl), and
    (h) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring;
Ring B is a benzene ring optionally further substituted by 1 to 3 substituents, in addition to $R^1$ and $R^2$, selected from
    (a) a halogen atom (e.g., a fluorine atom, a chlorine atom, a bromine atom),
    (b) a cyano group,
    (c) a $C_{1-6}$ alkyl group (e.g., methyl, ethyl) optionally substituted by 1 to 3 halogen atoms (e.g., a fluorine atom),
    (d) a $C_{1-6}$ alkoxy group (e.g., methoxy),
    (e) a $C_{3-10}$ cycloalkyl group (e.g., cyclobutyl),
    (f) a triazolyl group,
    (g) a pyrazolyl group,
    (h) a thiazolyl group, and
    (i) a pyrimidinyl group; and
Ring D is a 1,2,5-oxadiazepane ring optionally further substituted by 1 to 3 substituents selected from a $C_{1-6}$ alkyl group (e.g., methyl, ethyl) optionally substituted by 1 to 3 $C_{1-6}$ alkoxy groups (e.g., methoxy).
[Compound D-2]
Compound (I) wherein
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy), (6) a $C_{1-6}$ alkoxy-carbonyl group (e.g., methoxycarbonyl),
(7) a $C_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
   (i) a halogen atom (e.g., a fluorine atom), and
   (ii) a $C_{1-6}$ alkyl group (e.g., methyl),
(17) an oxadiazolyl group optionally substituted by 1 to 3 $C_{1-6}$ alkyl groups (e.g., methyl),
(18) a pyridyl group, or
(19) a pyrimidinyl group optionally substituted by 1 to 3 halogen atoms (e.g., a fluorine atom);
$R^2$ is
(1) a hydrogen atom,
(2) a halogen atom (e.g., a fluorine atom, a chlorine atom),
(3) a cyano group,
(4) a $C_{1-6}$ alkoxy group (e.g., methoxy), or
(5) a phenyl group; or
$R^1$ and $R^2$ are optionally bonded to each other to form, together with the adjacent carbon atoms,
(1) a benzene ring,
(2) a cyclopentene ring,
(3) a pyridine ring,
(4) a pyrimidine ring optionally substituted by 1 to 3 $C_{1-6}$ alkyl groups (e.g., methyl),
(5) a pyrrole ring optionally substituted by 1 to 3 $C_{1-6}$ alkyl groups (e.g., methyl),
(6) a pyrazole ring optionally substituted by 1 to 3 $C_{1-6}$ alkyl groups (e.g., methyl),
(7) an oxazole ring optionally substituted by 1 to 3 $C_{1-6}$ alkyl groups (e.g., methyl),
(8) a thiadiazole ring,
(9) a dihydrofuran ring optionally substituted by 1 to 3 $C_{1-6}$ alkyl groups (e.g., methyl), or
(10) a pyrroline ring optionally substituted by 1 to 3 substituents selected from
   (a) a $C_{1-6}$ alkyl group (e.g., methyl), and
   (b) an oxo group
[preferably
$R^1$ is
(1) a hydrogen atom,
(2) a halogen atom (e.g., a fluorine atom, a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy, ethoxy),
(6) a $C_{1-6}$ alkoxy-carbonyl group (e.g., methoxycarbonyl),
(7) a $C_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
   (i) a halogen atom (e.g., a fluorine atom), and
   (ii) a $C_{1-6}$ alkyl group (e.g., methyl),
(17) an oxadiazolyl group optionally substituted by 1 to 3 $C_{1-6}$ alkyl groups (e.g., methyl),
(18) a pyridyl group, or
(19) a pyrimidinyl group optionally substituted by 1 to 3 halogen atoms (e.g., a fluorine atom); and
$R^2$ is
(1) a hydrogen atom,
(2) a halogen atom (e.g., a fluorine atom, a chlorine atom),
(3) a cyano group,
(4) a $C_{1-6}$ alkoxy group (e.g., methoxy), or
(5) a phenyl group];
Ring A is
(1) a benzene ring optionally substituted by 1 to 3 substituents selected from
   (a) a halogen atom (e.g., a fluorine atom, a chlorine atom),
   (b) a cyano group, and
   (c) a $C_{1-6}$ alkoxy group (e.g., methoxy),
(2) a thiazole ring optionally substituted by 1 to 3 $C_{1-6}$ alkyl groups (e.g., methyl),
(3) a pyridine ring optionally substituted by 1 to 3 substituents selected from
   (a) a halogen atom (e.g., a fluorine atom, a chlorine atom),
   (b) a cyano group,
   (c) a $C_{1-6}$ alkyl group (e.g., methyl) optionally substituted by 1 to 3 substituents selected from
      (i) a halogen atom (e.g., a fluorine atom), and
      (ii) a hydroxy group,
   (d) a $C_{1-6}$ alkoxy group (e.g., methoxy), and
   (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
   (a) a halogen atom (e.g., a fluorine atom, a chlorine atom),
   (b) a hydroxy group,
   (c) a cyano group,
   (d) a $C_{1-6}$ alkyl group (e.g., methyl, ethyl, tert-butyl) optionally substituted by 1 to 3 halogen atoms (e.g., a fluorine atom),
   (e) a $C_{1-6}$ alkoxy group (e.g., methoxy),
   (f) a $C_{1-6}$ alkoxy-carbonyl group (e.g., methoxycarbonyl, ethoxycarbonyl),
   (g) a $C_{3-10}$ cycloalkyl group (e.g., cyclopropyl) optionally substituted by 1 to 3 $C_{1-6}$ alkyl groups (e.g., methyl), and
   (h) a $C_{6-14}$ aryl group (e.g., phenyl) optionally substituted by 1 to 3 halogen atoms (e.g., a fluorine atom),
(5) a pyridazine ring optionally substituted by 1 to 3 $C_{1-6}$ alkyl groups (e.g., methyl),
(6) a triazine ring optionally substituted by 1 to 3 $C_{1-6}$ alkoxy groups (e.g., methoxy),
(7) a quinazoline ring,
(8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring;
Ring B is a benzene ring optionally further substituted by 1 to 3 substituents, in addition to $R^1$ and $R^2$, selected from
   (a) a halogen atom (e.g., a fluorine atom, a chlorine atom, a bromine atom),
   (b) a cyano group,
   (c) a $C_{1-6}$ alkyl group (e.g., methyl, ethyl) optionally substituted by 1 to 3 halogen atoms (e.g., a fluorine atom), (d) a C$_{1-6}$ alkoxy group (e.g., methoxy), and
(e) a C$_{3-10}$ cycloalkyl group (e.g., cyclobutyl); and Ring D is a 1,2,5-oxadiazepane ring optionally further substituted by 1 to 3 substituents selected from a C$_{1-6}$ alkyl group (e.g., methyl, ethyl) optionally substituted by 1 to 3 C$_{1-6}$ alkoxy groups (e.g., methoxy).

[Compound D-2a]

Compound (Ia) wherein

R$^1$ is (1) a hydrogen atom,
(2) a halogen atom (e.g., a fluorine atom, a chlorine atom),
(3) a cyano group,
(4) a C$_{1-6}$ alkyl group (e.g., methyl) optionally substituted by 1 to 3 halogen atoms (e.g., a fluorine atom),
(5) a C$_{1-6}$ alkoxy group (e.g., methoxy, ethoxy),
(6) a C$_{1-6}$ alkoxy-carbonyl group (e.g., methoxycarbonyl),
(7) a C$_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
   (i) a halogen atom (e.g., a fluorine atom), and
   (ii) a C$_{1-6}$ alkyl group (e.g., methyl),
(17) an oxadiazolyl group optionally substituted by 1 to 3 C$_{1-6}$ alkyl groups (e.g., methyl),
(18) a pyridyl group, or
(19) a pyrimidinyl group optionally substituted by 1 to 3 halogen atoms (e.g., a fluorine atom);

R$^2$ is (1) a hydrogen atom,
(2) a halogen atom (e.g., a fluorine atom, a chlorine atom),
(3) a cyano group,
(4) a C$_{1-6}$ alkoxy group (e.g., methoxy), or
(5) a phenyl group; or R$^1$ and R$^2$ are optionally bonded to each other to form, together with the adjacent carbon atoms, (1) a benzene ring,
(2) a cyclopentene ring,
(3) a pyridine ring,
(4) a pyrimidine ring optionally substituted by 1 to 3 C$_{1-6}$ alkyl groups (e.g., methyl),
(5) a pyrrole ring optionally substituted by 1 to 3 C$_{1-6}$ alkyl groups (e.g., methyl),
(6) a pyrazole ring optionally substituted by 1 to 3 C$_{1-6}$ alkyl groups (e.g., methyl),
(7) an oxazole ring optionally substituted by 1 to 3 C$_{1-6}$ alkyl groups (e.g., methyl),
(8) a thiadiazole ring,
(9) a dihydrofuran ring optionally substituted by 1 to 3 C$_{1-6}$ alkyl groups (e.g., methyl), or
(10) a pyrroline ring optionally substituted by 1 to 3 substituents selected from
   (a) a C$_{1-6}$ alkyl group (e.g., methyl), and
   (b) an oxo group

[preferably

R$^1$ is (1) a hydrogen atom,
(2) a halogen atom (e.g., a fluorine atom, a chlorine atom),
(3) a cyano group,
(4) a C$_{1-6}$ alkyl group (e.g., methyl) optionally substituted by 1 to 3 halogen atoms (e.g., a fluorine atom),
(5) a C$_{1-6}$ alkoxy group (e.g., methoxy, ethoxy),
(6) a C$_{1-6}$ alkoxy-carbonyl group (e.g., methoxycarbonyl),
(7) a C$_{3-10}$ cycloalkyl group (e.g., cyclobutyl),
(8) a phenyl group,
(9) a triazolyl group,
(10) a pyrrolyl group,
(11) a furyl group,
(12) a thienyl group,
(13) an imidazolyl group,
(14) a pyrazolyl group,
(15) a tetrazolyl group,
(16) a thiazolyl group optionally substituted by 1 to 3 substituents selected from
   (i) a halogen atom (e.g., a fluorine atom), and
   (ii) a C$_{1-6}$ alkyl group (e.g., methyl),
(17) an oxadiazolyl group optionally substituted by 1 to 3 C$_{1-6}$ alkyl groups (e.g., methyl),
(18) a pyridyl group, or
(19) a pyrimidinyl group optionally substituted by 1 to 3 halogen atoms (e.g., a fluorine atom); and R$^2$ is (1) a hydrogen atom,
(2) a halogen atom (e.g., a fluorine atom, a chlorine atom),
(3) a cyano group,
(4) a C$_{1-6}$ alkoxy group (e.g., methoxy), or
(5) a phenyl group];

Ring A is (1) a benzene ring optionally substituted by 1 to 3 substituents selected from
   (a) a halogen atom (e.g., a fluorine atom, a chlorine atom),
   (b) a cyano group, and
   (c) a C$_{1-6}$ alkoxy group (e.g., methoxy),
(2) a thiazole ring optionally substituted by 1 to 3 C$_{1-6}$ alkyl groups (e.g., methyl),
(3) a pyridine ring optionally substituted by 1 to 3 substituents selected from
   (a) a halogen atom (e.g., a fluorine atom, a chlorine atom),
   (b) a cyano group,
   (c) a C$_{1-6}$ alkyl group (e.g., methyl) optionally substituted by 1 to 3 substituents selected from
      (i) a halogen atom (e.g., a fluorine atom), and
      (ii) a hydroxy group,
   (d) a C$_{1-6}$ alkoxy group (e.g., methoxy), and
   (e) a 5- to 14-membered aromatic heterocyclic group (preferably a 5- or 6-membered monocyclic aromatic heterocyclic group (e.g., pyrazolyl)),
(4) a pyrimidine ring optionally substituted by 1 to 3 substituents selected from
   (a) a halogen atom (e.g., a fluorine atom, a chlorine atom),
   (b) a hydroxy group,
   (c) a cyano group,
   (d) a C$_{1-6}$ alkyl group (e.g., methyl, ethyl, tert-butyl) optionally substituted by 1 to 3 halogen atoms (e.g., a fluorine atom),
   (e) a C$_{1-6}$ alkoxy group (e.g., methoxy),
   (f) a C$_{1-6}$ alkoxy-carbonyl group (e.g., methoxycarbonyl, ethoxycarbonyl),
   (g) a C$_{3-10}$ cycloalkyl group (e.g., cyclopropyl) optionally substituted by 1 to 3 C$_{1-6}$ alkyl groups (e.g., methyl), and
   (h) a C$_{6-14}$ aryl group (e.g., phenyl) optionally substituted by 1 to 3 halogen atoms (e.g., a fluorine atom),
(5) a pyridazine ring optionally substituted by 1 to 3 C$_{1-6}$ alkyl groups (e.g., methyl),
(6) a triazine ring optionally substituted by 1 to 3 C$_{1-6}$ alkoxy groups (e.g., methoxy),
(7) a quinazoline ring, (8) a thienopyrimidine ring,
(9) a benzoxazole ring optionally substituted by 1 to 3 halogen atoms (e.g., a chlorine atom),
(10) an imidazopyridine ring,
(11) a pyrrolopyrimidine ring optionally substituted by 1 to 3 $C_{1-6}$ alkyl groups (e.g., methyl), or
(12) a pyrazolopyrimidine ring;

Ring B is a benzene ring optionally further substituted by 1 to 3 substituents, in addition to $R^1$ and $R^2$, selected from
  (a) a halogen atom (e.g., a fluorine atom, a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom),
  (d) a $C_{1-6}$ alkoxy group (e.g., methoxy), and
  (e) a $C_{3-10}$ cycloalkyl group (e.g., cyclobutyl);

$R^a$ is a hydrogen atom;
$R^b$ is
(1) a hydrogen atom, or
(2) a $C_{1-6}$ alkyl group (e.g., methyl, ethyl) optionally substituted by 1 to 3 $C_{1-6}$ alkoxy groups (e.g., methoxy);
$R^c$ is
(1) a hydrogen atom, or
(2) a $C_{1-6}$ alkyl group (e.g., methyl, ethyl); and
$R^d$ is
(1) a hydrogen atom, or
(2) a $C_{1-6}$ alkyl group (e.g., methyl).

[Compound E-2]
Compound (I) wherein
$R^1$ is
(1) a triazolyl group,
(2) a thiazolyl group, or
(3) a pyrimidinyl group;
$R^2$ is a hydrogen atom;
Ring A is a pyrimidine ring substituted by 1 to 3 (preferably 2) substituents selected from a $C_{1-6}$ alkyl group (e.g., methyl) optionally substituted by 1 to 3 halogen atoms (e.g., a fluorine atom);
Ring B is a benzene ring optionally further substituted by 1 to 3 (preferably 1 or 2) substituents, in addition to $R^1$ and $R^2$, selected from
  (a) a halogen atom (e.g., a fluorine atom, a chlorine atom), and
  (b) a $C_{1-6}$ alkyl group (e.g., methyl, ethyl) optionally substituted by 1 to 3 halogen atoms (e.g., a fluorine atom); and
Ring D is a 1,2,5-oxadiazepane ring optionally further substituted by 1 to 3 (preferably 1 or 2) $C_{1-6}$ alkyl groups (e.g., methyl).

[Compound E-2a]
Compound (Ia) wherein
$R^1$ is
(1) a triazolyl group,
(2) a thiazolyl group, or
(3) a pyrimidinyl group;
$R^2$ is a hydrogen atom;
Ring A is a pyrimidine ring substituted by 1 to 3 (preferably 2) substituents selected from a $C_{1-6}$ alkyl group (e.g., methyl) optionally substituted by 1 to 3 halogen atoms (e.g., a fluorine atom);
Ring B is a benzene ring optionally further substituted by 1 to 3 (preferably 1 or 2) substituents, in addition to $R^1$ and $R^2$, selected from
  (a) a halogen atom (e.g., a fluorine atom, a chlorine atom), and
  (b) a $C_{1-6}$ alkyl group (e.g., methyl, ethyl) optionally substituted by 1 to 3 halogen atoms (e.g., a fluorine atom);

$R^a$ is a hydrogen atom;
$R^b$ is
(1) a hydrogen atom, or
(2) a $C_{1-6}$ alkyl group (e.g., methyl);
$R^c$ is
(1) a hydrogen atom, or
(2) a $C_{1-6}$ alkyl group (e.g., methyl); and
$R^d$ is
(1) a hydrogen atom, or
(2) a $C_{1-6}$ alkyl group (e.g., methyl).

[Compound F-2]
Compound (I) wherein
$R^1$ is
(1) a triazolyl group, or
(2) a pyrimidinyl group;
$R^2$ is a hydrogen atom;
Ring A is a pyrimidine ring substituted by two $C_{1-6}$ alkyl groups (e.g., methyl);
Ring B is a benzene ring optionally further substituted by 1 or 2 substituents, in addition to $R^1$ and $R^2$, selected from
  (a) a halogen atom (e.g., a fluorine atom, a chlorine atom), and
  (b) a $C_{1-6}$ alkyl group (e.g., methyl); and
Ring D is a 1,2,5-oxadiazepane ring optionally further substituted by one $C_{1-6}$ alkyl group (e.g., methyl).

[Compound F-2a]
Compound (Ia) wherein
$R^1$ is
(1) a triazolyl group, or
(2) a pyrimidinyl group;
$R^2$ is a hydrogen atom;
Ring A is a pyrimidine ring substituted by two $C_{1-6}$ alkyl groups (e.g., methyl);
Ring B is a benzene ring optionally further substituted by 1 or 2 substituents, in addition to $R^1$ and $R^2$, selected from
  (a) a halogen atom (e.g., a fluorine atom, a chlorine atom), and
  (b) a $C_{1-6}$ alkyl group (e.g., methyl);
$R^a$ is a hydrogen atom;
$R^b$ is
(1) a hydrogen atom, or
(2) a $C_{1-6}$ alkyl group (e.g., methyl);
$R^c$ is
(1) a hydrogen atom, or
(2) a $C_{1-6}$ alkyl group (e.g., methyl); and
$R^d$ is a hydrogen atom.

When compound (I) is in a form of a salt, examples thereof include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline-earth metal salts such as calcium salt, magnesium salt, barium salt and the like; an aluminium salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among them, a pharmaceutically acceptable salt is preferable. For example, when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like, and when a compound has an acidic functional group, examples thereof include inorganic salts such alkali metal salts (e.g., sodium salt, potassium salt, etc.), alkaline-earth metal salts (e.g., calcium salt, magnesium salt, barium salt, etc.) and the like, an ammonium salt and the like.

Compound (I) may be in the crystal form. Either single crystalline form or crystalline mixture are encompassed in compound (I).

Compound (I) may be a pharmaceutically acceptable co-crystal or a co-crystal salt. The co-crystal or co-crystal salt as used herein means a crystalline material composed of two or more unique solids at room temperature, each of which has distinctive physical characteristics (e.g., structure, melting point, heats of fusion, hygroscopicity, solubility, stability, etc.). A co-crystal or a co-crystal salt can be produced according to co-crystallization method known per se.

Compound (I) encompass a solvate (e.g., a hydrate) or a non-solvate. In addition, compound (I) may be a compound labeled with or substituted by isotopes (e.g., $^{2}H$, $^{3}H$, $^{11}C$, $^{14}C$, $^{18}F$, $^{35}S$, $^{125}I$ etc.) and the like. The compound labeled with or substituted by isotopes can be used as, for example, a tracer used for Positron Emission Tomography (PET) (PET tracer), and are expected to be useful in the field of medical diagnosis and the like.

When compound (I) of the present invention has an asymmetric center, isomers such as enantiomer and diastereomer and the like may be exist. Such isomer and mixtures thereof are all encompassed in the present invention. In addition, when an isomer due to conformation tautomer is exist, such isomer and mixtures thereof are also all encompassed in compound (I) of the present invention.

The production method of the compound of the present invention is explained in the following.

The starting materials and reagents used in each step in the following production method, and the compounds obtained therein each may form a salt. Examples of the salt include those similar to the above-mentioned salts of the compound of the present invention, and the like.

When the compound obtained in each step is a free compound, it can be converted to a desired salt according to a method known per se. Conversely, when the compound obtained in each step is a salt, it can be converted to a free form or a desired other kind of salt according to a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds used in each step are commercially available, the commercially available products can be directly used.

In the reaction of each step, while the reaction time varies depending on the reagents and solvents to be used, unless otherwise specified, it is generally 1 min to 48 hr, preferably 10 min to 8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm to 20 atm, preferably 1 atm to 3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature to 300° C., preferably 50° C. to 250° C. While the reaction time varies depending on the reagents and solvents to be used, unless otherwise specified, it is generally 1 min to 48 hr, preferably 1 min to 8 hr.

In the reaction of each step, unless otherwise specified, a reagent is used in 0.5 equivalent to 20 equivalents, preferably 0.8 equivalent to 5 equivalents, relative to the substrate. When a reagent is used as a catalyst, the reagent is used in 0.001 equivalent to 1 equivalent, preferably 0.01 equivalent to 0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

The above-mentioned solvent can be used in a mixture of two or more kinds thereof in an appropriate ratio.

When a base is used in the reaction of each step, for example, bases shown below or those described in Examples are used.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13 to vol. 19 (The Chemical Society of Japan ed.); Shinjikken Kagaku Kouza (Courses in Experimental Chemistry), vol. 14 and vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I to VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1 to Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate protecting groups such as acetate and the like; sulfonate protecting groups such as methanesulfonate and the like; carbonate protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as 0-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid, triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride and a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., inorganic bases, organic bases and the like) are used as the reagent.

A microwave synthetic apparatus such as initiator manufactured by Biotage, and the like may be used in each step.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include arylmagnesium halides such as phenylmagnesium bromide and the like; and alkylmagnesium halides such as methylmagnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When the Mitsunobu reaction is performed in each step, azodicarbonyldipiperazine (ADDP) and tributylphosphine are also used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; phosphorous condensing agents such as 2,4,6-tripropyl-1,3,5,2,4,6-trioxatriphosphinane 2,4,6-trioxide (T3P), diethyl cyanophosphate, diphenylphosphoryl azide (DPPA) and the like; benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphate (HATU); fluoro-N,N,N',N'-tetramethylformamidinium hexafluorophosphorate (TFFH); sulfuric acid; a combination thereof and the like.

When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris (triphenylphosphine)rhodium(III) chloride and the like; a cobalt compound; copper compounds such as copper oxide, copper(I) iodide and the like; a platinum compound and the like. In addition, a base may be added to the reaction system. Examples of the base include inorganic bases, metal alkoxides and the like.

When a coupling reaction is performed in each step, examples of the metal catalyst also include palladium compounds such as palladium(II) chloride, chloro(2-dicyclohexylphosphino-2',4',6'-triisopropyl-1,1'-biphenyl)[2-(2-aminoethyl)phenyl)]palladium(II), chloro[2-(di-tert-butylphosphino)-2',4',6'-triisopropyl-1,1'-biphenyl][2-(2-aminoethyl)phenyl)]palladium(II), chloro(2-dicyclohexylphosphino-2',6'-dimethoxy-1,1'-biphenyl)[2-(2-aminoethylphenyl)]palladium(II) methyl-tert-butyl ether adduct, chloro-(2-dicyclohexylphosphino-2',6'-diisopropoxy-1,1'-biphenyl)[2-(2-aminoethyl)phenyl]palladium (II), chloro[2-(2-dicyclohexylphosphino)-3,6-dimethoxy-2', 4',6'-triisopropyl-1,1'-biphenyl)][2-(2-aminoethyl)phenyl)] palladium(II), chloro(2-dicyclohexylphosphino-2',4',6'-triisopropyl-1,1'-biphenyl)[2-(2'-amino-1,1'-biphenyl)] palladium(II), chloro(2-dicyclohexylphosphino-2',6'-dimethoxy-1,1'-biphenyl)[2-(2'-amino-1,1'-biphenyl)] palladium(II), chloro(2-dicyclohexylphosphino-2',6'-diisopropoxy-1,1'-biphenyl)[2-(2'-amino-1,1'-biphenyl)] palladium(II) and the like.

When a coupling reaction is performed in each step, where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropylbiphenyl, 2-dicyclohexylphosphino-2',6'-dimethoxybiphenyl, 2-dicyclohexylphosphino-2',6'-diisopropoxybiphenyl, 2-(dicyclohexylphosphino)-3,6-dimethoxy-2',4',6'-triisopropyl-1,1'-biphenyl, 2-di-tert-butylphosphino-2',4', 6'-triisopropylbiphenyl, triphenylphosphine, tri-tert-butylphosphine, N,N'-dimethylethylene diamine, proline, L-proline, D-proline, trans-1,2-cyclohexyldiamine, phenanthroline etc.) may be added, and a metal oxide (e.g., copper oxide, silver oxide etc.) may be used as a cocatalyst, in addition to the above-mentioned metal catalyst. In addition, a base may be added to the reaction system. Examples of the base include inorganic bases and the like. In this step, a microwave synthetic apparatus such as initiator manufactured by Biotage, and the like may be used.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Of compound (I), a compound represented by the formula (I-A)

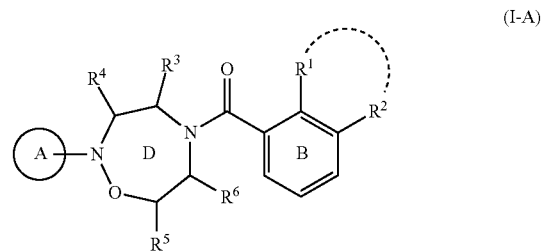

wherein each symbol is as defined above (hereinafter to be referred to as compound (I-A)) can be produced according to the following Method A or a method analogous thereto. When the raw material compound used in each method are commercially available, the commercially available product can be directly used, or the raw material compound can also be synthesized according to a method known per se a method analogous thereto. In each step in the following production methods, the raw material compounds may be in a form of a salt, and examples of such salt include those exemplified as the salts of compound (I).

[Method A]

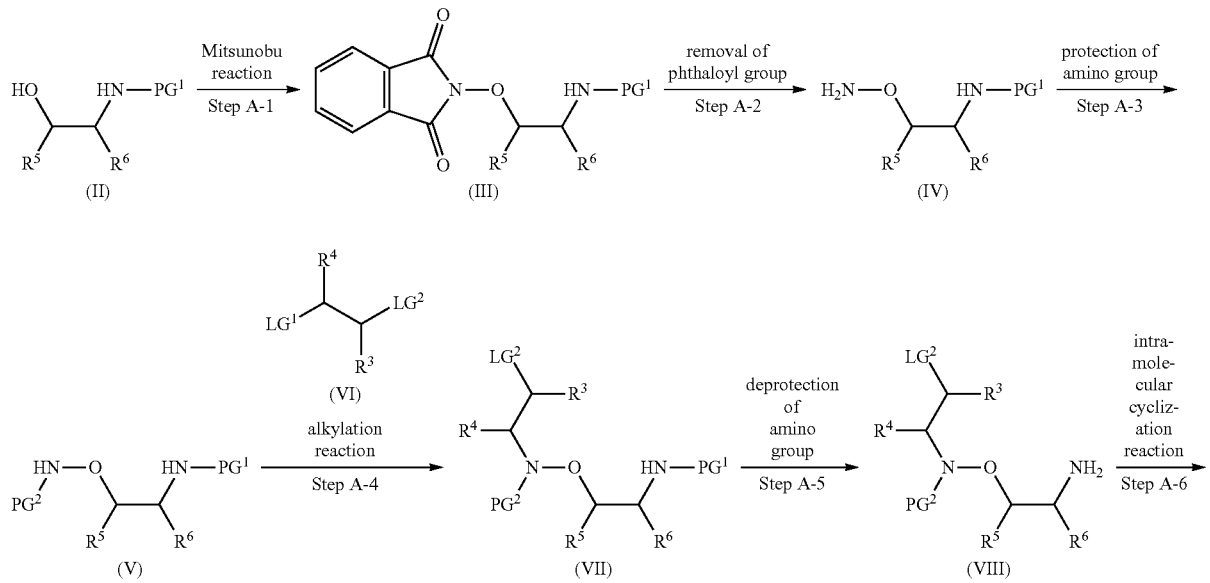

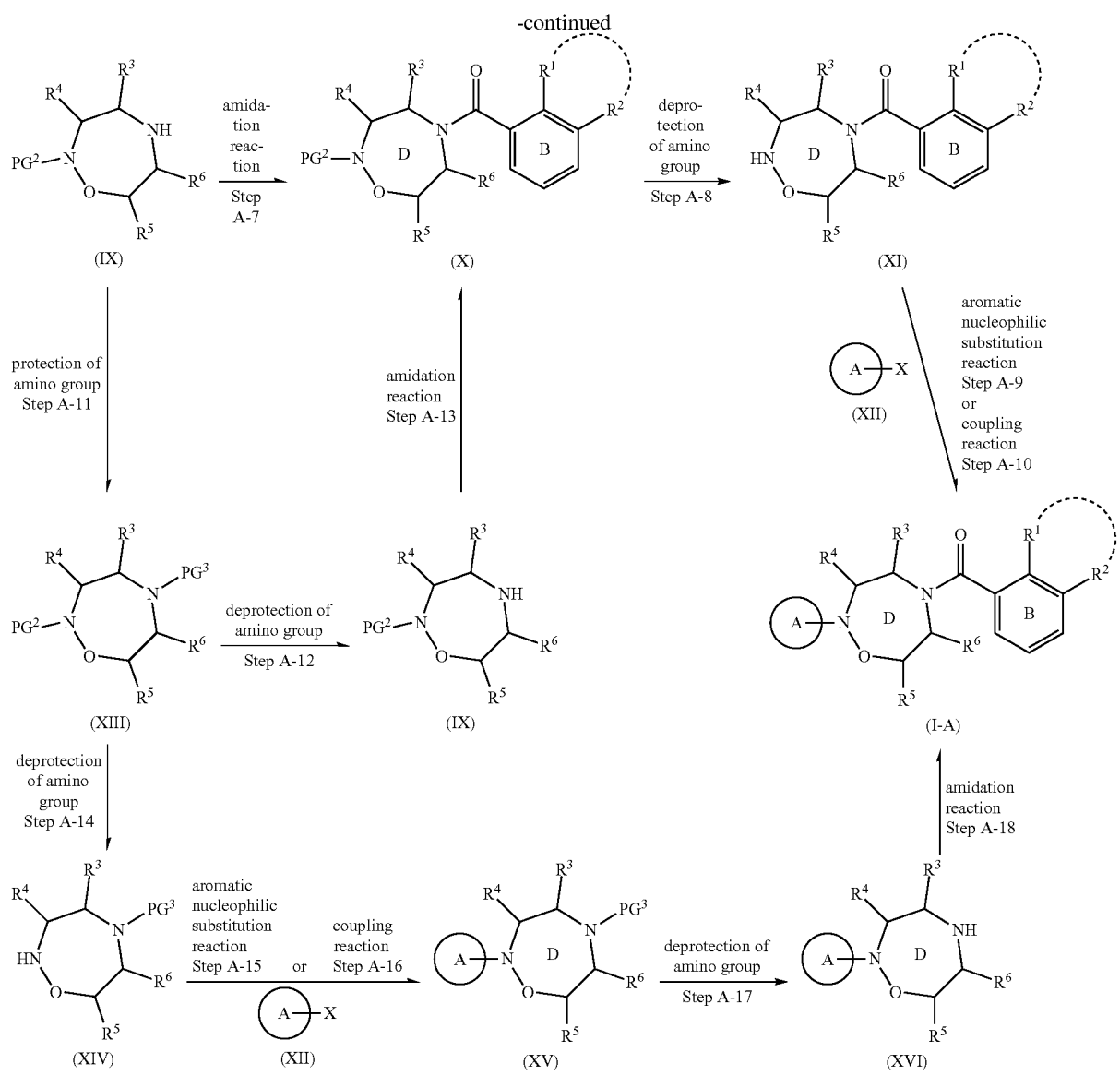

wherein $R^3$, $R^4$, $R^5$ and $R^6$ are each independently a hydrogen atom or an optionally substituted $C_{1-6}$ alkyl group, X is a halogen atom, $PG^1$, $PG^2$ and $PG^3$ are each independently an amino-protecting group, $LG^1$ and $LG^2$ are each independently a leaving group, and the other symbols are as defined above.

Examples of the leaving group represented by $LG^1$ or $LG^2$ include a halogen atom (e.g., a fluorine atom, a chlorine atom, a bromine atom, an iodine atom) and the like.

Compound (II), compound (VI) and compound (XII), which are used as a raw material in the method, may be commercially available products, or can also be produced according to a method known per se or a method analogous thereto.

(Step A-4)

This step is a step of converting compound (V) to compound (VII) by subjecting compound (V) to an alkylation reaction with compound (VI) and a base. Examples of the base include potassium hydride, sodium hydride and the like.

(Step A-6)

This step is a step of converting compound (VIII) to compound (IX) by subjecting compound (VIII) to intramolecular cyclization reaction with an base. Examples of the base include sodium hydroxide, potassium hydroxide, sodium carbonate, potassium carbonate, cesium carbonate, triethylamine, diisopropylethylamine and the like.

Compound (XIII) can also be produced according to the following Method B.

[Method B]

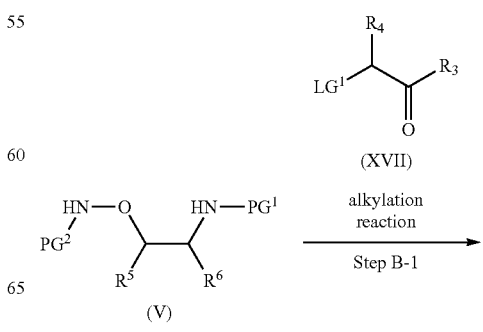

-continued

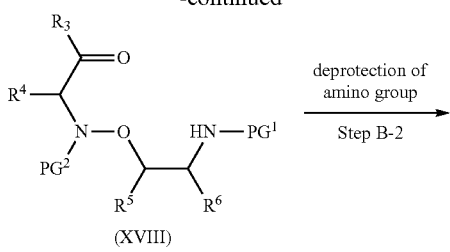

(XVIII)

deprotection of amino group
Step B-2

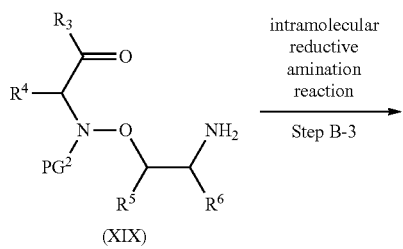

(XIX)

intramolecular reductive amination reaction
Step B-3

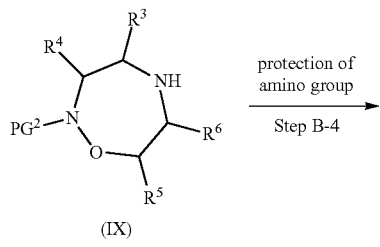

(IX)

protection of amino group
Step B-4

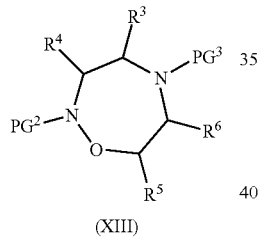

(XIII)

wherein each symbol is as defined above.

Compound (XVII), which is used as a raw material in the method, may be a commercially available product, or can also be produced according to a method known per se or a method analogous thereto.

(Step B-1)

This step is a step of converting compound (V) to compound (XVIII) by subjecting compound (V) to an alkylation reaction with compound (XVII) and a base. Examples of the base include sodium carbonate, potassium carbonate, cesium carbonate and the like.

(Step B-3)

This step is a step of converting compound (XIX) to compound (IX) by subjecting compound (XIX) to an intramolecular reductive amination reaction with a reducing agent. Examples of the reducing agent to be used include sodium triacetoxyborohydride, sodium cyanoborohydride and the like.

Compound (XIII'), which is compound (XIII) wherein R⁶ is a hydrogen atom, can also be produced according to the following Method C.

[Method C]

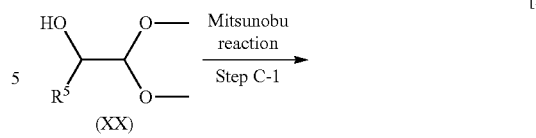

(XX)

Mitsunobu reaction
Step C-1

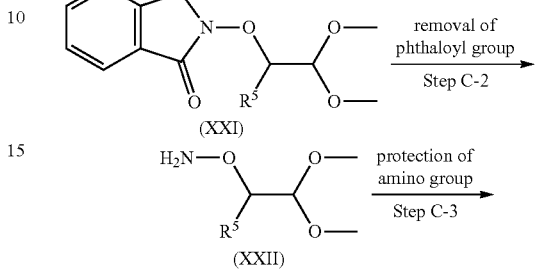

(XXI)

removal of phthaloyl group
Step C-2

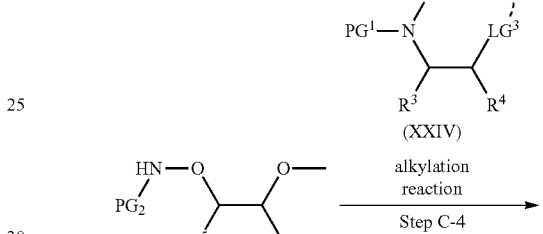

(XXII)

protection of amino group
Step C-3

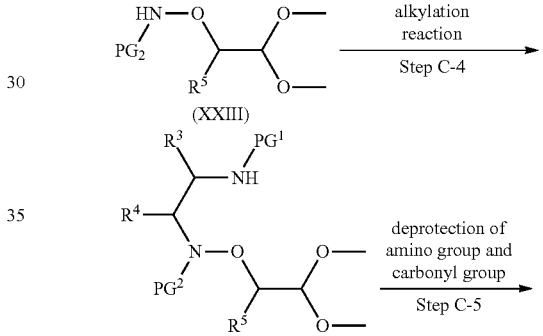

(XXIII)

alkylation reaction
Step C-4

(XXIV)

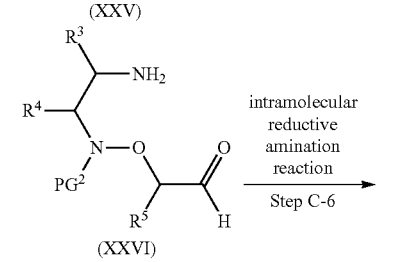

(XXV)

deprotection of amino group and carbonyl group
Step C-5

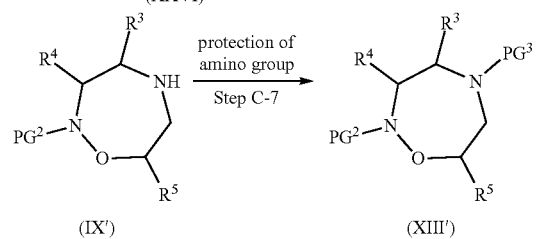

(XXVI)

intramolecular reductive amination reaction
Step C-6

(IX')

protection of amino group
Step C-7

(XIII')

wherein LG³ is a leaving group, R⁷ is a hydrogen atom, or R⁷ and LG³ in combination form a heterocycle (e.g., 2,2-dioxido-1,2,3-oxathiazolidine ring etc.), and the other symbols are as defined above.

Examples of the leaving group represented by LG³ include a halogen atom (e.g., a fluorine atom, a chlorine atom, a bromine atom, an iodine atom), a substituted sulfonyloxy group (e.g., a $C_{1-6}$ alkylsulfonyloxy group optionally substituted by 1 to 3 halogen atoms (e.g., a methanesulfonyloxy group, an ethanesulfonyloxy group, a trifluoromethanesulfonyloxy group etc.); a $C_{6-14}$ arylsulfonyloxy group optionally substituted by 1 to 3 $C_{1-6}$ alkyl groups (e.g., a benzenesulfonyloxy group, a p-toluenesulfonyloxy group etc.); a $C_{7-14}$ aralkylsulfonyloxy group (e.g., a benzylsulfonyloxy group etc.) etc.) and the like.

Compound (XX) and compound (XXIV), which are used as a raw material in the method, may be commercially available products, or can also be produced according to a method known per se [Journal of Organic Chemistry, 2002, vol. 67, page 5164, and the like] or a method analogous thereto.

(Step C-4)

This step is a step of converting compound (XXIII) to compound (XXV) by subjecting compound (XXIII) to an alkyl reaction with compound (XXIV) and a base. Examples of the base include potassium hydride, sodium hydride and the like.

(Step C-6)

This step is a step of converting compound (XXVI) to compound (IX') by subjecting compound (XXVI) to an intramolecular reductive amination reaction with a reducing agent. Examples of the reducing agent to be used include sodium triacetoxyborohydride, sodium cyanoborohydride and the like.

In addition, compound (XIII) can also be produced according to the following Method D.

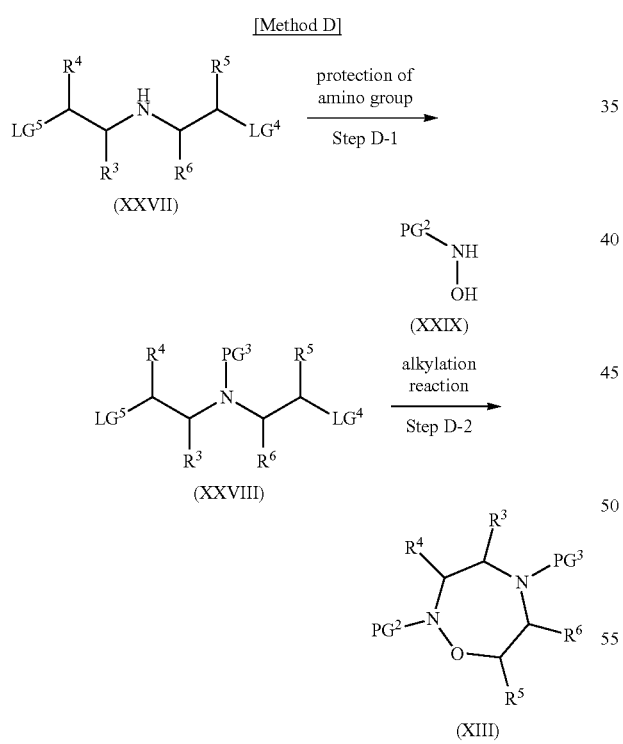

wherein $LG^4$ and $LG^5$ are each independently a leaving group, and the other symbols are as defined above.

Examples of the leaving group represented by $LG^4$ or $LG^5$ include a halogen atom (e.g., a fluorine atom, a chlorine atom, a bromine atom, an iodine atom) and the like.

Compound (XXVII) and compound (XXIX), which are used as a raw material in the method, may be commercially available products, or can also be produced according to a method known per se or a method analogous thereto.

(Step D-2)

This step is a step of converting compound (XXVIII) to compound (XIII) by subjecting compound (XXVIII) to an alkylation reaction with compound (XXIX) and a base. Examples of the base include potassium hydride, sodium hydride and the like.

Compound (I) (including compound (I-A)) can also be produced according to a single reaction or a combination of two or more reaction, selected from the above-mentioned reactions, the reactions in Examples, reactions known per se and reactions analogous thereto.

In addition, compound (I-A) can also be produced according to the following Method E.

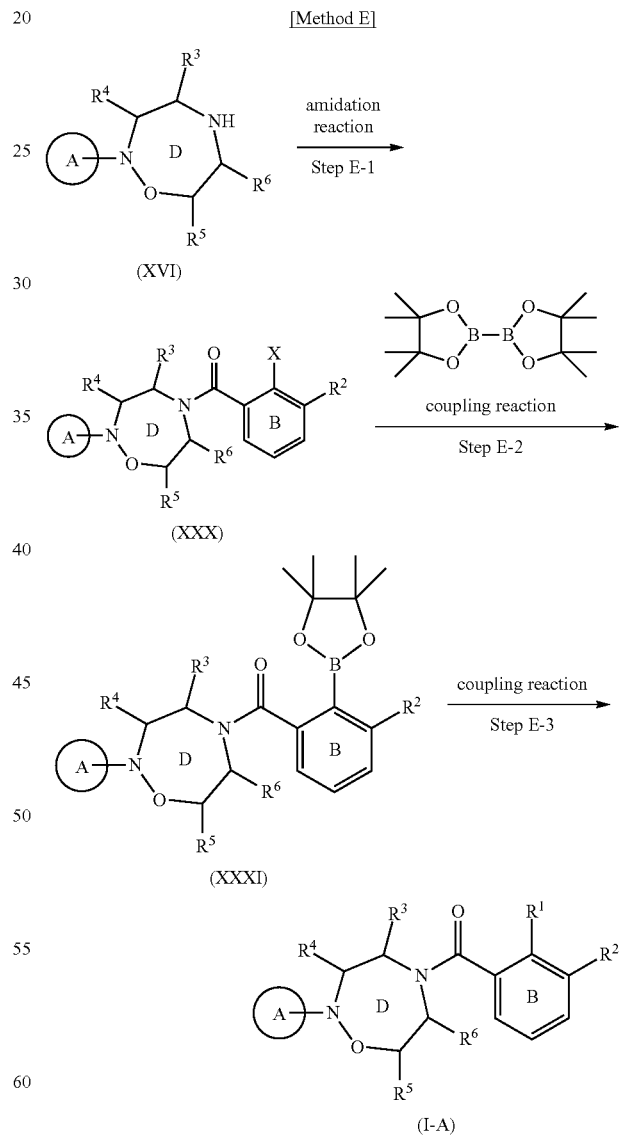

wherein each symbol is as defined above.

Moreover, compound (I-A) can also be produced according to the following Method F.

[Method F]

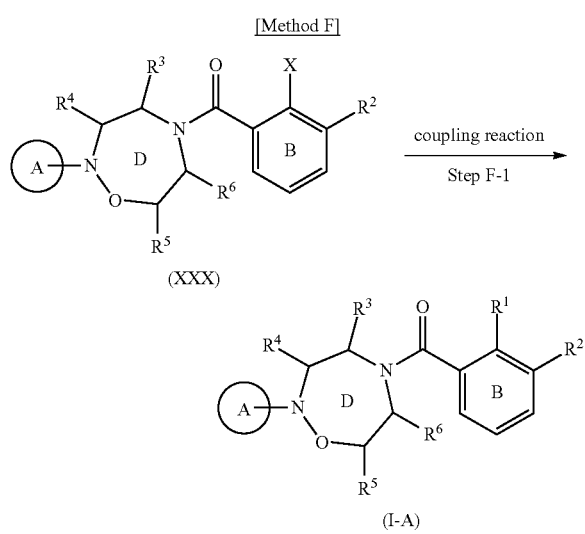

wherein each symbol is as defined above.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.
1) Fractional Recrystallization Method A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.
2) Chiral Column Method A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series manufactured by Daicel Corporation and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.
3) Diastereomer Method A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, t-butylation and the like);
a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);
a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be a crystal, and a single crystal form and a mixture of crystal forms are both encompassed in compound (I) of the present invention. The crystal can be produced by crystallizing according to a crystallization method known per se.

Compound (I) is expected to be effective for mammals (e.g., mouse, rat, hamster, rabbit, cat, dog, bovine, sheep, monkey, human etc.) as an agent for the prophylaxis or treatment of diseases, for example,
(1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, fragile X syndrome, Rett syndrome, adjustment disorder, bipolar disorder, neurosis, schizophrenia (e.g., positive symptom, negative symptom, cognitive symptom), chronic fatigue syndrome, anxiety neurosis, compulsive neurosis, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression],
(2) neurodegenerative diseases [e.g., Alzheimer's disease, Alzheimer-type senile dementia, Parkinson's disease, Huntington's disease, multi-infarct dementia, frontotemporal dementia, Parkinson's type frontotemporal dementia, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis, neuromyelitis optica (NMO)],
(3) age-related cognition memory disorders [e.g., age-related memory disorders, senile dementia],
(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome],
(5) respiratory depression caused by anesthetics, traumatic disease, or neurodegenerative disease and the like,
(6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania (drug dependence), drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus and the like,
(7) pain,
and the like. Compound (I) is particularly preferably expected to be effective as an orexin receptor antagonist and as an agent for the prophylaxis or treatment of sleep disorder, depression, anxiety disorder, panic disorder, schizophrenia, drug dependence, Alzheimer's disease and the like.

Since compound (I) has an excellent orexin receptor antagonistic activity, an excellent prophylactic or therapeutic effect for the above-mentioned diseases may be expected.

Since compound (I) has an excellent orexin receptor antagonistic activity, it has also an excellent sedative action, in addition to an excellent prophylactic or therapeutic effect for the above-mentioned diseases, and therefore an excellent effect as a sedative drug may be expected.

Since compound (I) is expected to be superior in vivo kinetics (e.g., plasma drug half-life, intracerebral migration, metabolic stability), to show low toxicity (e.g., more excellent as a medicament in terms of acute toxicity, chronic toxicity, genetic toxicity, reproductive toxicity, cardiotoxicity, drug interaction, carcinogenicity, phototoxicity and the like), and also to have excellent properties as a pharmaceutical product such as a few side effects and the like, it may be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

Compound (I) may have an excellent water-soluble property.

A preparation containing compound (I) may be any of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the preparation of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, white soft sugar, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain fatty acid triglyceride (e.g., miglyol 812 etc.) to give an injection to be actually used.

While the dose of compound (I) varies depending on the administration subject, administration route and symptom, it is not limited. For example, when compound (I) is orally administered to a patient with schizophrenia (adult, body weight 40 to 80 kg, for example, 60 kg), it is, for example, 0.001 to 1000 mg/kg body weight/day, preferably 0.01 to 100 mg/kg body weight/day, more preferably 0.1 to 10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-hydroxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01 to 100% (w/w), preferably 0.1 to 95% (w/w), of the total amount of the preparation.

The compound of the present invention may be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (Cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole, neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for hypoparathyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, an excellent effect such as (1) the dose may be reduced as compared to single administration of the compound of the present invention or a concomitant drug,
(2) the drug to be combined with the compound of the present invention may be selected according to the condition of patients (mild case, severe case and the like),
(3) the period of treatment may be set longer by selecting a concomitant drug having different action and mechanism from the compound of the present invention,
(4) a sustained treatment effect may be designed by selecting a concomitant drug having different action and mechanism from the compound of the present invention,
(5) a synergistic effect may be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions may be administered safely orally or non-orally (e.g., topical, rectal, intravenous administration etc.). Injection may be administered intravenously, intramuscularly, subcutaneously, or by intraorgan administration or directly to the lesion.

Examples of the pharmacologically acceptable carriers usable for the production of a combination agent of the present invention, may include various organic or inorganic carrier substances conventionally used as preparation materials. For solid preparations, for example, excipient, lubricant, binder and disintegrant may be used. For liquid preparations, for example, solvent, solubilizing agent, suspending agent, isotonic agent, buffering agent, soothing agent and the like may be used. Where necessary, an appropriate amount of conventional preservative, antioxidant, colorant, sweetening agent, adsorbent, wetting agent and the like may be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-hydroxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel, Diol means use of 3-(2,3-dihydroxypropoxy)propylsilane-bonded silica gel, and DiNH means use of N-(2-aminoethyl)-3-aminopropylsilane-bonded silica gel. In HPLC (high performance liquid chromatography), C18 means use of octadecyl-bonded silica gel. The ratios of elution solvents are volume mixing ratios, unless otherwise specified.

In Examples, the following abbreviations are used.
mp: melting point
MS: mass spectrum
[M+H]$^+$, [M−H]$^-$: molecular ion peak
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: ElectroSpray Ionization
APCI: Atmospheric Pressure Chemical Ionization
THF: tetrahydrofuran
DME: 1,2-dimethoxyethane
DMF: N,N-dimethylformamide
DMA: N,N-dimethylacetamide HATU: 2-(7-azabenzotriazol-1-yl)-1,1,3,3-tetramethyluronium hexafluorophosphate
HOBt: 1-hydroxybenzotriazole $^1$H NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates actual measured value (found). Generally, molecular ion peaks are observed. For example, in the case of a compound having a tert-butoxycarbonyl group, a peak after elimination of a tert-butoxycarbonyl group or a tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

The powder X-RAY diffraction measurement in Examples 1, 2 and 102 was performed under the following conditions.
measurement apparatus: RIGAKU Ultima IV
measurement condition
Cu-Kα ray: λ=1.5418 Å
tube voltage: 40 kV
tube current: 50 mA
scan speed: 6°/min
scan angle (2θ): 2 to 35°

Reference Example 1

5-fluoro-2-(2H-1,2,3-triazol-2-yl)benzoic acid

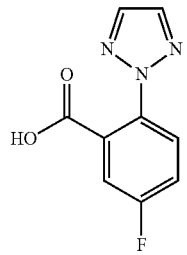

A) 5-fluoro-2-iodobenzoic acid

To a mixture of 2-amino-5-fluorobenzoic acid (10 g) in a mixed solvent of acetic acid (150 mL), water (50 mL) and conc. hydrochloric acid (5.0 mL) was added dropwise a solution of sodium nitrite (6.67 g) in water (50 mL) in a water bath, and the mixture was stirred at 0° C. for 0.5 hr. To the reaction mixture was added potassium iodide (32.1 g) at 0° C., and the mixture was stirred at room temperature for 5 hr. To the reaction mixture was added 1N aqueous hydrochloric acid solution at 0° C., and the mixture was extracted with ethyl acetate. The obtained organic layer was washed with saturated aqueous sodium thiosulfate solution and saturated brine, and dried over anhydrous magnesium sulfate, and the solvent was evaporated under reduced pressure to give the title compound (14.2 g).

$^1$H NMR (300 MHz, DMSO-d$_6$) δ 7.17 (1H, td, J=8.5, 3.0 Hz), 7.55 (1H, dd, J=9.5, 3.0 Hz), 7.99 (1H, dd, J=8.7, 5.7 Hz), 13.59 (1H, brs).

B) 5-fluoro-2-(2H-1,2,3-triazol-2-yl)benzoic acid

To a solution of 5-fluoro-2-iodobenzoic acid (17 g) obtained in Step A of Reference Example 1, copper(I) iodide (2.434 g), potassium carbonate (26.5 g) and N,N,N',N'-tetramethylethylene diamine (3.83 mL) in N,N-dimethylformamide (200 mL) was added 1H-1,2,3-triazole (11.11 mL), and the mixture was stirred overnight at 100° C. The reaction mixture was filtered through Celite, to the filtrate was added 6N aqueous hydrochloric acid solution at 0° C., and the mixture was extracted with ethyl acetate. The obtained organic layer was washed successively with saturated aqueous sodium thiosulfate solution and saturated brine, and dried over anhydrous magnesium sulfate, and the solvent was evaporated under reduced pressure. The residue was purified by silica gel column chromatography (hexane/ethyl acetate) to give the title compound (5.6 g).

$^1$H NMR (300 MHz, DMSO-d$_6$) δ 7.52-7.69 (2H, m), 7.81 (1H, dd, J=8.7, 4.9 Hz), 8.08 (2H, s), 13.35 (1H, brs).

Reference Example 2

2-(2H-1,2,3-triazol-2-yl)benzoic acid

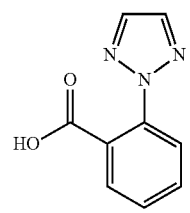

The title compound (1.77 g) was obtained using 2-iodobenzoic acid in the same manner as in Step B of Reference Example 1.

$^1$H NMR (300 MHz, DMSO-d$_6$) δ 7.54-7.64 (1H, m), 7.68-7.85 (3H, m), 8.08 (2H, s), 13.05 (1H, brs).

Reference Example 3

5-chloro-2-(2H-1,2,3-triazol-2-yl)benzoic acid

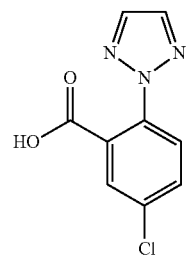

The title compound (1.45 g) was obtained using 5-chloro-2-iodobenzoic acid in the same manner as in Step B of Reference Example 1.

$^1$H NMR (300 MHz, DMSO-d$_6$) δ 7.71-7.85 (3H, m), 8.12 (2H, s), 13.40 (1H, brs).

Reference Example 4

2-(1,3-thiazol-2-yl)benzoic acid

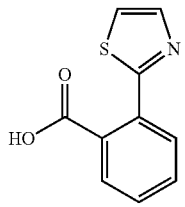 [SMILES: O=C(O)c1ccccc1-c1nccs1]

A) ethyl 2-(1,3-thiazol-2-yl)benzoate

To a solution of 2-bromo-1,3-thiazole (4.0 g), ethyl 2-(4,4,5,5-tetramethyl-1,3,2-dioxaborolan-2-yl)benzoate (7.94 g) and 2M aqueous cesium carbonate solution (30 mL) in 1,2-dimethoxyethane (150 mL) was added tetrakis(triphenylphosphine)palladium(0) (1.41 g), and the mixture was stirred overnight at 80° C. under argon atmosphere. To the reaction mixture was added saturated aqueous sodium hydrogencarbonate solution (100 mL), and the mixture was extracted twice with ethyl acetate (150 mL). The obtained organic layer was washed with saturated brine (30 mL), and dried over anhydrous magnesium sulfate, and the solvent was evaporated under reduced pressure. The residue was purified by silica gel column chromatography (NH, hexane/ethyl acetate) to give the title compound (3.99 g).
MS: [M+H]$^+$ 234.0.

B) 2-(1,3-thiazol-2-yl)benzoic acid

To a solution of ethyl 2-(1,3-thiazol-2-yl)benzoate (3.9 g) obtained in Step A of Reference Example 4 in tetrahydrofuran (40 mL)/methanol (40 mL) was added 8N aqueous sodium hydroxide solution (6.5 mL), and the mixture was stirred at room temperature for 5 hr. The reaction solution was acidified with 6N aqueous hydrogen chloride solution, and the solvent was evaporated under reduced pressure. To the residue was added water (50 mL), and the mixture was stirred at 0° C. for 0.5 hr, and the precipitate was collected by filtration to give the title compound (3.1 g).
MS: [M+H]$^+$ 206.0.

Reference Example 5

2-chloro-4-(4-fluorophenyl)-6-methylpyrimidine

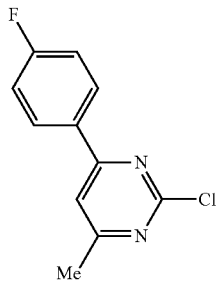 [SMILES: Cc1cc(-c2ccc(F)cc2)nc(Cl)n1]

To a mixture of 2,4-dichloro-6-methylpyrimidine (502.1 mg), (4-fluorophenyl)boronic acid (478 mg) and potassium carbonate (848 mg) in a mixed solvent of 1,2-dimethoxyethane (10 mL)/water (3.0 mL) was added 1,1'-bis(diphenylphosphino)ferrocene-palladium(II) dichloride-dichloromethane complex (126 mg), and the mixture was stirred overnight at 90° C. To the reaction mixture was added saturated aqueous sodium hydrogencarbonate solution (30 mL), and the mixture was extracted three times with ethyl acetate (30 mL). The obtained organic layer was washed with saturated brine (10 mL), and dried over anhydrous magnesium sulfate, and the solvent was evaporated under reduced pressure. The residue was purified by silica gel column chromatography (hexane/ethyl acetate) to give the title compound (433 mg).
MS: [M+H]$^+$ 223.0.

Reference Example 6

4,5-difluoro-2-(2H-1,2,3-triazol-2-yl)benzoic acid

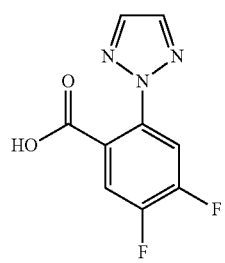

A) 4,5-difluoro-2-iodobenzoic acid

The title compound (8.28 g) was obtained using 2-amino-4,5-difluorobenzoic acid in the same manner as in Step A of Reference Example 1.
$^1$H NMR (300 MHz, DMSO-d$_6$) δ 7.83 (1H, dd, J=11.4, 8.3 Hz), 8.11 (1H, dd, J=10.0, 7.8 Hz), 13.32 (1H, brs).

B) methyl 4,5-difluoro-2-(2H-1,2,3-triazol-2-yl)benzoate

To a solution of 4,5-difluoro-2-iodobenzoic acid (8.5 g) obtained in Step A of Reference Example 6, copper(I) iodide (1.14 g), potassium carbonate (12.41 g) and N,N,N',N'-tetramethylethylene diamine (1.792 mL) in N,N-dimethylformamide (100 mL) was added 1H-1,2,3-triazole (5.2 mL), and the mixture was stirred overnight at 100° C. The reaction mixture was filtered through Celite, to the filtrate was added 6N aqueous hydrochloric acid solution at 0° C., and the mixture was extracted with ethyl acetate. The obtained organic layer was washed successively with saturated aqueous sodium thiosulfate solution and saturated brine, and dried over anhydrous magnesium sulfate, and the solvent was evaporated under reduced pressure. The residue was purified by silica gel column chromatography (hexane/ethyl acetate). To a solution of the obtained crude product in methanol (20 mL) was added thionyl chloride (1.095 mL) at room temperature, and the mixture was stirred overnight at 50° C. The solvent was evaporated under reduced pressure, and the residue was cooled to 0° C. Saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (1.16 g).

$^1$H NMR (300 MHz, DMSO-d$_6$) δ 3.67 (3H, s), 7.80-8.09 (2H, m), 8.15 (2H, s).

C) 4,5-difluoro-2-(2H-1,2,3-triazol-2-yl)benzoic acid

To a solution of methyl 4,5-difluoro-2-(2H-1,2,3-triazol-2-yl)benzoate (1.12 g) obtained in Step B of Reference Example 6 in methanol (5.0 mL) was added 2M aqueous sodium hydroxide solution (4.68 mL), and the mixture was stirred overnight at room temperature. The solvent was evaporated under reduced pressure, and the mixture was neutralized with 1N aqueous hydrogen chloride solution, and extracted with ethyl acetate. The obtained organic layer was washed successively with water and saturated brine, and dried over anhydrous magnesium sulfate, and the solvent was evaporated under reduced pressure to give the title compound (1.0 g).

$^1$H NMR (300 MHz, DMSO-d$_6$) δ 7.93 (2H, ddd, J=12.3, 10.6, 7.8 Hz), 8.12 (2H, s), 13.42 (1H, brs).

Reference Example 7

2-fluoro-6-(2H-1,2,3-triazol-2-yl)benzoic acid

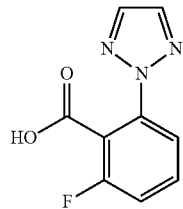 [SMILES: O=C(O)c1c(F)cccc1-n1nccn1]

To a solution of 2-fluoro-6-iodobenzoic acid (502.5 mg), copper(I) iodide (36.5 mg), cesium carbonate (1.25 g) and trans-N,N'-dimethylcyclohexane-1,2-diamine (0.047 mL) in N,N-dimethylformamide (2.0 mL) was added 1H-1,2,3-triazole (330.3 mg), and the mixture was stirred at 100° C. for 0.5 hr. To the reaction mixture were added ethyl acetate and water. The obtained aqueous layer was neutralized with 1N aqueous hydrogen chloride solution, and extracted with ethyl acetate. The obtained organic layer was washed successively with water and saturated brine, and dried over anhydrous magnesium sulfate, and the solvent was evaporated under reduced pressure to give the title compound (445.6 mg).

MS: [M+H]$^+$ 208.1.

Reference Example 9 potassium 2-cyclobutylbenzoate

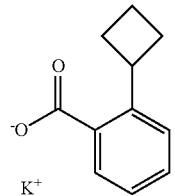

A) methyl 2-cyclobutylbenzoate

A mixture of methyl 2-iodobenzoate (634 mg), a solution of 0.5M cyclobutylzinc bromide in tetrahydrofuran (6.78 mL) and tetrakis(triphenylphosphine)palladium(0) (280 mg) was stirred in a microwave reactor at 50° C. for 1 hr. To the reaction mixture was added saturated aqueous sodium hydrogencarbonate solution, and the mixture was extracted with ethyl acetate. The obtained organic layer was washed successively with water and saturated brine, and dried over anhydrous sodium sulfate, and the solvent was evaporated under reduced pressure. The residue was purified by silica gel column chromatography (hexane/ethyl acetate) to give the title compound (450 mg).

MS: [M+H]$^+$ 191.1.

B) potassium 2-cyclobutylbenzoate

To a solution of methyl 2-cyclobutylbenzoate (450 mg) obtained in Step A of Reference Example 9 in tetrahydrofuran (5.0 mL) was added trimethyl(potassiooxy)silane (607 mg), and the mixture was stirred overnight at room temperature. The solvent was evaporated under reduced pressure to give the title compound (950 mg).

Reference Example 10 potassium 5-chloro-2-cyclobutylbenzoate

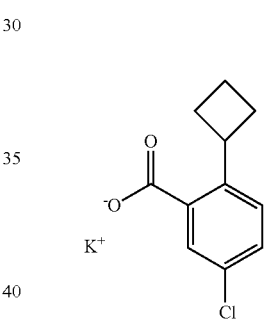

The title compound (450 mg) was obtained using methyl 5-chloro-2-iodobenzoate in the same manner as in Reference Example 9.

Reference Example 11

2-(thiophen-2-yl)benzoic acid

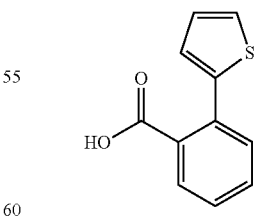

To a solution of 2-iodobenzoic acid (2.0 g) in DME (10 mL) were added 2-thienylboronic acid (1.548 g), bis(triphenylphosphine)palladium(II) dichloride (566 mg) and 2M aqueous sodium hydroxide solution (8.06 mL), and the mixture was stirred in a microwave reactor at 130° C. for 1 hr. To the reaction mixture was added 1N aqueous hydrogen chloride solution, and the mixture was extracted with ethyl acetate. The obtained organic layer was washed successively with water and saturated brine, and dried over anhydrous sodium sulfate, and the solvent was evaporated under reduced pressure. The residue was purified by silica gel column chromatography (hexane/ethyl acetate) to give the title compound (510 mg).

MS: [M−H]⁻ 203.0.

Reference Example 12

5-bromo-2-(2H-1,2,3-triazol-2-yl)benzoic acid

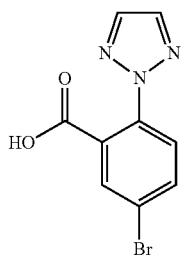

The title compound (1.42 g) was obtained using 5-bromo-2-iodobenzoic acid (4.0 g) in the same manner as in Step B of Reference Example 1.
MS: [M+H]⁺ 267.9.

Reference Example 13

5-fluoro-2-(pyrimidin-2-yl)benzoic acid

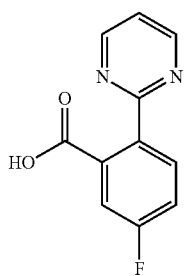

A) ethyl 5-fluoro-2-(pyrimidin-2-yl)benzoate

To a mixture of 2-bromopyrimidine (1.5 g), (2-(ethoxycarbonyl)-4-fluorophenyl)boronic acid (2.39 g) and potassium carbonate (2.7 g) in a mixed solvent of 1,2-dimethoxyethane (150 mL)/water (6.0 mL) was added 1,1'-bis(diphenylphosphino)ferrocene-palladium(II) dichloride-dichloromethane complex (389.3 mg), and the mixture was stirred overnight at 80° C. To the reaction mixture was added saturated aqueous sodium hydrogencarbonate solution (50 mL), and the precipitate was filtered through Celite. The filtrate was extracted three times with ethyl acetate (30 mL). The obtained organic layer was washed with saturated brine (20 mL), and dried over anhydrous magnesium sulfate, and the solvent was evaporated under reduced pressure. The residue was purified by silica gel column chromatography (hexane/ethyl acetate) to give the title compound (1.06 g).
MS: [M+H]⁺ 234.0.

B) 5-fluoro-2-(pyrimidin-2-yl)benzoic acid

To a solution of ethyl 5-fluoro-2-(pyrimidin-2-yl)benzoate (1.05 g) obtained in Step A of Reference Example 13 in tetrahydrofuran (8.0 mL)/methanol (8.0 mL) was added 8N aqueous sodium hydroxide solution (1.6 mL), and the mixture was stirred at room temperature for 5 hr. The reaction solution was acidified with 6N aqueous hydrogen chloride solution, and the solvent was evaporated under reduced pressure. To the residue was added water (50 mL), the mixture was stirred at 0° C. for 0.5 hr, and the precipitate was collected by filtration to give the title compound (538 mg).
MS: [M+H]⁺ 219.0.

Reference Example 14

5-fluoro-2-(1H-pyrazol-1-yl)benzoic acid

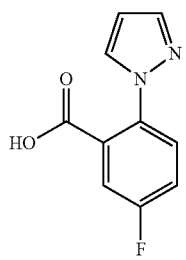 [SMILES: O=C(O)c1cc(F)ccc1-n1cccn1]

The title compound (1.07 g) was obtained using 5-fluoro-2-iodobenzoic acid obtained in Step A of Reference Example 1 and 1H-pyrazole in the same manner as in Step B of Reference Example 1.
MS: [M+H]⁺ 207.0.

Reference Example 15

2-(5-fluoro-1,3-thiazol-2-yl)benzoic acid

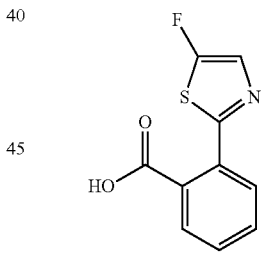

To a solution of 2-(1,3-thiazol-2-yl)benzoic acid (214.1 mg) obtained in Reference Example 4 in tetrahydrofuran (2.0 mL) was added dropwise n-butyl lithium (1.6 M hexane solution, 2.0 mL) at −78° C., and the mixture was stirred for 0.5 hr. To the reaction mixture was added dropwise a solution of N-fluoro-N-(phenylsulfonyl)benzenesulfonamide (1.09 g) in tetrahydrofuran (3.0 mL), and the mixture was stirred at −78° C. for 1 hr. To the reaction mixture were added ethyl acetate and saturated aqueous sodium hydrogencarbonate solution. The obtained aqueous layer was neutralized with 2M aqueous hydrogen chloride solution, and extracted twice with ethyl acetate. The obtained organic layer was washed successively with water and saturated brine, and dried over anhydrous magnesium sulfate, and the solvent was evaporated under reduced pressure to give the title compound (354.6 mg).
MS: [M+H]⁺ 224.0.

Reference Example 16

2-(2H-tetrazol-2-yl)benzoic acid

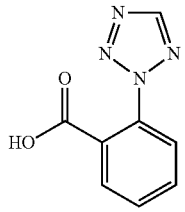 [SMILES: O=C(O)c1ccccc1-n1ncnn1]

To a solution of 2-iodobenzoic acid (1.85 g) and copper(I) iodide (128 mg) in N,N-dimethylacetamide (5.5 mL) was added cesium carbonate (4.06 g), the mixture was stirred at room temperature for 5 min, and N,N-dimethylglycine (131 mg) and 1H-tetrazole (1.291 g) were added thereto. To the reaction mixture was added N,N-dimethylacetamide (3.5 mL), and the mixture was stirred at room temperature for 10 min. The reaction mixture was stirred in a microwave reactor at 100° C. for 1 hr. To the reaction mixture were added water, ethyl acetate and 1N aqueous sodium hydroxide solution. The obtained aqueous layer was neutralized with 6N aqueous hydrogen chloride solution, and extracted twice with ethyl acetate. The obtained organic layer was washed successively with water and saturated brine, and dried over anhydrous sodium sulfate, and the solvent was evaporated under reduced pressure. The residue was purified by silica gel column chromatography (hexane/ethyl acetate) to give the title compound (0.12 g).
MS: [M+H]$^+$ 191.0.

Reference Example 17

2-(1,3-thiazol-5-yl)benzoic acid

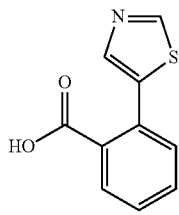 [SMILES: O=C(O)c1ccccc1-c1cncs1]

A) ethyl 2-(1,3-thiazol-5-yl)benzoate

To a mixture of ethyl 2-iodobenzoate (1.15 g) in a mixed solvent of tetrahydrofuran (10 mL)/water (2.0 mL) were added 6-methyl-2-(1,3-thiazol-5-yl)-1,3,6,2-dioxaazaborocane-4,8-dione (1.0 g), palladium(II) acetate (94 mg), dicyclohexyl(2',6'-dimethoxybiphenyl-2-yl)phosphine (342 mg) and tripotassium phosphate (1.769 g), and the mixture was stirred overnight at 80° C. under nitrogen atmosphere. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (157 mg).
MS: [M+H]$^+$ 234.1.

B) 2-(1,3-thiazol-5-yl)benzoic acid

The title compound (113 mg) was obtained using ethyl 2-(1,3-thiazol-5-yl)benzoate obtained in Step A of Reference Example 17 in the same manner as in Step C of Reference Example 6.
MS: [M+H]$^+$ 206.0.

Reference Example 18

5-fluoro-2-(1,3-thiazol-2-yl)benzoic acid

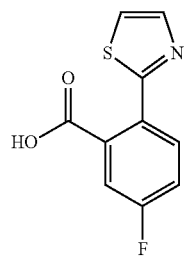 [SMILES: O=C(O)c1cc(F)ccc1-c1nccs1]

The title compound (542.7 mg) was obtained using ethyl 5-fluoro-2-(4,4,5,5-tetramethyl-1,3,2-dioxaborolan-2-yl) benzoate in the same manner as in Reference Example 4.
MS: [M+H]$^+$ 224.0.

Reference Example 19

5-chloro-2-(1,3-thiazol-2-yl)benzoic acid

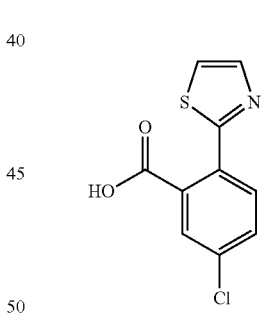

A) ethyl 5-chloro-2-(4,4,5,5-tetramethyl-1,3,2-dioxaborolan-2-yl)benzoate

To a solution of methyl 2-bromo-5-chlorobenzoate (1.99 g), 4,4,4',4',5,5,5',5'-octamethyl-2,2'-bi-1,3,2-dioxaborolane (2.63 g) and potassium acetate (1.56 g) in DME (40 mL) was added 1,1'-bis(diphenylphosphino)ferrocene-palladium(II) dichloride (324 mg), and the mixture was stirred overnight at 80° C. To the reaction mixture was added saturated aqueous sodium hydrogencarbonate solution (100 mL), and the insoluble substance was filtered through Celite. The obtained aqueous layer was extracted twice with ethyl acetate (50 mL), the obtained organic layer was washed with saturated brine (50 mL), and dried over anhydrous magnesium sulfate, and the solvent was evaporated under reduced pressure. The residue was purified by silica gel column chromatography (hexane/ethyl acetate) to give the title compound (1.56 g).

MS: [M+H]⁺ 297.1.

B) 5-chloro-2-(1,3-thiazol-2-yl)benzoic acid

The title compound (642 mg) was obtained using ethyl 5-chloro-2-(4,4,5,5-tetramethyl-1,3,2-dioxaborolan-2-yl)benzoate obtained in Step A of Reference Example 19 in the same manner as in Reference Example 4.

MS: [M+H]⁺ 239.9.

Reference Example 20

4-chloro-6-(difluoromethyl)-2-methylpyrimidine

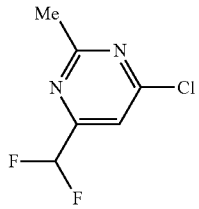

A) 6-(difluoromethyl)-2-methylpyrimidin-4(1H)-one

To a solution of ethyl 4,4-difluoro-3-oxobutanoate (5.7 g) in toluene (100 mL) were added ethanimidamide hydrochloride (3.24 g) and 20% sodium ethoxide ethanol solution (42.9 mL), and the mixture was stirred overnight at 80° C. The reaction mixture was neutralized with 1M aqueous hydrogen chloride solution, and extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (1.622 g).

MS: [M+H]⁺ 161.0.

B) 4-chloro-6-(difluoromethyl)-2-methylpyrimidine

To a solution of 6-(difluoromethyl)-2-methylpyrimidin-4(1H)-one (1.62 g) obtained in Step A of Reference Example 20 in acetonitrile (20 mL) was added phosphoryl chloride (2.83 mL), and the mixture was stirred overnight at 80° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (866 mg).

MS: [M+H]⁺ 179.0.

Reference Example 21

4-chloro-2-cyclopropyl-6-(difluoromethyl)pyrimidine

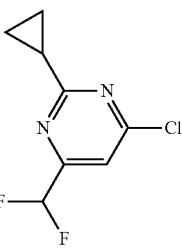

The title compound (2.95 g) was obtained using cyclopropanecarboximidamide hydrochloride in the same manner as in Reference Example 20.

¹H NMR (300 MHz, DMSO-d₆) δ 0.95-1.08 (2H, m), 1.15-1.30 (2H, m), 2.13-2.36 (1H, m), 6.92 (1H, t, J=52.0 Hz), 7.73 (1H, s).

Reference Example 22

4-chloro-2,6-dicyclopropylpyrimidine

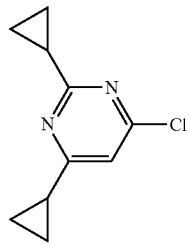 [SMILES: Clc1cc(C2CC2)nc(C2CC2)n1]

The title compound (100 mg) was obtained using ethyl 3-cyclopropyl-3-oxopropanoate and cyclopropanecarboximidamide hydrochloride in the same manner as in Reference Example 20.

MS: [M+H]⁺ 195.1.

Reference Example 23

4-chloro-2-cyclopropyl-6-(trifluoromethyl)pyrimidine

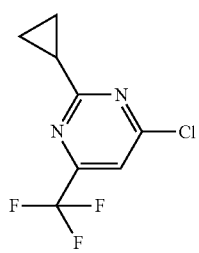 [SMILES: FC(F)(F)c1cc(Cl)nc(C2CC2)n1]

The title compound (1.96 g) was obtained using ethyl 4,4,4-trifluoro-3-oxobutanoate and cyclopropanecarboximidamide hydrochloride in the same manner as in Reference Example 20.

$^1$H NMR (300 MHz, DMSO-d$_6$) δ 1.01-1.12 (2H, m), 1.18-1.27 (2H, m), 2.32 (1H, tt, J=8.2, 4.5 Hz), 8.05 (1H, s).

Reference Example 24

5-chloropyrazolo[1,5-a]pyrimidine

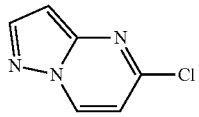

A) pyrazolo[1,5-a]pyrimidin-5-ol

To a solution of 1H-pyrazol-3-amine (500.6 mg) in N,N-dimethylformamide (10 mL) were added ethyl (2E)-3-ethoxyacrylate (1.3 mL) and cesium carbonate (2.93 g), and the mixture was stirred overnight at 110° C. The reaction mixture was neutralized with 2M aqueous hydrogen chloride solution, and extracted three times with ethyl acetate. Then, to the aqueous layer was added sodium chloride, and the mixture was extracted three times with tetrahydrofuran (15 mL)/ethyl acetate (15 mL). The obtained organic layer was washed with saturated brine (20 mL), and dried over anhydrous magnesium sulfate, and the solvent was evaporated under reduced pressure. The residue was purified by silica gel column chromatography (hexane/ethyl acetate/methanol) to give the title compound (226.3 mg).
MS: [M+H]$^+$ 136.0.

B) 5-chloropyrazolo[1,5-a]pyrimidine

The title compound (183.6 mg) was obtained using pyrazolo[1,5-a]pyrimidin-5-ol obtained in Step A of Reference Example 24 in the same manner as in Step B of Reference Example 20.
MS: [M+H]$^+$ 154.0.

Reference Example 25

2-(pyrimidin-2-yl)benzoic acid

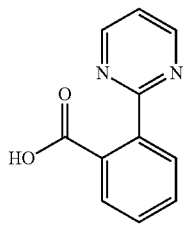

A) ethyl 2-(pyrimidin-2-yl)benzoate

To a mixture of ethyl 2-(4,4,5,5-tetramethyl-1,3,2-dioxaborolan-2-yl)benzoate (1.79 g) in a mixed solvent of toluene (20 mL)/water (4.0 mL) were added 2-bromopyrimidine (1.0 g), palladium(II) acetate (72.2 mg), dicyclohexyl(2',6'-dimethoxybiphenyl-2-yl)phosphine (258.6 mg) and cesium carbonate (4.18 g), and the mixture was stirred overnight at 100° C., and then stirred at 80° C. for 2 days. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (460 mg).
MS: [M+H]$^+$ 229.1.

B) 2-(pyrimidin-2-yl)benzoic acid

The title compound (1.43 g) was obtained using ethyl 2-(pyrimidin-2-yl)benzoate obtained in Step A of Reference Example 25 in the same manner as in Step B of Reference Example 4.
MS: [M+H]$^+$ 201.0.

Reference Example 26

2-(4-methyl-1,3-thiazol-2-yl)benzoic acid

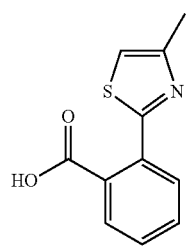

The title compound (1.12 g) was obtained using 2-bromo-4-methyl-1,3-thiazole in the same manner as in Reference Example 4.
MS: [M+H]$^+$ 220.0.

Reference Example 27

2-tert-butyl-4-chloro-6-methylpyrimidine

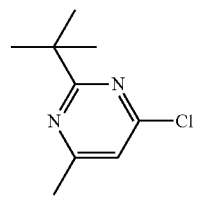

The title compound (0.87 g) was obtained using 2,2-dimethylpropaneimidamide hydrochloride and methyl 3-oxobutanoate in the same manner as in Reference Example 20.
MS: [M+H]$^+$ 185.1.

Reference Example 28

4-chloro-6-methyl-2-(1-methylcyclopropyl)pyrimidine

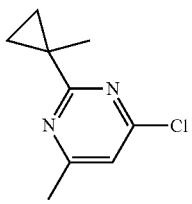

The title compound (1.5 g) was obtained using 1-methylcyclopropanecarboximidamide hydrochloride and methyl 3-oxobutanoate in the same manner as in Reference Example 20.

MS: [M+H]$^+$ 183.0.

Reference Example 29

2-chloro-5-fluoro-4,6-dimethylpyrimidine

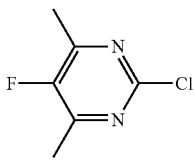

A) 5-fluoropyrimidine-2,4,6-triol

To a solution of diethyl fluoromalonate (3.0 g) and urea (1.02 g) in ethanol (17 mL) was added 20% sodium ethoxide ethanol solution (11.5 g), and the mixture was stirred overnight at 90° C. To the reaction mixture was added hexane (20 mL) at room temperature, and the precipitate was collected by filtration, and washed with a mixed solvent of hexane/diisopropanol. To a solution of the obtained residue in water (60 mL) was added conc. hydrochloric acid at 0° C., and the precipitate was collected by filtration to give the title compound (1.24 g).

$^1$H NMR (300 MHz, DMSO-d$_6$) δ 9.00 (1H, brs).

B) 2-chloro-5-fluoro-4,6-dimethylpyrimidine

To 5-fluoropyrimidine-2,4,6-triol (1.23 g) obtained in Step A of Reference Example 29 were added phosphoryl chloride (8.0 mL) and N,N-dimethylaniline (1.1 mL), and the mixture was stirred at 110° C. for 3 hr. To the reaction mixture were added phosphoryl chloride (8.0 mL) and N,N-dimethylaniline (1.5 mL), and the mixture was stirred overnight at 110° C. The reaction mixture was concentrated under reduced pressure, ice (10 g) and saturated aqueous sodium hydrogencarbonate solution (30 mL) were added thereto, and the mixture was extracted three times with diethyl ether (20 mL). The obtained organic layer was dried over anhydrous magnesium sulfate, and the solvent was evaporated under reduced pressure. The residue was purified by silica gel column chromatography (hexane/ethyl acetate). To a mixture of the obtained crude product (700 mg) and acetylacetone iron(III) (125.5 mg) in a mixed solvent of tetrahydrofuran (22 mL)/N-methyl-2-pyrrolidone (2.0 mL) was added dropwise 3M methylmagnesium bromide ether solution (3.48 mL) at 0° C., and the reaction mixture was stirred at 0° C. for 0.5 hr. Saturated aqueous ammonium chloride solution (50 mL) was added thereto, and the mixture was extracted five times with diethyl ether (20 mL). The obtained organic layer was dried over anhydrous magnesium sulfate, and the solvent was evaporated under reduced pressure. The residue was purified by silica gel column chromatography (hexane/ethyl acetate) to give the title compound (188.5 mg).

MS: [M+H]$^+$ 161.0.

Reference Example 30

2,5-dichloro-4,6-dimethylpyrimidine

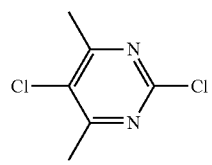

The title compound (309.4 mg) was obtained using 5-chloro-4,6-dimethylpyrimidin-2-ol in the same manner as in Step B of Reference Example 20.

MS: [M+H]$^+$ 177.0.

Reference Example 31

4,5-difluoro-2-(pyrimidin-2-yl)benzoic acid

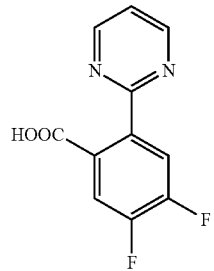 [SMILES: O=C(O)c1cc(F)c(F)cc1-c1ncccn1]

A) ethyl 4,5-difluoro-2-(pyrimidin-2-yl)benzoate

To a mixture of 2-bromopyrimidine (4.92 g), ethyl 4,5-difluoro-2-(4,4,5,5-tetramethyl-1,3,2-dioxaborolan-2-yl)benzoate (12.6 g) and potassium carbonate (8.56 g) in 1,2-dimethoxyethane (90 mL)/water (30 mL) was added 1,1'-bis(diphenylphosphino)ferrocene-palladium(II) dichloride-dichloromethane complex (1.26 g), and the mixture was stirred overnight at 80° C. To the reaction mixture was added saturated aqueous sodium hydrogencarbonate solution, and the precipitate was filtered through Celite, and washed with ethyl acetate. The organic layer of the filtrate was separated, and the aqueous layer was extracted with ethyl acetate. The obtained organic layer was washed with saturated brine, and dried over anhydrous sodium sulfate, and the solvent was evaporated under reduced pressure. The residue was purified by silica gel column chromatography (hexane/ethyl acetate) to give the title compound (7.09 g).

$^1$H NMR (300 MHz, DMSO-$d_6$) δ 1.04 (3H, t, J=7.08 Hz), 4.13 (2H, q, J=7.11 Hz), 7.53 (1H, t, J=4.91 Hz), 7.80 (1H, dd, J=10.58, 7.93 Hz), 8.01 (1H, dd, J=11.33, 7.93 Hz), 8.91 (2H, d, J=4.91 Hz).

MS: [M+H]$^+$ 265.0.

B) 4,5-difluoro-2-(pyrimidin-2-yl)benzoic acid

To a solution of ethyl 4,5-difluoro-2-(pyrimidin-2-yl)benzoate (333 mg) obtained in Step A of Reference Example 31 in ethanol (5 mL) was added 8N aqueous sodium hydroxide solution (0.63 mL), and the mixture was stirred at room temperature for 3 hr. The solvent was evaporated under reduced pressure, and the residue was acidified with 6N hydrochloric acid, and diluted with water. The precipitate was collected by filtration to give the title compound (220 mg).

$^1$H NMR (300 MHz, DMSO-$d_6$) δ 7.51 (1H, t, J=4.91 Hz), 7.77 (1H, dd, J=10.76, 7.93 Hz), 7.89 (1H, dd, J=11.33, 7.74 Hz), 8.89 (2H, d, J=5.10 Hz), 13.10 (1H, br.s.).

MS: [M+H]$^+$ 237.0.

Reference Example 32

4-bromo-2-(2H-1,2,3-triazol-2-yl)benzoic acid

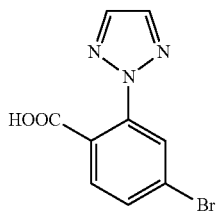 [SMILES: O=C(O)c1ccc(Br)cc1-n1nccn1]

To a solution of 4-bromo-2-iodobenzoic acid (10.2 g) in tetrahydrofuran (100 mL)/N,N-dimethylformamide (20 mL) were added copper(I) iodide (0.592 g) and potassium carbonate (10.7 g) at room temperature, and the mixture was stirred at 40° C. for 10 min. To the reaction mixture was added 2H-1,2,3-triazole (4.29 g), and the mixture was stirred at 70° C. for 12 hr under nitrogen atmosphere. The solvent was evaporated under reduced pressure, the residue was diluted with water, and 6N hydrochloric acid (40 mL) was added thereto at 0° C. The precipitate was collected by filtration, washed with water, and added to warm ethyl acetate (300 mL). The insoluble substance was removed by filtration, the filtrate was washed with saturated brine, and dried over anhydrous magnesium sulfate, and the solvent was evaporated under reduced pressure. The residue was dissolved in tetrahydrofuran (250 mL), and sodium tert-butoxide (3.29 g) was added thereto at 0° C. The mixture was stirred at room temperature for 16 hr under dried atmosphere, and the precipitate was collected by filtration, and washed with tetrahydrofuran (50 mL). The obtained solid was dissolved in water (40 mL), to the aqueous solution was added 1N hydrochloric acid (31 mL) at 0° C., and the mixture was stirred at the same temperature for 2 hr. The precipitate was collected by filtration, washed with cold water (20 mL), and dried to give the title compound (5.33 g).

MS: [M+H]$^+$ 267.9, 269.9.

Reference Example 33

2-methyl-6-(pyrimidin-2-yl)benzoic acid

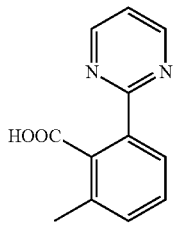 [SMILES: Cc1cccc(-c2ncccn2)c1C(=O)O]

A) methyl 2-methyl-6-(pyrimidin-2-yl)benzoate

To a solution of methyl (2-bromo-6-methyl)benzoate (2.50 g) in N,N-dimethylformamide (25 mL) were added cesium fluoride (3.32 g), copper(I) iodide (0.416 g), tetrakis(triphenylphosphine)palladium(0) (1.26 g) and 2-(tributylstannyl)pyrimidine (5.24 g), and the mixture was stirred at 120° C. for 6 hr. The reaction mixture was filtered, the filtrate was poured into saturated aqueous ammonium chloride solution, and the mixture was extracted with ethyl acetate. The obtained organic layer was dried over anhydrous sodium sulfate, and the solvent was evaporated under reduced pressure. The residue was purified by silica gel column chromatography (hexane/ethyl acetate) to give the title compound (1.48 g).

$^1$H NMR (300 MHz, CDCl$_3$) δ 2.42 (3H, s), 3.83 (3H, s), 7.19 (1H, t, J=4.9 Hz), 7.30-7.38 (1H, m), 7.39-7.49 (1H, m), 8.09-8.20 (1H, m), 8.78 (2H, d, J=4.5 Hz).

B) 2-methyl-6-(pyrimidin-2-yl)benzoic acid

The title compound (911 mg) was obtained using methyl 2-methyl-6-(pyrimidin-2-yl)benzoate obtained in Step A of Reference Example 33 in the same manner as in Step B of Reference Example 3.

$^1$H NMR (300 MHz, DMSO-$d_6$) δ 2.37 (3H, s), 7.31-7.54 (3H, m), 7.95 (1H, dd, J=7.3, 1.4 Hz), 8.87 (2H, d, J=4.9 Hz), 12.75 (1H, s).

Reference Example 34

4-chloro-2-(1H-1,2,3-triazol-1-yl)benzoic acid

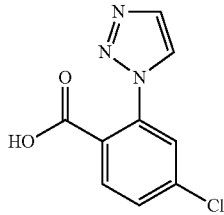 [SMILES: O=C(O)c1ccc(Cl)cc1-n1ccnn1]

A mixture of 2-bromo-4-chlorobenzoic acid (1.39 g), 1H-1,2,3-triazole (0.855 mL), copper(I) iodide (0.337 g), (1R,2R)—N,N'-dimethylcyclohexane-1,2-diamine (0.283 mL), cesium carbonate (3.85 g) and N,N-dimethylformamide (4 mL) was stirred in a microwave reactor at 100° C. for 10 min. To the reaction mixture was added 1N hydrochloric acid, and the mixture was extracted with ethyl acetate. The obtained organic layer was washed with water and saturated brine, and dried over anhydrous sodium sulfate, and the solvent was evaporated under reduced pressure. To the residue was added diisopropyl ether, and the obtained solid was collected by filtration to give the title compound (0.345 g).

$^1$H NMR (300 MHz, DMSO-d$_6$) δ 7.62-7.87 (2H, m), 7.87-8.03 (2H, m), 8.56 (1H, s), 13.30 (1H, brs).

Example 1

((7S)-2-(2,6-dimethylpyrimidin-4-yl)-7-methyl-1,2, 5-oxadiazepan-5-yl)(5-fluoro-2-(2H-1,2,3-triazol-2-yl)phenyl)methanone

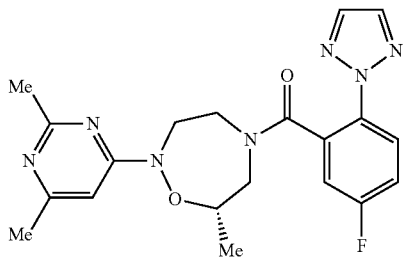 [SMILES: Cc1cc(N2CCN(C(=O)c3cc(F)ccc3-n3nccn3)C[C@H](C)O2)nc(C)n1]

A) tert-butyl ((2R)-2-hydroxypropyl)carbamate

To a solution of (R)-(−)-1-amino-2-propanol (10.53 mL) in tetrahydrofuran (200 mL) was added di-tert-butyl dicarbonate (34 mL) under ice-cooling, and the mixture was stirred overnight at room temperature. The solvent was evaporated under reduced pressure, and the residue was purified by silica gel column chromatography (hexane/ethyl acetate) to give the title compound (24.7 g).

$^1$H NMR (300 MHz, DMSO-d$_6$) δ 0.98 (3H, d, J=6.1 Hz), 1.37 (9H, s), 2.75-2.99 (2H, m), 3.49-3.74 (1H, m), 4.55 (1H, d, J=4.5 Hz), 6.53-6.74 (1H, m).

B) tert-butyl ((2S)-2-((1,3-dioxo-1,3-dihydro-2H-isoindol-2-yl)oxy)propyl) carbamate To a solution of 2-hydroxy-1H-isoindole-1,3(2H)-dione (10 g), tert-butyl ((2R)-2-hydroxypropyl)carbamate (11.69 g) obtained in Step A of Example 1 and tributylphosphine (18 mL) in tetrahydrofuran (200 mL) was added 1,1'-(azodicarbonyl)dipiperidine (18.47 g) at 0° C., and the mixture was stirred overnight at room temperature. The insoluble substance was removed by filtration, and the solvent was evaporated under reduced pressure. The residue was purified by silica gel column chromatography (hexane/ethyl acetate) to give the title compound (18.66 g).

$^1$H NMR (300 MHz, DMSO-d$_6$) δ 1.23 (3H, d, J=6.4 Hz), 1.37 (9H, s), 3.03-3.18 (1H, m), 3.19-3.30 (1H, m), 4.21-4.42 (1H, m), 6.76 (1H, t, J=5.9 Hz), 7.87 (4H, s).

MS: [M+H]$^+$ 343.0.

C) benzyl (((2S)-1-((tert-butoxycarbonyl)amino) propan-2-yl)oxy)carbamate

To a solution of tert-butyl ((2S)-2-((1,3-dioxo-1,3-dihydro-2H-isoindol-2-yl)oxy)propyl)carbamate (18.64 g) obtained in Step B of Example 1 in ethanol (250 mL) was added hydrazine monohydrate (8.5 mL), and the mixture was stirred at 50° C. for 5 hr. The insoluble substance was removed by filtration, and the solvent was evaporated under reduced pressure. To the residue was added saturated aqueous sodium hydrogencarbonate solution (200 mL), and the mixture was extracted three times with ethyl acetate (100 mL). The obtained organic layer was washed with saturated brine (30 mL), and dried over anhydrous magnesium sulfate, and the solvent was evaporated under reduced pressure. To a solution of the residue in pyridine (120 mL) was added dropwise benzyl chloroformate (12 mL) at 0° C., and the mixture was stirred overnight at room temperature. The solvent was evaporated under reduced pressure, to the residue was added saturated aqueous sodium hydrogencarbonate solution (200 mL), and the mixture was extracted twice with ethyl acetate (150 mL). The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (17.39 g).

$^1$H NMR (300 MHz, DMSO-d$_6$) δ 1.05 (3H, d, J=6.4 Hz), 1.37 (9H, s), 2.88-3.20 (2H, m), 3.77 (1H, q, J=5.7 Hz), 5.09 (2H, s), 6.63 (1H, t, J=5.9 Hz), 7.23-7.47 (5H, m), 10.23 (1H, brs).

MS: [M+H]$^+$ 347.1.

D) benzyl (2-bromoethyl)(((2S)-1-((tert-butoxycarbonyl)amino)propan-2-yl)oxy)carbamate To a solution of benzyl (((2S)-1-((tert-butoxycarbonyl) amino)propan-2-yl)oxy)carbamate (17.39 g) obtained in Step C of Example 1 in N,N-dimethylformamide (200 mL) was added sodium hydride (60% in mineral oil, 2.35 g) in an ice bath, and the mixture was stirred at room temperature for 30 min. To the reaction mixture was added 1,2-dibromoethane (5.5 mL) at 0° C., and the mixture was stirred overnight at room temperature. To the reaction mixture was added saturated aqueous sodium hydrogencarbonate solution (300 mL), and the mixture was extracted twice with ethyl acetate (200 mL). The obtained organic layer was washed successively with water (100 mL) and saturated brine (50 mL), and dried over anhydrous magnesium sulfate, and the solvent was evaporated under reduced pressure. The residue was purified by silica gel column chromatography (hexane/ethyl acetate) to give the title compound (16.38 g).

$^1$H NMR (300 MHz, DMSO-d$_6$) δ 1.08 (3H, d, J=6.4 Hz), 1.37 (9H, s), 2.88-3.18 (2H, m), 3.52-3.70 (2H, m), 3.75-4.07 (3H, m), 5.06-5.23 (2H, m), 6.81 (1H, t, J=5.5 Hz), 7.25-7.49 (5H, m).

MS: [M+H−Boc]$^+$ 331.0.

E) 2-benzyl 5-tert-butyl (7S)-7-methyl-1,2,5-oxadiazepane-2,5-dicarboxylate

To benzyl (2-bromoethyl)(((2S)-1-((tert-butoxycarbonyl) amino)propan-2-yl)oxy)carbamate (11.4 g) obtained in Step D of Example 1 was added trifluoroacetic acid (40 mL), and the mixture was stirred at room temperature for 1 hr. The solvent was evaporated under reduced pressure, to a solution of the residue in N,N-dimethylformamide (250 mL) was added N,N-diisopropylethylamine (23.08 mL), and the mixture was stirred overnight at room temperature. To the reaction mixture was added di-tert-butyl dicarbonate (9.20 mL), and the mixture was stirred at room temperature for 2 hr. The solvent was evaporated under reduced pressure, saturated aqueous sodium hydrogencarbonate solution was added thereto at 0° C., and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (hexane/ethyl acetate) to give the title compound (8.17 g).

$^1$H NMR (300 MHz, DMSO-d$_6$) δ 1.09 (3H, d, J=6.4 Hz), 1.36 (9H, s), 2.74-3.10 (1H, m), 3.15-3.30 (1H, m), 3.42-3.59 (1H, m), 3.63-4.12 (4H, m), 5.12 (2H, s), 7.14-7.55 (5H, m).

MS: [M+H−Boc]$^+$ 251.2.

F) benzyl (7S)-7-methyl-1,2,5-oxadiazepane-2-carboxylate hydrochloride

To a mixture of 2-benzyl 5-tert-butyl (7S)-7-methyl-1,2,5-oxadiazepane-2,5-dicarboxylate (10.1 g) obtained in Step E of Example 1 in a mixed solvent of tetrahydrofuran (130 mL) and ethanol (30 mL) was added a solution of 4M hydrogen chloride in cyclopentyl methyl ether (100 mL), and the mixture was stirred overnight at room temperature. The solvent was evaporated under reduced pressure to give the title compound (8.20 g).

G) benzyl (7S)-5-(5-fluoro-2-(2H-1,2,3-triazol-2-yl)benzoyl)-7-methyl-1,2,5-oxadiazepane-2-carboxylate To a solution of 5-fluoro-2-(2H-1,2,3-triazol-2-yl)benzoic acid (3.88 g) obtained in Reference Example 1 in a mixed solvent of tetrahydrofuran (60 mL) and N,N-dimethylformamide (1 mL) was added oxalyl chloride (2.5 mL), and the mixture was stirred at room temperature for 1 hr. The solvent was evaporated under reduced pressure, a solution of the residue in N,N-dimethylacetamide (20 mL) was added dropwise to a mixture of benzyl (7S)-7-methyl-1,2,5-oxadiazepane-2-carboxylate hydrochloride (4.13 g) obtained in Step F of Example 1 in a mixture of N,N-dimethylacetamide (40 mL) and triethylamine (7.0 mL) at 0° C., and the mixture was stirred overnight at room temperature. To the reaction mixture was added saturated aqueous sodium hydrogencarbonate solution (150 mL), and the mixture was extracted three times with ethyl acetate (100 mL). The obtained organic layer was washed with saturated brine, and dried over anhydrous magnesium sulfate, and the solvent was evaporated under reduced pressure. The residue was purified by silica gel column chromatography (NH, hexane/ethyl acetate) and silica gel column chromatography (hexane/ethyl acetate) to give the title compound (5.76 g).

$^1$H NMR (300 MHz, DMSO-d$_6$) δ 0.88-1.28 (3H, m), 2.79-3.30 (2H, m), 3.37-4.41 (5H, m), 4.92-5.31 (2H, m), 7.08-8.20 (10H, m).

MS: [M+H]$^+$ 440.2.

H) ((7S)-2-(2,6-dimethylpyrimidin-4-yl)-7-methyl-1,2,5-oxadiazepan-yl) (5-fluoro-2-(2H-1,2,3-triazol-2-yl)phenyl)methanone To benzyl (7S)-5-(5-fluoro-2-(2H-1,2,3-triazol-2-yl)benzoyl)-7-methyl-1,2,5-oxadiazepane-2-carboxylate (5.75 g) obtained in Step G of Example 1 was added 5.1M hydrogen bromide acetic acid solution (60 mL), and the mixture was stirred at room temperature for 1 hr. The solvent was evaporated under reduced pressure, to a solution of the residue in 2-propanol (60 mL) was added 4-chloro-2,6-dimethylpyrimidine (2.07 g), and the mixture was stirred at 70° C. for 2 hr. To the reaction mixture was added saturated aqueous sodium hydrogencarbonate solution (200 mL), and the mixture was extracted three times with ethyl acetate (100 mL). The obtained organic layer was washed with saturated brine (30 mL), and dried over anhydrous magnesium sulfate, and the solvent was evaporated under reduced pressure. The residue was purified by silica gel column chromatography (NH, hexane/ethyl acetate), and crystallized (hexane/ethyl acetate) to give the title compound (4.49 g).

$^1$H NMR (300 MHz, DMSO-d$_6$) δ 1.02-1.38 (3H, m), 2.20-2.46 (6H, m), 3.11-3.28 (1H, m), 3.41-3.74 (3H, m), 3.75-4.53 (3H, m), 6.37-6.75 (1H, m), 6.95-7.83 (3H, m), 7.84-8.04 (1H, m), 8.10 (1H, d, J=3.8 Hz).

MS: [M+H]$^+$ 412.2.

d value (or d-spacing) of specific peak in powder X-ray diffraction pattern=15.8, 7.9, 7.4, 5.6, 5.2, 4.4, 4.0, 3.7, 3.61, 3.56, 3.51, 3.46 A.

Example 2

((7S)-2-(2,6-dimethylpyrimidin-4-yl)-7-methyl-1,2,5-oxadiazepan-5-yl)(2-(2H-1,2,3-triazol-2-yl)phenyl)methanone

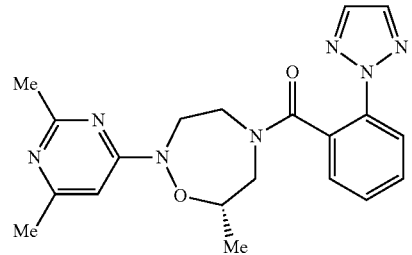 [SMILES: Cc1cc(N2CCN(C(=O)c3ccccc3-n3nccn3)C[C@H](C)O2)nc(C)n1]

A) benzyl (7S)-7-methyl-5-(2-(2H-1,2,3-triazol-2-yl)benzoyl)-1,2,5-oxadiazepane-2-carboxylate To 2-benzyl 5-tert-butyl (7S)-7-methyl-1,2,5-oxadiazepane-2,5-dicarboxylate (4.1 g) obtained in Step E of Example 1 was added 4M hydrogen chloride ethyl acetate (30 mL) solution, and the mixture was stirred at room temperature for 1 hr. The solvent was evaporated under reduced pressure to give benzyl (7S)-7-methyl-1,2,5-oxadiazepane-2-carboxylate hydrochloride. To a solution of 2-(2H-1,2,3-triazol-2-yl)benzoic acid (2.88 g) obtained in Reference Example 2 in tetrahydrofuran (40 mL) were added thionyl chloride (1.698 mL) and N,N-dimethylformamide (0.010 mL), and the mixture was stirred at room temperature for 1 hr. The solvent was evaporated under reduced pressure, a solution of the residue in tetrahydrofuran (20 mL) was added dropwise to a solution of benzyl (7S)-7-methyl-1,2,5-oxadiazepane-2-carboxylate hydrochloride in a mixture of tetrahydrofuran (40 mL) and triethylamine (6.54 mL) at 0° C., and the mixture was stirred overnight at room temperature. To the reaction mixture was added saturated aqueous sodium hydrogencarbonate solution at 0° C., and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (4.44 g).

$^1$H NMR (300 MHz, DMSO-$d_6$) δ 0.91-1.31 (3H, m), 2.79-3.22 (1H, m), 3.36-3.81 (4H, m), 3.94-4.48 (2H, m), 4.91-5.22 (2H, m), 7.10-8.37 (11H, m).

MS: [M+H]$^+$ 422.0.

B) ((7S)-2-(2,6-dimethylpyrimidin-4-yl)-7-methyl-1, 2,5-oxadiazepan-5-yl)(2-(2H-1,2,3-triazol-2-yl)phenyl)methanone To benzyl (7S)-7-methyl-5-(2-(2H-1,2,3-triazol-2-yl)benzoyl)-1,2,5-oxadiazepane-2-carboxylate (4.4 g) obtained in Step A of Example 2 was added 5.1M hydrogen bromide acetic acid solution (30 mL), and the mixture was stirred at room temperature for 1 hr. The solvent was evaporated under reduced pressure, to a solution of the residue in 2-propanol (40 mL) was added 4-chloro-2,6-dimethylpyrimidine (2.23 g), and the mixture was stirred at 70° C. for 10 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (heptane/ethyl acetate) to give the title compound (2.30 g).

$^1$H NMR (300 MHz, DMSO-$d_6$) δ 1.02-1.50 (3H, m), 2.16-2.46 (6H, m), 2.95-3.29 (1H, m), 3.40-3.75 (3H, m), 3.79-4.74 (3H, m), 6.31-6.77 (1H, m), 7.05-8.30 (6H, m).

MS: [M+H]$^+$ 394.1.

d value (or d-spacing) of specific peak in powder X-ray diffraction pattern=15.5, 7.9, 7.7, 7.4, 6.5, 5.6, 5.1, 4.3, 4.0, 3.67, 3.62, 3.57, 3.52 A.

Example 3

(5-chloro-2-(2H-1,2,3-triazol-2-yl)phenyl)((7S)-7-methyl-2-(2-methyl-6-(trifluoromethyl)pyrimidin-4-yl)-1,2,5-oxadiazepan-5-yl)methanone

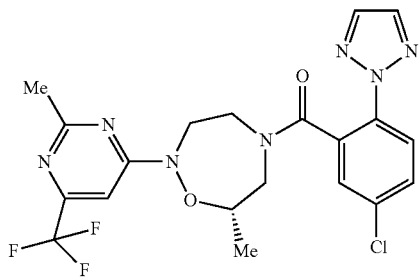 [SMILES: Cc1nc(N2CCN(C(=O)c3cc(Cl)ccc3-n3nccn3)C[C@H](C)O2)cc(C(F)(F)F)n1]

A) benzyl (7S)-5-(5-chloro-2-(2H-1,2,3-triazol-2-yl) benzoyl)-7-methyl-1,2,5-oxadiazepane-2-carboxylate To a solution of 5-chloro-2-(2H-1,2,3-triazol-2-yl)benzoic acid (3.2 g) obtained in Reference Example 3 in tetrahydrofuran (40 mL) were added thionyl chloride (1.56 mL) and N,N-dimethylformamide (0.010 mL), and the mixture was stirred at room temperature for 1 hr. The solvent was evaporated under reduced pressure, a solution of the residue in tetrahydrofuran (20 mL) was added dropwise to a solution of benzyl (7S)-7-methyl-1,2,5-oxadiazepane-2-carboxylate hydrochloride (4.1 g) obtained in Step F of Example 1 in a mixture of tetrahydrofuran (30 mL) and triethylamine (7.99 mL) at 0° C., and the mixture was stirred overnight at room temperature. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (5.1 g).

$^1$H NMR (300 MHz, DMSO-$d_6$) δ 0.94-1.29 (3H, m), 2.81-3.26 (1H, m), 3.36-3.82 (4H, m), 4.07-4.46 (2H, m), 4.89-5.38 (2H, m), 7.22-8.21 (10H, m).

MS: [M+H]$^+$ 455.9.

B) (5-chloro-2-(2H-1,2,3-triazol-2-yl)phenyl)((7S)-7-methyl-2-(2-methyl-6-(trifluoromethyl)pyrimidin-4-yl)-1,2,5-oxadiazepan-5-yl)methanone To benzyl (7S)-5-(5-chloro-2-(2H-1,2,3-triazol-2-yl)benzoyl)-7-methyl-1,2,5-oxadiazepane-2-carboxylate (5.1 g) obtained in Step A of Example 3 was added 5.1M hydrogen bromide acetic acid solution (30 mL), and the mixture was stirred at room temperature for 1 hr. The solvent was evaporated under reduced pressure, to a solution of the residue in 2-propanol (40 mL) was added 4-chloro-2-methyl-6-(trifluoromethyl)pyrimidine (3.3 g), and the mixture was stirred at 80° C. for 3 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (heptane/diisopropyl ether) to give the title compound (3.08 g).

$^1$H NMR (300 MHz, DMSO-$d_6$) δ 1.05-1.43 (3H, m), 2.50-2.63 (3H, m), 2.99-3.32 (1H, m), 3.42-3.94 (3H, m), 4.01-4.67 (3H, m), 6.68-8.28 (6H, m).

MS: [M+H]$^+$ 482.1.

Example 4

(2-(2,6-dimethylpyrimidin-4-yl)-1,2,5-oxadiazepan-5-yl)(5-methyl-2-(2H-1,2,3-triazol-2-yl)phenyl)methanone

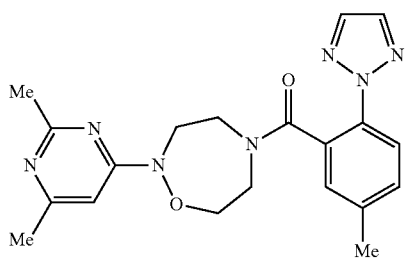 [SMILES: Cc1ccc(-n2nccn2)c(C(=O)N2CCON(c3cc(C)nc(C)n3)CC2)c1]

A) benzyl bis(2-chloroethyl)carbamate

To an aqueous solution (200 mL) of 2-chloro-N-(2-chloroethyl)ethanamine hydrochloride (19.3 g) and benzyl chloroformate (15.44 mL) was added dropwise 2M aqueous sodium hydroxide solution (108 mL) at 0° C., and the mixture was stirred at 0° C. for 3 hr. To the reaction mixture was added water, and the mixture was extracted with ethyl acetate. The obtained organic layer was washed with saturated brine, and dried over anhydrous magnesium sulfate, and the solvent was evaporated under reduced pressure to give the title compound (28 g).

$^1$H NMR (300 MHz, DMSO-d$_6$) δ 3.53-3.66 (4H, m), 3.68-3.83 (4H, m), 5.11 (2H, s), 7.21-7.55 (5H, m).

B) 5-benzyl 2-tert-butyl 1,2,5-oxadiazepane-2,5-dicarboxylate

To a solution of tert-butyl hydroxycarbamate (13.5 g) in N,N-dimethylformamide (200 mL) was added sodium hydride (60% in mineral oil, 8.92 g), and the mixture was stirred at 0° C. for 20 min. To the reaction mixture was added dropwise a solution of benzyl bis(2-chloroethyl)carbamate (28 g) obtained in Step A of Example 4 in N,N-dimethylformamide (200 mL), and the mixture was stirred at 0° C. for 20 min, and then at 100° C. for 1 hr. The solvent was evaporated under reduced pressure, to the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (14.4 g).

$^1$H NMR (300 MHz, DMSO-d$_6$) δ 1.40 (9H, s), 3.49-3.69 (6H, m), 3.83-3.93 (2H, m), 5.10 (2H, s), 7.31-7.42 (5H, m).
MS: [M+H−Boc]$^+$ 237.2.

C) benzyl 2-(2,6-dimethylpyrimidin-4-yl)-1,2,5-oxadiazepane-5-carboxylate

To 5-benzyl 2-tert-butyl 1,2,5-oxadiazepane-2,5-dicarboxylate (5.0 g) obtained in Step B of Example 4 was added 4M hydrogen chloride ethyl acetate (50 mL) solution, and the mixture was stirred at room temperature for 1 hr. The solvent was evaporated under reduced pressure, and the residue was washed with ethyl acetate to give benzyl 1,2,5-oxadiazepane-5-carboxylate hydrochloride (4.01 g). To a solution of the obtained benzyl 1,2,5-oxadiazepane-5-carboxylate hydrochloride (4.01 g) in 2-propanol (40 mL) was added 4-chloro-2,6-dimethylpyrimidine (2.23 g), and the mixture was stirred at 50° C. for 2 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (4.35 g).

$^1$H NMR (300 MHz, DMSO-d$_6$) δ 2.30 (3H, s), 2.38 (3H, d, J=2.3 Hz), 3.50-3.76 (4H, m), 3.82-3.92 (2H, m), 3.95-4.01 (2H, m), 5.11 (2H, s), 6.70 (1H, s), 7.27-7.42 (5H, m).
MS: [M+H]$^+$ 343.3.

D) 2-(2,6-dimethylpyrimidin-4-yl)-1,2,5-oxadiazepane dihydrobromide

To benzyl 2-(2,6-dimethylpyrimidin-4-yl)-1,2,5-oxadiazepane-5-carboxylate (4.35 g) obtained in Step C of Example 4 was added 5.1M hydrogen bromide acetic acid solution (30 mL), and the mixture was stirred at room temperature for 40 min. The solvent was evaporated under reduced pressure, and the residue was washed with ethyl acetate to give the title compound (4.3 g).

$^1$H NMR (300 MHz, DMSO-d$_6$) δ 2.50-2.51 (3H, m), 2.59 (3H, s), 3.24-3.67 (5H, m), 4.19-4.34 (2H, m), 4.36-4.57 (2H, m), 7.13 (1H, s), 9.39 (2H, brs).
MS: [M+H−2HBr]$^+$ 209.2.

E) (2-(2,6-dimethylpyrimidin-4-yl)-1,2,5-oxadiazepan-5-yl)(5-methyl-2-(2H-1,2,3-triazol-2-yl)phenyl)methanone To a solution of 5-methyl-2-(2H-1,2,3-triazol-2-yl)benzoic acid (2.64 g) in tetrahydrofuran (30 ml) were added oxalyl chloride (1.85 mL) and N,N-dimethylformamide (0.020 mL) at 0° C., and the mixture was stirred at room temperature for 1 hr. The solvent was evaporated under reduced pressure, a solution of the residue in tetrahydrofuran (15 mL) was added dropwise to a solution of 2-(2,6-dimethylpyrimidin-4-yl)-1,2,5-oxadiazepane dihydrobromide (4.0 g) obtained in Step D of Example 4 in a mixture of tetrahydrofuran (30 mL) and triethylamine (6.03 mL) at 0° C., and the mixture was stirred at room temperature for 3 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and recrystallized (heptane/ethyl acetate/ethanol) to give the title compound (3.52 g).

$^1$H NMR (300 MHz, DMSO-d$_6$) δ 2.25-2.45 (9H, m), 3.36-3.57 (2H, m), 3.58-4.34 (6H, m), 6.51-6.76 (1H, m), 6.95-7.31 (1H, m), 7.35-7.57 (1H, m), 7.72-7.90 (2H, m), 7.96 (1H, s).
MS: [M+H]$^+$ 394.3.

Example 5

((4S,6R)-2-(2,6-dimethylpyrimidin-4-yl)-4,6-dimethyl-1,2,5-oxadiazepan-5-yl)(2-(1,3-thiazol-2-yl)phenyl)methanone

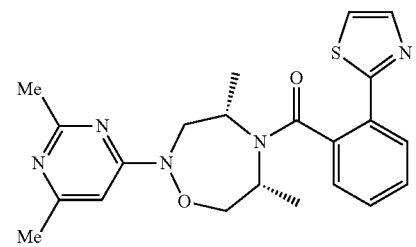 [SMILES: Cc1cc(N2C[C@H](C)N(C(=O)c3ccccc3-c3nccs3)[C@H](C)CO2)nc(C)n1]

A) tert-butyl ((2R)-1-((1,3-dioxo-1,3-dihydro-2H-isoindol-2-yl)oxy)propan-2-yl)carbamate To a solution of 2-hydroxy-1H-isoindole-1,3(2H)-dione (9.96 g), tert-butyl ((2R)-1-hydroxypropan-2-yl)carbamate (10.7 g) and tributylphosphine (19.63 mL) in tetrahydrofuran (200 mL) was added 1,1'-(azodicarbonyl)dipiperidine (18.49 g) at 0° C., and the mixture was stirred overnight. The insoluble substance was removed by filtration, and the solvent was evaporated under reduced pressure. The residue was purified by silica gel column chromatography (hexane/ethyl acetate) to give the title compound (12.65 g).

$^1$H NMR (300 MHz, DMSO-d$_6$) δ 1.16-1.23 (3H, m), 1.36 (9H, s), 3.78 (1H, dt, J=13.3, 6.6 Hz), 3.88-4.10 (2H, m), 6.87 (1H, d, J=8.0 Hz), 7.87 (4H, s).

MS: [M+H−Boc]$^+$ 221.0.

B) benzyl (((2R)-2-((tert-butoxycarbonyl)amino)propyl)oxy)carbamate

To a solution of tert-butyl ((2R)-1-((1,3-dioxo-1,3-dihydro-2H-isoindol-2-yl)oxy)propan-2-yl)carbamate (12.65 g) obtained in Step A of Example 5 in ethanol (250 mL) was added hydrazine monohydrate (13 mL), and the mixture was stirred at 50° C. for 1 hr. The insoluble substance was removed by filtration, and the solvent was evaporated under reduced pressure. To the residue was added saturated aqueous sodium hydrogencarbonate solution at 0° C., and the mixture was extracted with ethyl acetate. The obtained organic layer was washed with saturated brine, and dried over anhydrous magnesium sulfate, and the solvent was evaporated under reduced pressure. To a solution of the residue in pyridine (100 mL) was added dropwise benzyl chloroformate (11.27 mL) at 0° C., and the mixture was stirred overnight at room temperature. The solvent was evaporated under reduced pressure, to the residue was added 1N aqueous hydrogen chloride solution at 0° C., and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (11.5 g).

$^1$H NMR (300 MHz, DMSO-d$_6$) δ 1.04 (3H, d, J=6.8 Hz), 1.37 (9H, s), 3.41-3.55 (1H, m), 3.59-3.84 (2H, m), 5.09 (2H, s), 6.72 (1H, d, J=7.6 Hz), 7.23-7.60 (5H, m), 10.40 (1H, brs).

MS: [M+H−Boc]$^+$ 225.1.

C) benzyl (((2R)-2-((tert-butoxycarbonyl)amino)propyl)oxy)(2-oxopropyl)carbamate To a solution of benzyl (((2R)-2-((tert-butoxycarbonyl)amino)propyl)oxy)carbamate (6.0 g) obtained in Step B of Example 5 in N,N-dimethylformamide (60 mL) were added potassium carbonate (2.56 g) and 1-bromoacetone (2.33 mL), and the mixture was stirred overnight at room temperature. To the reaction mixture was added saturated aqueous sodium hydrogencarbonate solution at 0° C., and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (5.61 g).

$^1$H NMR (300 MHz, DMSO-d$_6$) δ 0.98 (3H, d, J=6.1 Hz), 1.37 (9H, s), 2.07 (3H, s), 3.52-3.78 (3H, m), 4.42 (2H, s), 5.13 (2H, s), 6.76 (1H, d, J=6.8 Hz), 7.13-7.49 (5H, m).

MS: [M+H−Boc]$^+$ 281.0.

D) benzyl (4S,6R)-4,6-dimethyl-1,2,5-oxadiazepane-2-carboxylate

To benzyl (((2R)-2-((tert-butoxycarbonyl)amino)propyl)oxy)(2-oxopropyl)carbamate (5.6 g) obtained in Step C of Example 5 was added trifluoroacetic acid (40 mL) under ice-cooling, and the mixture was stirred at room temperature for 1 hr. The solvent was evaporated under reduced pressure, to a solution of the residue in a mixed solvent of ethyl acetate (60 mL) and acetic acid (60 mL) was added sodium triacetoxyborohydride (9.36 g), and the mixture was stirred overnight at room temperature. The solvent was evaporated under reduced pressure, and the residue was cooled to 0° C. Saturated aqueous sodium hydrogencarbonate solution was added thereto, and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (NH, hexane/ethyl acetate) to give the title compound (2.8 g).

$^1$H NMR (300 MHz, DMSO-d$_6$) δ 0.89 (3H, d, J=6.4 Hz), 1.02 (3H, d, J=6.4 Hz), 2.04 (1H, s), 2.86-3.04 (2H, m), 3.16 (1H, dd, J=12.7, 10.8 Hz), 3.36 (1H, s), 3.67 (1H, dd, J=12.7, 4.0 Hz), 4.02 (1H, dd, J=11.4, 4.2 Hz), 5.12 (2H, s), 7.20-7.48 (5H, m).

MS: [M+H]$^+$ 265.1.

E) benzyl (4S,6R)-4,6-dimethyl-5-(2-(1,3-thiazol-2-yl)benzoyl)-1,2,5-oxadiazepane-2-carboxylate To a solution of 2-(1,3-thiazol-2-yl)benzoic acid (2.83 g) obtained in Reference Example 4 in tetrahydrofuran (30 mL) were added thionyl chloride (1.55 mL) and N,N-dimethylformamide (0.010 mL), and the mixture was stirred at room temperature for 1 hr. The solvent was evaporated under reduced pressure, a solution of the residue in tetrahydrofuran (10 mL) was added dropwise to a solution of benzyl (4S,6R)-4,6-dimethyl-1,2,5-oxadiazepane-2-carboxylate (2.8 g) obtained in Step D of Example 5 in a mixture of tetrahydrofuran (30 mL) and triethylamine (5.91 mL) at 0° C., and the mixture was stirred overnight at room temperature. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) and silica gel column chromatography (NH, hexane/ethyl acetate) to give the title compound (0.934 g).

$^1$H NMR (300 MHz, DMSO-d$_6$) δ 1.03-1.50 (6H, m), 3.58-4.10 (4H, m), 4.18-4.44 (1H, m), 4.69-4.90 (1H, m), 4.92-5.38 (2H, m), 6.91-8.30 (11H, m).

MS: [M+H]$^+$ 452.0.

F) ((4S,6R)-2-(2,6-dimethylpyrimidin-4-yl)-4,6-dimethyl-1,2,5-oxadiazepan-5-yl)(2-(1,3-thiazol-2-yl)phenyl)methanone To benzyl (4S,6R)-4,6-dimethyl-5-(2-(1,3-thiazol-2-yl)benzoyl)-1,2,5-oxadiazepane-2-carboxylate (0.934 g)

obtained in Step E of Example 5 was added 5.1M hydrogen bromide acetic acid solution (10 mL), and the mixture was stirred at 0° C. for 1 hr. The solvent was evaporated under reduced pressure, to a solution of the residue in 2-propanol (10 mL) was added 4-chloro-2,6-dimethylpyrimidine (442 mg), and the mixture was stirred at 70° C. for 10 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (heptane/ethyl acetate) to give the title compound (750 mg).

$^1$H NMR (300 MHz, DMSO-d$_6$) δ 0.93-1.51 (6H, m), 2.14-2.43 (6H, m), 3.61-4.28 (4H, m), 4.31-5.36 (2H, m), 6.23-6.83 (1H, m), 6.95-7.62 (4H, m), 7.73-8.17 (2H, m).

MS: [M+H]$^+$ 424.0.

Example 6

((6R)-2-(2,6-dimethylpyrimidin-4-yl)-6-methyl-1,2, 5-oxadiazepan-5-yl)(5-methyl-2-(2H-1,2,3-triazol-2-yl)phenyl)methanone

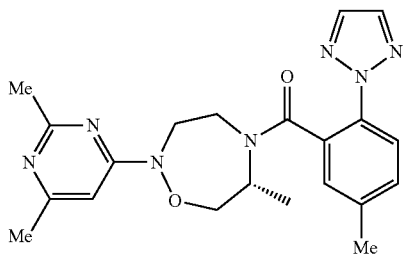 [SMILES: Cc1ccc(-n2nccn2)c(C(=O)N2CCN(c3cc(C)nc(C)n3)OC[C@H]2C)c1]

A) benzyl (2-bromoethyl)(((2R)-2-((tert-butoxycarbonyl)amino)propyl)oxy)carbamate To a solution of benzyl (((2R)-2-((tert-butoxycarbonyl)amino)propyl)oxy)carbamate (3.8 g) obtained in Step B of Example 5 in N,N-dimethylformamide (40 mL) was added sodium hydride (60% in mineral oil, 0.49 g) in an ice bath, and the mixture was stirred at 0° C. for 20 min. To the reaction mixture was added 1,2-dibromoethane (1.51 mL) at 0° C., and the mixture was stirred at 0° C. for 20 min, and then overnight at room temperature. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (3.96 g).

$^1$H NMR (300 MHz, DMSO-d$_6$) δ 1.01 (3H, d, J=6.4 Hz), 1.37 (9H, s), 3.54-3.65 (2H, m), 3.66-3.79 (3H, m), 3.83-3.92 (2H, m), 5.15 (2H, s), 6.82 (1H, d, J=8.0 Hz), 7.15-7.72 (5H, m).

MS: [M+H−Boc]$^+$ 331.1.

B) 2-benzyl 5-tert-butyl (6R)-6-methyl-1,2,5-oxadiazepane-2,5-dicarboxylate

To benzyl (2-bromoethyl)(((2R)-2-((tert-butoxycarbonyl)amino)propyl)oxy)carbamate (3.96 g) obtained in Step A of Example 6 was added trifluoroacetic acid (20 mL), and the mixture was stirred at room temperature for 1 hr. The solvent was evaporated under reduced pressure, to a solution of the residue in N,N-dimethylformamide (70 mL) was added potassium carbonate (6.34 g), and the mixture was stirred at room temperature for 5 hr. To the reaction mixture was added di-tert-butyl dicarbonate (4.26 mL), and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (hexane/ethyl acetate) to give the title compound (2.64 g).

$^1$H NMR (300 MHz, DMSO-d$_6$) δ 1.10 (3H, d, J=6.8 Hz), 1.38 (9H, s), 3.33-3.49 (1H, m), 3.55-3.85 (4H, m), 3.95-4.33 (2H, m), 5.13 (2H, s), 7.27-7.46 (5H, m).

MS: [M+H−Boc]$^+$ 251.2.

C) benzyl (6R)-6-methyl-5-(5-methyl-2-(2H-1,2,3-triazol-2-yl)benzoyl)-1,2,5-oxadiazepane-2-carboxylate To 2-benzyl 5-tert-butyl (6R)-6-methyl-1,2,5-oxadiazepane-2,5-dicarboxylate (400 mg) obtained in Step B of Example 6 was added 4M hydrogen chloride ethyl acetate (8.0 mL) solution, and the mixture was stirred at room temperature for 2 hr. The solvent was evaporated under reduced pressure to give benzyl (6R)-6-methyl-1,2,5-oxadiazepane-2-carboxylate hydrochloride. To a solution of 5-methyl-2-(2H-1,2,3-triazol-2-yl)benzoic acid (278 mg) in tetrahydrofuran (5.0 mL) were added thionyl chloride (0.165 mL) and N,N-dimethylformamide (0.020 mL), and the mixture was stirred at room temperature for 1 hr. The solvent was evaporated under reduced pressure, a solution of the residue in tetrahydrofuran (1.0 mL) was added to a mixture of benzyl (6R)-6-methyl-1,2,5-oxadiazepane-2-carboxylate hydrochloride in a mixture of tetrahydrofuran (2.0 mL) and triethylamine (0.48 mL), and the mixture was stirred at room temperature for 3 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (404 mg).

$^1$H NMR (300 MHz, DMSO-d$_6$) δ 1.09-1.34 (3H, m), 2.30-2.41 (3H, m), 3.39-4.33 (7H, m), 5.10-5.30 (2H, m), 7.21-7.50 (7H, m), 7.62-7.89 (2H, m), 8.06 (1H, d, J=7.2 Hz).

MS: [M+H]$^+$ 436.1.

D) ((6R)-6-methyl-1,2,5-oxadiazepan-5-yl)(5-methyl-2-(2H-1,2,3-triazol-2-yl)phenyl)methanone hydrobromide To benzyl (6R)-6-methyl-5-(5-methyl-2-(2H-1,2,3-triazol-2-yl)benzoyl)-1,2,5-oxadiazepane-2-carboxylate (410 mg) obtained in Step C of Example 6 was added 5.1M hydrogen bromide acetic acid solution (6 mL), and the mixture was stirred at room temperature for 1 hr. The solvent was evaporated under reduced pressure, and the residue was washed with ethyl acetate to give the title compound (313 mg).

$^1$H NMR (300 MHz, DMSO-$d_6$) δ 0.99-1.28 (3H, m), 2.41 (3H, s), 3.29-3.93 (4H, m), 3.96-4.77 (3H, m), 7.21-7.54 (2H, m), 7.78-7.92 (1H, m), 8.03-8.16 (2H, m).

MS: [M+H−HBr]$^+$ 302.2.

E) ((6R)-2-(2,6-dimethylpyrimidin-4-yl)-6-methyl-1,2,5-oxadiazepan-5-yl)(5-methyl-2-(2H-1,2,3-triazol-2-yl)phenyl)methanone A mixture of ((6R)-6-methyl-1,2,5-oxadiazepan-5-yl)(5-methyl-2-(2H-1,2,3-triazol-2-yl)phenyl)methanone hydrobromide (90 mg) obtained in Step D of Example 6, 4-chloro-2,6-dimethylpyrimidine (36.9 mg) and ethanol (1.0 mL) was stirred in a microwave reactor at 150° C. for 1 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (hexane/ethyl acetate) to give the title compound (55 mg).

$^1$H NMR (300 MHz, DMSO-$d_6$) δ 0.74-1.32 (3H, m), 2.21-2.45 (9H, m), 3.38-4.92 (7H, m), 6.44-8.17 (6H, m).

MS: [M+H]$^+$ 408.2.

Example 7

(2-(4,6-dimethylpyrimidin-2-yl)-1,2,5-oxadiazepan-5-yl)(5-methyl-2-(2H-1,2,3-triazol-2-yl)phenyl)methanone

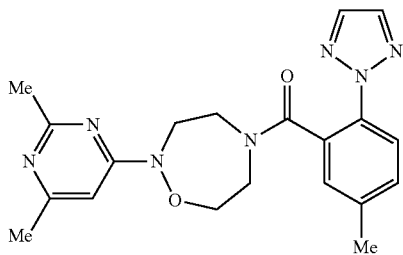 [SMILES: Cc1ccc(-n2nccn2)c(C(=O)N2CCON(c3cc(C)nc(C)n3)CC2)c1]

A) tert-butyl 1,2,5-oxadiazepane-2-carboxylate

To a solution of 5-benzyl 2-tert-butyl 1,2,5-oxadiazepane-2,5-dicarboxylate (5.0 g) obtained in Step B of Example 4 in ethanol (50 mL) was added 10% palladium-carbon (316 mg), and the mixture was stirred at room temperature for 5 hr under hydrogen atmosphere (normal pressure). The palladium on carbon was removed through Celite, and the solvent was evaporated under reduced pressure to give the title compound (2.98 g).

$^1$H NMR (300 MHz, DMSO-$d_6$) δ 1.42 (9H, s), 2.74-2.90 (4H, m), 3.31 (1H, brs), 3.43-3.54 (2H, m), 3.82 (2H, t, J=5.3 Hz).

B) tert-butyl 5-(5-methyl-2-(2H-1,2,3-triazol-2-yl)benzoyl)-1,2,5-oxadiazepane-2-carboxylate To a solution of tert-butyl 1,2,5-oxadiazepane-2-carboxylate (538 mg) obtained in Step A of Example 7 in N,N-dimethylacetamide (10 mL) were added 2-(7-azabenzotriazol-1-yl)-1,1,3,3-tetramethyluronium hexafluorophosphate (HATU) (1.52 g), diisopropylethylamine (0.91 mL) and 5-methyl-2-(2H-1,2,3-triazol-2-yl)benzoic acid (541 mg), and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed successively with water and saturated brine, and dried over magnesium sulfate, and the solvent was evaporated under reduced pressure. The residue was purified by column chromatography (hexane/ethyl acetate) to give the title compound (895 mg).

MS: [M+H−t−Bu]$^+$ 332.2.

C) (5-methyl-2-(2H-1,2,3-triazol-2-yl)phenyl)(1,2,5-oxadiazepan-5-yl)methanone

To tert-butyl 5-(5-methyl-2-(2H-1,2,3-triazol-2-yl)benzoyl)-1,2,5-oxadiazepane-2-carboxylate (875 mg) obtained in Step B of Example 7 was added 4M hydrogen chloride ethyl acetate (10 mL) solution, and the mixture was stirred at room temperature for 2 hr. The solvent was evaporated under reduced pressure, to the residue was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure to give the title compound (576 mg).

MS: [M+H]$^+$ 288.2.

D) (2-(4,6-dimethylpyrimidin-2-yl)-1,2,5-oxadiazepan-5-yl)(5-methyl-2-(2H-1,2,3-triazol-2-yl)phenyl)methanone A mixture of (5-methyl-2-(2H-1,2,3-triazol-2-yl)phenyl)(1,2,5-oxadiazepan-5-yl)methanone (50 mg) obtained in Step C of Example 7, 2-chloro-4,6-dimethylpyrimidine (37.2 mg), acetic acid (0.020 mL) and ethanol (1.0 mL) was stirred in a microwave reactor at 150° C. for 1 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (45 mg).

MS: [M+H]$^+$ 394.3.

The compounds of Examples 8 to 11 were produced using (5-methyl-2-(2H-1,2,3-triazol-2-yl)phenyl)(1,2,5-oxadiazepan-5-yl)methanone obtained in Step C of Example 7 and the reagents corresponding to the compounds of Examples 8 to 11 (the reagents can be produced according to a method known per se) according to the same method as in Step D of Example 7, or a method analogous thereto. MS in the tables means actual measured value.

TABLE 1

| Ex No. | IUPAC Name | Structure | Additive | MS | Reagent |
|---|---|---|---|---|---|
| 8 | (2-(4,6-dimethylpyrimidin-2-yl)-1,2,5-oxadiazepan-5-yl)(5-methyl-2-(2H-1,2,3-triazol-2-yl)phenyl)methanone hydrochloride | 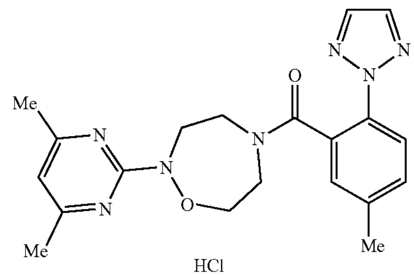 [SMILES: Cc1ccc(-n2nccn2)c(C(=O)N2CCON(c3nc(C)cc(C)n3)CC2)c1 ; Cl] | HCl HCl | 394.1 | |
| 9 | 5-methyl-2-(2H-1,2,3-triazol-2-yl)phenyl)(2-(5-(trifluoromethyl)pyrimidin-2-yl)-1,2,5-oxadiazepan-5-yl)methanone | 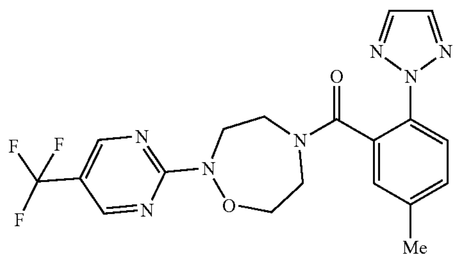 [SMILES: Cc1ccc(-n2nccn2)c(C(=O)N2CCON(c3ncc(C(F)(F)F)cn3)CC2)c1] | Free | 434.0 | |
| 10 | (2-(5-cyclopropylpyrimidin-2-yl)-1,2,5-oxadiazepan-5-yl)(5-methyl-2-(2H-1,2,3-triazol-2-yl)phenyl)methanone | 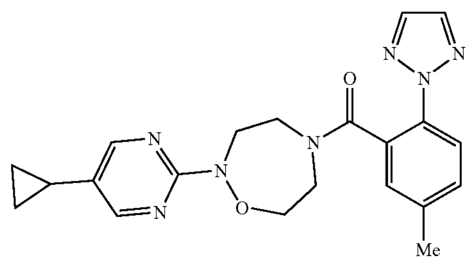 [SMILES: Cc1ccc(-n2nccn2)c(C(=O)N2CCON(c3ncc(C4CC4)cn3)CC2)c1] | Free | 406.1 | |
| 11 | (5-methyl-2-(2H-1,2,3-triazol-2-yl)phenyl)(2-(4-methyl-5-(trifluoromethyl)pyrimidin-2-yl)-1,2,5-oxadiazepan-5-yl)methanone | 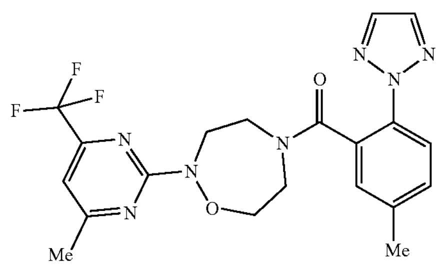 [SMILES: Cc1ccc(-n2nccn2)c(C(=O)N2CCON(c3nc(C)cc(C(F)(F)F)n3)CC2)c1] | Free | 448.0 | |

Example 12

(2-(4-(4-fluorophenyl)-6-methylpyrimidin-2-yl)-1,2,5-oxadiazepan-5-yl)(5-methyl-2-(2H-1,2,3-triazol-2-yl)phenyl)methanone

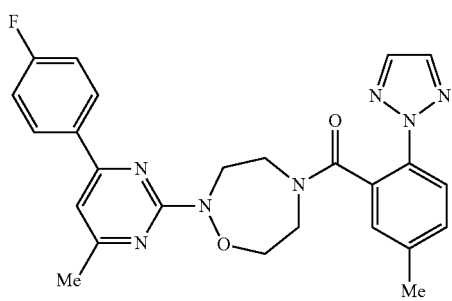 [SMILES: Cc1ccc(-n2nccn2)c(C(=O)N2CCON(c3nc(C)cc(-c4ccc(F)cc4)n3)CC2)c1]

To a solution of (5-methyl-2-(2H-1,2,3-triazol-2-yl)phenyl) (1,2,5-oxadiazepan-5-yl)methanone (50 mg) obtained in Step C of Example 7 in 2-propanol (1.0 mL) were added 2-chloro-4-(4-fluorophenyl)-6-methylpyrimidine (27.8 mg) obtained in Reference Example 5 and acetic acid (0.010 mL), and the mixture was stirred at 70° C. for 2 hr, and then overnight at 90° C. To the reaction mixture was added saturated aqueous sodium hydrogencarbonate solution (10 mL), and the mixture was extracted three times with ethyl acetate (10 mL). The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (40.9 mg).

MS: [M+H]⁺ 474.2.

Example 13

(2-(2,6-dimethylpyrimidin-4-yl)-1,2,5-oxadiazepan-5-yl)(5-methyl-2-(2H-1,2,3-triazol-2-yl)phenyl)methanone hydrochloride

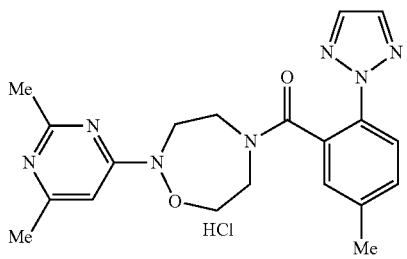 [SMILES: Cc1ccc(-n2nccn2)c(C(=O)N2CCON(c3cc(C)nc(C)n3)CC2)c1 ; Cl]

A) (5-methyl-2-(2H-1,2,3-triazol-2-yl)phenyl)(1,2,5-oxadiazepan-5-yl)methanone hydrochloride To tert-butyl 5-(5-methyl-2-(2H-1,2,3-triazol-2-yl)benzoyl)-1,2,5-oxadiazepane-2-carboxylate (3.44 g) obtained in Step B of Example 7 was added 4M hydrogen chloride ethyl acetate (35 mL) solution, and the mixture was stirred at 0° C. for 2 hr. The solvent was evaporated under reduced pressure, and the residue was washed with ethyl acetate to give the title compound (2.86 g).
MS: [M+H−HCl]+ 288.2.

B) (2-(2,6-dimethylpyrimidin-4-yl)-1,2,5-oxadiazepan-5-yl)(5-methyl-2-(2H-1,2,3-triazol-2-yl)phenyl)methanone hydrochloride To a solution of (5-methyl-2-(2H-1,2,3-triazol-2-yl)phenyl)(1,2,5-oxadiazepan-5-yl)methanone hydrochloride (2.8 g) obtained in Step A of Example 13 in 2-propanol (15 mL) was added 4-chloro-2,6-dimethylpyrimidine (1.36 g), and the mixture was stirred at 80° C. for 1 hr. The precipitate was collected by filtrate, and washed with ethyl acetate to give the title compound (3.27 g).
MS: [M+H−HCl]+ 394.3.

Example 14

(2-(2,6-dimethylpyrimidin-4-yl)-1,2,5-oxadiazepan-5-yl)(5-fluoro-2-(2H-1,2,3-triazol-2-yl)phenyl)methanone

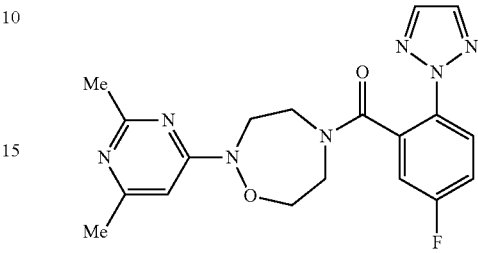

To a solution of 2-(2,6-dimethylpyrimidin-4-yl)-1,2,5-oxadiazepane dihydrobromide (100 mg) obtained in Step D of Example 4 in N,N-dimethylacetamide (1.0 mL) were added 2-(7-azabenzotriazol-1-yl)-1,1,3,3-hexafluorophosphate (HATU) (154 mg), diisopropylethylamine (0.142 mL) and 5-fluoro-2-(2H-1,2,3-triazol-2-yl)benzoic acid (84 mg) obtained in Reference Example 1, and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed successively with water and saturated brine, and dried over magnesium sulfate, and the solvent was evaporated under reduced pressure. The residue was purified by column chromatography (NH, hexane/ethyl acetate) to give the title compound (60 mg).
MS: [M+H]+ 398.1.

The compounds of Examples 15 to 32 were produced using 2-(2,6-dimethylpyrimidin-4-yl)-1,2,5-oxadiazepane dihydrobromide obtained in Step D of Example 4 and the reagents corresponding to the compounds of Examples 15 to 32 (the reagents can be produced according to a method known per se) according to the same method as in Example 14, or a method analogous thereto. MS in the tables means actual measured value.

TABLE 2-1

| Ex. No. | IUPAC Name | Structure |
|---|---|---|
| 15 | (4,5-difluoro-2-(2H-1,2,3-triazol-2-yl)phenyl) (2-(2,6-dimethylpyrimidin-4-yl)-1,2,5-oxadiazepan-5-yl)methanone | 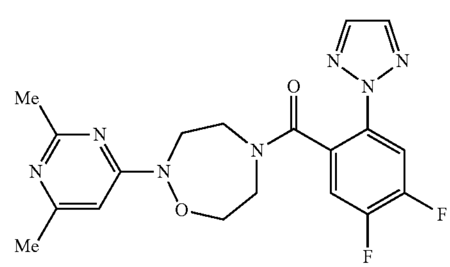 [SMILES: Cc1cc(N2CCN(C(=O)c3cc(F)c(F)cc3-n3nccn3)CCO2)nc(C)n1] |

TABLE 2-1-continued

| | | |
|---|---|---|
| 16 | (2-(2,6-dimethylpyrimidin-4-yl)-1,2,5-oxadiazepan-5-yl) (2-fluoro-6-(2H-1,2,3-triazol-2-yl)phenyl)methanone hydrochloride | |
| 17 | (2-(2,6-dimethylpyrimidin-4-yl)-1,2,5-oxadiazepan-5-yl) (2-(5-fluoro-1,3-thiazol-2-yl)phenyl)methanone | |
| 19 | (2-(2,6-dimethylpyrimidin-4-yl)-1,2,5-oxadiazepan-5-yl) (2-(2-methyl-1,3-thiazol-4-yl)phenyl)methanone | |
| 20 | (2-(2,6-dimethylpyrimidin-4-yl)-1,2,5-oxadiazepan-5-yl) (2-(2H-1,2,3-triazol-2-yl)phenyl)methanone | |
| 21 | (2-cyclobutylphenyl) (2-(2,6-dimethylpyrimidin-4-yl)-1,2,5-oxadiazepan-5-yl)methanone | |
| 22 | (5-chloro-2-cyclobutylphenyl) (2-(2,6-dimethylpyrimidin-4-yl)-1,2,5-oxadiazepan-5-yl)methanone | |

TABLE 2-1-continued
| 23 | (2-(2,6-dimethylpyrimidin-4-yl)-1,2,5-oxadiazepan-5-yl) (2-(2-thienyl)phenyl)methanone hydrochloride | 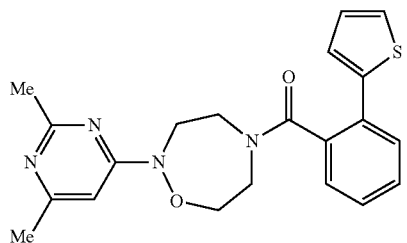 [SMILES: Cc1cc(N2CCN(C(=O)c3ccccc3-c3cccs3)CCO2)nc(C)n1] |
|---|---|---|
| Ex. No. | Additive | MS | Reagent |
|---|---|---|---|
| 15 | Free | 416.1 | 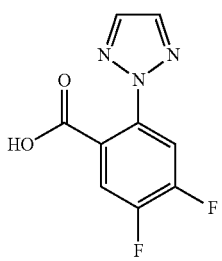 [SMILES: O=C(O)c1cc(F)c(F)cc1-n1nccn1] |
| 16 | Free | 398.2 | 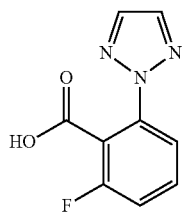 [SMILES: O=C(O)c1c(F)cccc1-n1nccn1] |
| 17 | Free | 414.1 | 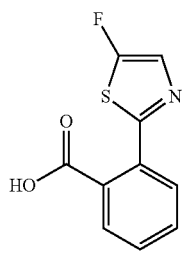 [SMILES: O=C(O)c1ccccc1-c1ncc(F)s1] |
| 19 | Free | 410.1 | 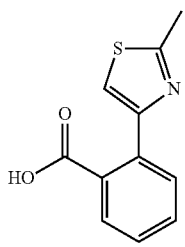 |
| 20 | Free | 380.2 | 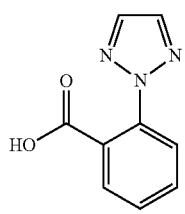 [SMILES: O=C(O)c1ccccc1-n1nccn1] |

TABLE 2-1-continued

| | | | |
|---|---|---|---|
| 21 | Free | 367.2 | 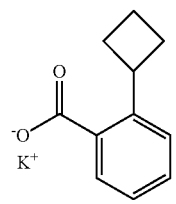 |
| 22 | Free | 401.1 | 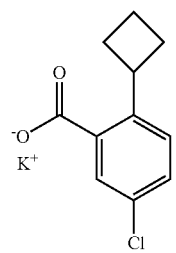 |
| 23 | HCl | 396.1 | 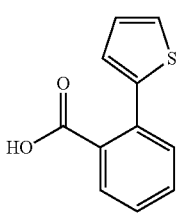 |

TABLE 2-2

| 24 | (2-(2,6-dimethyl-pyrimidin-4-yl)-1,2,5-oxadiazepan-5-yl) (2-(3-methyl-1,2,4-oxadiazol-5-yl)phenyl)methanone | 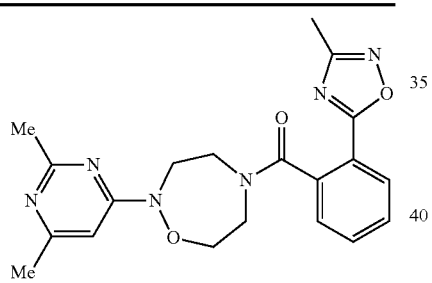 |
|---|---|---|
| 25 | (5-chloro-2-(2H-1,2,3-triazol-2-yl)phenyl) (2-(2,6-dimethyl-pyrimidin-4-yl)-1,2,5-oxadiazepan-5-yl)methanone | 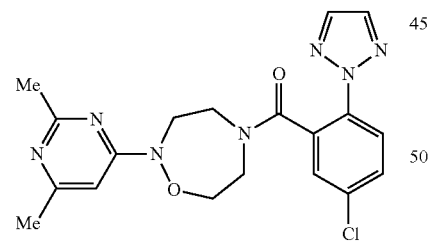 |
| 26 | (5-bromo-2-(2H-1,2,3-triazol-2-yl)phenyl) (2-(2,6-dimethyl-pyrimidin-4-yl)-1,2,5-oxadiazepan-5-yl)methanone | 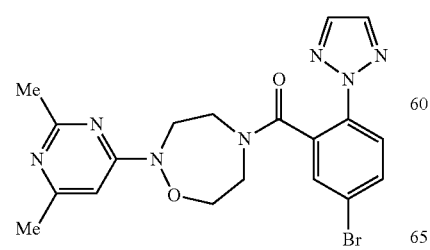 |

TABLE 2-2-continued

| 27 | (2-(2,6-dimethyl-pyrimidin-4-yl)-1,2,5-oxadiazepan-5-yl) (5-fluoro-2-(pyrimidin-2-yl)phenyl)methanone | 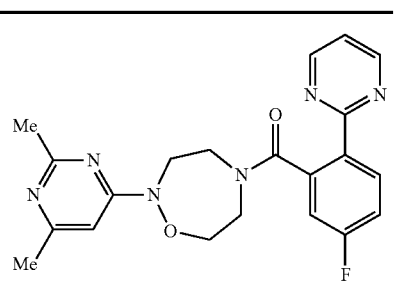 |
|---|---|---|
| 28 | (2-(2,6-dimethyl-pyrimidin-4-yl)-1,2,5-oxadiazepan-5-yl) (5-fluoro-2-(1H-pyrazol-1-yl)phenyl)methanone | 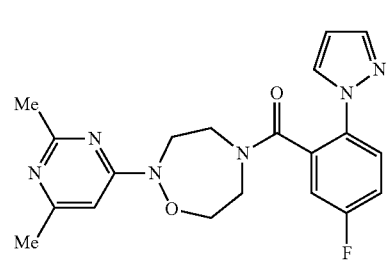 |
| 29 | (2-(2,6-dimethyl-pyrimidin-4-yl)-1,2,5-oxadiazepan-5-yl) (2-(1,3-thiazol-2-yl)phenyl)methanone | 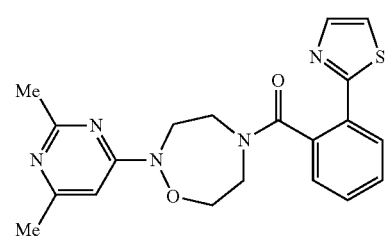 |

TABLE 2-2-continued

| | | | |
|---|---|---|---|
| 30 | (2-(2,6-dimethyl-pyrimidin-4-yl)-1,2,5-oxadiazepan-5-yl) (2-(1H-pyrazol-1-yl)phenyl) methanone | | |
| 31 | (2-(2,6-dimethyl-pyrimidin-4-yl)-1,2,5-oxadiazepan-5-yl) (2-(2H-tetrazol-2-yl)phenyl) methanone | | |
| 32 | (2-(2,6-dimethyl-pyrimidin-4-yl)-1,2,5-oxadiazepan-5-yl) (2-(1,3-thiazol-5-yl)phenyl) methanone | | |
| 24 | Free | 395.1 | |
| 25 | Free | 414.1 | |
| 26 | Free | 458.1 | |
| 27 | Free | 409.1 | |
| 28 | Free | 397.2 | |
| 29 | Free | 396.2 | |
| 30 | Free | 379.1 | |
| 31 | Free | 381.1 | |
| 32 | Free | 396.2 | |

Example 33

(2-(6-methylpyridin-2-yl)-1,2,5-oxadiazepan-5-yl)(5-methyl-2-(2H-1,2,3-triazol-2-yl)phenyl)methanone

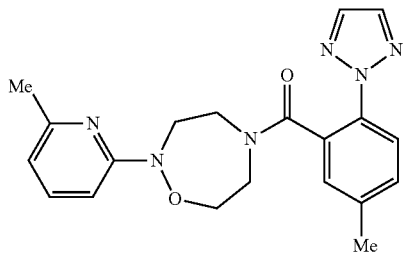 [SMILES: Cc1ccc(-n2nccn2)c(C(=O)N2CCON(c3cccc(C)n3)CC2)c1]

To a solution of (5-methyl-2-(2H-1,2,3-triazol-2-yl)phenyl) (1,2,5-oxadiazepan-5-yl)methanone (29.8 mg) obtained in Step C of Example 7 in toluene (0.70 mL) were added 2-bromo-6-methylpyridine (0.015 mL), sodium tert-butoxide (20.5 mg), 2,2'-bis(diphenylphosphino)-1,1'-binaphthyl (6.6 mg) and tris(dibenzylideneacetone)dipalladium(0) (5.1 mg), and the mixture was stirred overnight at 70° C. To the reaction mixture was added saturated aqueous sodium hydrogencarbonate solution, and the mixture was extracted with ethyl acetate. The obtained organic layer was dried over magnesium sulfate, and the solvent was evaporated under reduced pressure. The residue was purified by column chromatography (hexane/ethyl acetate) to give the title compound (37.8 mg).

MS: [M+H]$^+$ 379.1.

Example 34

(2-(4,6-dimethylpyridin-2-yl)-1,2,5-oxadiazepan-5-yl)(5-methyl-2-(2H-1,2,3-triazol-2-yl)phenyl)methanone

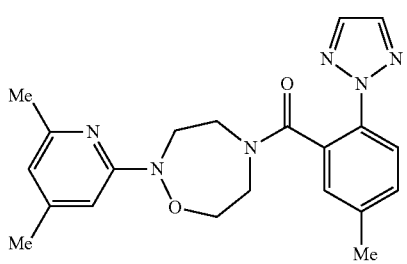

To a solution of (5-methyl-2-(2H-1,2,3-triazol-2-yl)phenyl) (1,2,5-oxadiazepan-5-yl)methanone (29.8 mg) obtained in Step C of Example 7 in toluene (0.70 mL) were added 2-chloro-4,6-dimethylpyridine (21.6 mg), sodium tert-butoxide (21.2 mg), 2,2'-bis(diphenylphosphino)-1,1'-binaphthyl (6.5 mg) and tris(dibenzylideneacetone)dipalladium(0) (4.9 mg), and the mixture was stirred overnight at 70° C. To the reaction mixture was added saturated aqueous sodium hydrogencarbonate solution, and the mixture was extracted with ethyl acetate. The obtained organic layer was dried over magnesium sulfate, and the solvent was evaporated under reduced pressure. The residue was purified by column chromatography (hexane/ethyl acetate) to give the title compound (31.6 mg).

MS: [M+H]$^+$ 393.1.

Example 35

(2-(2,6-dimethylpyridin-4-yl)-1,2,5-oxadiazepan-5-yl)(5-methyl-2-(2H-1,2,3-triazol-2-yl)phenyl)methanone

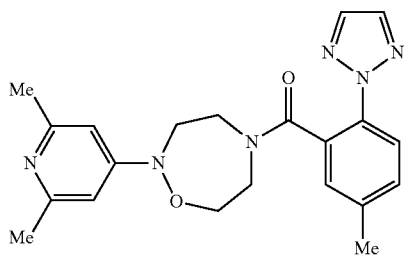 [SMILES: Cc1ccc(-n2nccn2)c(C(=O)N2CCON(c3cc(C)nc(C)c3)CC2)c1]

To a solution of (5-methyl-2-(2H-1,2,3-triazol-2-yl)phenyl) (1,2,5-oxadiazepan-5-yl)methanone (32.4 mg) obtained in Step C of Example 7 in toluene (0.70 mL) were added 4-bromo-2,6-dimethylpyridine (30.6 mg), sodium tert-butoxide (23.0 mg), 2,2'-bis(diphenylphosphino)-1,1'-binaphthyl (9.2 mg) and tris(dibenzylideneacetone)dipalladium(0) (6.6 mg), and the mixture was stirred overnight at 70° C. The reaction mixture was purified by column chromatography (hexane/ethyl acetate) to give the title compound (24.2 mg).

MS: [M+H]$^+$ 393.1.

Example 36

(2-(6-methoxypyridin-2-yl)-1,2,5-oxadiazepan-5-yl)(2-(1,3-thiazol-2-yl)phenyl)methanone

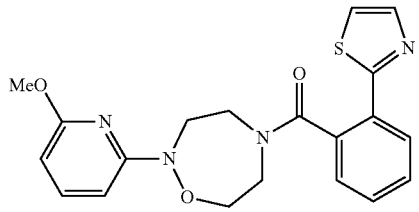 [SMILES: COc1cccc(N2CCN(C(=O)c3ccccc3-c3nccs3)CCO2)n1]

A) tert-butyl 5-(2-(1,3-thiazol-2-yl)benzoyl)-1,2,5-oxadiazepane-2-carboxylate To a solution of 2-(1,3-thiazol-2-yl)benzoic acid (201 mg) obtained in Reference Example 4 in N,N-dimethylformamide (3.0 mL) were added 2-(7-azabenzotriazol-1-yl)-1,1,3,3-hexafluorophosphate (HATU) (418 mg), diisopropylethylamine (0.548 mL) and tert-butyl 1,2,5-oxadiazepane-2-carboxylate (218 mg) obtained in Step A of Example 7, and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, dried over magnesium sulfate, and filtered through silica gel. The solvent was evaporated under reduced pressure to give the title compound (379 mg).

MS: [M+H]$^+$ 390.1.

B) 1,2,5-oxadiazepan-5-yl(2-(1,3-thiazol-2-yl)phenyl)methanone

To tert-butyl 5-(2-(1,3-thiazol-2-yl)benzoyl)-1,2,5-oxadiazepane-2-carboxylate (376 mg) obtained in Step A of Example 36 in acetic acid (5.0 mL) was added conc. hydrochloric acid (1.5 mL), and the mixture was stirred at room temperature for 3 hr. The solvent was evaporated under reduced pressure, to the residue was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure to give the title compound (193 mg).

MS: [M+H]$^+$ 290.0.

C) (2-(6-methoxypyridin-2-yl)-1,2,5-oxadiazepan-5-yl)(2-(1,3-thiazol-2-yl)phenyl)methanone A mixture of 1,2,5-oxadiazepan-5-yl(2-(1,3-thiazol-2-yl)phenyl)methanone (79.1 mg) obtained in Step B of Example 36, toluene (1.0 mL), 2-bromo-6-methoxypyridine (104.5 mg), potassium tert-butoxide (93.9 mg), dicyclohexyl(2',6'-diisopropoxybiphenyl-2-yl)phosphine (13.1 mg) and tris(dibenzylideneacetone)dipalladium(0) (13.2 mg) was stirred in a microwave reactor at 100° C. for 1.5 hr. To the reaction mixture was added saturated aqueous sodium hydrogencarbonate solution, and the mixture was extracted with ethyl acetate. The obtained organic layer was washed successively with water and saturated brine, and dried over anhydrous sodium sulfate, and the solvent was evaporated under reduced pressure. The residue was purified by silica gel column chromatography (hexane/ethyl acetate), and then purified by HPLC (C18, mobile phase: water/acetonitrile (containing 0.1% TFA)). To the obtained fraction was added saturated aqueous sodium hydrogencarbonate solution, and the solvent was evaporated under reduced pressure. The residue was extracted with ethyl acetate, and the obtained organic layer was dried over anhydrous magnesium sulfate, and concentrated under reduced pressure to give the title compound (40.3 mg).

MS: [M+H]$^+$ 397.1.

Example 37

(2-(2-methoxypyridin-4-yl)-1,2,5-oxadiazepan-5-yl)(2-(1,3-thiazol-2-yl)phenyl)methanone

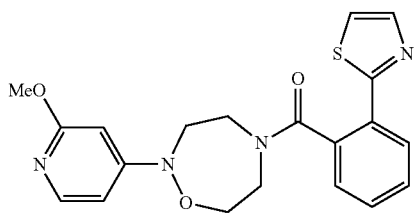 [SMILES: COc1cc(N2CCN(C(=O)c3ccccc3-c3nccs3)CCO2)ccn1]

The title compound (15 mg) was obtained using 1,2,5-oxadiazepan-5-yl(2-(1,3-thiazol-2-yl)phenyl)methanone (112.2 mg) obtained in Step B of Example 36 and 4-bromo-2-methoxypyridine (156.8 mg) in the same manner as in Step C of Example 36.

MS: [M+H]$^+$ 397.1.

Example 38

(5-methyl-2-(2H-1,2,3-triazol-2-yl)phenyl)(2-(quinazolin-2-yl)-1,2,5-oxadiazepan-5-yl)methanone

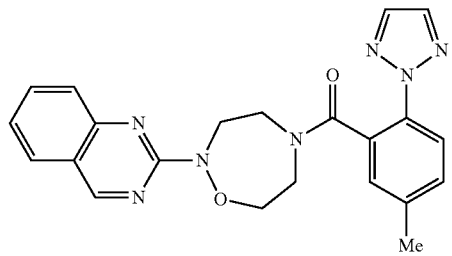 [SMILES: Cc1ccc(-n2nccn2)c(C(=O)N2CCON(c3ncc4ccccc4n3)CC2)c1]

A mixture of (5-methyl-2-(2H-1,2,3-triazol-2-yl)phenyl)(1,2,5-oxadiazepan-5-yl)methanone (50 mg) obtained in Step C of Example 7, 2-chloroquinazoline (34.4 mg), acetic acid (0.010 mL) and ethanol (1.0 mL) was stirred in a microwave reactor at 150° C. for 1 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate). The obtained crude product was purified by HPLC (C18, mobile phase: water/acetonitrile (containing 0.1% TFA)). To the obtained fraction was added saturated aqueous sodium hydrogencarbonate solution, and the solvent was evaporated under reduced pressure. The obtained mixture was extracted with ethyl acetate. The organic layer was dried over anhydrous magnesium sulfate, and concentrated under reduced pressure to give the title compound (15 mg).

MS: [M+H]$^+$ 416.3.

Example 39

(2-(6-chloro-1,3-benzoxazol-2-yl)-1,2,5-oxadiazepan-5-yl)(5-methyl-2-(2H-1,2,3-triazol-2-yl)phenyl)methanone

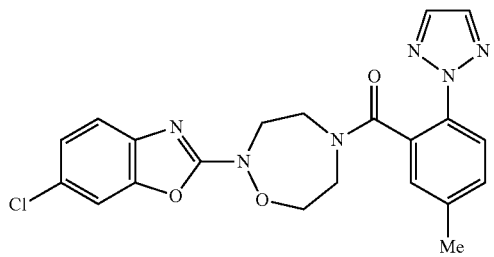 [SMILES: Cc1ccc(-n2nccn2)c(C(=O)N2CCON(c3nc4ccc(Cl)cc4o3)CC2)c1]

To a solution of (5-methyl-2-(2H-1,2,3-triazol-2-yl)phenyl) (1,2,5-oxadiazepan-5-yl)methanone (47.2 mg) obtained in Step C of Example 7 in N,N-dimethylformamide (1.0 mL) were added 2,6-dichloro-1,3-benzoxazole (36.2 mg) and diisopropylethylamine (0.057 mL), and the mixture was stirred overnight at room temperature, and then at 80° C. for 6 hr. To the reaction mixture was added saturated aqueous sodium hydrogencarbonate solution, and the mixture was extracted with ethyl acetate. The obtained organic layer was dried over magnesium sulfate, and the solvent was evaporated under reduced pressure. The residue was purified by column chromatography (hexane/ethyl acetate), and crystallized (hexane/ethyl acetate) to give the title compound (42.1 mg).

MS: [M+H]⁺ 439.1.

Example 40

(4-chlorophenyl)(2-(4,6-dimethylpyrimidin-2-yl)-1,2,5-oxadiazepan-5-yl)methanone

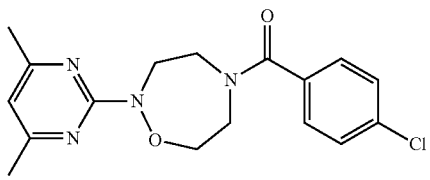 [SMILES: Cc1cc(C)nc(N2CCN(C(=O)c3ccc(Cl)cc3)CCO2)n1]

A) tert-butyl 5-(4-chlorobenzoyl)-1,2,5-oxadiazepane-2-carboxylate

To a solution of tert-butyl 1,2,5-oxadiazepane-2-carboxylate (335 mg) obtained in Step A of Example 7 in tetrahydrofuran (6.0 mL) were added diisopropylethylamine (0.566 mL) and 4-chlorobenzoyl chloride (0.223 mL), and the mixture was stirred at room temperature for 2 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over magnesium sulfate, and the solvent was evaporated under reduced pressure. The residue was purified by column chromatography (hexane/ethyl acetate) to give the title compound (493 mg).

MS: [M+H−Boc]⁺ 241.1.

B) (4-chlorophenyl)(1,2,5-oxadiazepan-5-yl)methanone

To tert-butyl 5-(4-chlorobenzoyl)-1,2,5-oxadiazepane-2-carboxylate (493 mg) obtained in Step A of Example 40 was added 4M hydrogen chloride ethyl acetate (10 mL) solution, and the mixture was stirred at room temperature for 2 hr. The solvent was evaporated under reduced pressure, to the residue was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure to give the title compound (280 mg).

MS: [M+H]⁺ 241.2.

C) (4-chlorophenyl)(2-(4,6-dimethylpyrimidin-2-yl)-1,2,5-oxadiazepan-5-yl)methanone The title compound (48 mg) was obtained using (4-chlorophenyl) (1,2,5-oxadiazepan-5-yl)methanone (50 mg) obtained in Step B of Example 40 and 2-chloro-4,6-dimethylpyrimidine (29.6 mg) in the same manner as in Step E of Example 6.

MS: [M+H]⁺ 347.2.

Example 41

(5-cyclobutyl-2-(2H-1,2,3-triazol-2-yl)phenyl)(2-(2,6-dimethylpyrimidin-4-yl)-1,2,5-oxadiazepan-5-yl)methanone

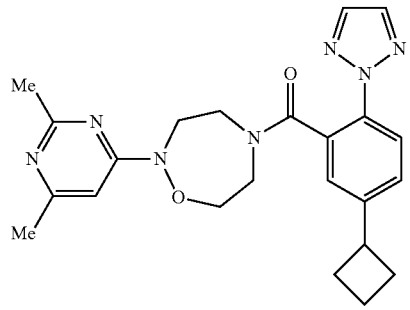 [SMILES: Cc1cc(N2CCN(C(=O)c3cc(C4CCC4)ccc3-n3nccn3)CCO2)nc(C)n1]

A mixture of (5-bromo-2-(2H-1,2,3-triazol-2-yl)phenyl)(2-(2,6-dimethylpyrimidin-4-yl)-1,2,5-oxadiazepan-5-yl)methanone (30 mg) obtained in Example 26, 0.5M cyclobutylzinc bromide in tetrahydrofuran (0.785 mL) solution and (1,1′-bis(diphenylphosphino)ferrocene)dichloropalladium (II) (9.58 mg) was stirred in a microwave reactor at 85° C. for 1 hr. To the reaction mixture was added saturated aqueous sodium hydrogencarbonate solution, and the mixture was extracted with ethyl acetate. The obtained organic layer was dried over anhydrous sodium sulfate, and the solvent was evaporated under reduced pressure. The residue was purified by silica gel column chromatography (ethyl acetate/methanol) to give the title compound (21.6 mg).

MS: [M+H]⁺ 434.2.

Example 42

(2-(2,6-dimethylpyrimidin-4-yl)-1,2,5-oxadiazepan-5-yl)(2-(pyrimidin-2-yl)phenyl)methanone

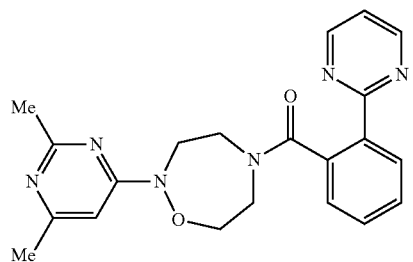 [SMILES: Cc1cc(N2CCN(C(=O)c3ccccc3-c3ncccn3)CCO2)nc(C)n1]

A) (2-(2,6-dimethylpyrimidin-4-yl)-1,2,5-oxadiazepan-5-yl)(2-iodophenyl)methanone The title compound (170 mg) was obtained using 2-(2,6-dimethylpyrimidin-4-yl)-1,2,5-oxadiazepane dihydrobromide (105 mg) obtained in Step D of Example 4 and 2-iodobenzoic acid (106 mg) in the same manner as in Example 14.

MS: [M+H]⁺ 439.0.

B) (2-(2,6-dimethylpyrimidin-4-yl)-1,2,5-oxadiaz-epan-5-yl)(2-(pyrimidin-2-yl)phenyl)methanone To a solution of (2-(2,6-dimethylpyrimidin-4-yl)-1,2,5-oxadiazepan-5-yl)(2-iodophenyl)methanone (124 mg) obtained in Step A of Example 42, 2-(tributylstannyl)pyrimidine (209 mg) and lithium chloride (120 mg) in N,N-dimethylformamide (3.0 mL) was added dichlorobis(triphenylphosphine)palladium(II) (19.86 mg) under argon atmosphere, and the mixture was stirred overnight at 90° C. To the reaction mixture was added aqueous potassium fluoride solution, and the precipitate was removed by filtration. The filtrate was extracted with ethyl acetate, and the obtained organic layer was washed with saturated brine, and dried over anhydrous sodium sulfate, and the solvent was evaporated under reduced pressure. The residue was purified by silica gel column chromatography (ethyl acetate/methanol), and recrystallized (hexane/ethyl acetate) to give the title compound (28.5 mg).

MS: [M+H]$^+$ 391.1.

Example 43

(2-(2,6-dimethylpyrimidin-4-yl)-1,2,5-oxadiazepan-5-yl)(2-(pyridin-2-yl)phenyl)methanone hydrochloride

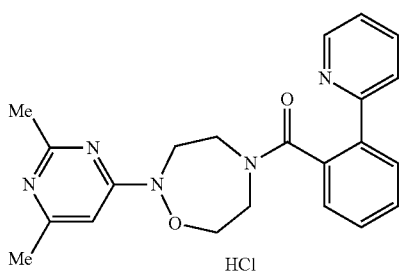 [SMILES: Cc1cc(N2CCN(C(=O)c3ccccc3-c3ccccn3)CCO2)nc(C)n1 ; Cl]

To a solution of (2-(2,6-dimethylpyrimidin-4-yl)-1,2,5-oxadiazepan-5-yl)(2-iodophenyl)methanone (118 mg) obtained in Step A of Example 42, 2-(tributylstannyl)pyridine (198 mg) and lithium chloride (114 mg) in N,N-dimethylformamide (3.0 mL) was added dichlorobis(triphenylphosphine)palladium(II) (18.9 mg) under argon atmosphere, and the mixture was stirred overnight at 90° C. To the reaction mixture was added aqueous potassium fluoride solution, and the precipitate was removed by filtration. The filtrate was extracted with ethyl acetate. The obtained organic layer was washed successively with saturated brine and saturated aqueous sodium hydrogencarbonate solution, and dried over anhydrous sodium sulfate, and the solvent was evaporated under reduced pressure. The residue was purified by silica gel column chromatography (NH, hexane/ethyl acetate). To a solution of the crude product in ethyl acetate (1.0 mL) was added 4M hydrogen chloride ethyl acetate (0.020 mL) solution. The precipitate was collected by filtration to give the title compound (2.2 mg).

MS: [M+H−HCl]$^+$ 390.1.

Example 44

3-((2-(2,6-dimethylpyrimidin-4-yl)-1,2,5-oxadiazepan-5-yl)carbonyl)-4-(2H-1,2,3-triazol-2-yl)benzonitrile

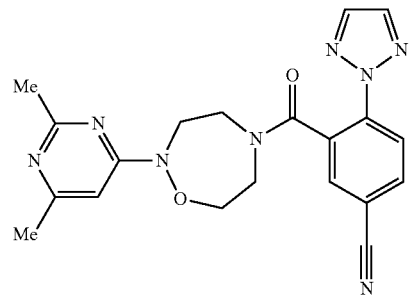 [SMILES: Cc1cc(N2CCN(C(=O)c3cc(C#N)ccc3-n3nccn3)CCO2)nc(C)n1]

To a solution of (5-bromo-2-(2H-1,2,3-triazol-2-yl)phenyl) (2-(2,6-dimethylpyrimidin-4-yl)-1,2,5-oxadiazepan-5-yl)methanone (50 mg) obtained in Example 26 in N,N-dimethylformamide (2.0 mL) were added zinc dicyanide (128 mg), 1,1'-bis(diphenylphosphino)ferrocene (48.4 mg) and tris(dibenzylideneacetone)dipalladium(0) (40 mg) under nitrogen atmosphere, and the mixture was stirred at 120° C. for 2 hr. The reaction mixture was purified by silica gel column chromatography (ethyl acetate/methanol) and then purified by silica gel column chromatography (NH, hexane/ethyl acetate) to give the title compound (4.9 mg).

MS: [M+H]$^+$ 405.1.

Example 45

2-((2-(4,6-dimethylpyrimidin-2-yl)-1,2,5-oxadiazepan-5-yl)carbonyl)benzonitrile

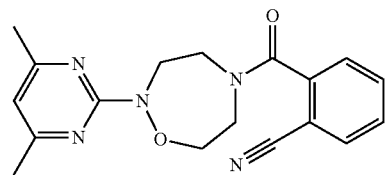 [SMILES: Cc1cc(C)nc(N2CCN(C(=O)c3ccccc3C#N)CCO2)n1]

A) benzyl 2-(4,6-dimethylpyrimidin-2-yl)-1,2,5-oxadiazepane-5-carboxylate

The title compound (1.4 g) was obtained using 5-benzyl 2-tert-butyl 1,2,5-oxadiazepane-2,5-dicarboxylate obtained in Step B of Example 4 and 2-chloro-4,6-dimethylpyrimidine in the same manner as in Step C of Example 4.

MS: [M+H]$^+$ 343.3.

B) 2-(4,6-dimethylpyrimidin-2-yl)-1,2,5-oxadiazepane dihydrobromide

The title compound (1.41 g) was obtained using benzyl 2-(4,6-dimethylpyrimidin-2-yl)-1,2,5-oxadiazepane-5-carboxylate (1.4 g) obtained in Step A of Example 45 in the same manner as in Step D of Example 4.

MS: [M+H−2HBr]$^+$ 209.2.

C) 2-((2-(4,6-dimethylpyrimidin-2-yl)-1,2,5-oxadiazepan-5-yl)carbonyl)benzonitrile To a solution of 2-(4,6-dimethylpyrimidin-2-yl)-1,2,5-oxadiazepane dihydrobromide (22 mg) obtained in Step B of Example 45 in N,N-dimethylacetamide (0.50 mL) were added 2-(7-azabenzotriazol-1-yl)-1,1,3,3-hexafluorophosphate (HATU) (46 mg), diisopropylethylamine (0.031 mL) and 2-cyanobenzoic acid (17.6 mg), and the mixture was stirred overnight at 80° C. The reaction mixture was cooled to 0° C., saturated aqueous sodium hydrogencarbonate solution was added thereto, and the mixture was extracted with ethyl acetate. The obtained organic layer was washed successively with water and saturated brine, and the solvent was evaporated under nitrogen stream. The residue was purified by HPLC (C18, mobile phase: water/acetonitrile (containing 10 mM NH$_4$HCO$_3$)), and the obtained fraction was concentrated under nitrogen stream to give the title compound (6.0 mg).

MS: [M+H]$^+$ 338.2.

The compounds of Examples 46 to 83 were produced using 2-(4,6-dimethylpyrimidin-2-yl)-1,2,5-oxadiazepane dihydrobromide obtained in Step B of Example 45 and the reagents corresponding to the compounds of Examples 46 to 83 (the reagents can be produced according to a method known per se) according to the same method as in Step C of Example 45, or a method analogous thereto. MS in the tables means actual measured value.

TABLE 3-1

| Ex. No. | IUPAC Name | Structure |
|---|---|---|
| 46 | (2-(4,6-dimethylpyrimidin-2-yl)-1,2,5-oxadiazepan-5-yl) (phenyl)methanone | 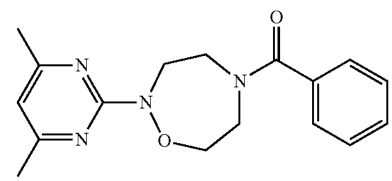 [SMILES: Cc1cc(C)nc(N2CCN(C(=O)c3ccccc3)CCO2)n1] |
| 47 | (2,6-dimethoxyphenyl) (2-(4,6-dimethylpyrimidin-2-yl)-1,2,5-oxadiazepan-5-yl)methanone | 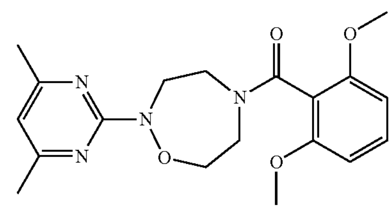 [SMILES: COc1cccc(OC)c1C(=O)N1CCON(c2nc(C)cc(C)n2)CC1] |
| 48 | (2-(4,6-dimethylpyrimidin-2-yl)-1,2,5-oxadiazepan-5-yl) (2-fluoro-6-methoxyphenyl)methanone | 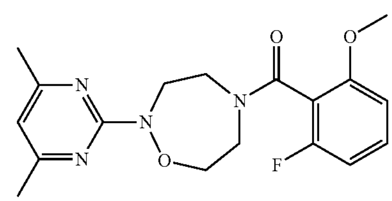 [SMILES: COc1cccc(F)c1C(=O)N1CCON(c2nc(C)cc(C)n2)CC1] |
| 49 | 3-((2-(4,6-dimethylpyrimidin-2-yl)-1,2,5-oxadiazepan-5-yl)carbonyl)benzonitrile | 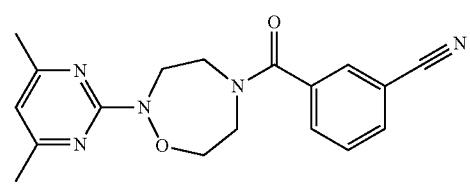 [SMILES: Cc1cc(C)nc(N2CCN(C(=O)c3cccc(C#N)c3)CCO2)n1] |
| 50 | 4-((2-(4,6-dimethylpyrimidin-2-yl)-1,2,5-oxadiazepan-5-yl)carbonyl)benzonitrile | 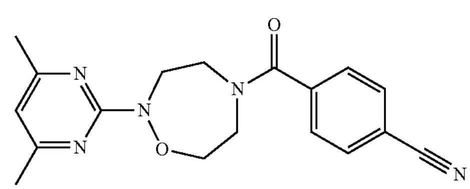 [SMILES: Cc1cc(C)nc(N2CCN(C(=O)c3ccc(C#N)cc3)CCO2)n1] |
| 51 | 2-(4,6-dimethylpyrimidin-2-yl)-1,2,5-oxadiazepan-5-yl) (2-methoxyphenyl)methanone | 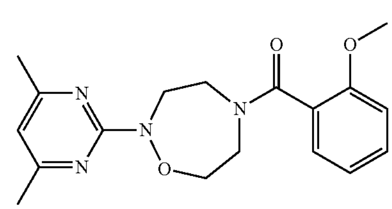 [SMILES: COc1ccccc1C(=O)N1CCON(c2nc(C)cc(C)n2)CC1] |

TABLE 3-1-continued

| Ex. No. | | Structure |
|---|---|---|
| 52 | (2-chloro-5-methoxyphenyl) (2-(4,6-dimethylpyrimidin-2-yl)-1,2,5-oxadiazepan-5-yl)methanone | 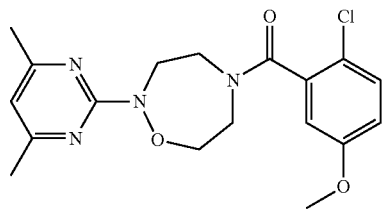 [SMILES: COc1ccc(Cl)c(C(=O)N2CCON(c3nc(C)cc(C)n3)CC2)c1] |
| 53 | (2-chlorophenyl) (2-(4,6-dimethylpyrimidin-2-yl)-1,2,5-oxadiazepan-5-yl)methanone | 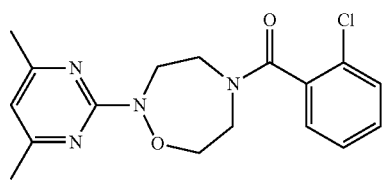 [SMILES: Cc1cc(C)nc(N2CCN(C(=O)c3ccccc3Cl)CCO2)n1] |
| 54 | (2,5-dichlorophenyl) (2-(4,6-dimethylpyrimidin-2-yl)-1,2,5-oxadiazepan-5-yl)methanone | 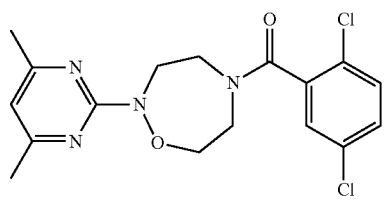 [SMILES: Cc1cc(C)nc(N2CCN(C(=O)c3cc(Cl)ccc3Cl)CCO2)n1] |

| Ex. No. | Additive | MS | Reagent |
|---|---|---|---|
| 46 | Free | 313.2 | benzoic acid |
| 47 | Free | 373.2 | 2,6-dimethoxybenzoic acid |
| 48 | Free | 361.2 | 2-fluoro-6-methoxybenzoic acid |
| 49 | Free | 338.2 | 3-cyanobenzoic acid |
| 50 | Free | 338.2 | 4-cyanobenzoic acid |

TABLE 3-1-continued
| | | | |
|---|---|---|---|
| 51 | Free | 343.2 | 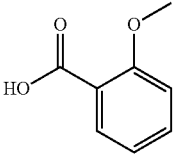 |
| 52 | Free | 377.2 | 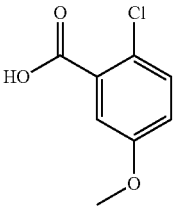 |
| 53 | Free | 347.2 | 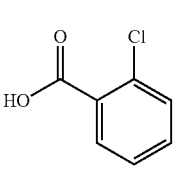 |
| 54 | Free | 381.1 | 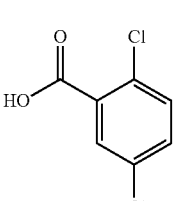 |
TABLE 3-2
| | | |
|---|---|---|
| 55 | (2,3-dichlorophenyl) (2-(4,6-dimethylpyrimidin-2-yl)-1,2,5-oxadiazepan-5-yl)methanone | 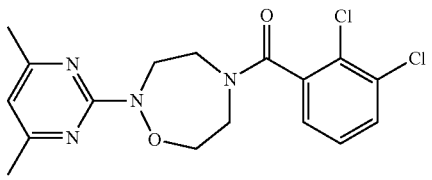 [SMILES: Cc1cc(C)nc(N2CCN(C(=O)c3cccc(Cl)c3Cl)CCO2)n1] |
| 56 | (3,5-dichlorophenyl) (2-(4,6-dimethylpyrimidin-2-yl)-1,2,5-oxadiazepan-5-yl)methanone | 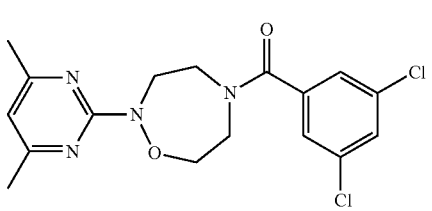 [SMILES: Cc1cc(C)nc(N2CCN(C(=O)c3cc(Cl)cc(Cl)c3)CCO2)n1] |
| 57 | (2-(4,6-dimethylpyrimidin-2-yl)-1,2,5-oxadiazepan-5-yl) (2-methylphenyl)methanone | 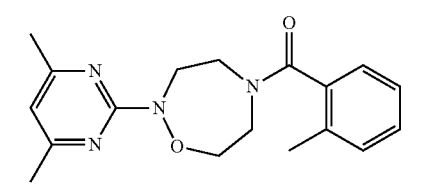 [SMILES: Cc1cc(C)nc(N2CCN(C(=O)c3ccccc3C)CCO2)n1] |
| 58 | (5-chloro-2-methoxyphenyl) (2-(4,6-dimethylpyrimidin-2-yl)-1,2,5-oxadiazepan-5-yl)methanone | 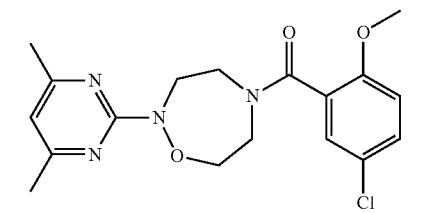 [SMILES: COc1ccc(Cl)cc1C(=O)N1CCON(c2nc(C)cc(C)n2)CC1] |

TABLE 3-2-continued

| | | |
|---|---|---|
| 59 | (2,4-dichlorophenyl) (2-(4,6-dimethylpyrimidin-2-yl)-1,2,5-oxadiazepan-5-yl)methanone | 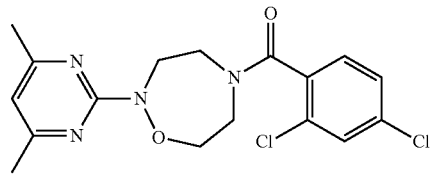 [SMILES: Cc1cc(C)nc(N2CCN(C(=O)c3ccc(Cl)cc3Cl)CCO2)n1] |
| 60 | (2-chloro-3-methoxyphenyl) (2-(4,6-dimethylpyrimidin-2-yl)-1,2,5-oxadiazepan-5-yl)methanone | 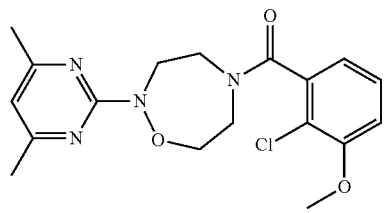 [SMILES: COc1cccc(C(=O)N2CCON(c3nc(C)cc(C)n3)CC2)c1Cl] |
| 61 | (2-(4,6-dimethylpyrimidin-2-yl)-1,2,5-oxadiazepan-5-yl) (2-ethoxyphenyl)methanone | 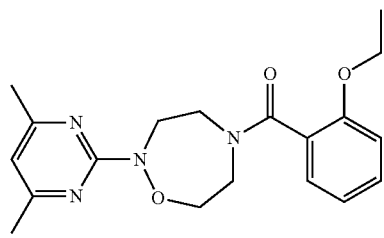 [SMILES: CCOc1ccccc1C(=O)N1CCON(c2nc(C)cc(C)n2)CC1] |
| 62 | (2-(4,6-dimethylpyrimidin-2-yl)-1,2,5-oxadiazepan-5-yl) (2-trifluoromethyl)phenyl)methanone | 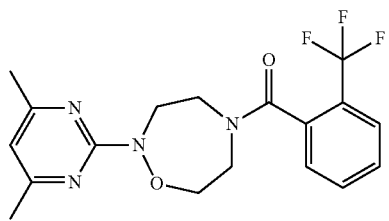 [SMILES: Cc1cc(C)nc(N2CCN(C(=O)c3ccccc3C(F)(F)F)CCO2)n1] |
| 63 | 3-((2-(4,6-dimethylpyrimidin-2-yl)-1,2,5-oxadiazepan-5-yl)carbonyl)-2-methoxybenzonitrile | 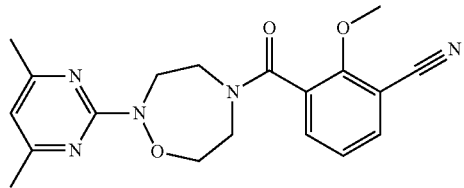 [SMILES: COc1c(C#N)cccc1C(=O)N1CCON(c2nc(C)cc(C)n2)CC1] |
| 55 | Free | 381.1 | 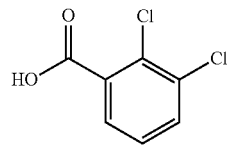 [SMILES: O=C(O)c1cccc(Cl)c1Cl] |
| 56 | Free | 381.1 | 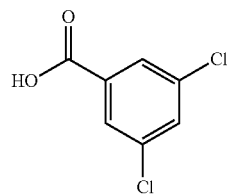 [SMILES: O=C(O)c1cc(Cl)cc(Cl)c1] |
| 57 | Free | 327.2 | 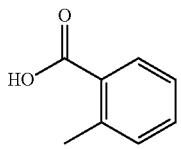 |

TABLE 3-2-continued
| 58 | Free | 377.2 | 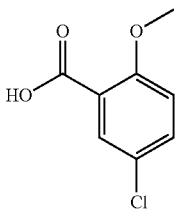 |
| 59 | Free | 381.1 | 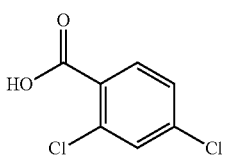 [SMILES: O=C(O)c1ccc(Cl)cc1Cl] |
| 60 | Free | 377.2 | 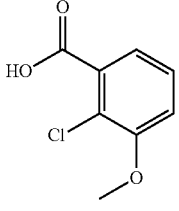 |
| 61 | Free | 357.2 | 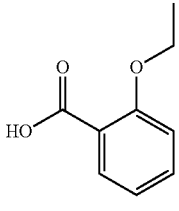 |
| 62 | Free | 381.2 | 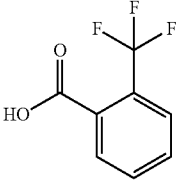 [SMILES: O=C(O)c1ccccc1C(F)(F)F] |
| 63 | Free | 368.1 | 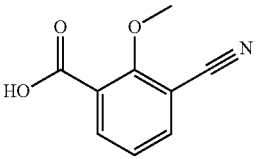 |
TABLE 3-3
| 64 | (2-(4,6-dimethylpyrimidin-2-yl)-1,2,5-oxadiazepan-5-yl) (1-naphthyl)methanone | 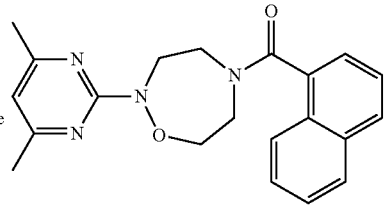 |
| 65 | (2-(4,6-dimethylpyrimidin-2-yl)-1,2,5-oxadiazepan-5-yl) (quinolin-5-yl)methanone | 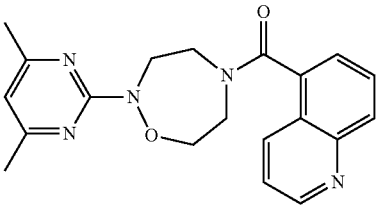 [SMILES: Cc1cc(C)nc(N2CCN(C(=O)c3cccc4ncccc34)CCO2)n1] |

TABLE 3-3-continued

| | | |
|---|---|---|
| 66 | (2-(4,6-dimethylpyrimidin-2-yl)-1,2,5-oxadiazepan-5-yl)(quinolin-8-yl)methanone | 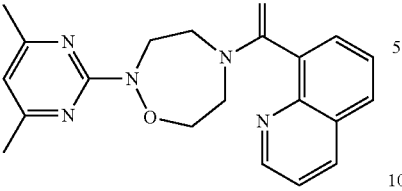 |
| 67 | (2-(4,6-dimethylpyrimidin-2-yl)-1,2,5-oxadiazepan-5-yl)(quinoxalin-5-yl)methanone | 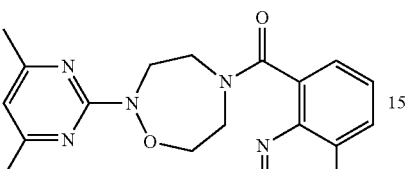 |
| 68 | (2-(4,6-dimethylpyrimidin-2-yl)-1,2,5-oxadiazepan-5-yl)(3-methylquinoxalin-5-yl)methanone | 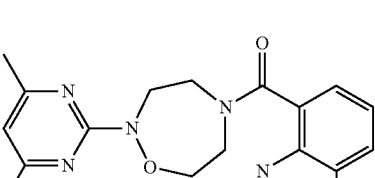 |
| 69 | (2-(4,6-dimethylpyrimidin-2-yl)-1,2,5-oxadiazepan-5-yl)(2-methyl-2H-indazol-4-yl)methanone | 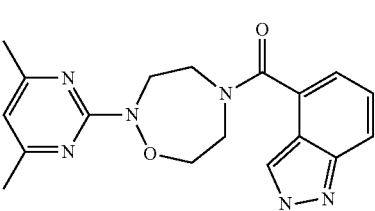 |
| 70 | (2-(4,6-dimethylpyrimidin-2-yl)-1,2,5-oxadiazepan-5-yl)(2-methyl-1,3-benzoxazol-7-yl)methanone | 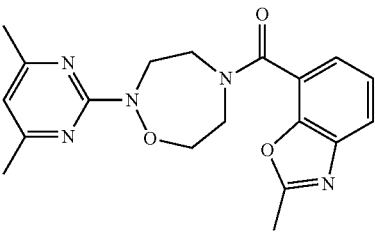 [SMILES: Cc1cc(C)nc(N2CCN(C(=O)c3cccc4nc(C)oc34)CCO2)n1] |
| 71 | (2-(4,6-dimethylpyrimidin-2-yl)-1,2,5-oxadiazepan-5-yl)(1-methyl-1H-indol-7-yl)methanone | 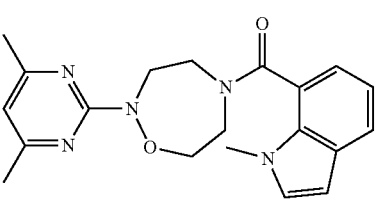 [SMILES: Cc1cc(C)nc(N2CCN(C(=O)c3cccc4ccn(C)c34)CCO2)n1] |
| 72 | (2-(4,6-dimethylpyrimidin-2-yl)-1,2,5-oxadiazepan-5-yl)(1-methyl-1H-indol-4-yl)methanone | 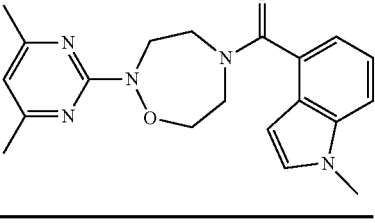 |

TABLE 3-3-continued

| | | | |
|---|---|---|---|
| 64 | Free | 363.2 | 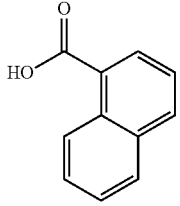 [SMILES: O=C(O)c1cccc2ccccc12] |
| 65 | Free | 364.2 | 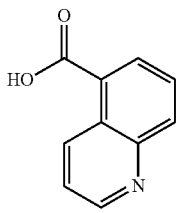 [SMILES: O=C(O)c1cccc2ncccc12] |
| 66 | Free | 364.2 | 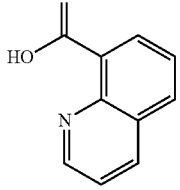 |
| 67 | Free | 366.1 | 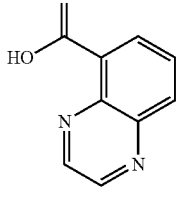 |
| 68 | Free | 379.2 | 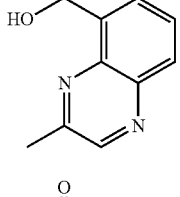 |
| 69 | Free | 367.1 | 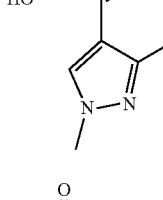 |
| 70 | Free | 368.1 | 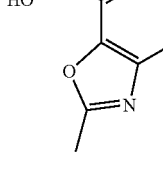 |

TABLE 3-3-continued

| 71 | Free | 366.1 | 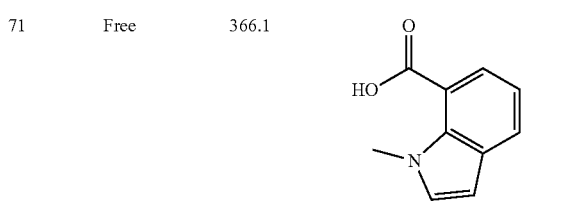 |

TABLE 3-3-continued

| 72 | Free | 366.1 | 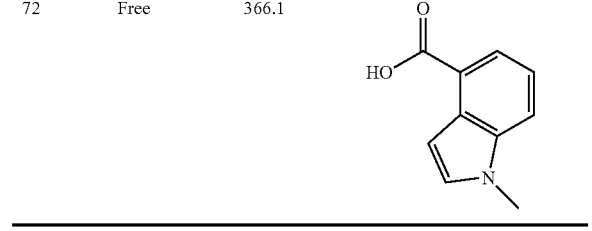 |

TABLE 3-4

| 73 | 2,1,3-benzothiadiazol-4-yl (2-(4,6-dimethylpyrimidin-2-yl)-1,2,5-oxadiazepan-5-yl)methanone | |
| 74 | 2,3-dihydro-1-benzofuran-7-yl (2-(4,6-dimethylpyrimidin-2-yl)-1,2,5-oxadiazepan-5-yl)methanone | |
| 75 | (2,2-dimethyl-2,3-dihydro-1-benzofuran-7-yl) (2-(4,6-dimethylpyrimidin-2-yl)-1,2,5-oxadiazepan-5-yl)methanone | |
| 76 | 7-((2-(4,6-dimethylpyrimidin-2-yl)-1,2,5-oxadiazepan-5-yl)carbonyl)-2-methylisoindolin-1-one | |
| 77 | (2-(4,6-dimethylpyrimidin-2-yl)-1,2,5-oxadiazepan-5-yl) (6-methoxy-2,3-dihydro-1H-inden-5-yl)methanone | |
| 78 | biphenyl-3-yl (2-(4,6-dimethylpyrimidin-2-yl)-1,2,5-oxadiazepan-5-yl)methanone | |

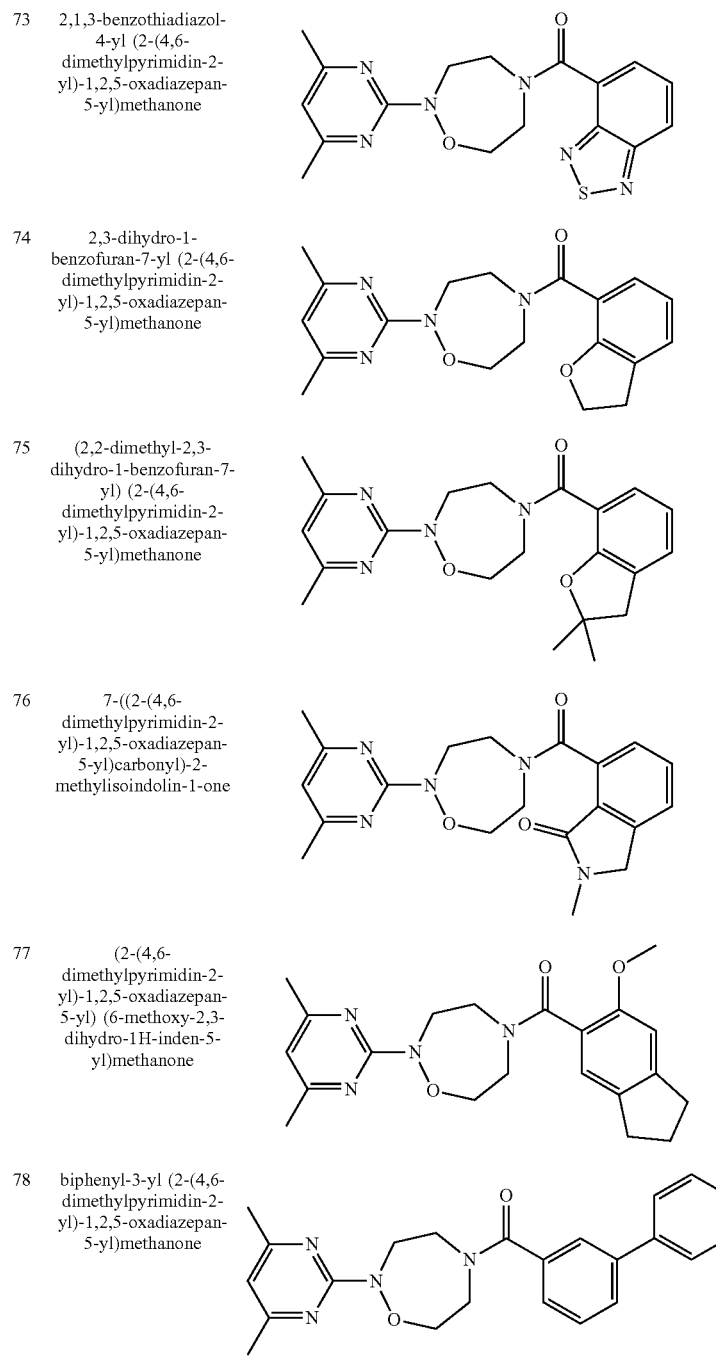

TABLE 3-4-continued
| | | |
|---|---|---|
| 79 | biphenyl-2-yl (2-(4,6-dimethylpyrimidin-2-yl)-1,2,5-oxadiazepan-5-yl)methanone | 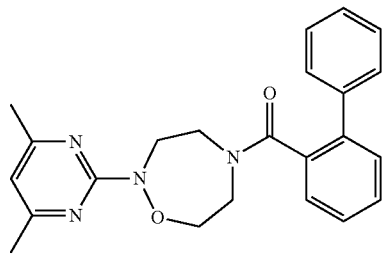 [SMILES: Cc1cc(C)nc(N2CCN(C(=O)c3ccccc3-c3ccccc3)CCO2)n1] |
| 80 | (2-(4,6-dimethylpyrimidin-2-yl)-1,2,5-oxadiazepan-5-yl) (2-(1H-pyrrol-1-yl)phenyl)methanone | 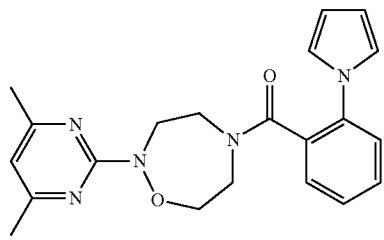 [SMILES: Cc1cc(C)nc(N2CCN(C(=O)c3ccccc3-n3cccc3)CCO2)n1] |
| 81 | (2-(4,6-dimethylpyrimidin-2-yl)-1,2,5-oxadiazepan-5-yl) (2-(2-furyl)phenyl)methanone | 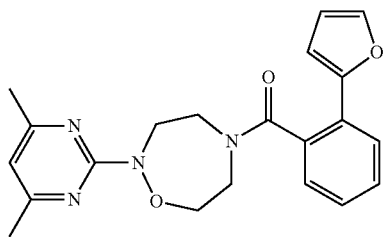 [SMILES: Cc1cc(C)nc(N2CCN(C(=O)c3ccccc3-c3ccco3)CCO2)n1] |
| 73 | Free | 371.1 | 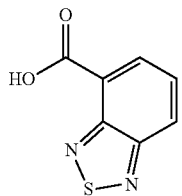 [SMILES: O=C(O)c1cccc2nsnc12] |
| 74 | Free | 366.2 | 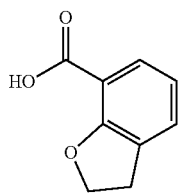 [SMILES: O=C(O)c1cccc2c1OCC2] |
| 75 | Free | 393.2 | 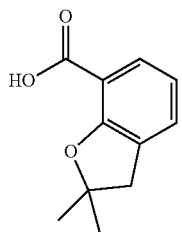 |
| 76 | Free | 382.2 |  |

TABLE 3-4-continued
| | | | |
|---|---|---|---|
| 77 | Free | 383.2 | 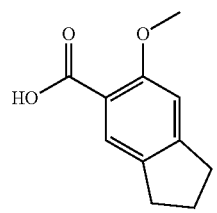 |
| 78 | Free | 389.2 | 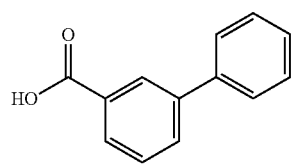 [SMILES: O=C(O)c1cccc(-c2ccccc2)c1] |
| 79 | Free | 389.2 | 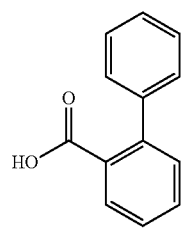 [SMILES: O=C(O)c1ccccc1-c1ccccc1] |
| 80 | Free | 378.2 | 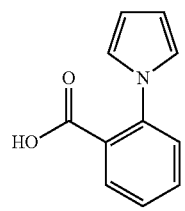 [SMILES: O=C(O)c1ccccc1-n1cccc1] |
| 81 | Free | 379.3 | 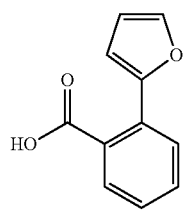 |
TABLE 3-5
| | | |
|---|---|---|
| 82 | (2-(4,6-dimethylpyrimidin-2-yl)-1,2,5-oxadiazepan-5-yl) (2-(1H-imidazol-2-yl)phenyl)methanone | 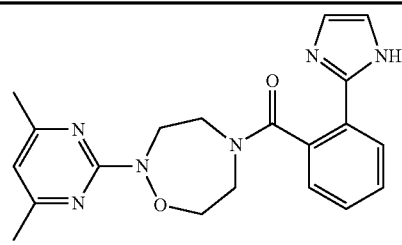 |

TABLE 3-5-continued

| | | | |
|---|---|---|---|
| 83 | 3-((2-(4,6-dimethylpyrimidin-2-yl)-1,2,5-oxadiazepan-5-yl)carbonyl)-4-methylbenzonitrile | | 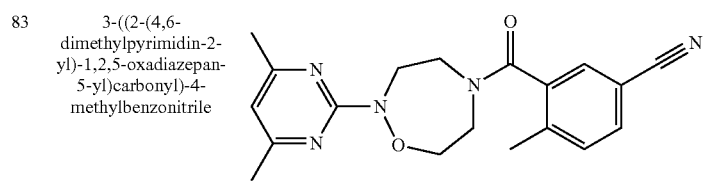 |
| 82 | Free | 379.3 | 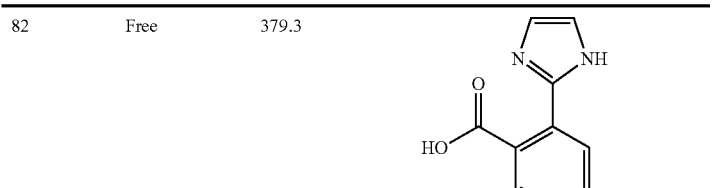 |
| 83 | Free | 362.2 | 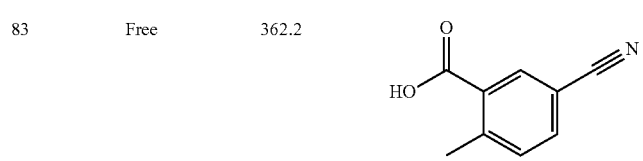 |

Example 84

((7S)-2-(2,6-dimethylpyrimidin-4-yl)-7-methyl-1,2,5-oxadiazepan-5-yl)(2-(1,3-thiazol-2-yl)phenyl)methanone

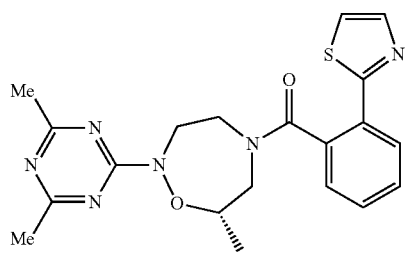 [SMILES: Cc1nc(C)nc(N2CCN(C(=O)c3ccccc3-c3nccs3)C[C@H](C)O2)n1]

A) benzyl (7S)-7-methyl-5-(2-(1,3-thiazol-2-yl)benzoyl)-1,2,5-oxadiazepane-2-carboxylate To 2-benzyl 5-tert-butyl (7S)-7-methyl-1,2,5-oxadiazepane-2,5-dicarboxylate (145 mg) obtained in Step E of Example 1 was added 4M hydrogen chloride ethyl acetate (4.0 mL) solution, and the mixture was stirred at room temperature for 2 hr. The solvent was evaporated under reduced pressure to give benzyl (7S)-7-methyl-1,2,5-oxadiazepane-2-carboxylate hydrochloride. To a solution of benzyl (7S)-7-methyl-1,2,5-oxadiazepane-2-carboxylate hydrochloride in N,N-dimethylacetamide (1.0 mL) were added 2-(7-azabenzotriazol-1-yl)-1,1,3,3-hexafluorophosphate (HATU) (236 mg), diisopropylethylamine (0.217 mL) and 2-(1,3-thiazol-2-yl)benzoic acid (85 mg) obtained in Reference Example 4, and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed successively with water and saturated brine, and dried over magnesium sulfate, and the solvent was evaporated under reduced pressure. The residue was purified by column chromatography (hexane/ethyl acetate) to give the title compound (56 mg).
MS: [M+H]$^+$ 438.1.

B) ((7S)-2-(2,6-dimethylpyrimidin-4-yl)-7-methyl-1,2,5-oxadiazepan-5-yl)(2-(1,3-thiazol-2-yl)phenyl)methanone The title compound (42 mg) was obtained using benzyl (7S)-7-methyl-5-(2-(1,3-thiazol-2-yl)benzoyl)-1,2,5-oxadiazepane-2-carboxylate (56 mg) obtained in Step A of Example 84 and 4-chloro-2,6-dimethylpyrimidine (27.4 mg) in the same manner as in Step F of Example 5.
MS: [M+H]$^+$ 410.2.

Example 85

((7S)-7-methyl-2-(2-methyl-6-(trifluoromethyl)pyrimidin-4-yl)-1,2,5-oxadiazepan-5-yl)(2-(1,3-thiazol-2-yl)phenyl)methanone

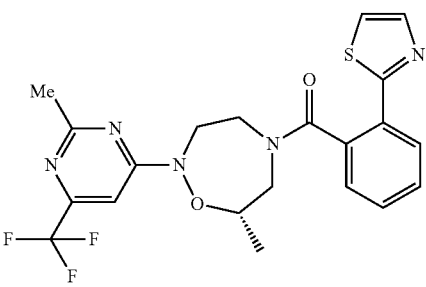 [SMILES: Cc1nc(N2CCN(C(=O)c3ccccc3-c3nccs3)C[C@H](C)O2)cc(C(F)(F)F)n1]

To benzyl (7S)-7-methyl-5-(2-(1,3-thiazol-2-yl)benzoyl)-1,2,5-oxadiazepane-2-carboxylate (88 mg) obtained in Step A of Example 84 was added 5.1M hydrogen bromide acetic acid solution (2.0 mL), and the mixture was stirred at room temperature for 1 hr. The solvent was evaporated under reduced pressure, and a mixture of the residue, ethanol (2.0 mL), acetic acid (0.012 mL) and 4-chloro-2-methyl-6-trifluoromethylpyrimidine (43.5 mg) was stirred in a microwave reactor at 150° C. for 0.5 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (hexane/diisopropyl ether) to give the title compound (45 mg).

MS: [M+H]$^+$ 464.0.

Example 86

((7S)-2-(2,6-dimethylpyrimidin-4-yl)-7-methyl-1,2,5-oxadiazepan-5-yl)(2-(1,3-thiazol-2-yl)phenyl)methanone hydrochloride

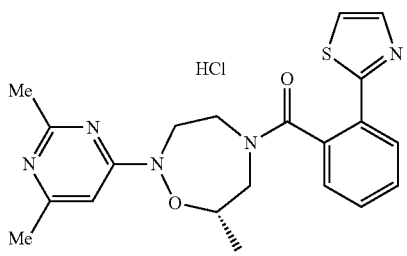 [SMILES: Cc1cc(N2CCN(C(=O)c3ccccc3-c3nccs3)C[C@H](C)O2)nc(C)n1 ; Cl]

To a solution of ((7S)-2-(2,6-dimethylpyrimidin-4-yl)-7-methyl-1,2,5-oxadiazepan-5-yl)(2-(1,3-thiazol-2-yl)phenyl)methanone (1.49 g) obtained in Step B of Example 84 in ethanol (15 mL) was added 4M hydrogen chloride ethyl acetate (2.0 mL) solution, and the mixture was stirred at room temperature for 1 hr. The solvent was evaporated under reduced pressure, and the residue was crystallized (ethyl acetate/ethanol) to give the title compound (1540 mg).

MS: [M+H–HCl]$^+$ 410.1.

Example 87

((7S)-2-(2,6-dimethylpyrimidin-4-yl)-7-methyl-1,2,5-oxadiazepan-5-yl)(5-fluoro-2-(1,3-thiazol-2-yl)phenyl)methanone hydrochloride

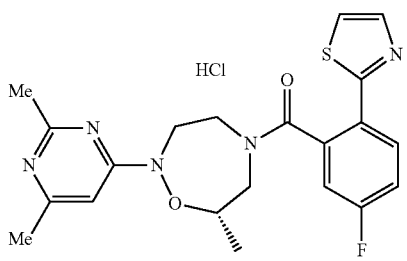 [SMILES: Cc1cc(N2CCN(C(=O)c3cc(F)ccc3-c3nccs3)C[C@H](C)O2)nc(C)n1 ; Cl]

A) benzyl (7S)-7-methyl-1,2,5-oxadiazepane-2-carboxylate

To benzyl (2-bromoethyl)(((2S)-1-((tert-butoxycarbonyl)amino)propan-2-yl)oxy)carbamate (14.68 g) obtained in Step D of Example 1 was added trifluoroacetic acid (50 mL), and the mixture was stirred at room temperature for 1 hr. The solvent was evaporated under reduced pressure, to a solution of the residue in N,N-dimethylformamide (200 mL) was added potassium carbonate (23.52 g) at 0° C., and the mixture was stirred overnight at room temperature. To the reaction mixture was added saturated aqueous sodium hydrogencarbonate solution, and the mixture was extracted with ethyl acetate and tetrahydrofuran. The obtained organic layer was washed with saturated brine, and dried over anhydrous magnesium sulfate, and the solvent was evaporated under reduced pressure. The residue was purified by silica gel column chromatography (NH, hexane/ethyl acetate) to give the title compound (4.19 g).

MS: [M+H]$^+$ 251.1.

B) benzyl (7S)-5-(5-fluoro-2-(1,3-thiazol-2-yl)benzoyl)-7-methyl-1,2,5-oxadiazepane-2-carboxylate The title compound (64.6 mg) was obtained using benzyl (7S)-7-methyl-1,2,5-oxadiazepane-2-carboxylate (102.5 mg) obtained in Step A of Example 87, 5-fluoro-2-(1,3-thiazol-2-yl)benzoic acid (107.6 mg) obtained in Reference Example 18 and oxalyl chloride (0.054 mL) in the same manner as in Step E of Example 5.

MS: [M+H]$^+$ 456.1.

C) ((7S)-2-(2,6-dimethylpyrimidin-4-yl)-7-methyl-1,2,5-oxadiazepan-5-yl)(5-fluoro-2-(1,3-thiazol-2-yl)phenyl)methanone hydrochloride The title compound (64.6 mg) was obtained using benzyl (7S)-5-(5-fluoro-2-(1,3-thiazol-2-yl)benzoyl)-7-methyl-1,2,5-oxadiazepane-2-carboxylate (108 mg) obtained in Step B of Example 87 and 4-chloro-2,6-dimethylpyrimidine (39.4 mg) in the same manner as in Step F of Example 5 and Example 86.

MS: [M+H–HCl]$^+$ 428.1.

Example 88

(5-chloro-2-(1,3-thiazol-2-yl)phenyl)((7S)-2-(2,6-dimethylpyrimidin-4-yl)-7-methyl-1,2,5-oxadiazepan-5-yl)methanone hydrochloride

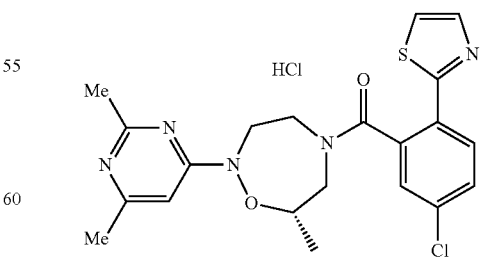

The title compound (86.6 mg) was obtained using 5-chloro-2-(1,3-thiazol-2-yl)benzoic acid obtained in Reference Example 19 in the same manner as in Example 87.

MS: [M+H–HCl]$^+$ 444.1.

Example 89

((7S)-7-methyl-2-(6-methylpyridin-2-yl)-1,2,5-oxadiazepan-5-yl) (2-(1,3-thiazol-2-yl)phenyl)methanone

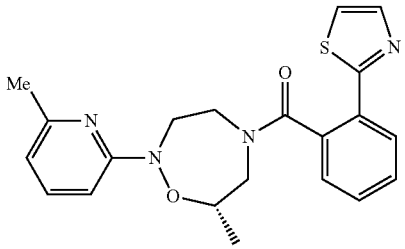 [SMILES: Cc1cccc(N2CCN(C(=O)c3ccccc3-c3nccs3)C[C@H](C)O2)n1]

A) ((7S)-7-methyl-1,2,5-oxadiazepan-5-yl)(2-(1,3-thiazol-2-yl)phenyl)methanone To benzyl (7S)-7-methyl-5-(2-(1,3-thiazol-2-yl)benzoyl)-1,2,5-oxadiazepane-2-carboxylate (785 mg) obtained in Step A of Example 84 was added 5.1M hydrogen bromide acetic acid solution (4.0 mL), and the mixture was stirred at room temperature for 2 hr. The solvent was evaporated under reduced pressure, to the residue was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (230.3 mg).
MS: [M+H]$^+$ 304.1.

B) ((7S)-7-methyl-2-(6-methylpyridin-2-yl)-1,2,5-oxadiazepan-5-yl)(2-(1,3-thiazol-2-yl)phenyl)methanone The title compound (38 mg) was obtained using ((7S)-7-methyl-1,2,5-oxadiazepan-5-yl)(2-(1,3-thiazol-2-yl)phenyl)methanone (52.4 mg) obtained in Step A of Example 89 and 2-bromo-6-methylpyridine (43.4 mg) in the same manner as in Example 33.
MS: [M+H]$^+$ 395.1.

Example 90

((7S)-2-(5-chloropyridin-2-yl)-7-methyl-1,2,5-oxadiazepan-5-yl)(2-(1,3-thiazol-2-yl)phenyl)methanone

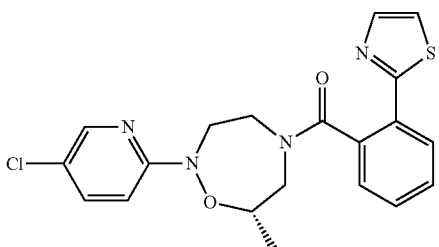

The title compound (46 mg) was obtained using 2-bromo-5-chloropyridine in the same manner as in Example 89.
MS: [M+H]$^+$ 415.0.

Example 91

((7S)-2-(4,6-dimethylpyridin-2-yl)-7-methyl-1,2,5-oxadiazepan-5-yl)(2-(1,3-thiazol-2-yl)phenyl)methanone

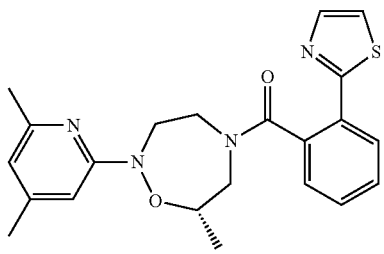 [SMILES: Cc1cc(C)nc(N2CCN(C(=O)c3ccccc3-c3nccs3)C[C@H](C)O2)c1]

The title compound (47 mg) was obtained using 2-chloro-4,6-dimethylpyridine in the same manner as in Example 89.
MS: [M+H]$^+$ 409.1.

Example 92

((7S)-7-methyl-2-(2-methyl-6-(trifluoromethyl)pyrimidin-4-yl)-1,2,5-oxadiazepan-5-yl)(2-(2H-1,2,3-triazol-2-yl)phenyl)methanone

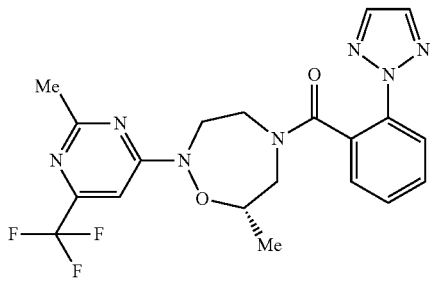 [SMILES: Cc1nc(N2CCN(C(=O)c3ccccc3-n3nccn3)C[C@H](C)O2)cc(C(F)(F)F)n1]

A) ((7S)-7-methyl-1,2,5-oxadiazepan-5-yl)(2-(2H-1,2,3-triazol-2-yl)phenyl)methanone hydrobromide To benzyl (7S)-7-methyl-5-(2-(2H-1,2,3-triazol-2-yl)benzoyl)-1,2,5-oxadiazepane-2-carboxylate (735 mg) obtained in Step A of Example 2 was added 5.1M hydrogen bromide acetic acid solution (5.0 mL), and the mixture was stirred at room temperature for 1 hr. The solvent was evaporated under reduced pressure to give the title compound (640 mg).
MS: [M+H−HBr]$^+$ 288.2.

B) ((7S)-7-methyl-2-(2-methyl-6-(trifluoromethyl)pyrimidin-4-yl)-1,2,5-oxadiazepan-5-yl)(2-(2H-1,2,3-triazol-2-yl)phenyl)methanone A mixture of ((7S)-7-methyl-1,2,5-oxadiazepan-5-yl)(2-(2H-1,2,3-triazol-2-yl)phenyl)methanone hydrobromide (100 mg) obtained in Step A of Example 92, 4-chloro-2-methyl-6-trifluoromethylpyrimidine (53.4 mg) and 2-propanol (2.0 mL) was stirred in a microwave reactor at 150° C.

for 1 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate), and crystallized (hexane/diisopropyl ether) to give the title compound (38 mg).

MS: [M+H]$^+$ 448.1.

The compounds of Examples 93 to 97 were produced using ((7S)-7-methyl-1,2,5-oxadiazepan-5-yl)(2-(2H-1,2,3-triazol-2-yl)phenyl)methanone hydrobromide obtained in Step A of Example 92 and the reagents corresponding to the compounds of Examples 93 to 97 (the reagents can be produced according to a method known per se) according to the same method as in Step B of Example 92, or a method analogous thereto. MS in the tables means actual measured value.

TABLE 4

| Ex. No. | IUPAC Name | Structure |
|---|---|---|
| 93 | ((7S)-2-(6-(difluoromethyl)-2-methylpyrimidin-4-yl)-7-methyl-1,2,5-oxadiazepan-5-yl) (2-(2H-1,2,3-triazol-2-yl)phenyl)methanone | 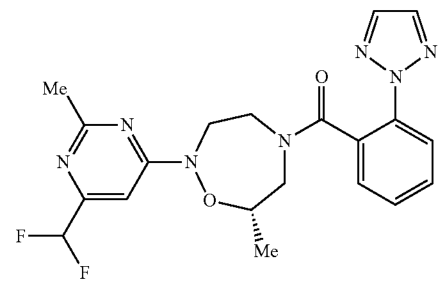 [SMILES: Cc1nc(C(F)F)cc(N2CCN(C(=O)c3ccccc3-n3nccn3)C[C@H](C)O2)n1] |
| 94 | ((7S)-7-methyl-2-(6-methyl-2-(trifluoromethyl)pyrimidin-4-yl)-1,2,5-oxadiazepan-5-yl) (2-(2H-1,2,3-triazol-2-yl)phenyl)methanone | 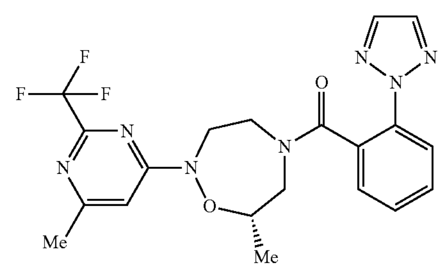 [SMILES: Cc1cc(N2CCN(C(=O)c3ccccc3-n3nccn3)C[C@H](C)O2)nc(C(F)(F)F)n1] |
| 95 | ((7S)-2-(2-cyclopropyl-6-(difluoromethyl)pyrimidin-4-yl)-7-methyl-1,2,5-oxadiazepan-5-yl) (2-(2H-1,2,3-triazol-2-yl)phenyl)methanone | 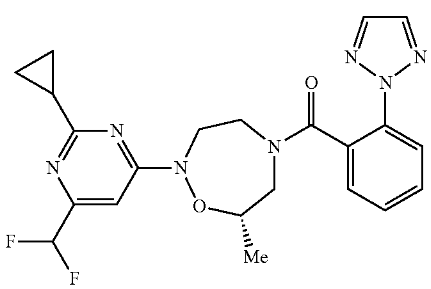 [SMILES: C[C@H]1CN(C(=O)c2ccccc2-n2nccn2)CCN(c2cc(C(F)F)nc(C3CC3)n2)O1] |
| 96 | ((7S)-2-(2,6-dicyclopropylpyrimidin-4-yl)-7-methyl-1,2,5-oxadiazepan-5-yl) (2-(2H-1,2,3-triazol-2-yl)phenyl)methanone | 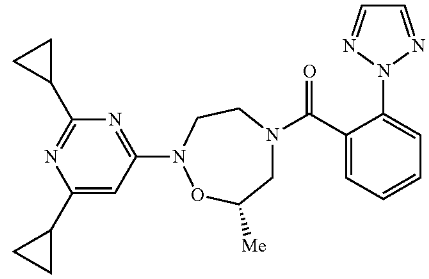 [SMILES: C[C@H]1CN(C(=O)c2ccccc2-n2nccn2)CCN(c2cc(C3CC3)nc(C3CC3)n2)O1] |

TABLE 4-continued
| 97 | ((7S)-2-(2-cyclopropyl-6-(trifluoromethyl)pyrimidin-4-yl)-7-methyl-1,2,5-oxadiazepan-5-yl) (2-(2H-1,2,3-triazol-2-yl)phenyl)methanone | 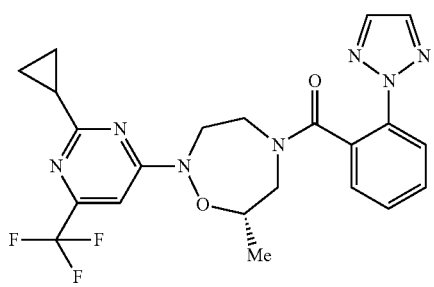 [SMILES: C[C@H]1CN(C(=O)c2ccccc2-n2nccn2)CCN(c2cc(C(F)(F)F)nc(C3CC3)n2)O1] |
| Ex. No. | Additive | MS | Reagent |
|---|---|---|---|
| 93 | Free | 430.1 | 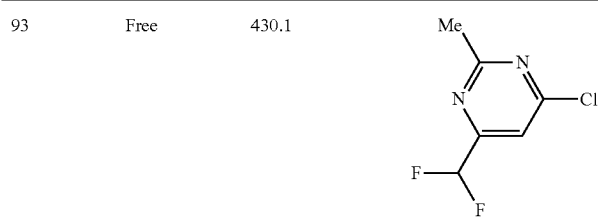 |
| 94 | Free | 448.1 | 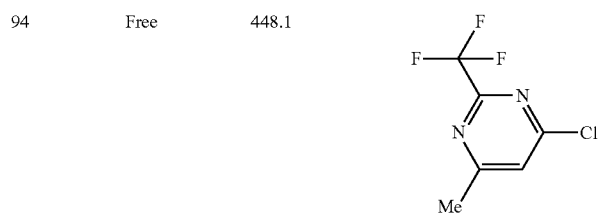 |
| 95 | Free | 456.1 | 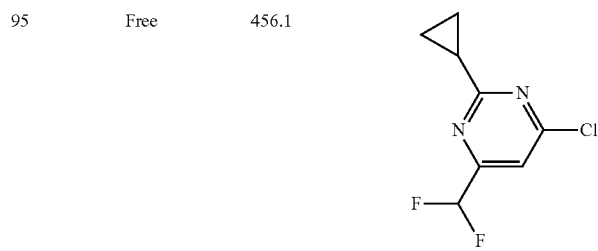 |
| 96 | Free | 446.2 |  |
| 97 | Free | 474.1 | 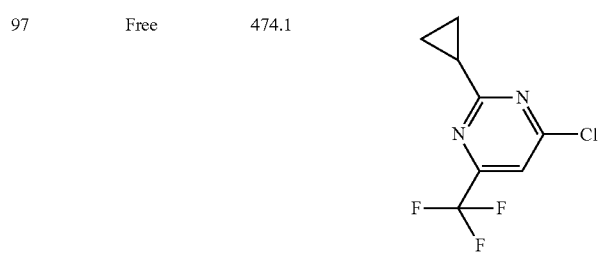 |

Example 98

((7S)-2-(5-chloropyridin-2-yl)-7-methyl-1,2,5-oxadiazepan-5-yl) (2-(2H-1,2,3-triazol-2-yl)phenyl)methanone

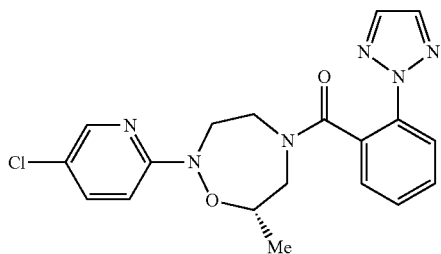 [SMILES: C[C@H]1CN(C(=O)c2ccccc2-n2nccn2)CCN(c2ccc(Cl)cn2)O1]

The title compound (59.6 mg) was obtained using ((7S)-7-methyl-1,2,5-oxadiazepan-5-yl)(2-(2H-1,2,3-triazol-2-yl)phenyl)methanone hydrobromide (105 mg) obtained in Step A of Example 92 and 2-bromo-5-chloropyridine (67.4 mg) in the same manner as in Example 33.
MS: [M+H]$^+$ 399.1.

Example 99

((7S)-7-methyl-2-(pyrazolo[1,5-a]pyrimidin-5-yl)-1,2,5-oxadiazepan-5-yl)(2-(2H-1,2,3-triazol-2-yl)phenyl)methanone

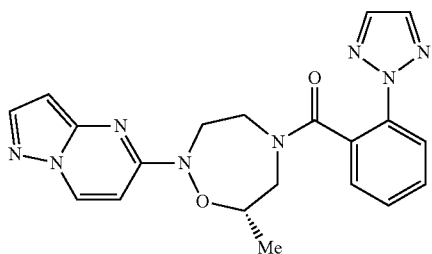 [SMILES: C[C@H]1CN(C(=O)c2ccccc2-n2nccn2)CCN(c2ccn3nccc3n2)O1]

The title compound (11.4 mg) was obtained using ((7S)-7-methyl-1,2,5-oxadiazepan-5-yl)(2-(2H-1,2,3-triazol-2-yl)phenyl)methanone hydrobromide (60 mg) obtained in Step A of Example 92 and 5-chloropyrazolo[1,5-a]pyrimidine (26.1 mg) obtained in Reference Example 24 in the same manner as in Step B of Example 2.
MS: [M+H]$^+$ 405.1.

Example 100

((7S)-2-(6-(difluoromethyl)-2-methylpyrimidin-4-yl)-7-methyl-1,2,5-oxadiazepan-5-yl)(5-fluoro-2-(2H-1,2,3-triazol-2-yl)phenyl)methanone

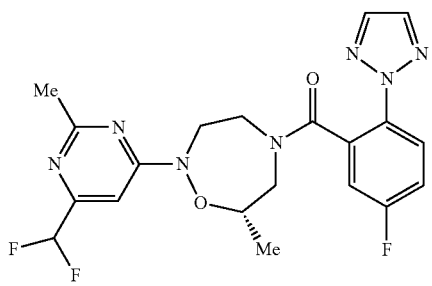 [SMILES: Cc1nc(C(F)F)cc(N2CCN(C(=O)c3cc(F)ccc3-n3nccn3)C[C@H](C)O2)n1]

The title compound (57 mg) was obtained using benzyl (7S)-5-(5-fluoro-2-(2H-1,2,3-triazol-2-yl)benzoyl)-7-methyl-1,2,5-oxadiazepane-2-carboxylate obtained in Step G of Example 1 and 4-chloro-6-(difluoromethyl)-2-methylpyrimidine obtained in Reference Example 20 in the same manner as in Step A and Step B of Example 92.
MS: [M+H]$^+$ 448.1.

Example 101

(5-fluoro-2-(2H-1,2,3-triazol-2-yl)phenyl)((7S)-7-methyl-2-(2-methyl-6-(trifluoromethyl)pyrimidin-4-yl)-1,2,5-oxadiazepan-5-yl)methanone

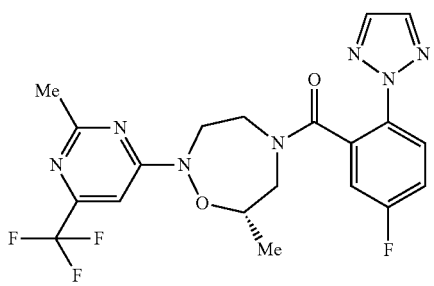 [SMILES: Cc1nc(N2CCN(C(=O)c3cc(F)ccc3-n3nccn3)C[C@H](C)O2)cc(C(F)(F)F)n1]

The title compound (69 mg) was obtained using benzyl (7S)-5-(5-fluoro-2-(2H-1,2,3-triazol-2-yl)benzoyl)-7-methyl-1,2,5-oxadiazepane-2-carboxylate obtained in Step G of Example 1 and 4-chloro-2-methyl-6-(trifluoromethyl)pyrimidine in the same manner as in Steps A and B of Example 92.
MS: [M+H]$^+$ 466.1.

Example 102

(5-chloro-2-(2H-1,2,3-triazol-2-yl)phenyl)((7S)-2-(2,6-dimethylpyrimidin-4-yl)-7-methyl-1,2,5-oxadiazepan-5-yl)methanone

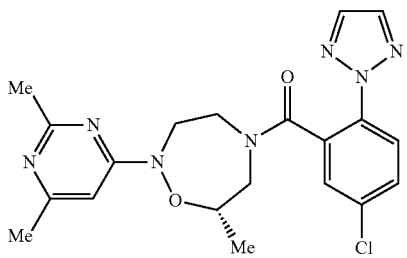 [SMILES: Cc1cc(N2CCN(C(=O)c3cc(Cl)ccc3-n3nccn3)C[C@H](C)O2)nc(C)n1]

A) tert-butyl {(2S)-2-[(1,3-dioxo-1,3-dihydro-2H-isoindol-2-yl)oxy]propyl}carbamate To a solution of 2-hydroxy-1H-isoindole-1,3(2H)-dione (10.0 g), tert-butyl [(2R)-2-hydroxypropyl]carbamate (11.7 g) and tributylphosphine (18.0 mL) in tetrahydrofuran (200 mL) was added 1,1'-(azodicarbonyl)dipiperidine (18.5 g) at 0° C., and the mixture was stirred overnight at room temperature. The insoluble substance was removed by filtration, and the solvent was evaporated under reduced pressure. The residue was purified by silica gel column chromatography (hexane/ethyl acetate) to give the title compound (18.7 g).

¹H NMR (300 MHz, DMSO-d₆) δ 1.23 (3H, d, J=6.4 Hz), 1.37 (9H, s), 3.03-3.18 (1H, m), 3.19-3.30 (1H, m), 4.21-4.42 (1H, m), 6.76 (1H, t, J=5.9 Hz), 7.87 (4H, s).
MS: [M+H−Boc]⁺ 221.0.

B) prop-2-en-1-yl ({(2S)-1-[(tert-butoxycarbonyl)amino]propan-2-yl}oxy)carbamate To a solution of tert-butyl {(2S)-2-[(1,3-dioxo-1,3-dihydro-2H-isoindol-2-yl)oxy]propyl}carbamate (16.2 g) obtained in Step A of Example 102 in ethanol (170 mL) was added hydrazine monohydrate (7.40 mL) at room temperature, and the mixture was stirred at 50° C. for 30 min. The insoluble substance was removed by filtration, and washed with ethanol, and the solvent was evaporated under reduced pressure. To the residue was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The obtained residue was dissolved in pyridine (170 mL), allyl chloroformate (7.50 mL) was added thereto while stirring at 0° C., and the mixture was stirred at the same temperature for 2 hr. The solvent was evaporated under reduced pressure, to the residue was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (13.7 g).
¹H NMR (300 MHz, DMSO-d₆) δ 1.06 (3H, d, J=6.4 Hz), 1.38 (9H, s), 2.89-3.18 (2H, m), 3.68-3.85 (1H, m), 4.54 (2H, dt, J=5.3, 1.5 Hz), 5.12-5.39 (2H, m), 5.80-6.04 (1H, m), 6.63 (1H, t, J=5.9 Hz), 10.17 (1H, brs).

C) prop-2-en-1-yl (2-bromoethyl)({(2S)-1-[(tert-butoxycarbonyl)amino]propan-2-yl}oxy)carbamate To a solution of prop-2-en-1-yl ({(2S)-1-[(tert-butoxycarbonyl)amino]propan-2-yl}oxy)carbamate (13.6 g) obtained in Step B of Example 102 in N,N-dimethylformamide (140 mL) was added sodium hydride (60% in mineral oil, 2.22 g) at 0° C., and the mixture was stirred at the same temperature for 1 hr. 1,2-Dibromoethane (5.20 mL) was added dropwise thereto at 0° C., and the mixture was stirred at room temperature for 2 hr. To the reaction mixture was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (14.9 g).
¹H NMR (300 MHz, DMSO-d₆) δ 1.10 (3H, d, J=6.1 Hz), 1.38 (9H, s), 2.93-3.18 (2H, m), 3.57-3.67 (2H, m), 3.81-3.90 (2H, m), 3.90-4.03 (1H, m), 4.59 (2H, d, J=5.3 Hz), 5.17-5.40 (2H, m), 5.83-6.04 (1H, m), 6.82 (1H, t, J=5.7 Hz).

D) 5-tert-butyl 2-prop-2-en-1-yl (7S)-7-methyl-1,2,5-oxadiazepane-2, 5-dicarboxylate To prop-2-en-1-yl (2-bromoethyl)({(2S)-1-[(tert-butoxycarbonyl)amino]propan-2-yl}oxy)carbamate (46.4 g) obtained in Step C of Example 102 was added trifluoroacetic acid (300 mL) at 0° C., and the mixture was stirred at room temperature for 1 hr. The mixture was concentrated under reduced pressure, and the residue was dissolved in N,N-dimethylformamide (800 mL). Diisopropylethylamine (106 mL) was added thereto at 0° C., and the mixture was stirred overnight at room temperature. Di-tert-butyl dicarbonate (42.4 mL) was added thereto, and the mixture was stirred at room temperature for 2 hr. The solvent was evaporated under reduced pressure, to the residue was added saturated aqueous sodium hydrogencarbonate solution at 0° C., and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (35.9 g).
¹H NMR (300 MHz, DMSO-d₆) δ 1.11 (3H, d, J=6.1 Hz), 1.38 (9H, s), 2.76-3.11 (1H, m), 3.24 (1H, ddd, J=14.5, 9.4, 5.7 Hz), 3.38-3.54 (1H, m), 3.56-3.91 (4H, m), 4.57 (2H, dt, J=5.3, 1.5 Hz), 5.21 (1H, dd, J=10.6, 1.5 Hz), 5.29 (1H, dq, J=17.2, 1.7 Hz), 5.92 (1H, ddt, J=17.2, 10.5, 5.3 Hz).
MS: [M+H−Boc]⁺ 201.2.

E) tert-butyl (7S)-7-methyl-1,2,5-oxadiazepane-5-carboxylate

To a solution of 5-tert-butyl 2-prop-2-en-1-yl (7S)-7-methyl-1,2,5-oxadiazepane-2,5-dicarboxylate (25.0 g) obtained in Step D of Example 102 and 1,3-dimethylpyrimidine-2,4,6(1H,3H, 5H)-trione (16.9 g) in tetrahydrofuran (500 mL) was added tetrakis(triphenylphosphine)palladium(0) (4.81 g) at room temperature, and the mixture was stirred for 4 hr under argon atmosphere. The reaction mixture was acidified with 1N hydrochloric acid, and extracted with ethyl acetate. The aqueous layer was basified with 8N aqueous sodium hydroxide solution, and extracted with ethyl acetate. The extracts were combined, washed with saturated brine, and dried over anhydrous magnesium sulfate, and the solvent was evaporated under reduced pressure to give the title compound (13.7 g).
¹H NMR (300 MHz, DMSO-d₆) δ 0.93-1.08 (3H, m), 1.39 (9H, s), 2.72-3.15 (4H, m), 3.47-3.70 (2H, m), 3.78-3.96 (1H, m), 6.63 (1H, d, J=15.9 Hz).

F) tert-butyl (7S)-2-(2,6-dimethylpyrimidin-4-yl)-7-methyl-1,2,5-oxadiazepane-5-carboxylate A solution of tert-butyl (7S)-7-methyl-1,2,5-oxadiazepane-5-carboxylate (146 mg) obtained in Step E of Example 102 and 4-chloro-2,6-dimethylpyrimidine (106 mg) in 2-propanol (3 mL) was stirred at 70° C. for 2 hr. The mixture was concentrated under reduced pressure, to the residue was added saturated aqueous sodium hydrogencarbonate solution, and the mixture was extracted with ethyl acetate. The obtained organic layer was dried over anhydrous sodium sulfate, and the solvent was evaporated under reduced pressure. The residue was purified by silica gel column chromatography (hexane/ethyl acetate) to give the title compound (212 mg).
¹H NMR (300 MHz, DMSO-d₆) δ 1.21 (3H, d, J=6.8 Hz), 1.37 (9H, d, J=3.0 Hz), 2.27-2.42 (6H, m), 2.87-3.22 (1H, m), 3.35-3.94 (4H, m), 3.95-4.35 (2H, m), 6.53-6.75 (1H, m).
MS: [M+H]⁺ 323.2.

G) (7S)-2-(2,6-dimethylpyrimidin-4-yl)-7-methyl-1,2,5-oxadiazepane dihydrochloride A mixture of tert-butyl (7S)-2-(2,6-dimethylpyrimidin-4-yl)-7-methyl-1,2,5-oxadiazepane-5-carboxylate (560 mg) obtained in Step F of Example 102 and 2N hydrochloric acid (2-propanol solution, 6.08 mL) was stirred at 50° C. for 3 hr. The mixture was concentrated under reduced pressure, and the obtained solid was collected by filtration, washed with ethyl acetate, and dried to give the title compound (504 mg).

$^1$H NMR (300 MHz, DMSO-d$_6$) δ 1.41 (3H, d, J=6.4 Hz), 2.54 (3H, s), 2.61 (3H, s), 3.05-4.18 (5H, m), 4.39-4.69 (2H, m), 6.94 (1H, s), 9.70-10.49 (2H, m), 14.40-15.49 (1H, m).

MS: [M+H]$^+$ 223.0.

H) [5-chloro-2-(2H-1,2,3-triazol-2-yl)phenyl][(7S)-2-(2,6-dimethylpyrimidin-4-yl)-7-methyl-1,2,5-oxadiazepan-5-yl]methanone To a solution of (7S)-2-(2,6-dimethylpyrimidin-4-yl)-7-methyl-1,2,5-oxadiazepane dihydrochloride (16.0 g) obtained in Step G of Example 102, 5-chloro-2-(2H-1,2,3-triazol-2-yl)benzoic acid (18.2 g) obtained in Reference Example 3 and 2-(7-azabenzotriazol-1-yl)-1,1,3,3-hexafluorophosphate (HATU) (30.9 g) in N,N-dimethylformamide (150 mL) was added triethylamine (22.7 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate), and crystallized (hexane/ethyl acetate) to give the title compound (19.0 g).

$^1$H NMR (300 MHz, DMSO-d$_6$) δ 1.01-1.38 (3H, m), 2.20-2.47 (6H, m), 2.93-3.31 (1H, m), 3.37-4.55 (6H, m), 6.37-6.76 (1H, m), 7.15-7.52 (1H, m), 7.55-8.05 (3H, m), 8.08-8.19 (1H, m).

MS: [M+H]$^+$ 428.0.

d value (or d-spacing) of specific peak in powder X-ray diffraction pattern=15.4, 8.6, 8.0, 7.3, 6.8, 5.4, 5.2, 4.7, 4.6, 4.3, 4.1, 4.0, 3.9, 3.7, 3.5, 3.23, 3.17 A.

Example 103

(5-chloro-2-(2H-1,2,3-triazol-2-yl)phenyl)((7S)-2-(6-(difluoromethyl)-2-methylpyrimidin-4-yl)-7-methyl-1,2,5-oxadiazepan-5-yl)methanone

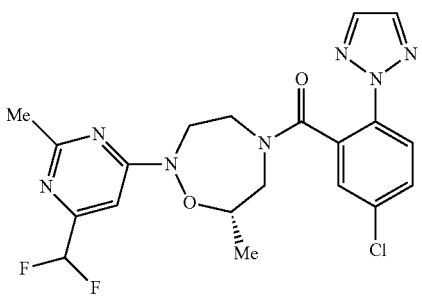 [SMILES: Cc1nc(C(F)F)cc(N2CCN(C(=O)c3cc(Cl)ccc3-n3nccn3)C[C@H](C)O2)n1]

A) (5-chloro-2-(2H-1,2,3-triazol-2-yl)phenyl)((7S)-7-methyl-1,2,5-oxadiazepan-5-yl)methanone hydrochloride To benzyl (7S)-5-(5-chloro-2-(2H-1,2,3-triazol-2-yl)benzoyl)-7-methyl-1,2,5-oxadiazepane-2-carboxylate (1.65 g) obtained in Step A of Example 3 was added 5.1M hydrogen bromide acetic acid solution (5.0 mL), and the mixture was stirred at room temperature for 1 hr. The solvent was evaporated under reduced pressure, saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate). To the crude product was added 4M hydrogen chloride ethyl acetate (5.0 mL) solution, and the solvent was evaporated under reduced pressure to give the title compound (745 mg).

MS: [M+H−HCl]$^+$ 322.0.

B) (5-chloro-2-(2H-1,2,3-triazol-2-yl)phenyl)((7S)-2-(6-(difluoromethyl)-2-methylpyrimidin-4-yl)-7-methyl-1,2,5-oxadiazepan-5-yl)methanone The title compound (87 mg) was obtained using (5-chloro-2-(2H-1,2,3-triazol-2-yl)phenyl)((7S)-7-methyl-1,2,5-oxadiazepan-5-yl)methanone hydrochloride (100 mg) obtained in Step A of Example 103 and 4-chloro-6-(difluoromethyl)-2-methylpyrimidine (49.8 mg) obtained in Reference Example 20 in the same manner as in Step B of Example 92.

MS: [M+H]$^+$ 464.0.

Example 104

(5-chloro-2-(2H-1,2,3-triazol-2-yl)phenyl)((7S)-7-methyl-2-(6-methyl-2-(trifluoromethyl)pyrimidin-4-yl)-1,2,5-oxadiazepan-5-yl)methanone

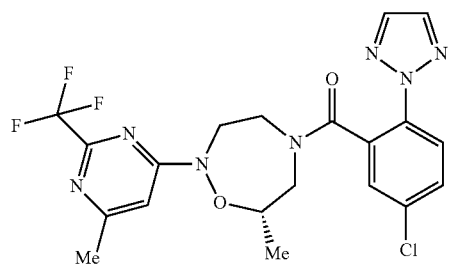 [SMILES: Cc1cc(N2CCN(C(=O)c3cc(Cl)ccc3-n3nccn3)C[C@H](C)O2)nc(C(F)(F)F)n1]

The title compound (46 mg) was obtained using (5-chloro-2-(2H-1,2,3-triazol-2-yl)phenyl)((7S)-7-methyl-1,2,5-oxadiazepan-5-yl)methanone hydrochloride (100 mg) obtained in Step A of Example 103 and 4-chloro-6-methyl-2-(trifluoromethyl)pyrimidine (60.4 mg) in the same manner as in Step B of Example 92.

MS: [M+H]$^+$ 482.0.

Example 105

(5-chloro-2-(2H-1,2,3-triazol-2-yl)phenyl)((7S)-2-(2-cyclopropyl-6-(difluoromethyl)pyrimidin-4-yl)-7-methyl-1,2,5-oxadiazepan-5-yl)methanone

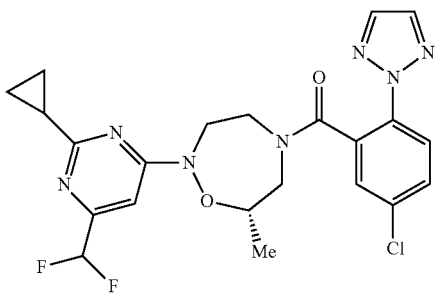 [SMILES: C[C@H]1CN(C(=O)c2cc(Cl)ccc2-n2nccn2)CCN(c2cc(C(F)F)nc(C3CC3)n2)O1]

The title compound (83 mg) was obtained using (5-chloro-2-(2H-1,2,3-triazol-2-yl)phenyl)((7S)-7-methyl-1,2,5-oxadiazepan-5-yl)methanone hydrochloride (100 mg) obtained in Step A of Example 103 and 4-chloro-2-cyclopropyl-6-(difluoromethyl)pyrimidine (57.1 mg) obtained in Reference Example 21 in the same manner as in Step B of Example 92.

MS: [M+H]$^+$ 490.0.

Example 106

(4,5-difluoro-2-(2H-1,2,3-triazol-2-yl)phenyl)((7S)-2-(2,6-dimethylpyrimidin-4-yl)-7-methyl-1,2,5-oxadiazepan-5-yl)methanone

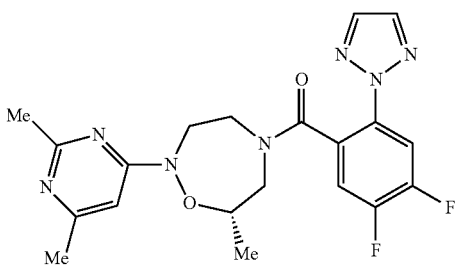 [SMILES: Cc1cc(N2CCN(C(=O)c3cc(F)c(F)cc3-n3nccn3)C[C@H](C)O2)nc(C)n1]

A) benzyl (7S)-5-(4,5-difluoro-2-(2H-1,2,3-triazol-2-yl)benzoyl)-7-methyl-1,2,5-oxadiazepane-2-carboxylate The title compound (486 mg) was obtained using 2-benzyl 5-tert-butyl (7S)-7-methyl-1,2,5-oxadiazepane-2,5-dicarboxylate (519 mg) obtained in Step E of Example 1 and 4,5-difluoro-2-(2H-1,2,3-triazol-2-yl)benzoic acid (500 mg) obtained in Reference Example 6 in the same manner as in Step A of Example 2.

MS: [M+H]$^+$ 457.9.

B) (4,5-difluoro-2-(2H-1,2,3-triazol-2-yl)phenyl)((7S)-2-(2,6-dimethylpyrimidin-4-yl)-7-methyl-1,2,5-oxadiazepan-5-yl)methanone The title compound (20 mg) was obtained using benzyl (7S)-5-(4,5-difluoro-2-(2H-1,2,3-triazol-2-yl)benzoyl)-7-methyl-1,2,5-oxadiazepane-2-carboxylate obtained in Step A of Example 106 and 4-chloro-2,6-dimethylpyrimidine in the same manner as in Steps A and B of Example 92.

MS: [M+H]$^+$ 430.0.

Example 107

(4,5-difluoro-2-(2H-1,2,3-triazol-2-yl)phenyl)((7S)-7-methyl-2-(2-methyl-6-(trifluoromethyl)pyrimidin-4-yl)-1,2,5-oxadiazepan-5-yl)methanone

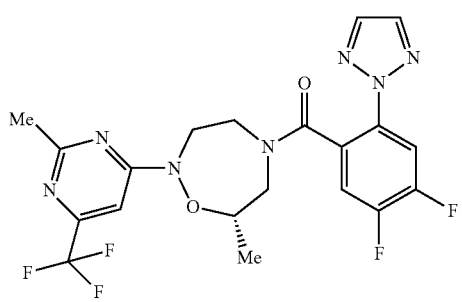 [SMILES: Cc1nc(N2CCN(C(=O)c3cc(F)c(F)cc3-n3nccn3)C[C@H](C)O2)cc(C(F)(F)F)n1]

The title compound (37 mg) was obtained using benzyl (7S)-5-(4,5-difluoro-2-(2H-1,2,3-triazol-2-yl)benzoyl)-7-methyl-1,2,5-oxadiazepane-2-carboxylate obtained in Step A of Example 106 and 4-chloro-2-methyl-6-(trifluoromethyl)pyrimidine in the same manner as in Steps A and B of Example 92.

MS: [M+H]$^+$ 484.0.

Example 108

(4,5-difluoro-2-(2H-1,2,3-triazol-2-yl)phenyl)((7S)-7-methyl-2-(6-methyl-2-(trifluoromethyl)pyrimidin-4-yl)-1,2,5-oxadiazepan-5-yl)methanone

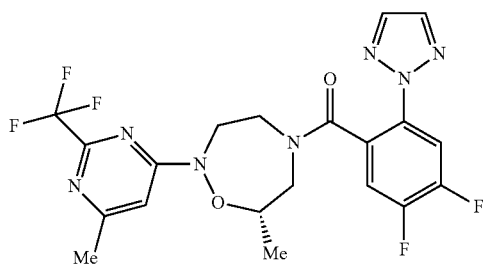 [SMILES: Cc1cc(N2CCN(C(=O)c3cc(F)c(F)cc3-n3nccn3)C[C@H](C)O2)nc(C(F)(F)F)n1]

The title compound (39 mg) was obtained using benzyl (7S)-5-(4,5-difluoro-2-(2H-1,2,3-triazol-2-yl)benzoyl)-7-methyl-1,2,5-oxadiazepane-2-carboxylate obtained in Step A of Example 106 and 4-chloro-6-methyl-2-(trifluoromethyl)pyrimidine in the same manner as in Steps A and B of Example 92.

MS: [M+H]$^+$ 483.8.

Example 109

((7S)-2-(2,6-dimethylpyrimidin-4-yl)-7-methyl-1,2,5-oxadiazepan-5-yl)(2-(pyrimidin-2-yl)phenyl)methanone

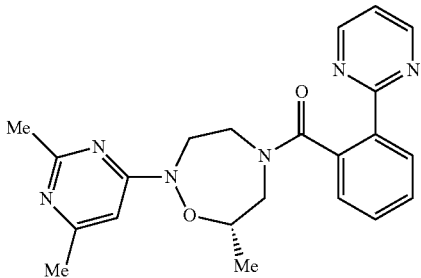 [SMILES: Cc1cc(N2CCN(C(=O)c3ccccc3-c3ncccn3)C[C@H](C)O2)nc(C)n1]

A) benzyl (7S)-7-methyl-5-(2-(pyrimidin-2-yl)benzoyl)-1,2,5-oxadiazepane-2-carboxylate To a solution of benzyl (7S)-7-methyl-1,2,5-oxadiazepane-2-carboxylate hydrochloride (120 mg) obtained in Step F of Example 1 in N,N-dimethylformamide (2.0 mL) were added 2-(pyrimidin-2-yl)benzoic acid (100.6 mg) obtained in Reference Example 25, N,N-diisopropylethylamine (0.368 mL) and a solution of 1.7M 2,4,6-tripropyl-1,3,5,2,4,6-trioxatriphosphorinane-2,4,6-trioxide in ethyl acetate (0.88 mL), and the mixture was stirred overnight at room temperature. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (78.8 mg).

MS: [M+H]$^+$ 433.1.

B) ((7S)-2-(2,6-dimethylpyrimidin-4-yl)-7-methyl-1,2,5-oxadiazepan-5-yl)(2-(pyrimidin-2-yl)phenyl)methanone The title compound (7.8 mg) was obtained using benzyl (7S)-7-methyl-5-(2-(pyrimidin-2-yl)benzoyl)-1,2,5-oxadiazepane-2-carboxylate obtained in Step A of Example 109 and 4-chloro-2,6-dimethylpyrimidine in the same manner as in Steps A and B of Example 92.

MS: [M+H]$^+$ 405.2.

Example 110

((7S)-2-(2,6-dimethylpyrimidin-4-yl)-7-methyl-1,2,5-oxadiazepan-5-yl)(2-(4-methyl-1,3-thiazol-2-yl)phenyl)methanone

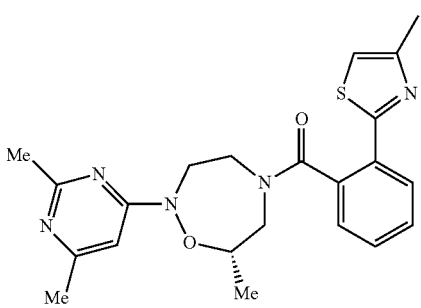 [SMILES: Cc1cc(N2CCN(C(=O)c3ccccc3-c3nc(C)cs3)C[C@H](C)O2)nc(C)n1]

A) benzyl (7S)-7-methyl-5-(2-(4-methyl-1,3-thiazol-2-yl)benzoyl)-1,2,5-oxadiazepane-2-carboxylate The title compound (194 mg) was obtained using benzyl (7S)-7-methyl-1,2,5-oxadiazepane-2-carboxylate hydrochloride (123 mg) obtained in Step F of Example 1 and 2-(4-methyl-1,3-thiazol-2-yl)benzoic acid (242.1 mg) obtained in Reference Example 26 in the same manner as in Example 14.

MS: [M+H]$^+$ 452.2.

B) ((7S)-2-(2,6-dimethylpyrimidin-4-yl)-7-methyl-1,2,5-oxadiazepan-5-yl)(2-(4-methyl-1,3-thiazol-2-yl)phenyl)methanone The title compound (185 mg) was obtained using benzyl (7S)-7-methyl-5-(2-(4-methyl-1,3-thiazol-2-yl)benzoyl)-1,2,5-oxadiazepane-2-carboxylate obtained in Step A of Example 110 and 4-chloro-2,6-dimethylpyrimidine in the same manner as in Steps A and B of Example 92.

MS: [M+H]$^+$ 424.2.

Example 111

((7S)-7-methyl-2-(2-methyl-6-(trifluoromethyl)pyrimidin-4-yl)-1,2,5-oxadiazepan-5-yl)(2-(3-methyl-1,2,4-oxadiazol-5-yl)phenyl)methanone

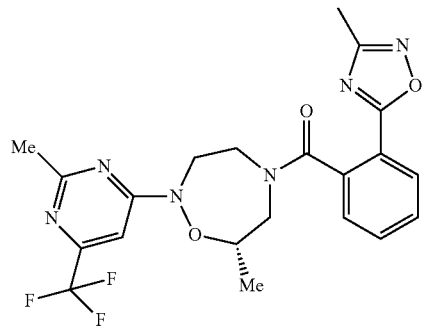 [SMILES: Cc1nc(N2CCN(C(=O)c3ccccc3-c3nc(C)no3)C[C@H](C)O2)cc(C(F)(F)F)n1]

A) benzyl (7S)-7-methyl-5-(2-(3-methyl-1,2,4-oxadiazol-5-yl)benzoyl)-1,2,5-oxadiazepane-2-carboxylate The title compound (638.8 mg) was obtained using benzyl (7S)-7-methyl-1,2,5-oxadiazepane-2-carboxylate hydrochloride (436 mg) obtained in Step F of Example 1 and 2-(3-methyl-1,2,4-oxadiazol-5-yl)benzoic acid (372 mg) in the same manner as in Example 14.

MS: [M+H]$^+$ 437.0.

B) ((7S)-7-methyl-2-(2-methyl-6-(trifluoromethyl)pyrimidin-4-yl)-1,2,5-oxadiazepan-5-yl)(2-(3-methyl-1,2,4-oxadiazol-5-yl)phenyl)methanone The title compound (49.8 mg) was obtained using benzyl (7S)-7-methyl-5-(2-(3-methyl-1,2,4-oxadiazol-5-yl)benzoyl)-1,2,5-oxadiazepane-2-carboxylate obtained in Step A of Example 111 and 4-chloro-2-methyl-6-(trifluoromethyl)pyrimidine in the same manner as in Step A and Step B of Example 92.

MS: [M+H]$^+$ 463.0.

Example 112

(2-(2,6-dimethylpyrimidin-4-yl)-7-ethyl-1,2,5-oxadiazepan-5-yl)(2-(2H-1,2,3-triazol-2-yl)phenyl)methanone

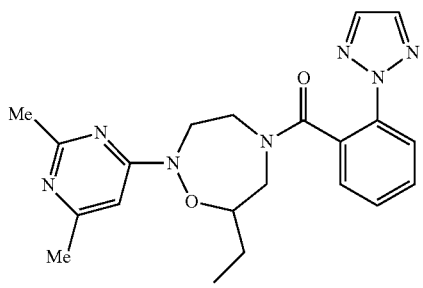 [SMILES: CCC1CN(C(=O)c2ccccc2-n2nccn2)CCN(c2cc(C)nc(C)n2)O1]

The title compound (62.6 mg) was obtained using 1-amino-2-butanol in the same manner as in Steps A, B, C and D of Example 1, Step B of Example 6, Step A of Example 13, Example and Step B of Example 2.

MS: [M+H]$^+$ 408.2.

Example 113

(2-(2,6-dimethylpyrimidin-4-yl)-7-(methoxymethyl)-1,2,5-oxadiazepan-5-yl)(2-(2H-1,2,3-triazol-2-yl)phenyl)methanone

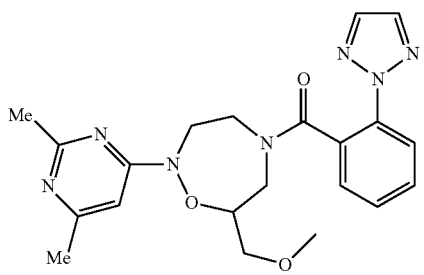 [SMILES: COCC1CN(C(=O)c2ccccc2-n2nccn2)CCN(c2cc(C)nc(C)n2)O1]

A) tert-butyl (3-((tert-butyl(dimethyl)silyl)oxy)-2-hydroxypropyl) carbamate

To a solution of tert-butyl (2,3-dihydroxypropyl)carbamate (10 g) and imidazole (5.34 g) in N,N-dimethylformamide (150 mL) was added tert-butyldimethylchlorosilane (9.46 g), and the mixture was stirred overnight at room temperature. The reaction mixture was poured into water, and extracted with diethyl ether. The obtained organic layer was washed with water and saturated brine, and dried over anhydrous magnesium sulfate, and the solvent was evaporated under reduced pressure. The residue was purified by silica gel column chromatography (hexane/ethyl acetate) to give the title compound (15 g).

MS: [M+H−Boc]$^+$ 206.2.

B) 2-benzyl 5-tert-butyl 7-(hydroxymethyl)-1,2,5-oxadiazepane-2,5-dicarboxylate

The title compound (200 mg) was obtained using tert-butyl (3-((tert-butyl(dimethyl)silyl)oxy)-2-hydroxypropyl) carbamate obtained in Step A of Example 113 in the same manner as in Steps B, C and D of Example 1 and Step B of Example 6.

$^1$H NMR (300 MHz, DMSO-d$_6$) δ 1.19-1.62 (9H, m), 2.92-3.94 (10H, m), 5.07-5.24 (2H, m), 7.23-7.48 (5H, m).

MS: [M+H−Boc]$^+$ 267.1.

C) 2-benzyl 5-tert-butyl 7-(methoxymethyl)-1,2,5-oxadiazepane-2,5-dicarboxylate

To a solution of 2-benzyl 5-tert-butyl 7-(hydroxymethyl)-1,2,5-oxadiazepane-2,5-dicarboxylate (200 mg) obtained in Step B of Example 113 in N,N-dimethylformamide (3.0 mL) was added sodium hydride (60% in mineral oil, 24.01 mg) in an ice bath, and the mixture was stirred at 0° C. for 30 min. To the reaction mixture was added methyl iodide (0.051 mL) at 0° C., and the mixture was stirred overnight at room temperature. To the reaction mixture was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (95 mg).

MS: [M+H−Boc]$^+$ 281.1.

D) (2-(2,6-dimethylpyrimidin-4-yl)-7-(methoxymethyl)-1,2,5-oxadiazepan-5-yl)(2-(2H-1,2,3-triazol-2-yl)phenyl)methanone The title compound (13 mg) was obtained using 2-benzyl 5-tert-butyl 7-(methoxymethyl)-1,2,5-oxadiazepane-2,5-dicarboxylate obtained in Step C of Example 113 in the same manner as in Step A of Example 13, Example 20 and Step B of Example 2.

MS: [M+H]$^+$ 424.1.

The compounds of Examples 114 to 116 were produced using ((6R)-6-methyl-1,2,5-oxadiazepan-5-yl)(5-methyl-2-(2H-1,2,3-triazol-2-yl)phenyl)methanone hydrobromide obtained in Step D of Example 6 and the reagents corresponding to the compounds of Examples 114 to 116 (the reagents can be produced according to a method known per se) according to the same method as in Step B of Example 92, or a method analogous thereto. MS in the tables means actual measured value.

TABLE 5
| Ex. No. | IUPAC Name | Structure |
|---|---|---|
| 114 | ((6R)-2-(4,6-dimethylpyrimidin-2-yl)-6-methyl-1,2,5-oxadiazepan-5-yl) (5-methyl-2-(2H-1,2,3-triazol-2-yl)phenyl)methanone | 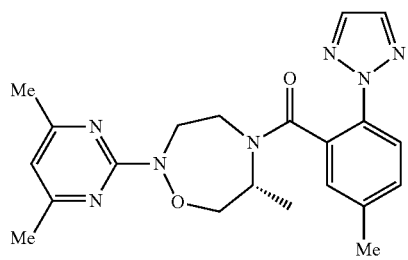 [SMILES: Cc1ccc(-n2nccn2)c(C(=O)N2CCN(c3nc(C)cc(C)n3)OC[C@H]2C)c1] |
| 115 | 6-methyl-2-((6R)-6-methyl-5-(5-methyl-2-(2H-1,2,3-triazol-2-yl)benzoyl)-1,2,5-oxadiazepan-2-yl)pyrimidine-4-carbonitrile | 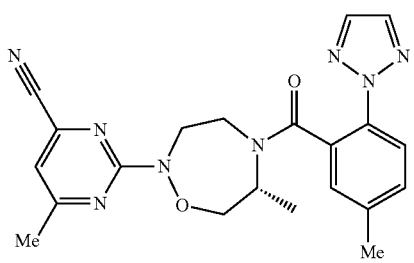 [SMILES: Cc1ccc(-n2nccn2)c(C(=O)N2CCN(c3nc(C)cc(C#N)n3)OC[C@H]2C)c1] |
| 116 | ((6R)-6-methyl-2-(thieno[3,2-d]pyrimidin-2-yl)-1,2,5-oxadiazepan-5-yl) (5-methyl-2-(2H-1,2,3-triazol-2-yl)phenyl)methanone | 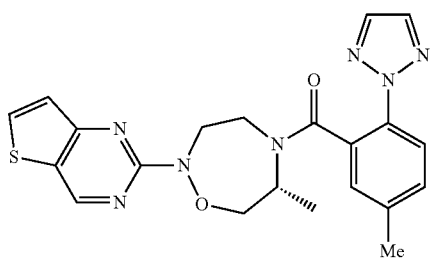 [SMILES: Cc1ccc(-n2nccn2)c(C(=O)N2CCN(c3ncc4sccc4n3)OC[C@H]2C)c1] |
| Ex. No. | Additive | MS | Reagent |
|---|---|---|---|
| 114 | Free | 408 | 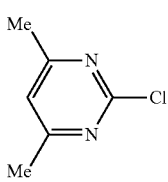 |
| 115 | Free | 419.2 | 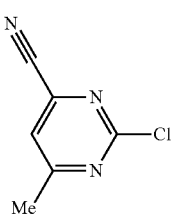 |
| 116 | Free | 436.1 | 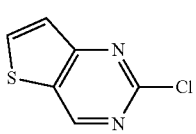 |

Example 117

((6R)-2-(5-fluoro-4-methoxypyrimidin-2-yl)-6-methyl-1,2,5-oxadiazepan-5-yl)(5-methyl-2-(2H-1,2,3-triazol-2-yl)phenyl)methanone hydrochloride

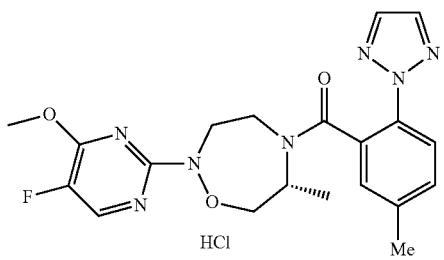 [SMILES: COc1nc(N2CCN(C(=O)c3cc(C)ccc3-n3nccn3)[C@H](C)CO2)ncc1F ; Cl]

The title compound (10 mg) was obtained using ((6R)-6-methyl-1,2,5-oxadiazepan-5-yl)(5-methyl-2-(2H-1,2,3-triazol-2-yl)phenyl)methanone hydrobromide (80 mg) obtained in Step D of Example 6 and 2-chloro-5-fluoro-4-methoxypyrimidine (51 mg) in the same manner as in Example 33.

MS: [M+H−HCl]$^+$ 428.2.

Example 118

((6R)-2-(5-chloro-1,3-benzoxazol-2-yl)-6-methyl-1,2,5-oxadiazepan-5-yl)(5-methyl-2-(2H-1,2,3-triazol-2-yl)phenyl)methanone

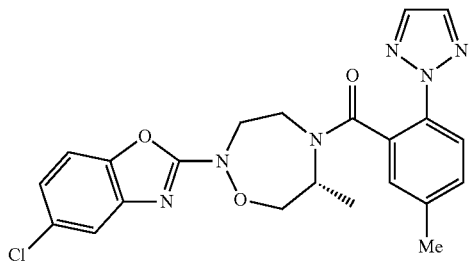 [SMILES: Cc1ccc(-n2nccn2)c(C(=O)N2CCN(c3nc4cc(Cl)ccc4o3)OC[C@H]2C)c1]

The title compound (16.2 mg) was obtained using ((6R)-6-methyl-1,2,5-oxadiazepan-5-yl)(5-methyl-2-(2H-1,2,3-triazol-2-yl)phenyl)methanone hydrobromide (52.3 mg) obtained in Step D of Example 6 and 2,5-dichloro-1,3-benzoxazole (31.8 mg) in the same manner as in Example 39.

MS: [M+H]$^+$ 453.1.

Example 119

((6R)-2-(5-fluoropyridin-2-yl)-6-methyl-1,2,5-oxadiazepan-5-yl)(5-methyl-2-(2H-1,2,3-triazol-2-yl)phenyl)methanone

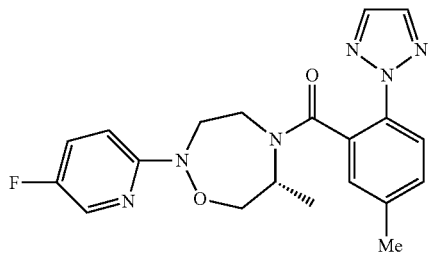 [SMILES: Cc1ccc(-n2nccn2)c(C(=O)N2CCN(c3ccc(F)cn3)OC[C@H]2C)c1]

To a solution of ((6R)-6-methyl-1,2,5-oxadiazepan-5-yl)(5-methyl-2-(2H-1,2,3-triazol-2-yl)phenyl)methanone hydrobromide (31 mg) obtained in Step D of Example 6 in toluene (1.0 mL) were added 2-chloro-5-fluoropyridine (21 mg), potassium tert-butoxide (27 mg), 2-dicyclohexylphosphino-2',6'-diisopropoxybiphenyl (1.867 mg) and tris(dibenzylideneacetone)dipalladium(0) (15 mg), and the mixture was stirred in a microwave reactor at 90° C. for 1 hr. To the reaction mixture was added saturated aqueous sodium hydrogencarbonate solution, and the mixture was extracted with ethyl acetate. The obtained organic layer was washed successively with water and saturated brine, and the solvent was evaporated under nitrogen stream. The residue was purified by HPLC (C18, mobile phase: water/acetonitrile (containing 10 mM NH$_4$HCO$_3$)), and the obtained fraction was concentrated under nitrogen stream to give the title compound (7.0 mg).

MS: [M+H]$^+$ 397.2.

The compounds of Examples 120 to 146 were produced using ((6R)-6-methyl-1,2,5-oxadiazepan-5-yl)(5-methyl-2-(2H-1,2,3-triazol-2-yl)phenyl)methanone hydrobromide obtained in Step D of Example 6 and the reagents corresponding to the compounds of Examples 120 to 146 (the reagents can be produced according to a method known per se) according to the same method as in Example 119, or a method analogous thereto. MS in the tables means actual measured value.

TABLE 6-1

| Ex. No. | IUPAC Name | Structure |
|---|---|---|
| 120 | ((6R)-2-(3-methoxyphenyl)-6-methyl-1,2,5-oxadiazepan-5-yl) (5-methyl-2-(2H-1,2,3-triazol-2-yl)phenyl)methanone | 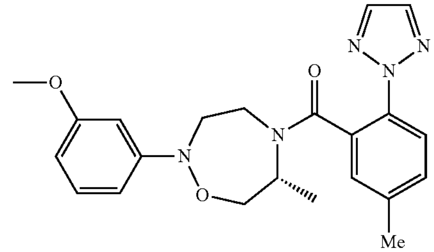 [SMILES: COc1cccc(N2CCN(C(=O)c3cc(C)ccc3-n3nccn3)[C@H](C)CO2)c1] |

TABLE 6-1-continued

| | | |
|---|---|---|
| 121 | ((6R)-2-(5-chloropyridin-2-yl)-6-methyl-1,2,5-oxadiazepan-5-yl) (5-methyl-2-(2H-1,2,3-triazol-2-yl)phenyl)methanone | 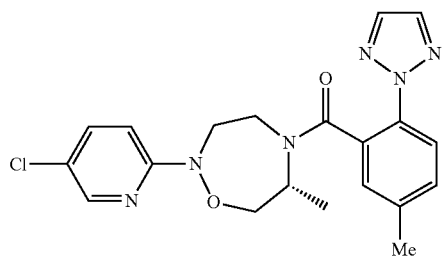 [SMILES: Cc1ccc(-n2nccn2)c(C(=O)N2CCN(c3ccc(Cl)cn3)OC[C@H]2C)c1] |
| 122 | ((6R)-2-(3-chloropyridin-2-yl)-6-methyl-1,2,5-oxadiazepan-5-yl) (5-methyl-2-(2H-1,2,3-triazol-2-yl)phenyl)methanone | 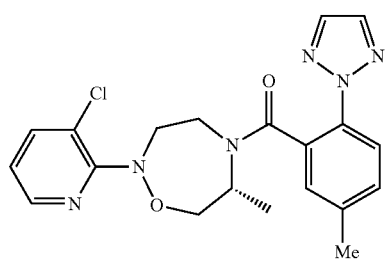 [SMILES: Cc1ccc(-n2nccn2)c(C(=O)N2CCN(c3ncccc3Cl)OC[C@H]2C)c1] |
| 123 | ((6R)-2-(3-methoxypyridin-2-yl)-6-methyl-1,2,5-oxadiazepan-5-yl) (5-methyl-2-(2H-1,2,3-triazol-2-yl)phenyl)methanone | 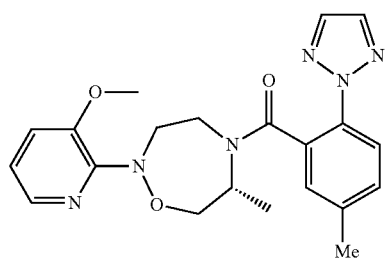 [SMILES: COc1cccnc1N1CCN(C(=O)c2cc(C)ccc2-n2nccn2)[C@H](C)CO1] |
| 124 | ((6R)-6-methyl-2-(6-methylpyridin-2-yl)-1,2,5-oxadiazepan-5-yl) (5-methyl-2-(2H-1,2,3-triazol-2-yl)phenyl)methanone | 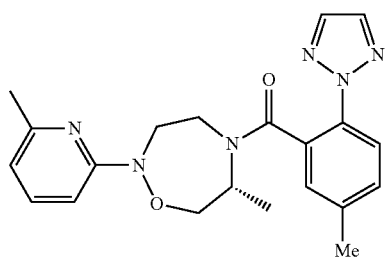 [SMILES: Cc1ccc(-n2nccn2)c(C(=O)N2CCN(c3cccc(C)n3)OC[C@H]2C)c1] |
| 125 | ((6R)-6-methyl-2-(4-methylpyridin-2-yl)-1,2,5-oxadiazepan-5-yl) (5-methyl-2-(2H-1,2,3-triazol-2-yl)phenyl)methanone | 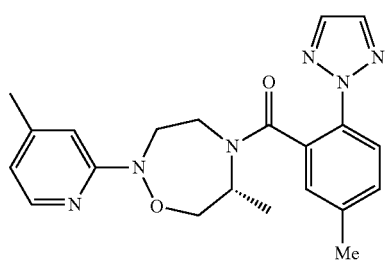 [SMILES: Cc1ccnc(N2CCN(C(=O)c3cc(C)ccc3-n3nccn3)[C@H](C)CO2)c1] |
| 126 | ((6R)-2-(6-methoxypyridin-2-yl)-6-methyl-1,2,5-oxadiazepan-5-yl) (5-methyl-2-(2H-1,2,3-triazol-2-yl)phenyl)methanone | 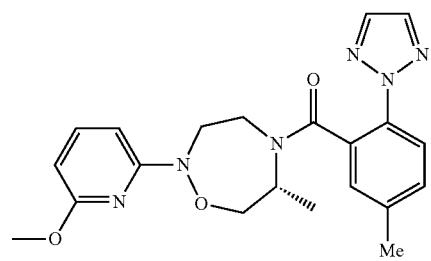 [SMILES: COc1cccc(N2CCN(C(=O)c3cc(C)ccc3-n3nccn3)[C@H](C)CO2)n1] |

TABLE 6-1-continued
| 127 | (5-methyl-2-(2H-1,2,3-triazol-2-yl)phenyl) ((6R)-6-methyl-2-(4-(trifluoromethyl)pyridin-2-yl)-1,2,5-oxadiazepan-5-yl)methanone | 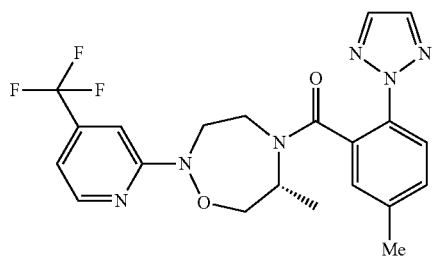 [SMILES: Cc1ccc(-n2nccn2)c(C(=O)N2CCN(c3cc(C(F)(F)F)ccn3)OC[C@H]2C)c1] |
| --- | --- | --- |
| 128 | (5-methyl-2-(2H-1,2,3-triazol-2-yl)phenyl) ((6R)-6-methyl-2-(6-(trifluoromethyl)pyridin-2-yl)-1,2,5-oxadiazepan-5-yl)methanone | 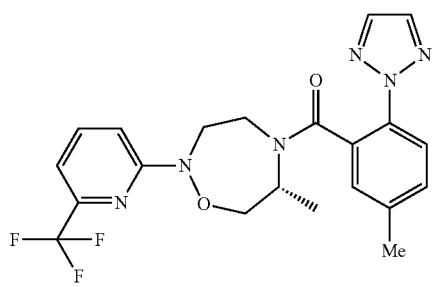 [SMILES: Cc1ccc(-n2nccn2)c(C(=O)N2CCN(c3cccc(C(F)(F)F)n3)OC[C@H]2C)c1] |
| Ex. No. | Additive | MS | Reagent |
| --- | --- | --- | --- |
| 120 | Free | 408.2 | 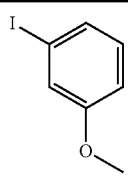 |
| 121 | Free | 413.1 | 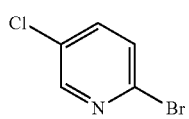 |
| 122 | Free | 413.1 | 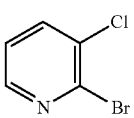 |
| 123 | Free | 409.2 | 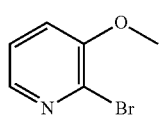 |
| 124 | Free | 393.2 | 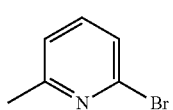 |
| 125 | Free | 393.2 | 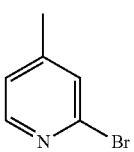 |
| 126 | Free | 409.2 | 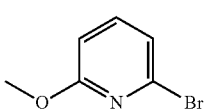 |

TABLE 6-1-continued
| 127 | Free | 447.1 | 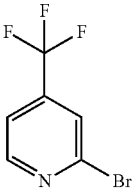 |
| 128 | Free | 447.1 | 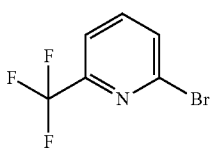 |
TABLE 6-2
| 129 | ((6R)-2-(3,6-dimethylpyrazin-2-yl)-6-methyl-1,2,5-oxadiazepan-5-yl) (5-methyl-2-(2H-1,2,3-triazol-2-yl)phenyl)methanone | 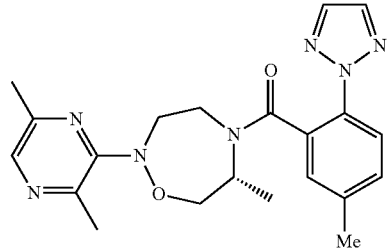 |
| 130 | ((6R)-2-(imidazo[1,2-a]pyridin-2-yl)-6-methyl-1,2,5-oxadiazepan-5-yl) (5-methyl-2-(2H-1,2,3-triazol-2-yl)phenyl)methanone | 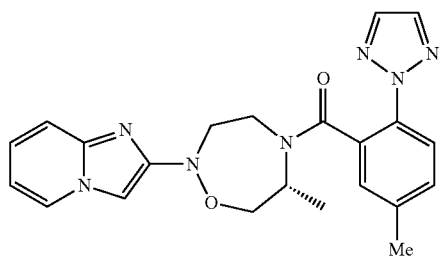 |
| 131 | ((6R)-6-methyl-2-(5-methylpyridin-3-yl)-1,2,5-oxadiazepan-5-yl) (5-methyl-2-(2H-1,2,3-triazol-2-yl)phenyl)methanone | 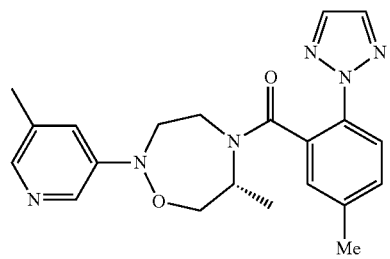 |
| 132 | ((6R)-2-(5-methoxypyridin-3-yl)-6-methyl-1,2,5-oxadiazepan-5-yl) (5-methyl-2-(2H-1,2,3-triazol-2-yl)phenyl)methanone | 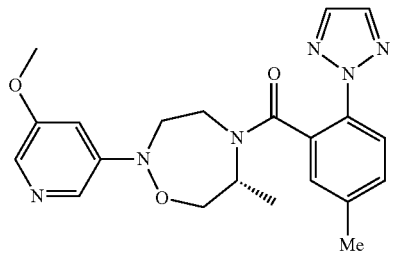 |

TABLE 6-2-continued

| 133 | ((6R)-2-(5-chloropyridin-3-yl)-6-methyl-1,2,5-oxadiazepan-5-yl) (5-methyl-2-(2H-1,2,3-triazol-2-yl)phenyl)methanone | 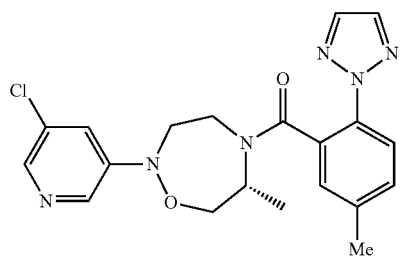 |
| --- | --- | --- |
| 134 | ((6R)-2-(3-chloro-4-fluorophenyl)-6-methyl-1,2,5-oxadiazepan-5-yl) (5-methyl-2-(2H-1,2,3-triazol-2-yl)phenyl)methanone | 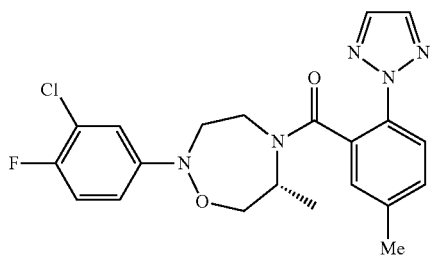 [SMILES: Cc1ccc(-n2nccn2)c(C(=O)N2CCN(c3ccc(F)c(Cl)c3)OC[C@H]2C)c1] |
| 135 | ((6R)-2-(4-fluorophenyl)-6-methyl-1,2,5-oxadiazepan-5-yl) (5-methyl-2-(2H-1,2,3-triazol-2-yl)phenyl)methanone | 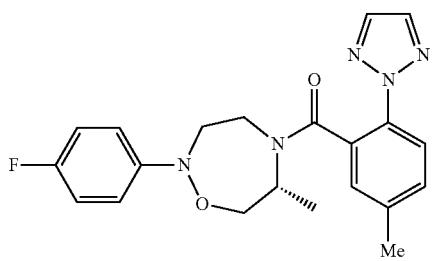 [SMILES: Cc1ccc(-n2nccn2)c(C(=O)N2CCN(c3ccc(F)cc3)OC[C@H]2C)c1] |
| 136 | 2-((6R)-6-methyl-5-(5-methyl-2-(2H-1,2,3-triazol-2-yl)benzoyl)-1,2,5-oxadiazepan-2-yl)isonicotinonitrile | 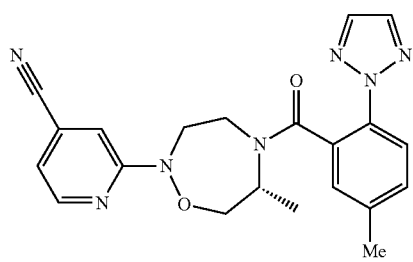 [SMILES: Cc1ccc(-n2nccn2)c(C(=O)N2CCN(c3cc(C#N)ccn3)OC[C@H]2C)c1] |
| 137 | ((6R)-2-(4-methoxypyridin-2-yl)-6-methyl-1,2,5-oxadiazepan-5-yl) (5-methyl-2-(2H-1,2,3-triazol-2-yl)phenyl)methanone | 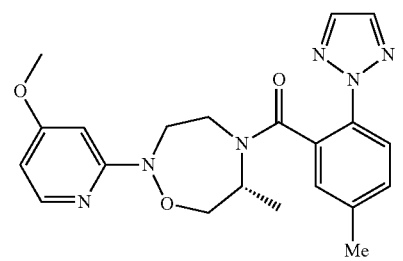 [SMILES: COc1ccnc(N2CCN(C(=O)c3cc(C)ccc3-n3nccn3)[C@H](C)CO2)c1] |
| 129 | Free | 408.2 | 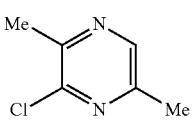 |
| 130 | Free | 418.1 | 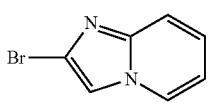 |

TABLE 6-2-continued
| 131 | Free | 393.2 | 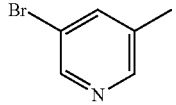 |
| 132 | Free | 409.2 | 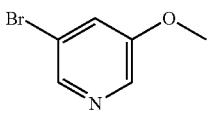 |
| 133 | Free | 413.1 | 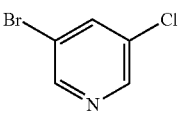 |
| 134 | Free | 430.2 | 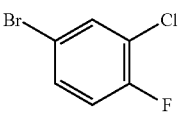 |
| 135 | Free | 396.2 | 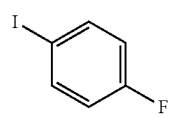 |
| 136 | Free | 404.2 | 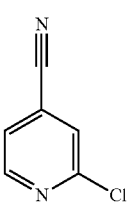 |
| 137 | Free | 409.2 | 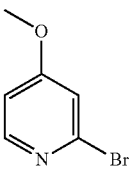 |
TABLE 6-3
| 138 | ((6R)-6-methyl-2-(6-(1H-pyrazol-1-yl)pyridin-2-yl)-1,2,5-oxadiazepan-5-yl) (5-methyl-2-(2H-1,2,3-triazol-2-yl)phenyl)methanone | 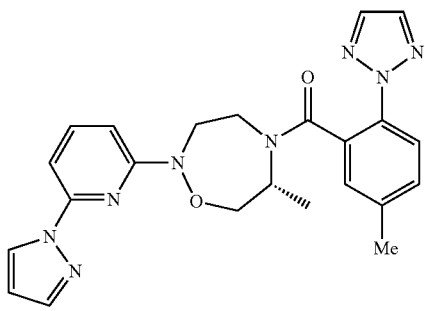 [SMILES: Cc1ccc(-n2nccn2)c(C(=O)N2CCN(c3cccc(-n4cccn4)n3)OC[C@H]2C)c1] |
| 139 | ((6R)-2-(4-(difluoromethyl)pyridin-2-yl)-6-methyl-1,2,5-oxadiazepan-5-yl) (5-methyl-2-(2H-1,2,3-triazol-2-yl)phenyl)methanone | 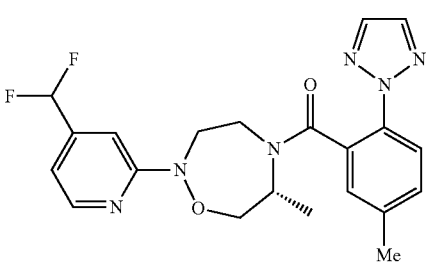 [SMILES: Cc1ccc(-n2nccn2)c(C(=O)N2CCN(c3cc(C(F)F)ccn3)OC[C@H]2C)c1] |

TABLE 6-3-continued

| | | |
|---|---|---|
| 140 | 3-((6R)-6-methyl-5-(5-methyl-2-(2H-1,2,3-triazol-2-yl)benzoyl)-1,2,5-oxadiazepan-2-yl)benzonitrile | 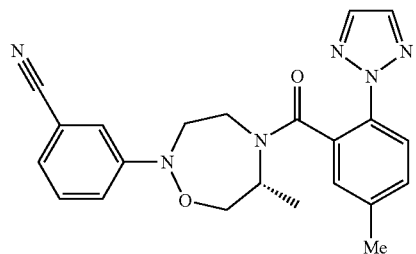 |
| 141 | ((6R)-6-methyl-2-(5-methylpyridin-2-yl)-1,2,5-oxadiazepan-5-yl) (5-methyl-2-(2H-1,2,3-triazol-2-yl)phenyl)methanone | 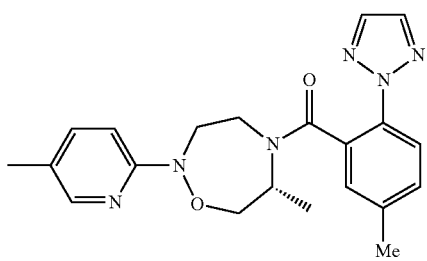 [SMILES: Cc1ccc(N2CCN(C(=O)c3cc(C)ccc3-n3nccn3)[C@H](C)CO2)nc1] |
| 142 | ((6R)-2-(4,6-dimethylpyridin-2-yl)-6-methyl-1,2,5-oxadiazepan-5-yl) (5-methyl-2-(2H-1,2,3-triazol-2-yl)phenyl)methanone | 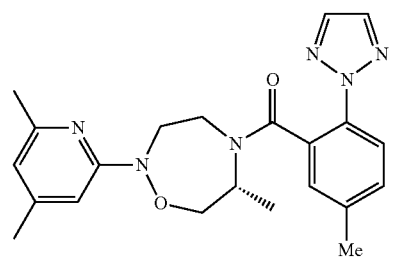 [SMILES: Cc1cc(C)nc(N2CCN(C(=O)c3cc(C)ccc3-n3nccn3)[C@H](C)CO2)c1] |
| 143 | ((6R)-2-(2,6-dimethylpyridin-4-yl)-6-methyl-1,2,5-oxadiazepan-5-yl) (5-methyl-2-(2H-1,2,3-triazol-2-yl)phenyl)methanone | 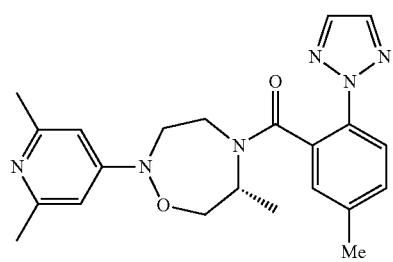 [SMILES: Cc1ccc(-n2nccn2)c(C(=O)N2CCN(c3cc(C)nc(C)c3)OC[C@H]2C)c1] |
| 144 | ((6R)-6-methyl-2-(2-methylpyridin-4-yl)-1,2,5-oxadiazepan-5-yl) (5-methyl-2-(2H-1,2,3-triazol-2-yl)phenyl)methanone | 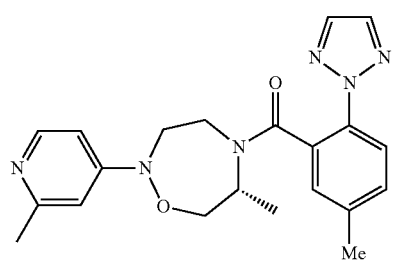 |
| 145 | ((6R)-6-methyl-2-(3-methylpyridin-2-yl)-1,2,5-oxadiazepan-5-yl) (5-methyl-2-(2H-1,2,3-triazol-2-yl)phenyl)methanone | 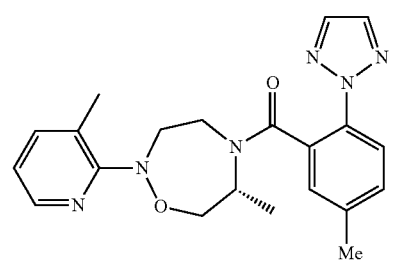 [SMILES: Cc1ccc(-n2nccn2)c(C(=O)N2CCN(c3ncccc3C)OC[C@H]2C)c1] |

TABLE 6-3-continued
| 146 | (5-methyl-2-(2H-1,2,3-triazol-2-yl)phenyl) ((6R)-6-methyl-2-(2-(trifluoromethyl)pyridin-4-yl)-1,2,5-oxadiazepan-5-yl)methanone | | 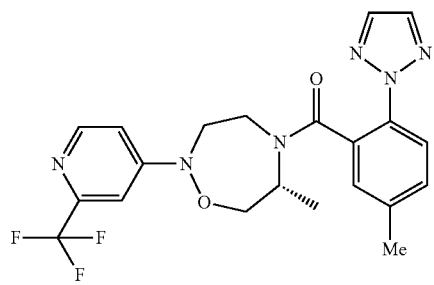 [SMILES: Cc1ccc(-n2nccn2)c(C(=O)N2CCN(c3ccnc(C(F)(F)F)c3)OC[C@H]2C)c1] |
|---|---|---|---|
| 138 | Free | 445.2 | 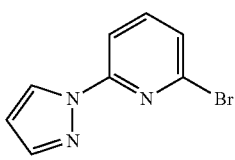 [SMILES: Brc1cccc(-n2cccn2)n1] |
| 139 | Free | 429.2 | 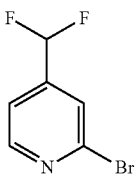 |
| 140 | Free | 403.2 | 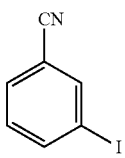 |
| 141 | Free | 393.2 | 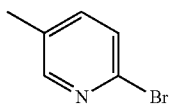 |
| 142 | Free | 407.2 | 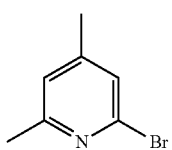 |
| 143 | Free | 407.2 | 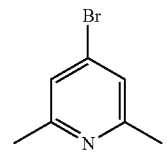 |
| 144 | Free | 393.2 | 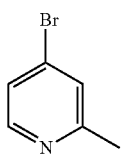 |
| 145 | Free | 393.2 | 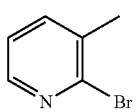 |

TABLE 6-3-continued

| 146 | Free | 447.1 | 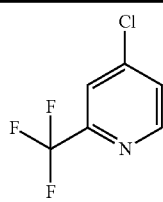 |

The compounds of Examples 147 to 152 were produced using 2-benzyl 5-tert-butyl (6R)-6-methyl-1,2,5-oxadiazepane-2,5-dicarboxylate obtained in Step B of Example 6 and the reagents corresponding to the compounds of Examples 147 to 152 (the reagents can be produced according to a method known per se) according to the same method as in Step A of Example 2 and Steps D and E of Example 6, or a method analogous thereto. MS in the tables means actual measured value.

TABLE 7

| Ex. No. | IUPAC Name | Structure |
|---|---|---|
| 147 | ((6R)-2-(4,6-dimethylpyrimidin-2-yl)-6-methyl-1,2,5-oxadiazepan-5-yl) (2-(2H-1,2,3-triazol-2-yl)phenyl)methanone | 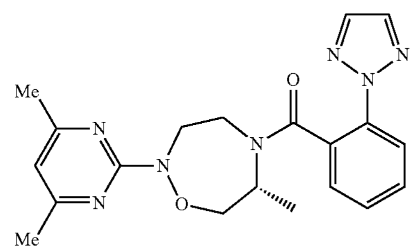 [SMILES: Cc1cc(C)nc(N2CCN(C(=O)c3ccccc3-n3nccn3)[C@H](C)CO2)n1] |
| 148 | ((6R)-2-(2,6-dimethylpyrimidin-4-yl)-6-methyl-1,2,5-oxadiazepan-5-yl) (2-(2H-1,2,3-triazol-2-yl)phenyl)methanone | 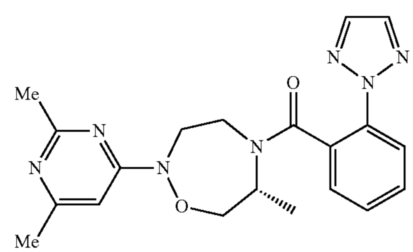 [SMILES: Cc1cc(N2CCN(C(=O)c3ccccc3-n3nccn3)[C@H](C)CO2)nc(C)n1] |
| 149 | ((6R)-2-(5-fluoro-4-hydroxypyrimidin-2-yl)-6-methyl-1,2,5-oxadiazepan-5-yl) (2-(2H-1,2,3-triazol-2-yl)phenyl)methanone | 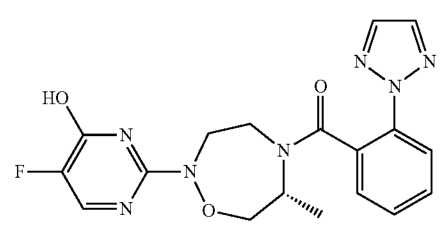 [SMILES: C[C@@H]1CON(c2ncc(F)c(O)n2)CCN1C(=O)c1ccccc1-n1nccn1] |
| 150 | ((6R)-2-(6-cyclopropylpyrimidin-4-yl)-6-methyl-1,2,5-oxadiazepan-5-yl) (2-(2H-1,2,3-triazol-2-yl)phenyl)methanone | 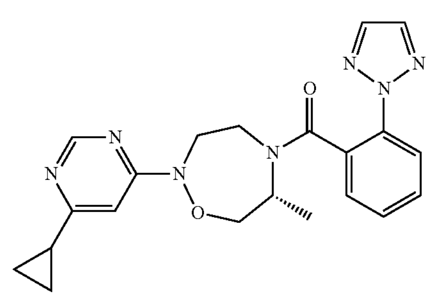 [SMILES: C[C@@H]1CON(c2cc(C3CC3)ncn2)CCN1C(=O)c1ccccc1-n1nccn1] |

TABLE 7-continued

| | | | |
|---|---|---|---|
| 151 | ((6R)-2-(4-ethylpyrimidin-2-yl)-6-methyl-1,2,5-oxadiazepan-5-yl) (2-(2H-1,2,3-triazol-2-yl)phenyl)methanone | 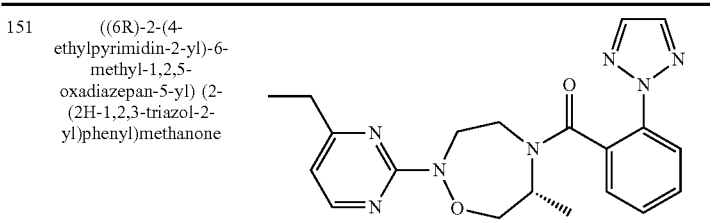 | |
| 152 | 6-methyl-2-((6R)-6-methyl-5-(2-(2H-1,2,3-triazol-2-yl)benzoyl)-1,2,5-oxadiazepan-2-yl)pyrimidine-4-carbonitrile | 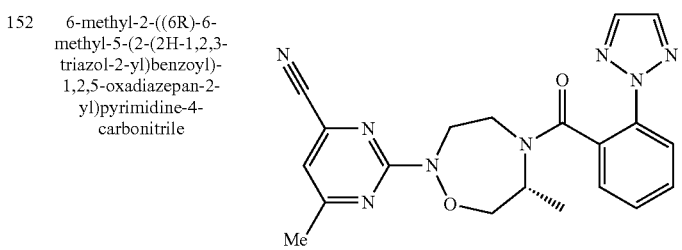 | |

| Ex. No. | Additive | MS | Reagent |
|---|---|---|---|
| 147 | Free | 394 | 2-chloro-4,6-dimethylpyrimidine |
| 148 | Free | 394.1 | 4-chloro-2,6-dimethylpyrimidine |
| 149 | Free | 400 | 2-chloro-5-fluoro-4-methoxypyrimidine |
| 150 | Free | 406.1 | 4-chloro-6-cyclopropylpyrimidine |
| 151 | Free | 394.2 | 2-chloro-4-ethylpyrimidine |
| 152 | Free | 405.1 | 2-chloro-6-methylpyrimidine-4-carbonitrile |

Example 153

((6R)-2-(2,6-dimethoxypyrimidin-4-yl)-6-methyl-1,2,5-oxadiazepan-5-yl)(2-(2H-1,2,3-triazol-2-yl)phenyl)methanone

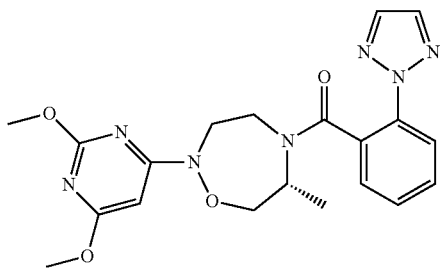 [SMILES: COc1cc(N2CCN(C(=O)c3ccccc3-n3nccn3)[C@H](C)CO2)nc(OC)n1]

A) ((6R)-6-methyl-1,2,5-oxadiazepan-5-yl)(2-(2H-1,2,3-triazol-2-yl)phenyl)methanone hydrobromide The title compound (1088 mg) was obtained using 2-benzyl 5-tert-butyl (6R)-6-methyl-1,2,5-oxadiazepane-2,5-dicarboxylate obtained in Step B of Example 6 and 2-(2H-1,2,3-triazol-2-yl)benzoic acid obtained in Reference Example 2 in the same manner as in Steps C and D of Example 6.

MS: [M+H−HBr]+ 288.2.

B) ((6R)-2-(2,6-dimethoxypyrimidin-4-yl)-6-methyl-1,2,5-oxadiazepan-5-yl)(2-(2H-1,2,3-triazol-2-yl)phenyl)methanone To a solution of ((6R)-6-methyl-1,2,5-oxadiazepan-5-yl)(2-(2H-1,2,3-triazol-2-yl)phenyl)methanone hydrobromide (90 mg) obtained in Step A of Example 153 in 2-propanol (3.0 mL) were added 4-chloro-2,6-dimethoxypyrimidine (85 mg) and acetic acid (33.8 mg), and the mixture was stirred at 100° C. for 2 hr. To the reaction mixture was added diisopropylethylamine (0.427 mL), the mixture was stirred overnight at 70° C., and the solvent was evaporated under reduced pressure. The residue was purified by column chromatography (hexane/ethyl acetate) and column chromatography (NH, hexane/ethyl acetate) to give the title compound (3.7 mg).

MS: [M+H]+ 426.1.

Example 154

((6R)-2-(2-tert-butyl-6-methylpyrimidin-4-yl)-6-methyl-1,2,5-oxadiazepan-5-yl)(2-(2H-1,2,3-triazol-2-yl)phenyl)methanone

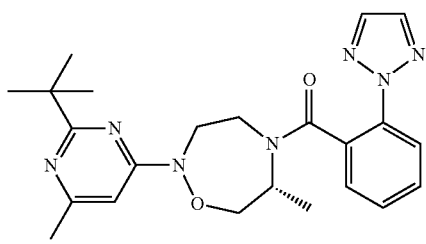 [SMILES: Cc1cc(N2CCN(C(=O)c3ccccc3-n3nccn3)[C@H](C)CO2)nc(C(C)(C)C)n1]

A mixture of ((6R)-6-methyl-1,2,5-oxadiazepan-5-yl)(2-(2H-1,2,3-triazol-2-yl)phenyl)methanone hydrobromide (90 mg) obtained in Step A of Example 153 and 2-tert-butyl-4-chloro-6-methylpyrimidine (90 mg) obtained in Reference Example 27 in 2-propanol (5.0 mL) was stirred at 100° C. for 2 hr, and then stirred overnight at 70° C. The solvent was evaporated under reduced pressure, saturated aqueous sodium hydrogencarbonate solution was added thereto, and the mixture was extracted with ethyl acetate. The obtained organic layer was dried over sodium sulfate, and the solvent was evaporated under reduced pressure. The residue was purified by column chromatography (hexane/ethyl acetate) to give the title compound (60 mg).

MS: [M+H]+ 436.2.

Example 155

((6R)-6-methyl-2-(6-methyl-2-(1-methylcyclopropyl)pyrimidin-4-yl-1,2,5-oxadiazepan-5-yl)(2-(2H-1,2,3-triazol-2-yl)phenyl)methanone hydrochloride

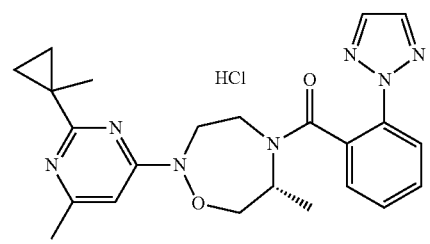 [SMILES: Cc1cc(N2CCN(C(=O)c3ccccc3-n3nccn3)[C@H](C)CO2)nc(C2(C)CC2)n1 ; Cl]

A mixture of ((6R)-6-methyl-1,2,5-oxadiazepan-5-yl)(2-(2H-1,2,3-triazol-2-yl)phenyl)methanone hydrobromide (74 mg) obtained in Step A of Example 153 and 4-chloro-6-methyl-2-(1-methylcyclopropyl)pyrimidine (147 mg) obtained in Reference Example 28 in 2-propanol (3.0 mL) was stirred at 100° C. for 2 hr, and then overnight at 70° C. The solvent was evaporated under reduced pressure, and the residue was purified by column chromatography (ethyl acetate/methanol). The crude product was crystallized (ethyl acetate/methanol), and to the precipitate was added 4M hydrogen chloride ethyl acetate (0.010 mL) solution. The solvent was evaporated under reduced pressure to give the title compound (50 mg).

MS: [M+H−HCl]+ 434.2.

Example 156

6-methyl-2-((6R)-6-methyl-5-(2-(2H-1,2,3-triazol-2-yl)benzoyl)-1,2,5-oxadiazepan-2-yl)nicotinonitrile

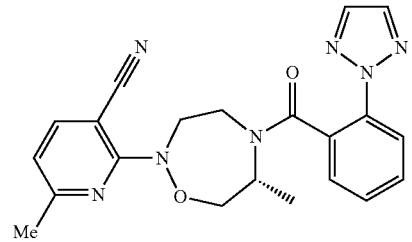 [SMILES: Cc1ccc(C#N)c(N2CCN(C(=O)c3ccccc3-n3nccn3)[C@H](C)CO2)n1]

To a solution of ((6R)-6-methyl-1,2,5-oxadiazepan-5-yl)(2-(2H-1,2,3-triazol-2-yl)phenyl)methanone hydrobromide (80 mg) obtained in Step A of Example 153 in toluene (2.0 mL) were added 2-chloro-6-methylnicotinonitrile (43.1 mg), sodium tert-butoxide (62.6 mg), 2,2'-bis(diphenylphosphino)-1,1'-binaphthyl (27.1 mg) and tris(dibenzylideneacetone)dipalladium(0) (19.89 mg), and the mixture was stirred overnight at 70° C. To the reaction mixture was added saturated aqueous sodium hydrogencarbonate solution, and the mixture was extracted with ethyl acetate. The obtained organic layer was dried over magnesium sulfate, and the solvent was evaporated under reduced pressure. The residue was purified by column chromatography (NH, hexane/ethyl acetate). The obtained crude product was purified by HPLC (C18, mobile phase: water/acetonitrile (containing 0.1% TFA)), to the obtained fraction was added saturated aqueous sodium hydrogencarbonate solution, and the solvent was evaporated under reduced pressure. The obtained mixture was extracted with ethyl acetate. The organic layer was dried over anhydrous magnesium sulfate, and concentrated under reduced pressure to give the title compound (7.0 mg).

MS: [M+H]$^+$ 404.1.

Example 157

((6R)-2-(6-methoxypyridin-2-yl)-6-methyl-1,2,5-oxadiazepan-5-yl)(2-(2H-1,2,3-triazol-2-yl)phenyl)methanone

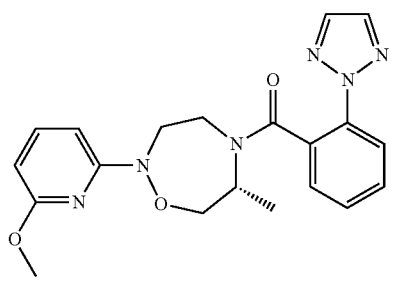 [SMILES: COc1cccc(N2CCN(C(=O)c3ccccc3-n3nccn3)[C@H](C)CO2)n1]

The title compound (52 mg) was obtained using ((6R)-6-methyl-1,2,5-oxadiazepan-5-yl)(2-(2H-1,2,3-triazol-2-yl)phenyl)methanone hydrobromide (100 mg) obtained in Step A of Example 153 and 2-bromo-6-methoxypyridine (0.067 mL) in the same manner as in Example 33.

MS: [M+H]$^+$ 395.2.

Example 158

((6R)-2-(6-(hydroxymethyl)pyridin-2-yl)-6-methyl-1,2,5-oxadiazepan-5-yl)(2-(2H-1,2,3-triazol-2-yl)phenyl)methanone

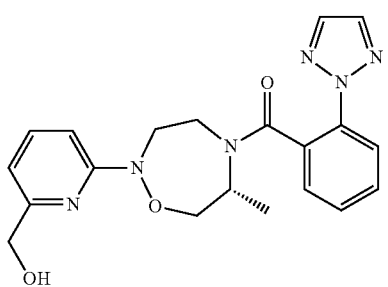 [SMILES: C[C@@H]1CON(c2cccc(CO)n2)CCN1C(=O)c1ccccc1-n1nccn1]

The title compound (4.0 mg) was obtained using ((6R)-6-methyl-1,2,5-oxadiazepan-5-yl)(2-(2H-1,2,3-triazol-2-yl)phenyl)methanone hydrobromide (20 mg) obtained in Step A of Example 153 and (6-bromopyridin-2-yl)methanol (25.5 mg) in the same manner as in Step C of Example 36.

MS: [M+H]$^+$ 395.1.

Example 159

((6R)-2-(4-methoxy-1,3,5-triazin-2-yl)-6-methyl-1,2,5-oxadiazepan-5-yl)(2-(2H-1,2,3-triazol-2-yl)phenyl)methanone

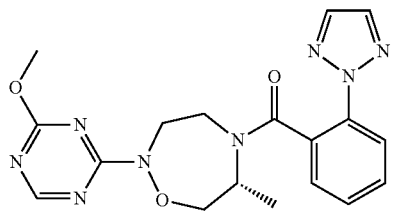 [SMILES: COc1ncnc(N2CCN(C(=O)c3ccccc3-n3nccn3)[C@H](C)CO2)n1]

To a solution of ((6R)-6-methyl-1,2,5-oxadiazepan-5-yl)(2-(2H-1,2,3-triazol-2-yl)phenyl)methanone hydrobromide (138 mg) obtained in Step A of Example 153 in acetone (10 mL) were added 2,4-dichloro-1,3,5-triazine (112 mg) and diisopropylethylamine (0.262 mL) under ice-cooling, and the mixture was stirred at 0° C. for 2 hr. The solvent was evaporated under reduced pressure, to a solution of the obtained residue in methanol (5.0 mL) was added 28% sodium methoxide methanol (1.0 mL) solution at 0° C., and the mixture was stirred for 0.5 hr. The reaction mixture was cooled to 0° C., water was added thereto, and the mixture was extracted with ethyl acetate. The obtained organic layer was dried over sodium sulfate, and the solvent was evaporated under reduced pressure. The residue was purified by column chromatography (ethyl acetate/methanol), and recrystallized (hexane/ethyl acetate) to give the title compound (37 mg).

MS: [M+H]$^+$ 397.1.

Example 160

((6R)-2-(6-methoxy-2-methylpyrimidin-4-yl)-6-methyl-1,2,5-oxadiazepan-5-yl)(2-(2H-1,2,3-triazol-2-yl)phenyl)methanone

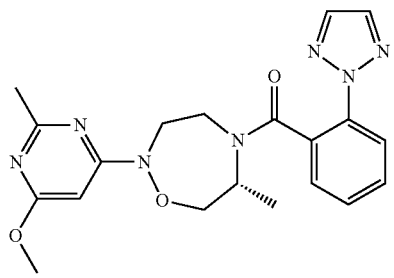 [SMILES: COc1cc(N2CCN(C(=O)c3ccccc3-n3nccn3)[C@H](C)CO2)nc(C)n1]

The title compound (6.2 mg) was obtained using ((6R)-6-methyl-1,2,5-oxadiazepan-5-yl)(2-(2H-1,2,3-triazol-2-yl)phenyl)methanone hydrobromide (12 mg) obtained in Step A of Example 153 and 4,6-dichloro-2-methylpyrimidine (10.62 mg) in the same manner as in Example 159.
MS: [M+H]⁺ 410.1.

Example 161

((6R)-2-(4,6-dimethylpyrimidin-2-yl)-6-methyl-1,2,5-oxadiazepan-5-yl)(5-fluoro-2-(2H-1,2,3-triazol-2-yl)phenyl)methanone hydrochloride

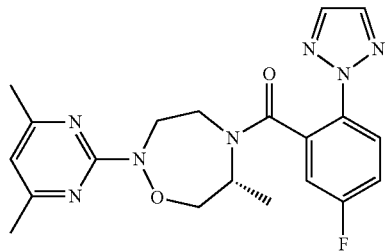 [SMILES: Cc1cc(C)nc(N2CCN(C(=O)c3cc(F)ccc3-n3nccn3)[C@H](C)CO2)n1]

A) (5-fluoro-2-(2H-1,2,3-triazol-2-yl)phenyl)((6R)-6-methyl-1,2,5-oxadiazepan-5-yl)methanone hydrobromide The title compound (1.099 g) was obtained using 2-benzyl 5-tert-butyl (6R)-6-methyl-1,2,5-oxadiazepane-2,5-dicarboxylate (1.538 g) obtained in Step B of Example 6 and 5-fluoro-2-(2H-1,2,3-triazol-2-yl)benzoic acid (1.0 g) obtained in Reference Example 1 in the same manner as in Steps C and D of Example 6.
MS: [M+H]⁺ 306.1.

B) ((6R)-2-(4,6-dimethylpyrimidin-2-yl)-6-methyl-1,2,5-oxadiazepan-5-yl)(5-fluoro-2-(2H-1,2,3-triazol-2-yl)phenyl)methanone hydrochloride The title compound (39 mg) was obtained using (5-fluoro-2-(2H-1,2,3-triazol-2-yl)phenyl)((6R)-6-methyl-1,2,5-oxadiazepan-5-yl)methanone hydrobromide (90 mg) obtained in Step A of Example 161 and 2-chloro-4,6-dimethylpyrimidine (36.5 mg) in the same manner as in Step E of Example 6.
MS: [M+H−HCl]⁺ 412.1.

Example 162

((6R)-2-(2,6-dimethylpyrimidin-4-yl)-6-methyl-1,2,5-oxadiazepan-5-yl)(5-fluoro-2-(2H-1,2,3-triazol-2-yl)phenyl)methanone

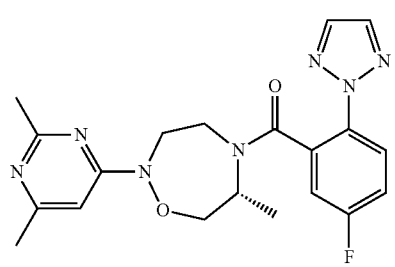 [SMILES: Cc1cc(N2CCN(C(=O)c3cc(F)ccc3-n3nccn3)[C@H](C)CO2)nc(C)n1]

The title compound (46 mg) was obtained using (5-fluoro-2-(2H-1,2,3-triazol-2-yl)phenyl)((6R)-6-methyl-1,2,5-oxadiazepan-5-yl)methanone hydrobromide (90 mg) obtained in Step A of Example 161 and 4-chloro-2,6-dimethylpyrimidine (36.5 mg) in the same manner as in Step E of Example 6.
MS: [M+H]⁺ 412.1.

Example 163

2-((6R)-5-(5-fluoro-2-(2H-1,2,3-triazol-2-yl)benzoyl)-6-methyl-1,2,5-oxadiazepan-2-yl)-6-methylpyrimidine-4-carbonitrile

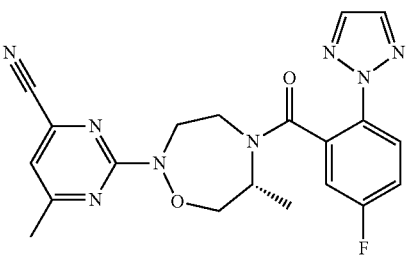 [SMILES: Cc1cc(C#N)nc(N2CCN(C(=O)c3cc(F)ccc3-n3nccn3)[C@H](C)CO2)n1]

The title compound (62 mg) was obtained using (5-fluoro-2-(2H-1,2,3-triazol-2-yl)phenyl)((6R)-6-methyl-1,2,5-oxadiazepan-5-yl)methanone hydrobromide (90 mg) obtained in Step A of Example 161 and 2-chloro-6-methylpyrimidine-4-carbonitrile (39.4 mg) in the same manner as in Step E of Example 6.
MS: [M+H]⁺ 423.1.

Example 164

(5-fluoro-2-(2H-1,2,3-triazol-2-yl)phenyl)((6R)-6-methyl-2-(4-methyl-1,3-thiazol-2-yl)-1,2,5-oxadiazepan-5-yl)methanone

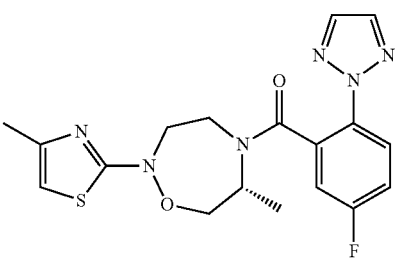 [SMILES: Cc1csc(N2CCN(C(=O)c3cc(F)ccc3-n3nccn3)[C@H](C)CO2)n1]

The title compound (11.7 mg) was obtained using (5-fluoro-2-(2H-1,2,3-triazol-2-yl)phenyl)((6R)-6-methyl-1,2,5-oxadiazepan-5-yl)methanone hydrobromide (50 mg) obtained in Step A of Example 161 and 2-chloro-4-methyl-1,3-thiazole (25.9 mg) in the same manner as in Example 33.
MS: [M+H]⁺ 403.1.

Example 165

(5-fluoro-2-(2H-1,2,3-triazol-2-yl)phenyl)((6R)-6-methyl-2-(5-methyl-5H-pyrrolo[3,2-d]pyrimidin-4-yl)-1,2,5-oxadiazepan-5-yl)methanone

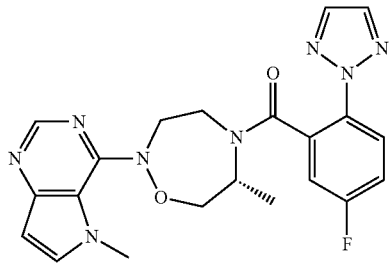 [SMILES: C[C@@H]1CON(c2ncnc3ccn(C)c23)CCN1C(=O)c1cc(F)ccc1-n1nccn1]

The title compound (43.9 mg) was obtained using (5-fluoro-2-(2H-1,2,3-triazol-2-yl)phenyl)((6R)-6-methyl-1,2,5-oxadiazepan-5-yl)methanone hydrobromide (67.8 mg) obtained in Step A of Example 161 and 4-chloro-5-methyl-5H-pyrrolo[3,2-d]pyrimidine (34.7 mg) in the same manner as in Step H of Example 1.
MS: [M+H]$^+$ 437.1.

Example 166

((6R)-2-(5-fluoro-4,6-dimethylpyrimidin-2-yl)-6-methyl-1,2,5-oxadiazepan-5yl)(5-fluoro-2-(2H-1,2,3-triazol-2-yl)phenyl)methanone

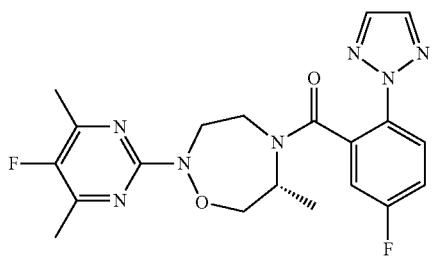 [SMILES: Cc1nc(N2CCN(C(=O)c3cc(F)ccc3-n3nccn3)[C@H](C)CO2)nc(C)c1F]

The title compound (22.6 mg) was obtained using (5-fluoro-2-(2H-1,2,3-triazol-2-yl)phenyl)((6R)-6-methyl-1,2,5-oxadiazepan-5-yl)methanone hydrobromide (70 mg) obtained in Step A of Example 161 and 2-chloro-5-fluoro-4,6-dimethylpyrimidine (60 mg) obtained in Reference Example 29 in the same manner as in Step H of Example 1.
MS: [M+H]$^+$ 430.1.

Example 167

((6R)-2-(5-chloro-4,6-dimethylpyrimidin-2-yl)-6-methyl-1,2,5-oxadiazepan-5-yl)(5-fluoro-2-(2H-1,2,3-triazol-2-yl)phenyl)methanone

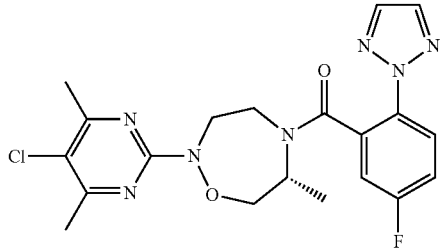 [SMILES: Cc1nc(N2CCN(C(=O)c3cc(F)ccc3-n3nccn3)[C@H](C)CO2)nc(C)c1Cl]

The title compound (36 mg) was obtained using (5-fluoro-2-(2H-1,2,3-triazol-2-yl)phenyl)((6R)-6-methyl-1,2,5-oxadiazepan-5-yl)methanone hydrobromide (73 mg) obtained in Step A of Example 161 and 2,5-dichloro-4,6-dimethylpyrimidine (42.8 mg) obtained in Reference Example 30 in the same manner as in Step H of Example 1.
MS: [M+H]$^+$ 446.1.

Example 168

((6R)-2-(2,6-dimethylpyrimidin-4-yl)-6-ethyl-1,2,5-oxadiazepan-5-yl)(2-(2H-1,2,3-triazol-2-yl)phenyl)methanone

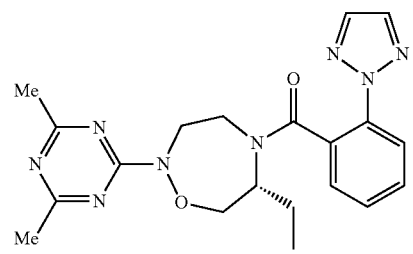 [SMILES: CC[C@@H]1CON(c2nc(C)nc(C)n2)CCN1C(=O)c1ccccc1-n1nccn1]

The title compound (129.1 mg) was obtained using (2R)-2-aminobutan-1-ol and 2-(2H-1,2,3-triazol-2-yl)benzoic acid obtained in Reference Example 2 in the same manner as in Steps A, B and C of Example 1, Step A of Example 6, Step A of Example 87 and Steps G and H of Example 1.
MS: [M+H]$^+$ 408.2.

Example 169

((6R)-2-(2,6-dimethylpyrimidin-4-yl)-6-ethyl-1,2,5-oxadiazepan-5-yl)(2-(1,3-thiazol-2-yl)phenyl)methanone

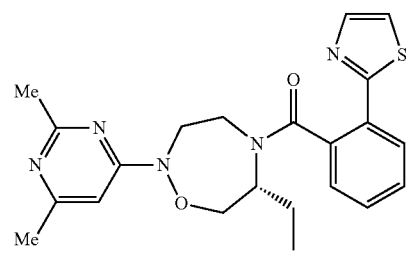 [SMILES: CC[C@@H]1CON(c2cc(C)nc(C)n2)CCN1C(=O)c1ccccc1-c1nccs1]

The title compound (117.4 mg) was obtained using (2R)-2-aminobutan-1-ol and 2-(1,3-thiazol-2-yl)benzoic acid obtained in Reference Example 4 in the same manner as in Steps A, B and C of Example 1, Step A of Example 6, Step A of Example 87 and Steps G and H of Example 1.
MS: [M+H]$^+$ 424.1.

Example 170

((6S)-2-(2,6-dimethylpyrimidin-4-yl)-6-methyl-1,2,5-oxadiazepan-5-yl)(2-(2H-1,2,3-triazol-2-yl)phenyl)methanone

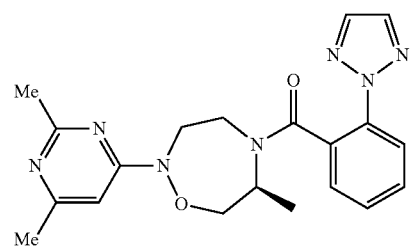 [SMILES: Cc1cc(N2CCN(C(=O)c3ccccc3-n3nccn3)[C@@H](C)CO2)nc(C)n1]

The title compound (20 mg) was obtained using tert-butyl ((2S)-1-hydroxypropan-2-yl)carbamate and 2-(2H-1,2,3-triazol-2-yl)benzoic acid obtained in Reference Example 2 in the same manner as in Steps A and B of Example 5 and Example 6.

MS: [M+H]$^+$ 394.1.

Example 171

((6S)-2-(2,6-dimethylpyrimidin-4-yl)-6-methyl-1,2,5-oxadiazepan-5-yl)(2-(1,3-thiazol-2-yl)phenyl)methanone

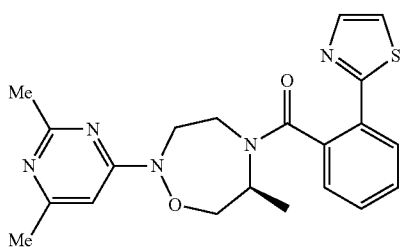 [SMILES: Cc1cc(N2CCN(C(=O)c3ccccc3-c3nccs3)[C@@H](C)CO2)nc(C)n1]

The title compound (50 mg) was obtained using tert-butyl ((2S)-1-hydroxypropan-2-yl)carbamate and 2-(1,3-thiazol-2-yl)benzoic acid obtained in Reference Example 4 in the same manner as in Steps A and B of Example 5 and Example 6.

MS: [M+H]$^+$ 410.2.

Example 172

((4S,6R)-2-(2,6-dimethylpyrimidin-4-yl)-4,6-dimethyl-1,2,5-oxadiazepan-5-yl)(2-(2H-1,2,3-triazol-2-yl)phenyl)methanone

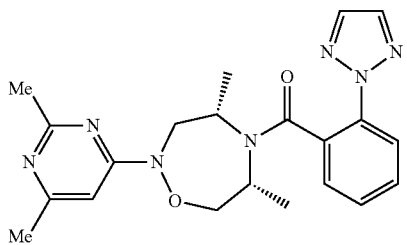 [SMILES: Cc1cc(N2C[C@H](C)N(C(=O)c3ccccc3-n3nccn3)[C@H](C)CO2)nc(C)n1]

A) benzyl (4S,6R)-4,6-dimethyl-5-(2-(2H-1,2,3-triazol-2-yl)benzoyl)-1,2,5-oxadiazepane-2-carboxylate The title compound (910 mg) was obtained using benzyl (4S,6R)-4,6-dimethyl-1,2,5-oxadiazepane-2-carboxylate (600 mg) obtained in Step D of Example 5 and 2-(2H-1,2,3-triazol-2-yl)benzoic acid (558 mg) obtained in Reference Example 2 in the same manner as in Step E of Example 5.

MS: [M+H]$^+$ 436.1.

B) ((4S,6R)-4,6-dimethyl-1,2,5-oxadiazepan-5-yl)(2-(2H-1,2,3-triazol-2-yl)phenyl)methanone hydrobromide The title compound (900 mg) was obtained using benzyl (4S,6R)-4,6-dimethyl-5-(2-(2H-1,2,3-triazol-2-yl)benzoyl)-1,2,5-oxadiazepane-2-carboxylate (910 mg) obtained in Step A of Example 172 in the same manner as in Step D of Example 6.

MS: [M+H–HBr]$^+$ 302.2.

C) ((4S,6R)-2-(2,6-dimethylpyrimidin-4-yl)-4,6-dimethyl-1,2,5-oxadiazepan-5-yl)(2-(2H-1,2,3-triazol-2-yl)phenyl)methanone The title compound (62 mg) was obtained using ((4S,6R)-4,6-dimethyl-1,2,5-oxadiazepan-5-yl)(2-(2H-1,2,3-triazol-2-yl)phenyl)methanone hydrobromide (100 mg) obtained in Step B of Example 172 and 4-chloro-2,6-dimethylpyrimidine (37.3 mg) in the same manner as in Step E of Example 6.

MS: [M+H]$^+$ 408.1.

The compounds of Examples 173 to 175 were produced using ((4S,6R)-4,6-dimethyl-1,2,5-oxadiazepan-5-yl)(2-(2H-1,2,3-triazol-2-yl)phenyl)methanone hydrobromide obtained in Step B of Example 172 and the reagents corresponding to the compounds of Examples 173 to 175 (the reagents can be produced according to a method known per se) according to the same method as in Step C of Example 172, or a method analogous thereto. MS in the tables means actual measured value.

TABLE 8

| Ex. No. | IUPAC Name | Structure |
|---|---|---|
| 173 | ((4S,6R)-4,6-dimethyl-2-(2-methylpyrimidin-4-yl)-1,2,5-oxadiazepan-5-yl) (2-(2H-1,2,3-triazol-2-yl)phenyl)methanone | 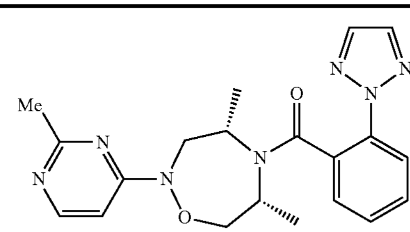 |

TABLE 8-continued

| | | | | |
|---|---|---|---|---|
| 174 | ((4S,6R)-4,6-dimethyl-2-(6-methylpyrimidin-4-yl)-1,2,5-oxadiazepan-5-yl) (2-(2H-1,2,3-triazol-2-yl)phenyl)methanone | | 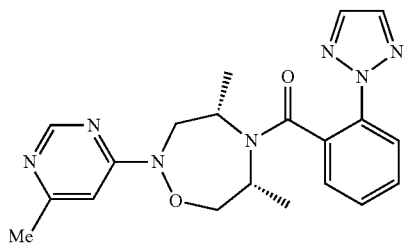 [SMILES: Cc1cc(N2C[C@H](C)N(C(=O)c3ccccc3-n3nccn3)[C@H](C)CO2)ncn1] | |
| 175 | ((4S,6R)-2-(2-cyclopropylpyrimidin-4-yl)-4,6-dimethyl-1,2,5-oxadiazepan-5-yl) (2-(2H-1,2,3-triazol-2-yl)phenyl)methanone | | 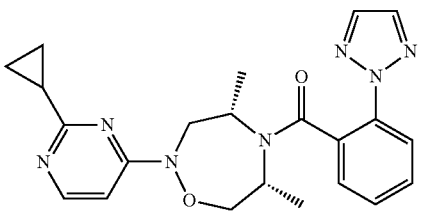 [SMILES: C[C@@H]1CON(c2ccnc(C3CC3)n2)C[C@H](C)N1C(=O)c1ccccc1-n1nccn1] | |

| Ex. No. | Additive | MS | Reagent | |
|---|---|---|---|---|
| 173 | Free | 394.2 | 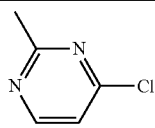 | |
| 174 | Free | 394.2 | 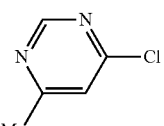 | |
| 175 | Free | 420.2 | 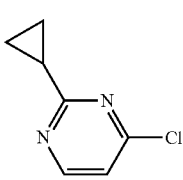 | |

Example 176

((4S,6R)-2-(2,6-dimethylpyrimidin-4-yl)-4,6-dimethyl-1,2,5-oxadiazepan-5-yl)(5-methyl-2-(2H-1,2,3-triazol-2-yl)phenyl)methanone

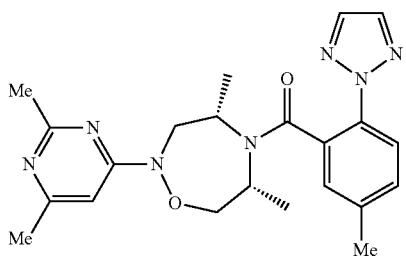 [SMILES: Cc1ccc(-n2nccn2)c(C(=O)N2[C@H](C)CON(c3cc(C)nc(C)n3)C[C@@H]2C)c1]

A) benzyl (4S,6R)-4,6-dimethyl-5-(5-methyl-2-(2H-1,2,3-triazol-2-yl)benzoyl)-1,2,5-oxadiazepane-2-carboxylate The title compound (117 mg) was obtained using benzyl (4S,6R)-4,6-dimethyl-1,2,5-oxadiazepane-2-carboxylate (76 mg) obtained in Step D of Example 5 and 5-methyl-2-(2H-1,2,3-triazol-2-yl)benzoic acid (70.1 mg) in the same manner as in Step E of Example 5.

MS: [M+H]$^+$ 450.1.

B) ((4S,6R)-2-(2,6-dimethylpyrimidin-4-yl)-4,6-dimethyl-1,2,5-oxadiazepan-5-yl)(5-methyl-2-(2H-1,2,3-triazol-2-yl)phenyl)methanone The title compound (68 mg) was obtained using benzyl (4S,6R)-4,6-dimethyl-5-(5-methyl-2-(2H-1,2,3-triazol-2-yl)benzoyl)-1,2,5-oxadiazepane-2-carboxylate (117 mg) obtained in Step A of Example 176 in the same manner as in Steps D and E of Example 6.

MS: [M+H]$^+$ 422.2.

The compounds of Examples 177 to 179 were produced using benzyl (4S,6R)-4,6-dimethyl-5-(5-methyl-2-(2H-1,2,3-triazol-2-yl)benzoyl)-1,2,5-oxadiazepane-2-carboxylate obtained in Step A of Example 176 and the reagents corresponding to the compounds of Examples 177 to 179 (the reagents can be produced according to a method known per se) according to the same method as in Step B of Example 176, or a method analogous thereto. MS in the tables means actual measured value.

TABLE 9

| Ex. No. | IUPAC Name | Structure |
|---|---|---|
| 177 | ((4S,6R)-4,6-dimethyl-2-(6-methyl-2-(trifluoromethyl)pyrimidin-4-yl)-1,2,5-oxadiazepan-5-yl) (5-methyl-2-(2H-1,2,3-triazol-2-yl)phenyl)methanone | 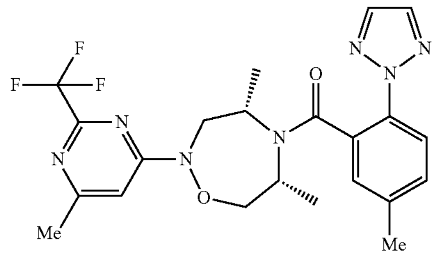 [SMILES: Cc1ccc(-n2nccn2)c(C(=O)N2[C@H](C)CON(c3cc(C)nc(C(F)(F)F)n3)C[C@@H]2C)c1] |
| 178 | ((4S,6R)-4,6-dimethyl-2-(2-methyl-6-(trifluoromethyl)pyrimidin-4-yl)-1,2,5-oxadiazepan-5-yl) (5-methyl-2-(2H-1,2,3-triazol-2-yl)phenyl)methanone | 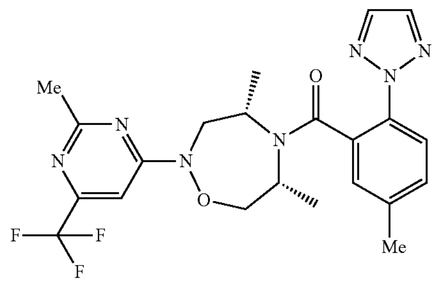 [SMILES: Cc1ccc(-n2nccn2)c(C(=O)N2[C@H](C)CON(c3cc(C(F)(F)F)nc(C)n3)C[C@@H]2C)c1] |
| 179 | ((4S,6R)-2-(6-(difluoromethyl)-2-methylpyrimidin-4-yl)-4,6-dimethyl-1,2,5-oxadiazepan-5-yl) (5-methyl-2-(2H-1,2,3-triazol-2-yl)phenyl)methanone | 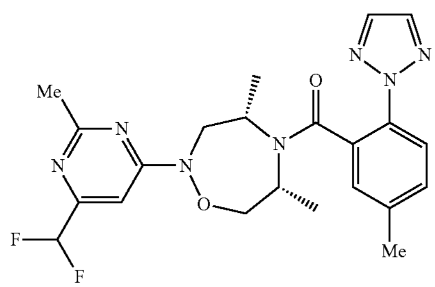 [SMILES: Cc1ccc(-n2nccn2)c(C(=O)N2[C@H](C)CON(c3cc(C(F)F)nc(C)n3)C[C@@H]2C)c1] |

| Ex. No. | Additive | MS | Reagent |
|---|---|---|---|
| 177 | Free | 476.3 | |
| 178 | Free | 476.2 | |
| 179 | Free | 458.2 | |

Example 180

((4S,6R)-2-(6-(difluoromethyl)-2-methylpyrimidin-4-yl)-4,6-dimethyl-1,2,5-oxadiazepan-5-yl)(5-fluoro-2-(2H-1,2,3-triazol-2-yl)phenyl)methanone

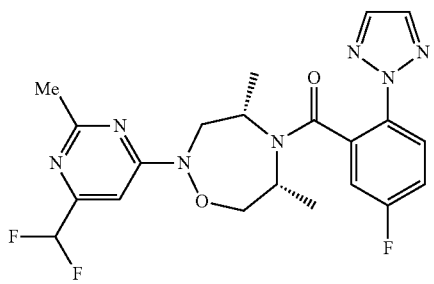 [SMILES: Cc1nc(C(F)F)cc(N2C[C@H](C)N(C(=O)c3cc(F)ccc3-n3nccn3)[C@H](C)CO2)n1]

The title compound (52 mg) was obtained using benzyl (4S,6R)-4,6-dimethyl-1,2,5-oxadiazepane-2-carboxylate (500 mg) obtained in Step D of Example 5, 5-fluoro-2-(2H-1,2,3-triazol-2-yl)benzoic acid (588 mg) obtained in Reference Example 1, and 4-chloro-6-(difluoromethyl)-2-methylpyrimidine (34.4 mg) obtained in Reference Example 20 in the same manner as in Step E of Example 5 and Steps D and E of Example 6.

MS: [M+H]$^+$ 462.1.

Example 181

((4S,6R)-4,6-dimethyl-2-(2-methyl-6-(trifluoromethyl)pyrimidin-4-yl)-1,2,5-oxadiazepan-5-yl)(5-fluoro-2-(2H-1,2,3-triazol-2-yl)phenyl)methanone

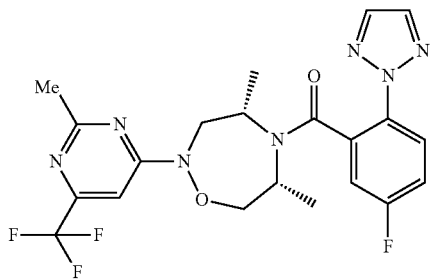 [SMILES: Cc1nc(N2C[C@H](C)N(C(=O)c3cc(F)ccc3-n3nccn3)[C@H](C)CO2)cc(C(F)(F)F)n1]

The title compound (50 mg) was obtained using benzyl (4S,6R)-4,6-dimethyl-1,2,5-oxadiazepane-2-carboxylate (500 mg) obtained in Step D of Example 5, 5-fluoro-2-(2H-1,2,3-triazol-2-yl)benzoic acid (588 mg) obtained in Reference Example 1 and 4-chloro-2-methyl-6-(trifluoromethyl)pyrimidine (37.8 mg) in the same manner as in Step E of Example 5 and Steps D and E of Example 6.

MS: [M+H]$^+$ 480.1.

Example 182

(5-chloro-2-(2H-1,2,3-triazol-2-yl)phenyl)((4S,6R)-2-(6-(difluoromethyl)-2-methylpyrimidin-4-yl)-4,6-dimethyl-1,2,5-oxadiazepan-5-yl)methanone

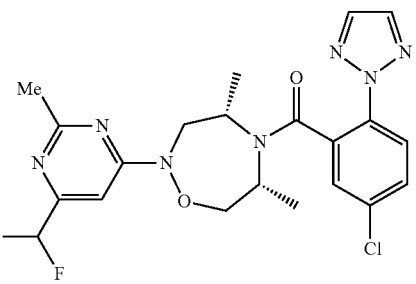

The title compound (76 mg) was obtained using benzyl (4S,6R)-4,6-dimethyl-1,2,5-oxadiazepane-2-carboxylate (500 mg) obtained in Step D of Example 5, 5-chloro-2-(2H-1,2,3-triazol-2-yl)benzoic acid (635 mg) obtained in Reference Example 3, and 4-chloro-6-(difluoromethyl)-2-methylpyrimidine (47.1 mg) obtained in Reference Example 20 in the same manner as in Step E of Example 5 and Steps D and E of Example 6.

MS: [M+H]$^+$ 478.1.

Example 183

(5-chloro-2-(2H-1,2,3-triazol-2-yl)phenyl)((4S,6R)-4,6-dimethyl-2-(2-methyl-6-(trifluoromethyl)pyrimidin-4-yl)-1,2,5-oxadiazepan-5-yl)methanone

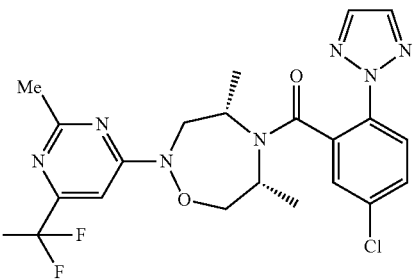

The title compound (41 mg) was obtained using benzyl (4S,6R)-4,6-dimethyl-1,2,5-oxadiazepane-2-carboxylate (500 mg) obtained in Step D of Example 5, 5-chloro-2-(2H-1,2,3-triazol-2-yl)benzoic acid (588 mg) obtained in Reference Example 3 and 4-chloro-2-methyl-6-(trifluoromethyl) pyrimidine (51.9 mg) in the same manner as in Step E of Example 5 and Steps D and E of Example 6.

MS: [M+H]$^+$ 496.0.

Example 184

((4S,6R)-4,6-dimethyl-2-(2-methylpyrimidin-4-yl)-1,2,5-oxadiazepan-5-yl)(2-(1,3-thiazol-2-yl)phenyl)methanone

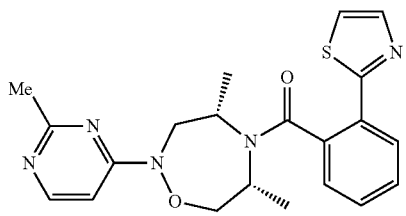 [SMILES: Cc1nccc(N2C[C@H](C)N(C(=O)c3ccccc3-c3nccs3)[C@H](C)CO2)n1]

The title compound (56 mg) was obtained using benzyl (4S,6R)-4,6-dimethyl-5-(2-(1,3-thiazol-2-yl)benzoyl)-1,2,5-oxadiazepane-2-carboxylate (277 mg) obtained in Step E of Example 5 and 4-chloro-2-methylpyrimidine (38.7 mg) in the same manner as in Steps D and E of Example 6.

MS: [M+H]$^+$ 410.2.

Example 185

((4R,6S)-2-(2,6-dimethylpyrimidin-4-yl)-4,6-dimethyl-1,2,5-oxadiazepan-5-yl)(2-(2H-1,2,3-triazol-2-yl)phenyl)methanone

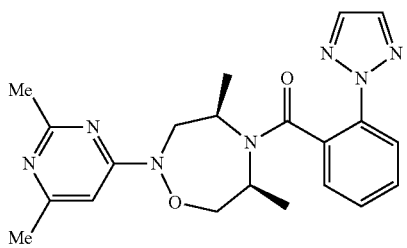 [SMILES: Cc1cc(N2C[C@@H](C)N(C(=O)c3ccccc3-n3nccn3)[C@@H](C)CO2)nc(C)n1]

The title compound (68 mg) was obtained using tert-butyl ((2S)-1-hydroxypropan-2-yl)carbamate and 2-(2H-1,2,3-triazol-2-yl)benzoic acid obtained in Reference Example 2 in the same manner as in Steps A, B, C, D and E of Example 5 and Steps D and E of Example 6.

MS: [M+H]$^+$ 408.2.

Example 186

((4R,6S)-2-(2,6-dimethylpyrimidin-4-yl)-4,6-dimethyl-1,2,5-oxadiazepan-5-yl)(2-(1,3-thiazol-2-yl)phenyl)methanone

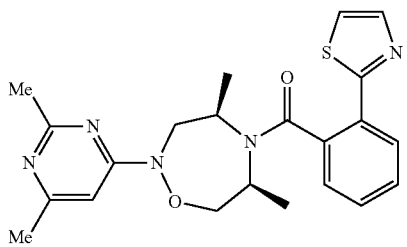 [SMILES: Cc1cc(N2C[C@@H](C)N(C(=O)c3ccccc3-c3nccs3)[C@@H](C)CO2)nc(C)n1]

The title compound (48 mg) was obtained using tert-butyl ((2S)-1-hydroxypropan-2-yl)carbamate and 2-(1,3-thiazol-2-yl)benzoic acid obtained in Reference Example 4 in the same manner as in Steps A, B, C, D and E of Example 5 and Steps D and E of Example 6.

MS: [M+H]$^+$ 424.1.

Example 187

(2-(2,6-dimethylpyrimidin-4-yl)-4-methyl-1,2,5-oxadiazepan-5-yl)(2-(2H-1,2,3-triazol-2-yl)phenyl)methanone

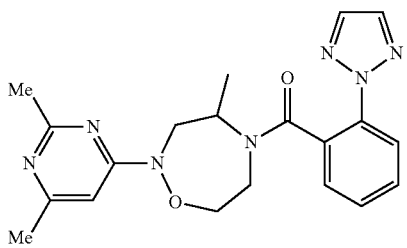 [SMILES: Cc1cc(N2CC(C)N(C(=O)c3ccccc3-n3nccn3)CCO2)nc(C)n1]

A) benzyl (2-((tert-butoxycarbonyl)amino)ethoxy)(2-oxopropyl)carbamate

The title compound (2.04 g) was obtained using tert-butyl (2-hydroxyethyl)carbamate in the same manner as in Steps B and C of Example 1 and Step C of Example 5.

$^1$H NMR (300 MHz, DMSO-d$_6$) δ 1.37 (9H, s), 2.07 (3H, s), 3.11 (2H, q, J=5.4 Hz), 3.79 (2H, t, J=5.7 Hz), 4.43 (2H, s), 5.13 (2H, s), 6.78 (1H, t, J=5.3 Hz), 7.33-7.37 (5H, m).

MS: [M+H−Boc]$^+$ 267.2.

B) 2-benzyl 5-tert-butyl 4-methyl-1,2,5-oxadiazepane-2,5-dicarboxylate

To benzyl (2-((tert-butoxycarbonyl)amino)ethoxy)(2-oxopropyl)carbamate (2.0 g) obtained in Step A of Example 187 was added trifluoroacetic acid (10 mL) under ice-cooling, and the mixture was stirred at room temperature for 1 hr. The solvent was evaporated under reduced pressure, to a solution of the residue in a mixed solvent of ethyl acetate (20 mL) and acetic acid (20 mL) was added sodium triacetoxyborohydride (3.47 g), and the mixture was stirred at room temperature for 3 hr. The solvent was evaporated under reduced pressure, the residue was cooled to 0° C., saturated aqueous sodium hydrogencarbonate solution was added thereto, and the mixture was extracted with ethyl acetate. The obtained organic layer was washed with water and saturated brine, and dried over anhydrous magnesium sulfate, and the solvent was evaporated under reduced pressure. To a solution of the obtained residue in tetrahydrofuran (20 mL) was added di-tert-butyl dicarbonate (2.53 mL), and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (0.88 g).

$^1$H NMR (300 MHz, DMSO-d$_6$) δ 1.05 (3H, d, J=4.9 Hz), 1.36 (9H, d, J=3.0 Hz), 3.22-3.49 (2H, m), 3.62-4.12 (4H, m), 4.15-4.46 (1H, m), 5.11 (2H, brs), 7.25-7.43 (5H, m).

MS: [M+H−Boc]$^+$ 251.2.

C) (2-(2,6-dimethylpyrimidin-4-yl)-4-methyl-1,2,5-oxadiazepan-5-yl)(2-(2H-1,2,3-triazol-2-yl)phenyl)methanone The title compound (44 mg) was obtained using 2-benzyl 5-tert-butyl 4-methyl-1,2,5-oxadiazepane-2,5-dicarboxylate obtained in Step B of Example 187 and 2-(2H-1,2,3-triazol-2-yl)benzoic acid obtained in Reference Example 2 in the same manner as in Steps C, D and E of Example 6.

MS: [M+H]$^+$ 394.1.

Example 188

(2-(2,6-dimethylpyrimidin-4-yl)-3-methyl-1,2,5-oxadiazepan-5-yl)(2-(2H-1,2,3-triazol-2-yl)phenyl)methanone

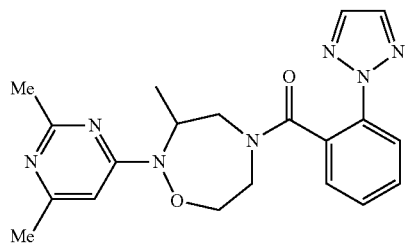 [SMILES: Cc1cc(N2OCCN(C(=O)c3ccccc3-n3nccn3)CC2C)nc(C)n1]

A) 2,2-dimethoxyethanol

To a solution of lithium aluminium hydride (3.4 g) in tetrahydrofuran (150 mL) was added dropwise a solution of methyldimethoxyacetate (9.83 mL) in tetrahydrofuran (50 mL) under ice-cooling, and the mixture was stirred at 0° C. for 3 hr. To the reaction mixture was added sodium sulfate decahydrate (45 g) at 0° C., and the mixture was filtered through Celite. The solvent was evaporated under reduced pressure to give the title compound (5.45 g).

$^1$H NMR (300 MHz, DMSO-d$_6$) δ 3.27 (6H, s), 3.32-3.37 (2H, m), 4.29 (1H, t, J=5.5 Hz), 4.69 (1H, t, J=6.1 Hz).

B) benzyl (2,2-dimethoxyethoxy)carbamate

The title compound (2.56 g) was obtained using 2,2-dimethoxyethanol obtained in Step A of Example 188 in the same manner as in Steps B and C of Example 1.

$^1$H NMR (300 MHz, DMSO-d$_6$) δ 3.27 (6H, s), 3.72 (2H, d, J=5.3 Hz), 4.54 (1H, t, J=5.1 Hz), 5.10 (2H, s), 7.24-7.50 (5H, m), 10.52 (1H, s).

C) benzyl (1-((tert-butoxycarbonyl)amino)propan-2-yl)(2,2-dimethoxyethoxy)carbamate To a solution of benzyl (2,2-dimethoxyethoxy)carbamate (0.978 g) obtained in Step B of Example 188 in N,N-dimethylformamide (10 mL) was added sodium hydride (60% in mineral oil, 199 mg) in an ice bath, and the mixture was stirred at 0° C. for 10 min. To the reaction mixture was added tert-butyl 5-methyl-1,2,3-oxathiazolidine-3-carboxylate 2,2-dioxide (1.0 g), and the mixture was stirred at 0° C. for 2 hr. To the reaction mixture was added 1N aqueous hydrogen chloride solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (1.5 g).

$^1$H NMR (300 MHz, DMSO-d$_6$) δ 1.06 (3H, d, J=6.4 Hz), 1.36 (9H, s), 2.87-3.16 (2H, m), 3.23 (3H, s), 3.25 (3H, s), 3.85 (2H, dd, J=5.3, 2.3 Hz), 4.05-4.20 (1H, m), 4.52 (1H, t, J=5.1 Hz), 5.06-5.27 (2H, m), 6.95 (1H, t, J=5.7 Hz), 7.25-7.51 (5H, m).

D) 2-benzyl 5-tert-butyl 3-methyl-1,2,5-oxadiazepane-2,5-dicarboxylate

To a solution of benzyl (1-((tert-butoxycarbonyl)amino)propan-2-yl)(2,2-dimethoxyethoxy)carbamate (270 mg) obtained in Step C of Example 188 in water (1.0 mL) was added 4M hydrogen chloride ethyl acetate (5.0 mL) solution under ice-cooling, and the mixture was stirred at room temperature for 1 hr. To the reaction mixture were added sodium triacetoxyborohydride (0.694 g) and acetic acid (1.0 mL), and the mixture was stirred at room temperature for 3 hr. The solvent was evaporated under reduced pressure, to a solution of the residue in tetrahydrofuran (2.0 mL) was added di-tert-butyl dicarbonate (0.304 mL), and the mixture was stirred overnight at room temperature. The reaction mixture was cooled to 0° C., saturated aqueous sodium hydrogencarbonate solution was added thereto, and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (hexane/ethyl acetate) to give the title compound (102 mg).

$^1$H NMR (300 MHz, DMSO-d$_6$) δ 1.04 (3H, d, J=6.1 Hz), 1.34 (9H, s), 2.81-3.25 (2H, m), 3.62-3.87 (3H, m), 3.92-4.04 (1H, m), 4.32-4.60 (1H, m), 5.01-5.28 (2H, m), 6.97-7.63 (5H, m).

MS: [M+H−Boc]$^+$ 251.2.

E) (2-(2,6-dimethylpyrimidin-4-yl)-3-methyl-1,2,5-oxadiazepan-5-yl)(2-(2H-1,2,3-triazol-2-yl)phenyl)methanone The title compound (23 mg) was obtained using 2-benzyl 5-tert-butyl 3-methyl-1,2,5-oxadiazepane-2,5-dicarboxylate obtained in Step D of Example 188 and 2-(2H-1,2,3-triazol-2-yl)benzoic acid obtained in Reference Example 2 in the same manner as in Steps C, D and E of Example 6.

MS: [M+H]$^+$ 394.1.

Example 189

((7S)-2-(2,6-dimethylpyrimidin-4-yl)-4,7-dimethyl-1,2,5-oxadiazepan-5-yl)(2-(2H-1,2,3-triazol-2-yl)phenyl)methanone

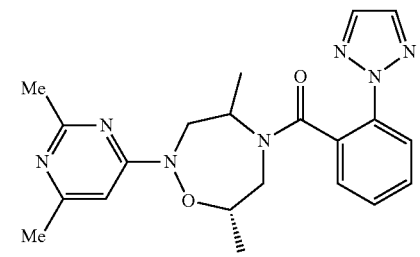 [SMILES: Cc1cc(N2CC(C)N(C(=O)c3ccccc3-n3nccn3)C[C@H](C)O2)nc(C)n1]

The title compound (83 mg) was obtained using benzyl (((2S)-1-((tert-butoxycarbonyl)amino)propan-2-yl)oxy)carbamate obtained in Step C of Example 1 in the same manner as in Steps C and D of Example 5, Step A of Example 2 and Steps D and E of Example 6.

MS: [M+H]+ 408.2.

Example 190

((4S)-2-(2,6-dimethylpyrimidin-4-yl)-4,7-dimethyl-1,2,5-oxadiazepan-5-yl)(2-(2H-1,2,3-triazol-2-yl)phenyl)methanone

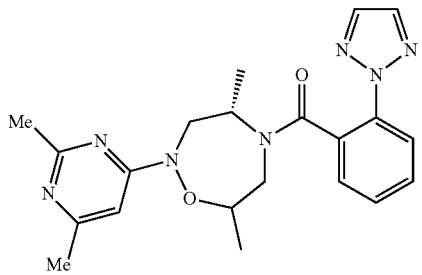 [SMILES: Cc1cc(N2C[C@H](C)N(C(=O)c3ccccc3-n3nccn3)CC(C)O2)nc(C)n1]

A) 1,1-dimethoxypropan-2-ol

To a mixture of 1,1-dimethoxyacetone (24.99 mL) in a mixed solvent of methanol (125 mL) and tetrahydrofuran (125 mL) was added sodium borohydride (8.81 g) under ice-cooling, and the mixture was stirred at room temperature for 4 hr. The solvent was evaporated under reduced pressure, to the residue was added saturated aqueous ammonium chloride solution, and the mixture was extracted twice with ethyl acetate. The obtained organic layer was washed with saturated brine, and dried over anhydrous magnesium sulfate, and the solvent was evaporated under reduced pressure to give the title compound (8.89 g).

$^1$H NMR (300 MHz, DMSO-$d_6$) δ 1.00 (3H, d, J=6.4 Hz), 3.30 (6H, s), 3.48-3.66 (1H, m), 3.98 (1H, d, J=5.7 Hz), 4.58 (1H, d, J=5.3 Hz).

B) benzyl (4S)-4,7-dimethyl-5-(2-(2H-1,2,3-triazol-2-yl)benzoyl)-1,2,5-oxadiazepane-2-carboxylate The title compound (61 mg) was obtained using 1,1-dimethoxypropan-2-ol obtained in Step A of Example 190, 2-(2H-1,2,3-triazol-2-yl)benzoic acid obtained in Reference Example 2 and tert-butyl (4S)-4-methyl-1,2,3-oxathiazolidine-3-carboxylate 2,2-dioxide in the same manner as in Steps B and C of Example 1, Steps C and D of Example 188 and Step C of Example 6.

MS: [M+H]+ 436.0.

C) ((4S)-2-(2,6-dimethylpyrimidin-4-yl)-4,7-dimethyl-1,2,5-oxadiazepan-5-yl)(2-(2H-1,2,3-triazol-2-yl)phenyl)methanone To benzyl (4S)-4,7-dimethyl-5-(2-(2H-1,2,3-triazol-2-yl)benzoyl)-1,2,5-oxadiazepane-2-carboxylate (63 mg) obtained in Step B of Example 190 was added 5.1M hydrogen bromide acetic acid solution (2.0 mL), and the mixture was stirred at room temperature for 0.5 hr. The solvent was evaporated under reduced pressure, a mixture of the residue, 4-chloro-2,6-dimethylpyrimidine (30.9 mg) and 2-propanol (2.0 mL) was stirred in a microwave reactor at 150° C. for 0.5 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (10 mg) as a lower polar component.

MS: [M+H]+ 408.1.

Example 191

((4S)-2-(2,6-dimethylpyrimidin-4-yl)-4,7-dimethyl-1,2,5-oxadiazepan-5-yl)(2-(2H-1,2,3-triazol-2-yl)phenyl)methanone

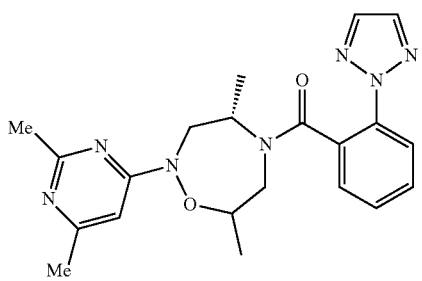 [SMILES: Cc1cc(N2C[C@H](C)N(C(=O)c3ccccc3-n3nccn3)CC(C)O2)nc(C)n1]

To benzyl (4S)-4,7-dimethyl-5-(2-(2H-1,2,3-triazol-2-yl)benzoyl)-1,2,5-oxadiazepane-2-carboxylate (63 mg) obtained in Step B of Example 190 was added 5.1M hydrogen bromide acetic acid solution (2.0 mL), and the mixture was stirred at room temperature for 0.5 hr. The solvent was evaporated under reduced pressure, a mixture of the residue, 4-chloro-2,6-dimethylpyrimidine (30.9 mg) and 2-propanol (2.0 mL) was stirred in a microwave reactor at 150° C. for 0.5 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (16 mg) as a higher polar component.

MS: [M+H]+ 408.1.

Example 192

(2-(2,6-dimethylpyrimidin-4-yl)-6,7-dimethyl-1,2,5-oxadiazepan-5-yl)(2-(2H-1,2,3-triazol-2-yl)phenyl)methanone

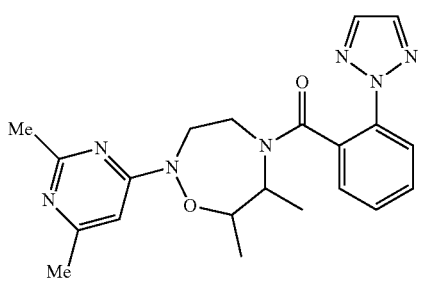 [SMILES: Cc1cc(N2CCN(C(=O)c3ccccc3-n3nccn3)C(C)C(C)O2)nc(C)n1]

A) tert-butyl (3-hydroxybutan-2-yl)carbamate

To a solution of 3-nitrobutan-2-ol (5.0 g) in methanol (50 mL) was added 10% palladium-carbon (511.7 mg), and the mixture was stirred under hydrogen atmosphere (normal pressure) at room temperature for 5 hr. The palladium on carbon was removed through Celite. The solvent was evaporated under reduced pressure, to a solution of the residue in tetrahydrofuran (100 mL) was added dropwise di-tert-butyl dicarbonate (11 mL) at 0° C., and the mixture was stirred for 3 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (3.81 g).

$^1$H NMR (300 MHz, DMSO-$d_6$) δ 0.84-1.10 (6H, m), 1.26-1.54 (9H, m), 2.76-2.96 (0.5H, m), 3.17-3.29 (0.5H, m), 3.36-3.73 (1H, m), 4.37-4.82 (1H, m), 6.22-6.56 (0.5H, m), 7.28-7.61 (0.5H, m).

B) benzyl 6,7-dimethyl-5-(2-(2H-1,2,3-triazol-2-yl)benzoyl)-1,2,5-oxadiazepane-2-carboxylate The title compound (176.8 mg) was obtained using tert-butyl (3-hydroxybutan-2-yl)carbamate obtained in Step A of Example 192 and 2-(2H-1,2,3-triazol-2-yl)benzoic acid obtained in Reference Example 2 in the same manner as in Steps B, C, D and E of Example 1 and Step C of Example 6. MS: [M+H]$^+$ 436.2.

C) (2-(2,6-dimethylpyrimidin-4-yl)-6,7-dimethyl-1,2,5-oxadiazepan-5-yl)(2-(2H-1,2,3-triazol-2-yl)phenyl)methanone To benzyl 6,7-dimethyl-5-(2-(2H-1,2,3-triazol-2-yl)benzoyl)-1,2,5-oxadiazepane-2-carboxylate (175 mg) obtained in Step B of Example 192 was added 5.1M hydrogen bromide acetic acid solution (3.0 mL), and the mixture was stirred at room temperature for 3 hr. The solvent was evaporated under reduced pressure, to a solution of the residue in 2-propanol (5.0 mL) was added 4-chloro-2,6-dimethylpyrimidine (63.3 mg), and the mixture was stirred at 70° C. for 2 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (52 mg) as a lower polar component.

MS: [M+H]$^+$ 408.2.

Example 193

(2-(2,6-dimethylpyrimidin-4-yl)-6,7-dimethyl-1,2,5-oxadiazepan-5-yl)(2-(2H-1,2,3-triazol-2-yl)phenyl)methanone

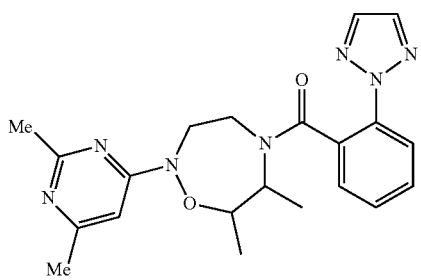 [SMILES: Cc1cc(N2CCN(C(=O)c3ccccc3-n3nccn3)C(C)C(C)O2)nc(C)n1]

(2-(2,6-dimethylpyrimidin-4-yl)-6,7-dimethyl-1,2,5-oxadiazepan-5-yl)(2-(2H-1,2,3-triazol-2-yl)phenyl)methanone To benzyl 6,7-dimethyl-5-(2-(2H-1,2,3-triazol-2-yl)benzoyl)-1,2,5-oxadiazepane-2-carboxylate (175 mg) obtained in Step B of Example 192 was added 5.1M hydrogen bromide acetic acid solution (3.0 mL), and the mixture was stirred at room temperature for 3 hr. The solvent was evaporated under reduced pressure, to a solution of the residue in 2-propanol (5.0 mL) was added 4-chloro-2,6-dimethylpyrimidine (63.3 mg), and the mixture was stirred at 70° C. for 2 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, hexane/ethyl acetate) to give the title compound (54.2 mg) as a higher polar component.

MS: [M+H]$^+$ 408.2.

Example 194

(5-chloro-2-(2H-1,2,3-triazol-2-yl)phenyl)((6R)-2-(2,6-dimethylpyrimidin-4-yl)-6-methyl-1,2,5-oxadiazepan-5-yl)methanone

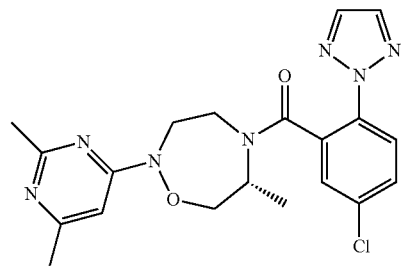 [SMILES: Cc1cc(N2CCN(C(=O)c3cc(Cl)ccc3-n3nccn3)[C@H](C)CO2)nc(C)n1]

A) tert-butyl ((2R)-1-((1,3-dioxo-1,3-dihydro-2H-isoindol-2-yl)oxy)propan-2-yl)carbamate To a solution of 2-hydroxy-1H-isoindole-1,3(2H)-dione (15.0 g) in tetrahydrofuran (300 mL) were added tert-butyl ((2R)-1-hydroxypropan-2-yl)carbamate (16.9 g), tributylphosphine (27.3 mL) and 1,1'-(azodicarbonyl)dipiperidine (27.8 g) at 0° C., and the mixture was stirred overnight at room temperature. The insoluble substance was removed by filtration, and the solvent was evaporated under reduced pressure. The residue was purified by silica gel column chromatography (hexane/ethyl acetate) to give the title compound (29.0 g).

$^1$H NMR (300 MHz, DMSO-$d_6$) δ 1.17 (3H, d, J=6.8 Hz), 1.36 (9H, s), 3.78 (1H, dt, J=13.2, 6.6 Hz), 3.94 (1H, dd, J=9.6, 6.6 Hz), 4.05-4.14 (1H, m), 6.87 (1H, d, J=7.9 Hz), 7.77-7.91 (4H, m).

MS: [M+H−Boc]$^+$ 221.2.

B) prop-2-en-1-yl ((2R)-2-((tert-butoxycarbonyl)amino)propoxy)carbamate

To a solution of tert-butyl ((2R)-1-((1,3-dioxo-1,3-dihydro-2H-isoindol-2-yl)oxy)propan-2-yl)carbamate (50.3 g) obtained in Step A of Example 194 in ethanol (500 mL) was added hydrazine monohydrate (22.9 mL) at room temperature, and the mixture was stirred at 50° C. for 30 min. The insoluble substance was removed by filtration, and washed with ethanol, and the solvent was evaporated under reduced pressure. To the residue was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The obtained residue was dissolved in pyridine (200 mL), allyl chloroformate (23.4 mL) was added thereto while stirring at 0° C., and the mixture was stirred at the same temperature for 2 hr. The solvent was evaporated under reduced pressure, to the residue was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (43.1 g).

$^1$H NMR (300 MHz, DMSO-$d_6$) δ 1.05 (3H, d, J=6.6 Hz), 1.38 (9H, s), 3.43-3.57 (1H, m), 3.58-3.78 (2H, m), 4.54 (2H, dt, J=5.3, 1.5 Hz), 5.20 (1H, dq, J=10.4, 1.4 Hz), 5.29 (1H, dq, J=17.3, 1.6 Hz), 5.91 (1H, ddt, J=17.2, 10.6, 5.3 Hz), 6.70 (1H, d, J=6.6 Hz), 10.33 (1H, brs).

MS: [M+H−Boc]$^+$ 175.1.

C) prop-2-en-1-yl (2-bromoethyl)((2R)-2-((tert-butoxycarbonyl)amino)propoxy)carbamate To a solution of prop-2-en-1-yl ((2R)-2-((tert-butoxycarbonyl)amino)propoxy)carbamate (43.1 g) obtained in Step B of Example 194 in N,N-dimethylformamide (500 mL) was added sodium hydride (60% in mineral oil, 9.43 g) at 0° C., and the mixture was stirred at the same temperature for 1 hr. 1,2-Dibromoethane (17.6 mL) was added dropwise thereto at 0° C., and the mixture was stirred at room temperature for 16 hr. To the reaction mixture was added saturated aqueous sodium hydrogencarbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (49.4 g).

$^1$H NMR (300 MHz, DMSO-$d_6$) δ 1.03 (3H, d, J=6.4 Hz), 1.38 (9H, d, J=2.6 Hz), 3.43-3.94 (6H, m), 4.43-4.73 (2H, m), 5.11-5.42 (2H, m), 5.82-6.04 (1H, m), 6.59-6.94 (1H, m).

D) 5-tert-butyl 2-prop-2-en-1-yl (6R)-6-methyl-1,2,5-oxadiazepane-2,5-dicarboxylate To prop-2-en-1-yl (2-bromoethyl)((2R)-2-((tert-butoxycarbonyl)amino)propoxy)carbamate (25.8 g) obtained in Step C of Example 194 was added trifluoroacetic acid (26.1 mL) at 0° C., and the mixture was stirred at room temperature for 2 hr. The mixture was concentrated under reduced pressure, and the residue was dissolved in N,N-dimethylformamide (500 mL). Diisopropylethylamine (45.0 mL) was added thereto at 0° C., and the mixture was stirred at room temperature over weekend. Di-tert-butyl dicarbonate (23.6 mL) was added thereto, and the mixture was stirred at room temperature for 3 hr. To the reaction mixture was added saturated aqueous sodium hydrogencarbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (16.2 g).

$^1$H NMR (300 MHz, DMSO-$d_6$) δ 1.10 (3H, d, J=6.99 Hz), 1.40 (9H, s), 3.33-3.44 (1H, m), 3.52-3.86 (4H, m), 3.97-4.32 (2H, m), 4.58 (2H, dt, J=5.29, 1.51 Hz), 5.11-5.40 (2H, m), 5.92 (1H, ddt, J=17.19, 10.58, 5.29 Hz).

E) tert-butyl (6R)-6-methyl-1,2,5-oxadiazepane-5-carboxylate

To a solution of 5-tert-butyl 2-prop-2-en-1-yl (6R)-6-methyl-1,2,5-oxadiazepane-2,5-dicarboxylate (16.2 g) obtained in Step D of Example 194 and 1,3-dimethylpyrimidine-2,4,6(1H,3H, 5H)-trione (11.0 g) in tetrahydrofuran (300 mL) was added tetrakis(triphenylphosphine)palladium(0) (3.12 g) at room temperature, and the mixture was stirred for 4 hr under argon atmosphere. The reaction mixture was acidified with 1N hydrochloric acid, and extracted with ethyl acetate. The aqueous layer was basified with 8N aqueous sodium hydroxide solution, and extracted with ethyl acetate. The obtained organic layer was washed with saturated brine, and dried over anhydrous magnesium sulfate, and the solvent was evaporated under reduced pressure to give the title compound (9.48 g).

$^1$H NMR (300 MHz, DMSO-$d_6$) δ 0.94-1.09 (3H, m), 1.40 (9H, s), 2.87 (2H, br.s.), 3.12-3.28 (1H, m), 3.41-3.74 (2H, m), 3.88-4.08 (2H, m), 6.99 (1H, d, J=12.3 Hz).

F) tert-butyl (6R)-2-(2,6-dimethylpyrimidin-4-yl)-6-methyl-1,2,5-oxadiazepane-5-carboxylate A solution of tert-butyl (6R)-6-methyl-1,2,5-oxadiazepane-5-carboxylate (4.40 g) obtained in Step E of Example 194 and 4-chloro-2,6-dimethylpyrimidine (3.19 g) in 2-propanol (45 mL) was stirred at 70° C. for 16 hr. The mixture was concentrated under reduced pressure, to the residue was added saturated aqueous sodium hydrogencarbonate solution, and the mixture was extracted with ethyl acetate. The obtained organic layer was dried over anhydrous sodium sulfate, and the solvent was evaporated under reduced pressure. The residue was purified by silica gel column chromatography (NH, hexane/ethyl acetate) to give the title compound (6.28 g).

$^1$H NMR (300 MHz, CDCl$_3$) δ 1.15-1.29 (3H, m), 1.47 (9H, s), 2.39 (3H, s), 2.51 (3H, s), 3.34-3.55 (1H, m), 3.70-4.60 (6H, m), 6.61 (1H, s).

MS: [M+H]$^+$ 323.1.

G) (6R)-2-(2,6-dimethylpyrimidin-4-yl)-6-methyl-1,2,5-oxadiazepane dihydrochloride A mixture of tert-butyl (6R)-2-(2,6-dimethylpyrimidin-4-yl)-6-methyl-1,2,5-oxadiazepane-5-carboxylate (6.28 g) obtained in Step F of Example 194 and 2N hydrochloric acid (2-propanol solution, 58.4 mL) was stirred at 50° C. for 3 hr. The mixture was concentrated under reduced pressure, and the obtained solid was collected by filtration, washed with ethyl acetate, and dried to give the title compound (5.43 g).

$^1$H NMR (300 MHz, DMSO-$d_6$) δ 1.26 (3H, d, J=6.6 Hz), 2.47-2.53 (3H, m), 2.60 (3H, s), 3.65 (3H, d, J=14.9 Hz), 3.94-4.26 (2H, m), 4.37-4.61 (2H, m), 7.05 (1H, s), 10.00 (1H, brs), 10.24 (1H, brs), 14.88 (1H, brs).

MS: [M+H]$^+$ 223.1.

H) (5-chloro-2-(2H-1,2,3-triazol-2-yl)phenyl)((6R)-2-(2,6-dimethylpyrimidin-4-yl)-6-methyl-1,2,5-oxadiazepan-5-yl)methanone To a solution of (6R)-2-(2,6-dimethylpyrimidin-4-yl)-6-methyl-1,2,5-oxadiazepane dihydrochloride (130 mg) obtained in Step G of Example 194, 5-chloro-2-(2H-1,2,3-triazol-2-yl)benzoic acid (98 mg) obtained in Reference Example 3 and 2-(7-azabenzotriazol-1-yl)-1,1,3,3-hexafluorophosphate (HATU) (251 mg) in N,N-dimethylformamide (5 mL) was added triethylamine (0.31 mL), and the mixture was stirred at room temperature for 3 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate), and crystallized (hexane/ethyl acetate) to give the title compound (125 mg).

$^1$H NMR (300 MHz, CDCl$_3$) δ 0.83-1.51 (3H, m), 2.31-2.66 (6H, m), 3.26-5.20 (7H, m), 6.37-6.73 (1H, m), 7.31-7.63 (3H, m), 7.74-7.87 (1H, m), 7.89-8.10 (1H, m).

MS: [M+H]$^+$ 428.1.

Example 195

(5-chloro-2-(pyrimidin-2-yl)phenyl)((6R)-2-(2,6-dimethylpyrimidin-4-yl)-6-methyl-1,2,5-oxadiazepan-5-yl)methanone

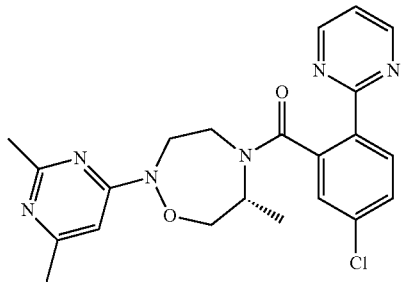 [SMILES: Cc1cc(N2CCN(C(=O)c3cc(Cl)ccc3-c3ncccn3)[C@H](C)CO2)nc(C)n1]

To a solution of (6R)-2-(2,6-dimethylpyrimidin-4-yl)-6-methyl-1,2,5-oxadiazepane dihydrochloride (800 mg) obtained in Step G of Example 194, 2-bromo-5-chlorobenzoic acid (638 mg) and 2-(7-azabenzotriazol-1-yl)-1,1,3,3-hexafluorophosphate (HATU) (1546 mg) in N,N-dimethylformamide (15 mL) was added triethylamine (1.89 mL), and the mixture was stirred at room temperature for 3 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate) to give a mixture (1.15 g) containing (2-bromo-5-chlorophenyl)[(6R)-2-(2,6-dimethylpyrimidin-4-yl)-6-methyl-1,2,5-oxadiazepan-5-yl]methanone as a main component. A mixture of the mixture (300 mg), 2-(tributylstannyl)pyrimidine (378 mg), dichlorobis(triphenylphosphine)palladium(II) (23.9 mg), lithium chloride (214 mg) and N,N-dimethylformamide (10 mL) was stirred in a microwave reactor at 140° C. for 1 hr. The reaction mixture was poured into aqueous potassium fluoride solution, and the suspension was stirred at room temperature for 1 hr. The precipitate was removed by filtration, and the filtrate was diluted with ethyl acetate. The obtained organic layer was washed with saturated brine, and dried over anhydrous sodium sulfate, and the solvent was evaporated under reduced pressure. The residue was purified by silica gel column chromatography (NH, hexane/ethyl acetate and ethyl acetate/methanol). The obtained crude product was purified by HPLC (C18, mobile phase: water/acetonitrile (containing 10 mM NH$_4$HCO$_3$)), the obtained fraction was concentrated, and the residue was crystallized (hexane/ethyl acetate) to give the title compound (38.0 mg).

$^1$H NMR (300 MHz, DMSO-d$_6$) δ 0.95-1.53 (3H, m), 2.19-2.70 (6H, m), 3.24-5.30 (7H, m), 6.41-6.71 (1H, m), 6.85-7.57 (3H, m), 8.22-8.64 (2H, m), 8.64-8.84 (1H, m).

MS: [M+H]$^+$ 439.1.

Example 196

((7S)-2-(2,6-dimethylpyrimidin-4-yl)-7-methyl-1,2,5-oxadiazepan-5-yl)(5-methyl-2-(pyrimidin-2-yl)phenyl)methanone

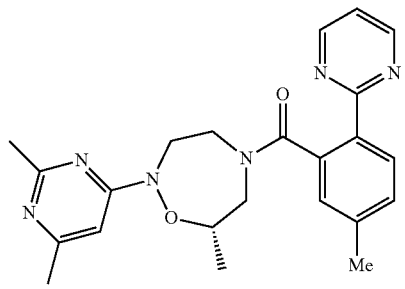 [SMILES: Cc1ccc(-c2ncccn2)c(C(=O)N2CCN(c3cc(C)nc(C)n3)O[C@@H](C)C2)c1]

A) (2-bromo-5-methylphenyl)((7S)-2-(2,6-dimethylpyrimidin-4-yl)-7-methyl-1,2,5-oxadiazepan-5-yl)methanone To a solution of (7S)-2-(2,6-dimethylpyrimidin-4-yl)-7-methyl-1,2,5-oxadiazepane dihydrochloride (250 mg) obtained in Step G of Example 102, 2-bromo-5-methylbenzoic acid (273 mg) and 2-(7-azabenzotriazol-1-yl)-1,1,3,3-hexafluorophosphate (HATU) (483 mg) in N,N-dimethylformamide (5 mL) was added triethylamine (0.59 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate) to give the title compound (349 mg).

$^1$H NMR (300 MHz, DMSO-d$_6$) δ 1.15 (1H, dd, J=6.4, 2.3 Hz), 1.31-1.43 (2H, m), 2.21-2.84 (9H, m), 3.06-4.93 (7H, m), 6.50-6.72 (1H, m), 6.97-7.14 (2H, m), 7.38-7.51 (1H, m).

MS: [M+H]$^+$ 419.0, 420.9.

B) ((7S)-2-(2,6-dimethylpyrimidin-4-yl)-7-methyl-1,2,5-oxadiazepan-5-yl)(5-methyl-2-(pyrimidin-2-yl)phenyl)methanone To a solution of (2-bromo-5-methylphenyl)((7S)-2-(2,6-dimethylpyrimidin-4-yl)-7-methyl-1,2,5-oxadiazepan-5-yl)methanone (349 mg) obtained in Step A of Example 196, 4,4,4',4',5,5,5',5'-octamethyl-2,2'-bi-1,3,2-dioxaborolane (317 mg) and potassium acetate (245 mg) in dimethyl sulfoxide (5 mL) was added 1,1'-bis(diphenylphosphino)ferrocene-palladium(II) dichloride (30.5 mg), and the mixture was stirred at 90° C. for 4 hr. To the reaction mixture was added saturated aqueous sodium hydrogencarbonate solution, and the insoluble substance was filtered through Celite, and washed with ethyl acetate. The filtrate was washed with saturated aqueous sodium hydrogencarbonate solution, and dried over anhydrous sodium sulfate, and the solvent was evaporated under reduced pressure. The residue was purified by silica gel column chromatography (hexane/ethyl acetate) to give a crude product (295 mg) containing ((7S)-2-(2,6-dimethylpyrimidin-4-yl)-7-methyl-1,2,5-oxadiazepan-5-yl)(5-methyl-2-(4,4,5,5-tetramethyl-1,3,2-dioxaborolan-2-yl)phenyl)methanone as a main component. A solution of the crude product (295 mg), 2-bromopyrimidine (121 mg), tetrakis(triphenylphosphine)palladium(0) (36.5 mg) and sodium carbonate (201 mg) in a mixed solvent of 1,2-dimethoxyethane (9 mL)/water (3 mL) was stirred at 100° C. for 3 hr under argon atmosphere. The reaction mixture was diluted with ethyl acetate, washed with saturated brine, and dried over sodium sulfate, and the solvent was evaporated under reduced pressure. The residue was purified by silica gel column chromatography (NH, hexane/ethyl acetate). The obtained crude product was purified by HPLC (C18, mobile phase: water/acetonitrile (containing 0.1% TFA)), the obtained fraction was concentrated, and the residue was crystallized (hexane/ethyl acetate) to give the title compound (71.0 mg).

$^1$H NMR (300 MHz, CDCl$_3$) δ 1.07 (1.1H, d, J=6.0 Hz), 1.39 (1.9H, d, J=6.4 Hz), 2.25-2.66 (9H, m), 2.82-5.03 (7H, m), 6.30-6.70 (1H, m), 6.77-7.42 (3H, m), 8.11-8.84 (3H, m).

MS: [M+H]$^+$ 419.1.

Example 197

(5-chloro-2-(pyrimidin-2-yl)phenyl)((7S)-2-(2,6-dimethylpyrimidin-4-yl)-7-methyl-1,2,5-oxadiazepan-5-yl)methanone

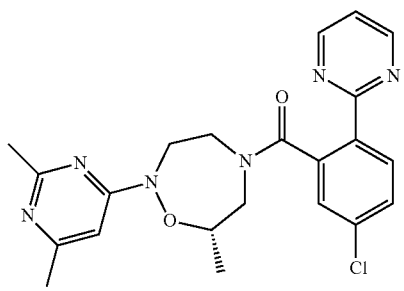 [SMILES: Cc1cc(N2CCN(C(=O)c3cc(Cl)ccc3-c3ncccn3)C[C@H](C)O2)nc(C)n1]

A) (2-bromo-5-chlorophenyl)[(7S)-2-(2,6-dimethylpyrimidin-4-yl)-7-methyl-1,2,5-oxadiazepan-5-yl]methanone To a solution of (7S)-2-(2,6-dimethylpyrimidin-4-yl)-7-methyl-1,2,5-oxadiazepane dihydrochloride (535 mg) obtained in Step G of Example 102, 2-bromo-5-chlorobenzoic acid (640 mg) and 2-(7-azabenzotriazol-1-yl)-1,1,3,3-hexafluorophosphate (HATU) (1034 mg) in N,N-dimethylformamide (15 mL) was added triethylamine (1.26 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate) to give the title compound (698 mg).

$^1$H NMR (300 MHz, CDCl$_3$) δ 1.10-1.44 (3H, m), 2.29-2.46 (3H, m), 2.46-2.65 (3H, m), 3.08-4.84 (7H, m), 6.52-6.72 (1H, m), 7.18-7.31 (2H, m), 7.47-7.57 (1H, m).

MS: [M+H]$^+$ 439.0, 441.0.

B) (5-chloro-2-(pyrimidin-2-yl)phenyl)((7S)-2-(2,6-dimethylpyrimidin-4-yl)-7-methyl-1,2,5-oxadiazepan-5-yl)methanone To a solution of (2-bromo-5-chlorophenyl)[(7S)-2-(2,6-dimethylpyrimidin-4-yl)-7-methyl-1,2,5-oxadiazepan-5-yl]methanone (695 mg) obtained in Step A of Example 197, 4,4,4',4',5,5,5',5'-octamethyl-2,2'-bi-1,3,2-dioxaborolane (602 mg) and potassium acetate (465 mg) in dimethyl sulfoxide (15 mL) was added 1,1'-bis(diphenylphosphino)ferrocene-palladium(II) dichloride (57.8 mg), and the mixture was stirred at 95° C. for 3 hr. 4,4,4',4',5,5,5',5'-Octamethyl-2,2'-bi-1,3,2-dioxaborolane (602 mg), potassium acetate (465 mg) and 1,1'-bis(diphenylphosphino)ferrocene-palladium(II) dichloride (57.8 mg) were added thereto, and the mixture was stirred at 95° C. for additional 3 hr. To the reaction mixture was added saturated aqueous sodium hydrogencarbonate solution, and the insoluble substance was filtered through Celite, and washed with ethyl acetate. The filtrate was washed with saturated aqueous sodium hydrogencarbonate solution, and dried over anhydrous sodium sulfate, and the solvent was evaporated under reduced pressure. To the residue was added a solution of 2-bromopyrimidine (302 mg), tetrakis(triphenylphosphine)palladium(0) (91.0 mg) and sodium carbonate (503 mg) in a mixed solvent of 1,2-dimethoxyethane (30 mL)/water (10 mL), and the mixture was stirred at 100° C. for 4 hr under argon atmosphere. The reaction mixture was diluted with ethyl acetate, washed with saturated brine, and dried over sodium sulfate, and the solvent was evaporated under reduced pressure. The residue was purified by silica gel column chromatography (NH, hexane/ethyl acetate). The obtained crude product was purified by HPLC (C18, mobile phase: water/acetonitrile (containing 10 mM NH$_4$HCO$_3$)), the obtained fraction was concentrated, and the residue was crystallized (hexane/ethyl acetate) to give the title compound (114 mg).

$^1$H NMR (300 MHz, DMSO-d$_6$) δ 1.08 (1H, d, J=6.4 Hz), 1.32 (2H, d, J=6.4 Hz), 2.12-2.48 (6H, m), 2.85-4.70 (7H, m), 6.41-6.79 (1H, m), 7.04-7.72 (3H, m), 8.10-9.02 (3H, m).

MS: [M+H]$^+$ 439.1.

Example 198

(4,5-difluoro-2-(pyrimidin-2-yl)phenyl)((7S)-2-(2,6-dimethylpyrimidin-4-yl)-7-methyl-1,2,5-oxadiazepan-5-yl)methanone

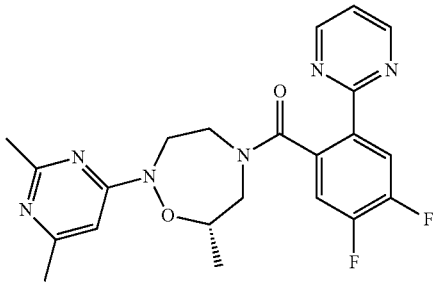 [SMILES: Cc1cc(N2CCN(C(=O)c3cc(F)c(F)cc3-c3ncccn3)C[C@H](C)O2)nc(C)n1]

To a mixture of (7S)-2-(2,6-dimethylpyrimidin-4-yl)-7-methyl-1,2,5-oxadiazepane dihydrochloride (3.00 g) obtained in Step G of Example 102, 4,5-difluoro-2-(pyrimidin-2-yl)benzoic acid (3.60 g) obtained in Reference Example 31, N,N-diisopropylethylamine (8.85 mL) and N,N-dimethylformamide (30 mL) was added dropwise 1.6M 2,4,6-tripropyl-1,3,5,2,4,6-trioxatriphosphorinane-2,4,6-trioxide ethyl acetate (19.1 mL) solution over 20 min at 0° C., and the mixture was stirred at room temperature for 16 hr. The reaction mixture was cooled to 0° C., saturated aqueous sodium hydrogencarbonate solution was added thereto, and the mixture was extracted with ethyl acetate. The obtained organic layer was washed successively with water and saturated brine, and dried over anhydrous sodium sulfate, and the solvent was evaporated under reduced pressure. The residue was purified by silica gel column chromatography (NH, hexane/ethyl acetate) to give the title compound (0.922 g).

$^1$H NMR (300 MHz, CDCl$_3$) δ 1.11 (1.1H, d, J=6.4 Hz), 1.39 (1.9H, d, J=6.4 Hz), 2.24-2.67 (6H, m), 2.85-4.95 (7H, m), 6.35-6.72 (1H, m), 6.82-7.36 (2H, m), 8.05-8.89 (3H, m).

MS: [M+H]$^+$ 441.1.

Example 199

((7S)-2-(2,6-dimethylpyrimidin-4-yl)-7-methyl-1,2,5-oxadiazepan-5-yl)(2-(2H-1,2,3-triazol-2-yl)-5-(trifluoromethyl)phenyl)methanone

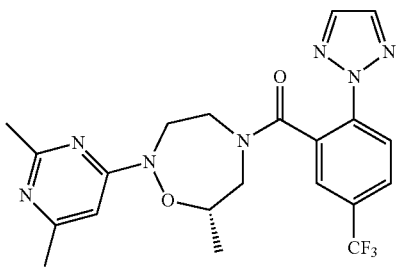 [SMILES: Cc1cc(N2CCN(C(=O)c3cc(C(F)(F)F)ccc3-n3nccn3)C[C@H](C)O2)nc(C)n1]

To a solution of (7S)-2-(2,6-dimethylpyrimidin-4-yl)-7-methyl-1,2,5-oxadiazepane dihydrochloride (150 mg) obtained in Step G of Example 102, 2-(2H-1,2,3-triazol-2-yl)-5-(trifluoromethyl)benzoic acid (144 mg) and 2-(7-azabenzotriazol-1-yl)-1,1,3,3-tetramethyluronium hexafluorophosphate (HATU) (290 mg) in N,N-dimethylformamide (5 mL) was added triethylamine (0.354 mL) at room temperature, and the mixture was stirred for 16 hr. To the reaction mixture was added saturated aqueous sodium hydrogencarbonate solution, and the mixture was extracted with ethyl acetate. The obtained organic layer was washed successively with water and saturated brine, and dried over anhydrous sodium sulfate, and the solvent was evaporated under reduced pressure. The residue was purified by silica gel column chromatography (NH, hexane/ethyl acetate), and crystallized (hexane/ethyl acetate) to give the title compound (174 mg).

$^1$H NMR (300 MHz, DMSO-d$_6$) δ 1.07 (1.3H, d, J=6.4 Hz), 1.32 (1.7H, d, J=6.2 Hz), 2.19-2.47 (6H, m), 2.92-4.63 (7H, m), 6.40-6.73 (1H, m), 7.43-7.69 (1H, m), 7.78-7.94 (1H, m), 7.94-8.09 (1H, m), 8.09-8.28 (2H, m).

MS: [M+H]$^+$ 462.1.

Example 200

(4-chloro-2-(2H-1,2,3-triazol-2-yl)phenyl)((7S)-2-(2,6-dimethylpyrimidin-4-yl)-7-methyl-1,2,5-oxadiazepan-5-yl)methanone

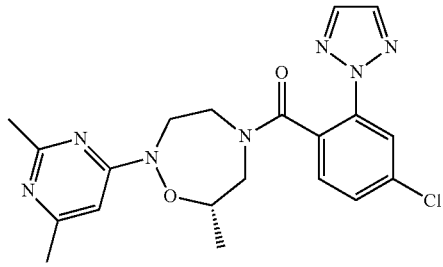 [SMILES: Cc1cc(N2CCN(C(=O)c3ccc(Cl)cc3-n3nccn3)C[C@H](C)O2)nc(C)n1]

To a solution of (7S)-2-(2,6-dimethylpyrimidin-4-yl)-7-methyl-1,2,5-oxadiazepane dihydrochloride (150 mg) obtained in Step G of Example 102, 4-chloro-2-(2H-1,2,3-triazol-2-yl)benzoic acid (125 mg) and 2-(7-azabenzotriazol-1-yl)-1,1,3,3-hexafluorophosphate (HATU) (290 mg) in N,N-dimethylformamide (5 mL) was added triethylamine (0.354 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate) to give the title compound (201 mg).

$^1$H NMR (300 MHz, DMSO-d$_6$) δ 1.01-1.14 (1.4H, m), 1.29 (1.6H, d, J=6.2 Hz), 2.12-2.46 (6H, m), 2.66-4.66 (7H, m), 6.37-8.31 (6H, m).

MS: [M+H]$^+$ 428.0.

Example 201

((7S)-2-(2,6-dimethylpyrimidin-4-yl)-7-methyl-1,2,5-oxadiazepan-5-yl)(5-ethyl-2-(2H-1,2,3-triazol-2-yl)phenyl)methanone

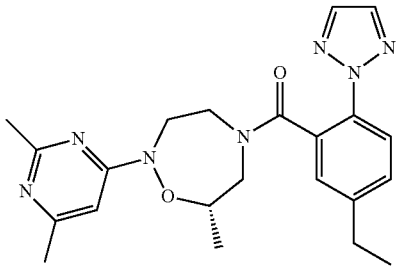 [SMILES: CCc1ccc(-n2nccn2)c(C(=O)N2CCN(c3cc(C)nc(C)n3)O[C@@H](C)C2)c1]

A) methyl 5-ethenyl-2-(2H-1,2,3-triazol-2-yl)benzoate

A solution of methyl 5-bromo-2-(2H-1,2,3-triazol-2-yl)benzoate (500 mg), 2-ethenyl-4,4,5,5-tetramethyl-1,3,2-dioxaborolane (300 mg) and sodium carbonate (564 mg) in a mixed solvent of 1,2-dimethoxyethane (10 mL)/water (10 mL) was stirred at room temperature for 15 min under nitrogen atmosphere. To this solution was added tetrakis(triphenylphosphine)palladium(0) (102 mg), and the mixture was stirred at 80° C. for 12 hr under nitrogen atmosphere. To the reaction mixture was added saturated brine, and the mixture was extracted with diisopropyl ether. The obtained organic layer was dried over anhydrous magnesium sulfate, and the solvent was evaporated under reduced pressure. The residue was purified by silica gel column chromatography (hexane/ethyl acetate) to give the title compound (175 mg).

$^1$H NMR (300 MHz, DMSO-$d_6$) δ 3.63-3.72 (3H, m), 5.44 (1H, d, J=10.95 Hz), 6.02 (1H, d, J=17.56 Hz), 6.86 (1H, dd, J=17.75, 10.95 Hz), 7.76-7.92 (3H, m), 8.11 (2H, s).

MS: [M+H]$^+$ 230.1.

B) ((7S)-2-(2,6-dimethylpyrimidin-4-yl)-7-methyl-1,2,5-oxadiazepan-5-yl)(5-ethyl-2-(2H-1,2,3-triazol-2-yl)phenyl)methanone A suspension of methyl 5-ethenyl-2-(2H-1,2,3-triazol-2-yl)benzoate (170 mg) obtained in Step A of Example 201 and 5% palladium-carbon (50 mg) in a mixed solvent of methanol (5 mL)/tetrahydrofuran (5 mL) was stirred at room temperature for 1 hr under hydrogen atmosphere (normal pressure). The palladium-carbon was removed by filtration, and the filtrate was concentrated under reduced pressure. The obtained residue was dissolved in a mixed solvent of methanol (3 mL)/tetrahydrofuran (3 mL), 1N aqueous sodium hydroxide solution (3 mL) was added thereto, and the mixture was stirred at 50° C. for 2.5 hr. To the reaction mixture were added 1N hydrochloric acid and saturated brine, and the organic layer was separated. The obtained organic layer was washed with saturated brine, and dried over anhydrous magnesium sulfate, and the solvent was evaporated under reduced pressure to give a crude product (160 mg) of 5-ethyl-2-(2H-1,2,3-triazol-2-yl)benzoic acid. To a solution of the crude product (77.0 mg), (7S)-2-(2,6-dimethylpyrimidin-4-yl)-7-methyl-1,2,5-oxadiazepane dihydrochloride (100 mg) obtained in Step G of Example 102 and 2-(7-azabenzotriazol-1-yl)-1,1,3,3-hexafluorophosphate (HATU) (135 mg) in N,N-dimethylformamide (2 mL) was added triethylamine (0.236 mL), and the mixture was stirred at room temperature for 24 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate), and crystallized (diisopropyl ether) to give the title compound (43 mg).

$^1$H NMR (300 MHz, DMSO-$d_6$) δ 1.03-1.32 (6H, m), 2.20-2.55 (6H, m), 2.65-2.75 (2H, m), 3.00-4.45 (7H, m), 6.44-6.68 (1.2H, m), 7.00-7.30 (1H, m), 7.39-7.52 (1.4H, m), 7.73-7.89 (1.4H, m), 8.07 (1H, br.s.).

MS: [M+H]$^+$ 422.1.

Example 202

(2-(2,6-dimethylpyrimidin-4-yl)-1,2,5-oxadiazepan-5-yl)(2-(2H-1,2,3-triazol-2-yl)-5-(trifluoromethyl)phenyl)methanone

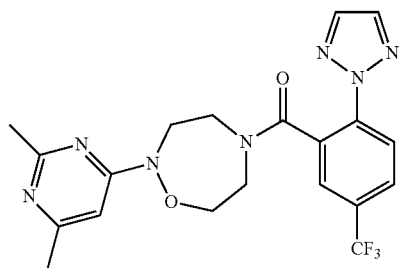 [SMILES: Cc1cc(N2CCN(C(=O)c3cc(C(F)(F)F)ccc3-n3nccn3)CCO2)nc(C)n1]

To a solution of 2-(2,6-dimethylpyrimidin-4-yl)-1,2,5-oxadiazepane dihydrobromide (180 mg) obtained in Step D of Example 4, 4-chloro-2-(2H-1,2,3-triazol-2-yl)benzoic acid (138 mg) and 2-(7-azabenzotriazol-1-yl)-1,1,3,3-hexafluorophosphate (HATU) (277 mg) in N,N-dimethylformamide (5 mL) was added triethylamine (0.339 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate), and crystallized (hexane/ethyl acetate) to give the title compound (215 mg).

$^1$H NMR (300 MHz, DMSO-$d_6$) δ 2.22-2.46 (6H, m), 3.15-4.28 (8H, m), 6.55-6.74 (1H, m), 7.61-7.84 (1H, m), 7.87 (1H, s), 7.96-8.10 (2H, m), 8.21 (1H, dd, J=14.6, 8.6 Hz).

MS: [M+H]$^+$ 448.1.

Example 203

(2-(2,6-dimethylpyrimidin-4-yl)-1,2,5-oxadiazepan-5-yl)(5-ethyl-2-(2H-1,2,3-triazol-2-yl)phenyl)methanone

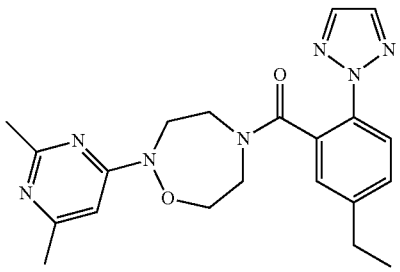 [SMILES: CCc1ccc(-n2nccn2)c(C(=O)N2CCON(c3cc(C)nc(C)n3)CC2)c1]

To a solution of 2-(2,6-dimethylpyrimidin-4-yl)-1,2,5-oxadiazepane dihydrobromide (125 mg) obtained in Step D of Example 4, the crude product (77.0 mg) of 5-ethyl-2-(2H-1,2,3-triazol-2-yl)benzoic acid (obtained as an intermediate in Step B of Example 201) and 2-(7-azabenzotriazol-1-yl)-1,1,3,3-hexafluorophosphate (HATU) (135 mg) in N,N-dimethylformamide (2 mL) was added triethylamine (0.235 mL), and the mixture was stirred at room temperature for 24 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate), and crystallized (diisopropyl ether) to give the title compound (122 mg).
$^1$H NMR (300 MHz, DMSO-$d_6$) δ 1.21 (3H, m), 2.30 (3H, s), 2.33 (1.5H, s), 2.49 (1.5H, s), 2.64-2.74 (2H, m), 3.26-4.15 (8H, m), 6.61 (0.5H, s), 6.70 (0.5H, s), 7.10 (0.5H, d, J=1.70 Hz), 7.24 (0.5H, d, J=1.89 Hz), 7.47 (1H, ddd, J=8.26, 5.90, 1.89 Hz), 7.76 (1H, s), 7.78-7.86 (1H, m), 7.96 (1H, s).
MS: [M+H]$^+$ 408.1.

Example 204

(4-chloro-2-(2H-1,2,3-triazol-2-yl)phenyl)(2-(2,6-dimethylpyrimidin-4-yl)-1,2,5-oxadiazepan-5-yl)methanone

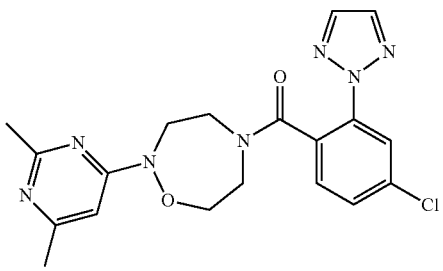 [SMILES: Cc1cc(N2CCN(C(=O)c3ccc(Cl)cc3-n3nccn3)CCO2)nc(C)n1]

To a solution of 2-(2,6-dimethylpyrimidin-4-yl)-1,2,5-oxadiazepane dihydrobromide (180 mg) obtained in Step D of Example 4, 4-chloro-2-(2H-1,2,3-triazol-2-yl)benzoic acid (120 mg) and 2-(7-azabenzotriazol-1-yl)-1,1,3,3-hexafluorophosphate (HATU) (277 mg) in N,N-dimethylformamide (5 mL) was added triethylamine (0.339 mL), and the mixture was stirred at room temperature for 16 hr. To the reaction mixture was added saturated aqueous sodium hydrogencarbonate solution, and the mixture was extracted with ethyl acetate. The obtained organic layer was washed successively with water and saturated brine, and dried over sodium sulfate, and the solvent was evaporated under reduced pressure. The residue was purified by silica gel column chromatography (NH, hexane/ethyl acetate) to give the title compound (188 mg).
$^1$H NMR (300 MHz, DMSO-$d_6$) δ 2.16-2.46 (6H, m), 3.15-4.20 (8H, m), 6.65 (1H, d, J=19.5 Hz), 7.31-7.51 (1H, m), 7.60 (1H, dd, J=8.3, 2.1 Hz), 7.81-8.06 (3H, m).
MS: [M+H]$^+$ 414.1.

Example 205

(4-bromo-2-(2H-1,2,3-triazol-2-yl)phenyl)((7S)-2-(2,6-dimethylpyrimidin-4-yl)-7-methyl-1,2,5-oxadiazepan-5-yl)methanone

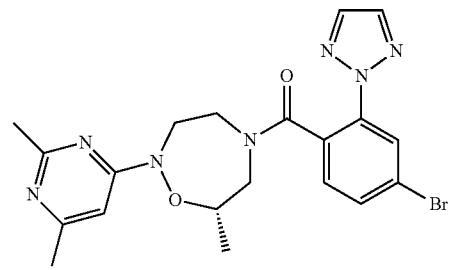 [SMILES: Cc1cc(N2CCN(C(=O)c3ccc(Br)cc3-n3nccn3)C[C@H](C)O2)nc(C)n1]

The title compound (238 mg) was obtained using (7S)-2-(2,6-dimethylpyrimidin-4-yl)-7-methyl-1,2,5-oxadiazepane dihydrochloride obtained in Step G of Example 102 and 4-bromo-2-(2H-1,2,3-triazol-2-yl)benzoic acid obtained in Reference Example 32 in the same manner as in Step H of Example 102.
MS: [M+H]$^+$ 472.0, 474.1.

Example 206

((7S)-7-methyl-2-(2-methylpyrimidin-4-yl)-1,2,5-oxadiazepan-5-yl)(2-(pyrimidin-2-yl)phenyl)methanone

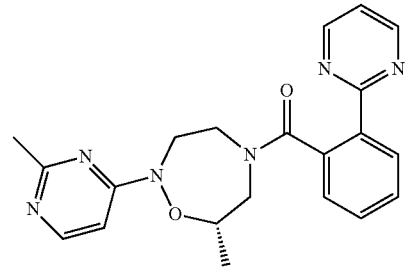 [SMILES: Cc1nccc(N2CCN(C(=O)c3ccccc3-c3ncccn3)C[C@H](C)O2)n1]

The title compound (48 mg) was obtained using (7S)-7-methyl-2-(2-methylpyrimidin-4-yl)-1,2,5-oxadiazepane dihydrochloride (obtained using tert-butyl (7S)-7-methyl-1, 2,5-oxadiazepane-5-carboxylate obtained in Step E of Example 102 and 4-chloro-2-methylpyrimidine in the same manner as in Steps F and G of Example 102), 2-(pyrimidin-2-yl)benzoic acid obtained in Reference Example 25 and TFFH as a condensing agent in the same manner as in Step H of Example 102.

MS: [M+H]$^+$ 391.1.

Example 207 methyl 6-((7S)-5-(5-chloro-2-(2H-1,2,3-triazol-2-yl)benzoyl)-7-methyl-1,2,5-oxadiazepan-2-yl)-2-methylpyrimidine-4-carboxylate

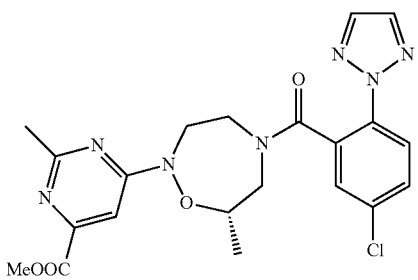 [SMILES: COC(=O)c1cc(N2CCN(C(=O)c3cc(Cl)ccc3-n3nccn3)C[C@H](C)O2)nc(C)n1]

The title compound (23 mg) was obtained using methyl 2-methyl-6-[(7S)-7-methyl-1,2,5-oxadiazepan-2-yl]pyrimidine-4-carboxylate dihydrochloride (obtained using tert-butyl (7S)-7-methyl-1,2,5-oxadiazepane-5-carboxylate obtained in Step E of Example 102 and methyl 6-chloro-2-methylpyrimidine-4-carboxylate in the same manner as in Steps F and G of Example 102) and 5-chloro-2-(2H-1,2,3-triazol-2-yl)benzoic acid obtained in Reference Example 3 in the same manner as in Step H of Example 102.

MS: [M+H]$^+$ 472.1.

Example 208 ethyl 6-((7S)-5-(5-chloro-2-(2H-1,2,3-triazol-2-yl)benzoyl)-7-methyl-1,2,5-oxadiazepan-2-yl)-2-methylpyrimidine-4-carboxylate

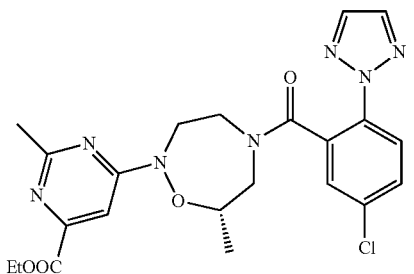 [SMILES: CCOC(=O)c1cc(N2CCN(C(=O)c3cc(Cl)ccc3-n3nccn3)C[C@H](C)O2)nc(C)n1]

The title compound (63 mg) was obtained using ethyl 2-methyl-6-[(7S)-7-methyl-1,2,5-oxadiazepan-2-yl]pyrimidine-4-carboxylate dihydrochloride (obtained using tert-butyl (7S)-7-methyl-1,2,5-oxadiazepane-5-carboxylate obtained in Step E of Example 102 and ethyl 6-chloro-2-methylpyrimidine-4-carboxylate in the same manner as in Steps F and G of Example 102) and 5-chloro-2-(2H-1,2,3-triazol-2-yl)benzoic acid obtained in Reference Example 3 in the same manner as in Step H of Example 102.

MS: [M+H]$^+$ 486.1.

Example 209

2-(((7S)-2-(2,6-dimethylpyrimidin-4-yl)-7-methyl-1,2,5-oxadiazepan-5-yl)carbonyl)benzonitrile

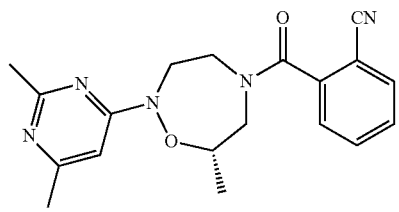 [SMILES: Cc1cc(N2CCN(C(=O)c3ccccc3C#N)C[C@H](C)O2)nc(C)n1]

The title compound (229 mg) was obtained using (7S)-2-(2,6-dimethylpyrimidin-4-yl)-7-methyl-1,2,5-oxadiazepane dihydrochloride obtained in Step G of Example 102 and 2-cyanobenzoic acid in the same manner as in Step H of Example 102.

MS: [M+H]$^+$ 352.0.

Example 210

((7S)-2-(2,6-dimethylpyrimidin-4-yl)-7-methyl-1,2,5-oxadiazepan-5-yl)(2-fluoro-6-(2H-1,2,3-triazol-2-yl)phenyl)methanone

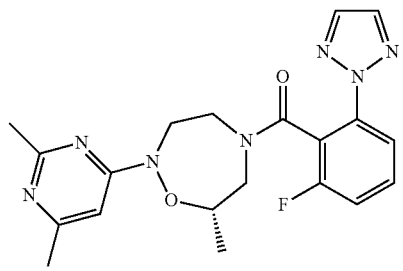 [SMILES: Cc1cc(N2CCN(C(=O)c3c(F)cccc3-n3nccn3)C[C@H](C)O2)nc(C)n1]

The title compound (122 mg) was obtained using (7S)-2-(2,6-dimethylpyrimidin-4-yl)-7-methyl-1,2,5-oxadiazepane dihydrochloride obtained in Step G of Example 102 and 2-fluoro-6-(2H-1,2,3-triazol-2-yl)benzoic acid obtained in Reference Example 7 in the same manner as in Step H of Example 102.

MS: [M+H]$^+$ 412.1.

Example 211

(4-chloro-2-(1H-1,2,3-triazol-1-yl)phenyl)((7S)-2-(2,6-dimethylpyrimidin-4-yl)-7-methyl-1,2,5-oxadiazepan-5-yl)methanone

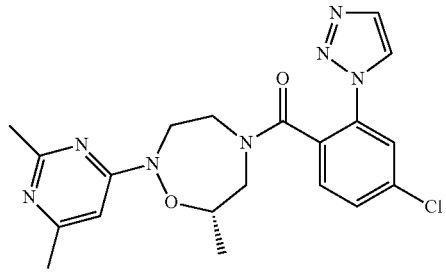 [SMILES: Cc1cc(N2CCN(C(=O)c3ccc(Cl)cc3-n3ccnn3)C[C@H](C)O2)nc(C)n1]

The title compound (191 mg) was obtained using (7S)-2-(2,6-dimethylpyrimidin-4-yl)-7-methyl-1,2,5-oxadiazepane dihydrochloride obtained in Step G of Example 102 and 4-chloro-2-(1H-1,2,3-triazol-1-yl)benzoic acid obtained in Reference Example 34 in the same manner as in Step H of Example 102.

MS: [M+H]⁺ 428.1.

Example 212

(5-chloro-2-(2H-1,2,3-triazol-2-yl)phenyl)((7R)-2-(2,6-dimethylpyrimidin-4-yl)-7-methyl-1,2,5-oxadiazepan-5-yl)methanone

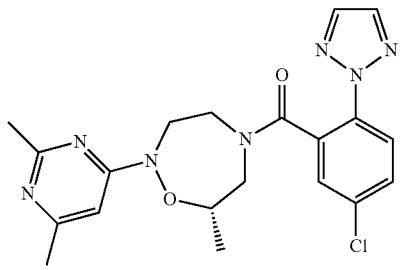 [SMILES: Cc1cc(N2CCN(C(=O)c3cc(Cl)ccc3-n3nccn3)C[C@H](C)O2)nc(C)n1]

The title compound (318 mg) was obtained using tert-butyl [(2S)-2-hydroxypropyl]carbamate in the same manner as in Steps A-H of Example 102.

MS: [M+H]⁺ 428.0.

Example 213

((6R)-2-(2,6-dimethylpyrimidin-4-yl)-6-methyl-1,2,5-oxadiazepan-5-yl)(2-(pyrimidin-2-yl)phenyl)methanone

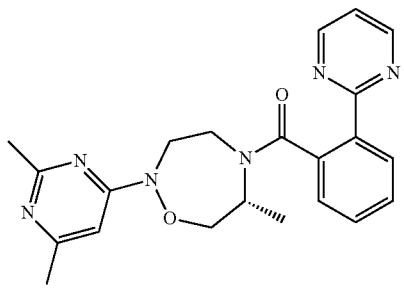 [SMILES: Cc1cc(N2CCN(C(=O)c3ccccc3-c3ncccn3)[C@H](C)CO2)nc(C)n1]

The title compound (12 mg) was obtained using (6R)-2-(2,6-dimethylpyrimidin-4-yl)-6-methyl-1,2,5-oxadiazepane dihydrochloride obtained in Step G of Example 194 and 2-(pyrimidin-2-yl)benzoic acid obtained in Reference Example 25 in the same manner as in Example 198.

MS: [M+H]⁺ 405.2.

Example 214

((6R)-6-methyl-2-(2-methyl-6-(trifluoromethyl)pyrimidin-4-yl)-1,2,5-oxadiazepan-5-yl)(2-(pyrimidin-2-yl)phenyl)methanone

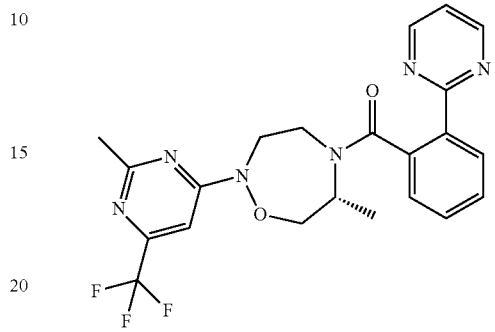

The title compound (58.5 mg) was obtained using (6R)-6-methyl-2-[2-methyl-6-(trifluoromethyl)pyrimidin-4-yl]-1,2,5-oxadiazepane dihydrochloride (obtained using tert-butyl (6R)-6-methyl-1,2,5-oxadiazepane-5-carboxylate obtained in Step E of Example 194 and 4-chloro-2-methyl-6-(trifluoromethyl)pyrimidine in the same manner as in Steps F and G of Example 102) and 2-(pyrimidin-2-yl)benzoic acid obtained in Reference Example 25 in the same manner as in Example 198.

MS: [M+H]⁺ 459.1.

Example 215

((6R)-2-(5-chloro-2-methylpyrimidin-4-yl)-6-methyl-1,2,5-oxadiazepan-5-yl)(5-chloro-2-(2H-1,2,3-triazol-2-yl)phenyl)methanone

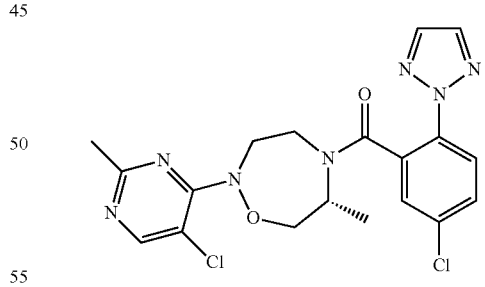

The title compound (132 mg) was obtained using (6R)-2-(5-chloro-2-methylpyrimidin-4-yl)-6-methyl-1,2,5-oxadiazepane dihydrochloride (obtained using tert-butyl (6R)-6-methyl-1,2,5-oxadiazepane-5-carboxylate obtained in Step E of Example 194 and 4,5-dichloro-2-methylpyrimidine in the same manner as in Steps F and G of Example 102) and 5-chloro-2-(2H-1,2,3-triazol-2-yl)benzoic acid obtained in Reference Example 3 in the same manner as in Step H of Example 102.

MS: [M+H]⁺ 448.0, 450.0.

Example 216

(2-(2,6-dimethylpyrimidin-4-yl)-1,2,5-oxadiazepan-5-yl)(2-methyl-6-(pyrimidin-2-yl)phenyl)methanone

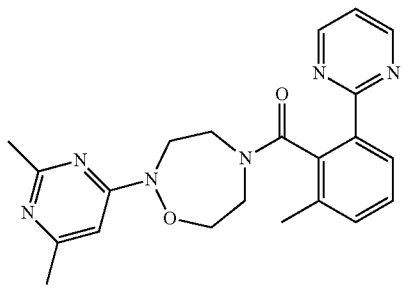 [SMILES: Cc1cc(N2CCN(C(=O)c3c(C)cccc3-c3ncccn3)CCO2)nc(C)n1]

The title compound (41 mg) was obtained using 2-(2,6-dimethylpyrimidin-4-yl)-1,2,5-oxadiazepane dihydrobromide obtained in Step D of Example 4 and 2-methyl-6-(pyrimidin-2-yl)benzoic acid obtained in Reference Example 33 in the same manner as in Example 198.
MS: [M+H]$^+$ 405.1.

Example 217

((7S)-2-(2,6-dimethylpyrimidin-4-yl)-7-methyl-1,2,5-oxadiazepan-5-yl)(4-methyl-2-(pyrimidin-2-yl)phenyl)methanone

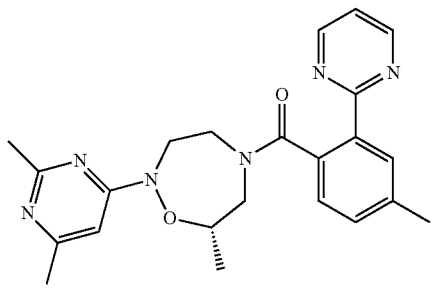

The title compound (142 mg) was obtained using 2-bromo-4-methylbenzoic acid in the same manner as in Steps A and B of Example 196.
MS: [M+H]$^+$ 419.1.

Example 218

((7S)-2-(2,6-dimethylpyrimidin-4-yl)-7-methyl-1,2,5-oxadiazepan-5-yl)(4-fluoro-2-(pyrimidin-2-yl)phenyl)methanone

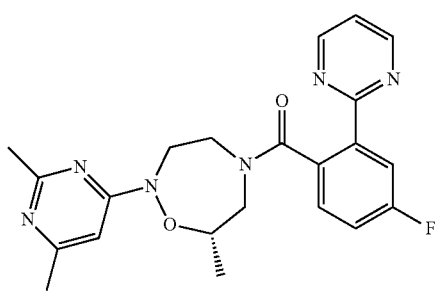 [SMILES: Cc1cc(N2CCN(C(=O)c3ccc(F)cc3-c3ncccn3)C[C@H](C)O2)nc(C)n1]

The title compound (88.0 mg) was obtained using 2-bromo-4-fluorobenzoic acid in the same manner as in Steps A and B of Example 196.
MS: [M+H]$^+$ 423.1.

Example 219

(5-chloro-2-(pyrimidin-2-yl)phenyl)((7S)-7-methyl-2-(2-methylpyrimidin-4-yl)-1,2,5-oxadiazepan-5-yl)methanone

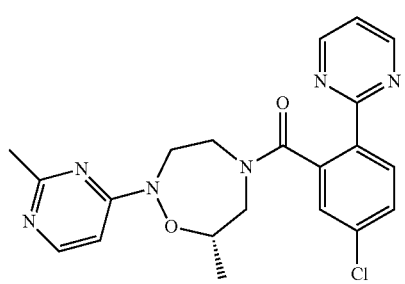 [SMILES: Cc1nccc(N2CCN(C(=O)c3cc(Cl)ccc3-c3ncccn3)C[C@H](C)O2)n1]

The title compound (46.0 mg) was obtained using (7S)-7-methyl-2-(2-methylpyrimidin-4-yl)-1,2,5-oxadiazepane dihydrochloride obtained as an intermediate in Example 206 and 2-bromo-5-chlorobenzoic acid in the same manner as in Steps A and B of Example 196.
MS: [M+H]$^+$ 425.1.

Example 220

((7S)-2-(2,6-dimethylpyrimidin-4-yl)-7-methyl-1,2,5-oxadiazepan-5-yl)(3-fluoro-2-(pyrimidin-2-yl)phenyl)methanone

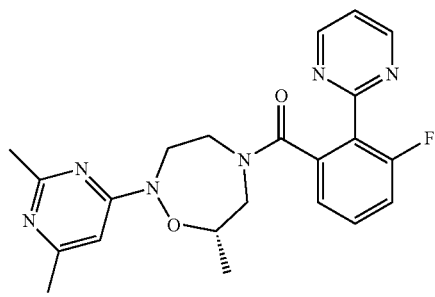 [SMILES: Cc1cc(N2CCN(C(=O)c3cccc(F)c3-c3ncccn3)C[C@H](C)O2)nc(C)n1]

The title compound (42.0 mg) was obtained using 2-bromo-3-fluorobenzoic acid in the same manner as in Steps A and B of Example 196.
MS: [M+H]$^+$ 423.1.

Example 221

(5-chloro-2-(5-fluoropyrimidin-2-yl)phenyl)((6R)-2-(2,6-dimethylpyrimidin-4-yl)-6-methyl-1,2,5-oxadiazepan-5-yl)methanone

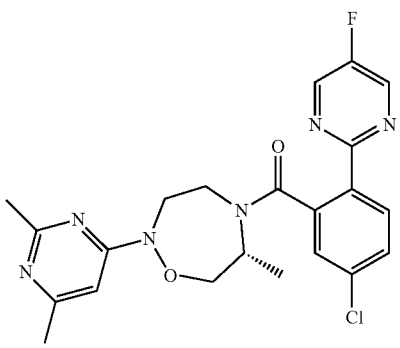 [SMILES: Cc1cc(N2CCN(C(=O)c3cc(Cl)ccc3-c3ncc(F)cn3)[C@H](C)CO2)nc(C)n1]

The title compound (96.0 mg) was obtained using (6R)-2-(2,6-dimethylpyrimidin-4-yl)-6-methyl-1,2,5-oxadiazepane dihydrochloride obtained in Step G of Example 194, 2-bromo-5-chlorobenzoic acid and 2-bromo-5-fluoropyrimidine in the same manner as in Steps A and B of Example 196.

MS: [M+H]$^+$ 457.1.

Example 222

(2-(2,6-dimethylpyrimidin-4-yl)-1,2,5-oxadiazepan-5-yl)(2-(5-fluoropyrimidin-2-yl)phenyl)methanone

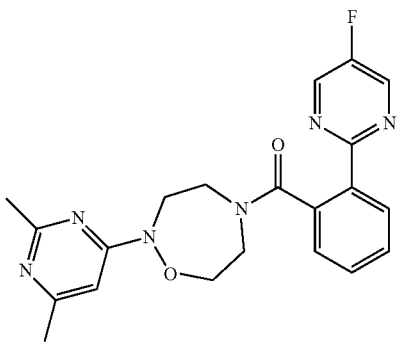 [SMILES: Cc1cc(N2CCN(C(=O)c3ccccc3-c3ncc(F)cn3)CCO2)nc(C)n1]

The title compound (24.0 mg) was obtained using 2-(2,6-dimethylpyrimidin-4-yl)-1,2,5-oxadiazepane dihydrobromide obtained in Step D of Example 4, 2-iodobenzoic acid and 2-bromo-5-fluoropyrimidine in the same manner as in Steps A and B of Example 196.

MS: [M+H]$^+$ 409.1.

Example 223

(4,5-difluoro-2-(5-fluoropyrimidin-2-yl)phenyl)(2-(2,6-dimethylpyrimidin-4-yl)-1,2,5-oxadiazepan-5-yl)methanone

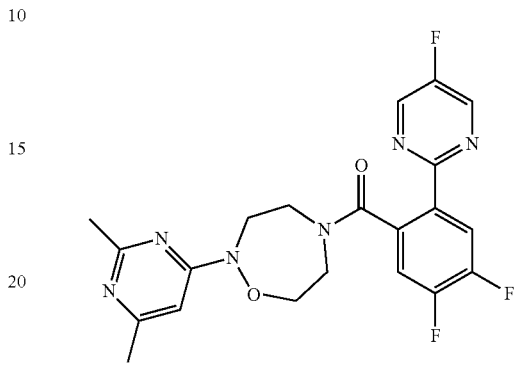

The title compound (26.0 mg) was obtained using 2-(2,6-dimethylpyrimidin-4-yl)-1,2,5-oxadiazepane dihydrobromide obtained in Step D of Example 4, 4,5-difluoro-2-iodobenzoic acid and 2-bromo-5-fluoropyrimidine in the same manner as in Steps A and B of Example 196.

MS: [M+H]$^+$ 445.1.

Example 224

(5-chloro-2-(5-fluoropyrimidin-2-yl)phenyl)(2-(2,6-dimethylpyrimidin-4-yl)-1,2,5-oxadiazepan-5-yl)methanone

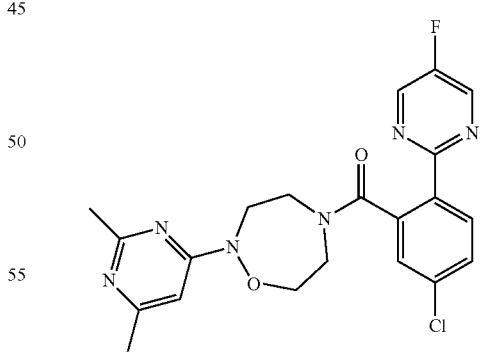

The title compound (86.0 mg) was obtained using 2-(2,6-dimethylpyrimidin-4-yl)-1,2,5-oxadiazepane dihydrobromide obtained in Step D of Example 4, 2-bromo-5-chlorobenzoic acid and 2-bromo-5-fluoropyrimidine in the same manner as in Steps A and B of Example 196.

MS: [M+H]$^+$ 443.1.

Example 225

(5-chloro-2-(pyrimidin-2-yl)phenyl)(2-(2-methyl-6-(trifluoromethyl)pyrimidin-4-yl)-1,2,5-oxadiazepan-5-yl)methanone

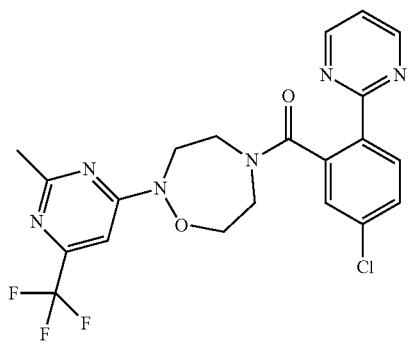 [SMILES: Cc1nc(N2CCN(C(=O)c3cc(Cl)ccc3-c3ncccn3)CCO2)cc(C(F)(F)F)n1]

The title compound (98.0 mg) was obtained using 2-(2-methyl-6-(trifluoromethyl)pyrimidin-4-yl)-1,2,5-oxadiazepane dihydrobromide (obtained using 4-chloro-2-methyl-6-(trifluoromethyl)pyrimidine in the same manner as in Steps C and D of Example 4) in the same manner as in Example 195.

MS: [M+H]$^+$ 479.1.

Example 226

(5-chloro-2-(pyrimidin-2-yl)phenyl)(2-(2,6-dimethylpyrimidin-4-yl)-1,2,5-oxadiazepan-5-yl)methanone

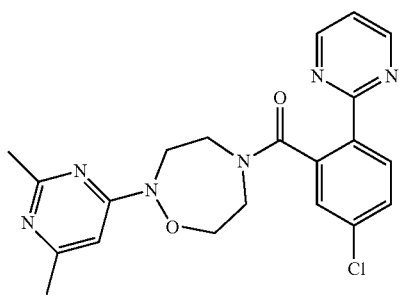 [SMILES: Cc1cc(N2CCN(C(=O)c3cc(Cl)ccc3-c3ncccn3)CCO2)nc(C)n1]

The title compound (74.0 mg) was obtained using 2-(2,6-dimethylpyrimidin-4-yl)-1,2,5-oxadiazepane dihydrobromide obtained in Step D of Example 4 and 2-bromo-5-chlorobenzoic acid in the same manner as in Example 195.

MS: [M+H]$^+$ 425.1.

Example 227

(4,5-difluoro-2-(pyrimidin-2-yl)phenyl)((7S)-7-methyl-2-(2-methyl-6-(trifluoromethyl)pyrimidin-4-yl)-1,2,5-oxadiazepan-5-yl)methanone

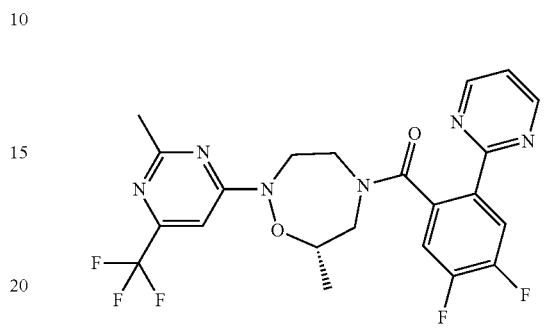

The title compound (13.0 mg) was obtained using (4,5-difluoro-2-iodophenyl){(7S)-7-methyl-2-[2-methyl-6-(trifluoromethyl)pyrimidin-4-yl]-1,2,5-oxadiazepan-5-yl}methanone (obtained using 4,5-difluoro-2-iodobenzoic acid and 4-chloro-2-methyl-6-(trifluoromethyl)pyrimidine in the same manner as in Steps A and B of Example 84) in the same manner as in Step B of Example 42.

MS: [M+H]$^+$ 495.2.

Example 228

(4,5-difluoro-2-(pyrimidin-2-yl)phenyl)(2-(2,6-dimethylpyrimidin-4-yl)-1,2,5-oxadiazepan-5-yl)methanone

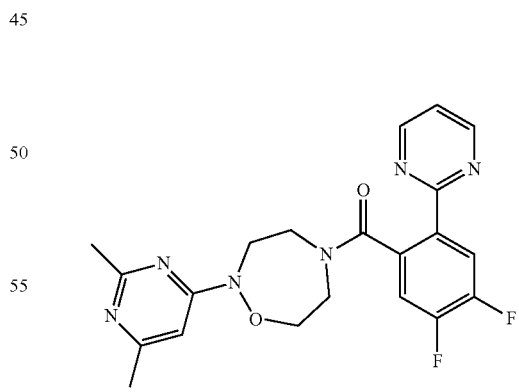

The title compound (20.0 mg) was obtained using 2-(2,6-dimethylpyrimidin-4-yl)-1,2,5-oxadiazepane dihydrobromide obtained in Step D of Example 4 and 4,5-difluoro-2-iodobenzoic acid in the same manner as in Example 195.

MS: [M+H]$^+$ 427.1.

Example 229

(5-chloro-2-(pyrimidin-2-yl)phenyl)(((6R)-6-methyl-2-(2-methylpyrimidin-4-yl)-1,2,5-oxadiazepan-5-yl)methanone

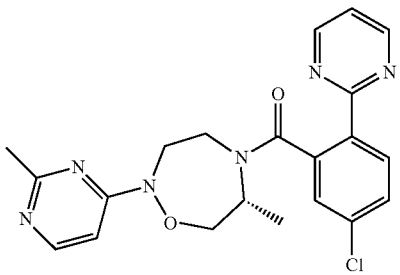 [SMILES: Cc1nccc(N2CCN(C(=O)c3cc(Cl)ccc3-c3ncccn3)[C@H](C)CO2)n1]

The title compound (11.5 mg) was obtained using (6R)-6-methyl-2-(2-methylpyrimidin-4-yl)-1,2,5-oxadiazepane dihydrochloride (obtained using 4-chloro-2-methylpyrimidine in the same manner as in Steps F and G of Example 194) in the same manner as in Example 195.
MS: [M+H]$^+$ 425.1.

Example 230

((6R)-2-(5-chloro-2-methylpyrimidin-4-yl)-6-methyl-1,2,5-oxadiazepan-5-yl)(5-chloro-2-(pyrimidin-2-yl)phenyl)methanone

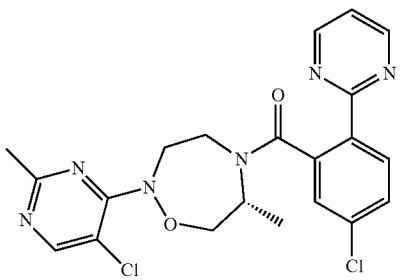 [SMILES: Cc1ncc(Cl)c(N2CCN(C(=O)c3cc(Cl)ccc3-c3ncccn3)[C@H](C)CO2)n1]

The title compound (16.0 mg) was obtained using (6R)-2-(5-chloro-2-methylpyrimidin-4-yl)-6-methyl-1,2,5-oxadiazepane dihydrochloride obtained as an intermediate in Example 215 in the same manner as in Example 195.
MS: [M+H]$^+$ 459.0, 461.0.

Example 231

(4,5-difluoro-2-(pyrimidin-2-yl)phenyl)(((6R)-2-(2,6-dimethylpyrimidin-4-yl)-6-methyl-1,2,5-oxadiazepan-5-yl)methanone

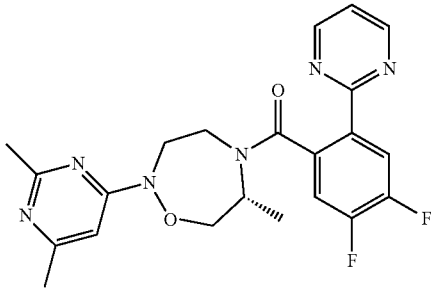 [SMILES: Cc1cc(N2CCN(C(=O)c3cc(F)c(F)cc3-c3ncccn3)[C@H](C)CO2)nc(C)n1]

The title compound (20.0 mg) was obtained using 4,5-difluoro-2-iodobenzoic acid in the same manner as in Example 195.
MS: [M+H]$^+$ 441.1.

Example 232

((7S)-2-(2,6-dimethylpyrimidin-4-yl)-7-methyl-1,2,5-oxadiazepan-5-yl)(2-(5-methyl-1,2,4-oxadiazol-3-yl)phenyl)methanone

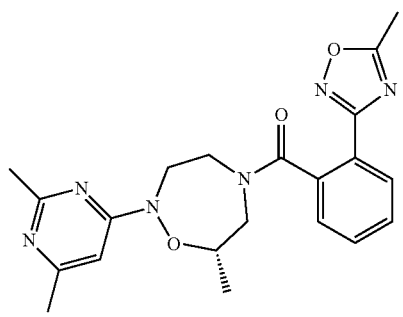

(S)-2-(2-(2,6-Dimethylpyrimidin-4-yl)-7-methyl-1,2,5-oxadiazepane-5-carbonyl)benzonitrile (229 mg) was obtained using 2-cyanobenzoic acid in the same manner as in Example 196. To a solution of the compound (200 mg) in methanol (10 mL) were added hydroxyamine hydrochloride (119 mg) and triethylamine (0.32 mL), and the mixture was stirred at 70° C. for 16 hr. The methanol was evaporated under reduced pressure, to the residue were added acetic anhydride (10.0 mL) and 4-methylbenzenesulfonic acid monohydrate (10.8 mg), and the mixture was stirred at 120° C. for 4 hr. The reaction mixture was concentrated under reduced pressure, to the residue was added saturated aqueous sodium hydrogencarbonate solution, and the mixture was extracted with ethyl acetate. The obtained organic layer was dried over sodium sulfate, and the solvent was evaporated under reduced pressure. The residue was purified by silica gel column chromatography (NH, hexane/ethyl acetate), the obtained crude product was purified by HPLC (C18, mobile phase: water/acetonitrile (containing 0.1% TFA)), and the obtained fraction was concentrated to give the title compound (31.0 mg).
MS: [M+H]$^+$ 409.1.

Example 233 methyl 2-(((7S)-2-(2,6-dimethylpyrimidin-4-yl)-7-methyl-1,2,5-oxadiazepan-5-yl)carbonyl)benzoate

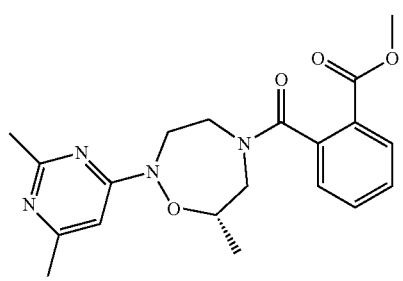 [SMILES: COC(=O)c1ccccc1C(=O)N1CCN(c2cc(C)nc(C)n2)O[C@@H](C)C1]

A solution of (7S)-2-(2,6-dimethylpyrimidin-4-yl)-7-methyl-1,2,5-oxadiazepane dihydrochloride (300 mg) obtained in Step G of Example 102, 2-benzofuran-1,3-dione (135 mg) and triethylamine (0.71 mL) in N,N-dimethylformamide (5 mL) was stirred overnight at room temperature. The reaction mixture was acidified with 1N hydrochloric acid, and concentrated under reduced pressure. To a solution of the obtained residue in toluene (4 mL)/tetrahydrofuran (4 mL)/methanol (1 mL) was added 0.6M (diazomethyl) (trimethyl)silane (6.12 mL) at 0° C., and the mixture was stirred overnight at room temperature. The reaction mixture was diluted with saturated aqueous sodium hydrogencarbonate solution, and extracted with ethyl acetate. The obtained organic layer was washed successively with water and saturated brine, and dried over anhydrous sodium sulfate, and the solvent was evaporated under reduced pressure. The residue was purified by silica gel column chromatography (ethyl acetate/methanol) to give the title compound (206 mg).

MS: $[M+H]^+$ 385.1.

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is passed through a 1 mm mesh sieve and granulated by using 10 wt % aqueous gelatin solution (30 mL) (3.0 g as gelatin), and the granules are dried at 40° C. and sieved again. The obtained granules are mixed with magnesium stearate (2.0 g), and the mixture is compressed. The obtained core tablets are coated with a sugar coating of an aqueous suspension of sucrose, titanium dioxide, talc and gum arabic. The coated tablets are glazed with beeswax to give 1000 coated tablets.

Formulation Example 2

| | |
|---|---|
| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), and the granules are dried and mixed with lactose (70.0 g) and cornstarch (50.0 g). The mixture is compressed to give 1000 tablets.

Experimental Example 1

Measurement of Orexin Receptor Antagonistic Activity

CHO cells forcibly expressing human OX1 receptor or human OX2 receptor were seeded in each well of 384 well black transparent bottom plate (BD Falcon) at 7,500 cells/well, and cultured for one day in a 5% $CO_2$ incubator at 37° C. After removal of the medium in the cell plate, assay buffer A (HBSS (Life Technologies), 20 mM HEPES (Life Technologies), 0.1% BSA (SIGMA), 2.5 µg/mL Fluo-4 AM (DOJINDO Chemical), 0.08% Pluronic F127 (DOJINDO Chemical), 1.25 mM probenecid (DOJINDO Chemical)) containing a calcium indicator was added at 20 µL/well. The plate was stood for 30 min in a 5% $CO_2$ incubator at 37° C., and further stood at room temperature for 30 min. A test compound prepared by diluting with assay buffer B (HBSS, 20 mM HEPES, 0.1% BSA) was added at 10 µL/well, and then OX-A (OX1 receptor, final concentration; 1 nM) or OX-A (OX2 receptor, final concentration; 0.3 nM) was added at 10 µL/well, and the fluorescence value was measured by FLIPRtetra (Molecular Devices) every one sec for 2 min. The inhibitory activity (%) of the test compound was calculated assuming that variation in the fluorescence value when DMSO was added instead of the test compound was 0% inhibition, and variation in the fluorescence value when buffer was added instead of OX-A was 100% inhibition.

TABLE 10

| Example No. | Human Orexin2 receptor inhibition (at 10 µM) | Human Orexin1 receptor inhibition (at 10 µM) |
|---|---|---|
| 1 | 98 | 47 |
| 2 | 101 | 68 |
| 3 | 100 | 87 |
| 4 | 96 | 62 |
| 5 | 99 | 101 |
| 6 | 96 | 88 |
| 7 | 92 | 62 |
| 9 | 74 | 91 |
| 10 | 94 | 93 |
| 11 | 95 | 89 |
| 12 | 93 | 101 |
| 14 | 91 | 23 |
| 15 | 102 | 5 |
| 16 | 98 | 21 |
| 17 | 102 | 41 |
| 19 | 100 | 36 |
| 20 | 101 | 25 |
| 21 | 99 | 19 |
| 22 | 99 | 54 |
| 23 | 101 | 88 |
| 24 | 99 | 13 |
| 25 | 98 | 61 |
| 26 | 100 | 83 |
| 27 | 102 | 45 |
| 28 | 74 | 23 |
| 29 | 100 | 88 |
| 30 | 101 | 1 |
| 31 | 100 | -2 |
| 32 | 96 | 38 |
| 33 | 99 | 44 |
| 34 | 99 | 97 |
| 35 | 5 | -4 |
| 36 | 100 | 67 |
| 37 | 85 | 19 |
| 38 | 90 | 92 |
| 39 | 98 | 100 |
| 40 | 4 | — |
| 41 | 56 | 10 |
| 42 | 101 | 41 |
| 43 | 91 | 35 |
| 44 | 103 | -16 |
| 45 | 19 | 16 |
| 46 | 36 | 4 |
| 47 | 97 | 23 |
| 48 | 73 | 10 |
| 49 | 14 | 9 |
| 50 | -3 | 3 |
| 51 | 68 | 22 |
| 52 | 96 | 16 |
| 53 | 57 | 9 |
| 54 | 84 | 16 |
| 55 | 96 | 18 |
| 56 | 96 | 21 |

TABLE 10-continued

| Example No. | Human Orexin2 receptor inhibition (at 10 μM) | Human Orexin1 receptor inhibition (at 10 μM) |
|---|---|---|
| 57 | 58 | 10 |
| 58 | 99 | 29 |
| 59 | 65 | 1 |
| 60 | 3 | −1 |
| 61 | 94 | 22 |
| 62 | 72 | 2 |
| 63 | 49 | 11 |
| 64 | 101 | 76 |
| 65 | 84 | 9 |
| 66 | 90 | 13 |
| 67 | 44 | 5 |
| 68 | 87 | 28 |
| 69 | 45 | 3 |
| 70 | 17 | −6 |
| 71 | 99 | 53 |
| 72 | 94 | 34 |
| 73 | 42 | 13 |
| 74 | 57 | 10 |
| 75 | 75 | 10 |
| 76 | 22 | 6 |
| 77 | 69 | 12 |
| 78 | 52 | 27 |
| 79 | 98 | 57 |
| 80 | 94 | 14 |
| 81 | 99 | 85 |
| 82 | 83 | 18 |
| 83 | 24 | 7 |
| 84 | 98 | 100 |
| 85 | 102 | 98 |
| 87 | 102 | 81 |
| 88 | 99 | 101 |
| 89 | 97 | 101 |
| 90 | 96 | 101 |
| 91 | 100 | 100 |
| 92 | 101 | 73 |
| 93 | 100 | 72 |
| 94 | 104 | 106 |
| 95 | 97 | 100 |
| 96 | 98 | 98 |
| 97 | 100 | 95 |
| 98 | 104 | 97 |
| 99 | 98 | 87 |
| 100 | 102 | 42 |
| 101 | 101 | 50 |
| 102 | 101 | 94 |
| 103 | 100 | 90 |
| 104 | 96 | 104 |
| 105 | 98 | 96 |
| 106 | 99 | 38 |
| 107 | 94 | 37 |
| 108 | 101 | 100 |
| 109 | 101 | 85 |
| 110 | 95 | 79 |
| 111 | 100 | 9 |
| 112 | 101 | 90 |
| 113 | 102 | 16 |
| 114 | 96 | 69 |
| 115 | 100 | 103 |
| 116 | 100 | 101 |
| 117 | 100 | 77 |
| 118 | 102 | 101 |
| 119 | 92 | 48 |
| 120 | 100 | 83 |
| 121 | 94 | 92 |
| 122 | 69 | 11 |
| 123 | 74 | 23 |
| 124 | 101 | 85 |
| 125 | 98 | 68 |
| 126 | 97 | 96 |
| 127 | 86 | 66 |
| 128 | 96 | 99 |
| 129 | 86 | 38 |
| 130 | 56 | 62 |
| 131 | 38 | −7 |
| 132 | 67 | 10 |
| 133 | 70 | 11 |
| 134 | 80 | 92 |
| 135 | 88 | 15 |
| 136 | 95 | 36 |
| 137 | 100 | 93 |
| 138 | 95 | 96 |
| 139 | 98 | 54 |
| 140 | 88 | 21 |
| 141 | 99 | 71 |
| 142 | 97 | 99 |
| 143 | 44 | 1 |
| 144 | 12 | 14 |
| 145 | 82 | 25 |
| 146 | 88 | 66 |
| 147 | 101 | 60 |
| 148 | 100 | 53 |
| 149 | −6 | 3 |
| 150 | 99 | 58 |
| 151 | 98 | 81 |
| 152 | 99 | 82 |
| 153 | 99 | 94 |
| 154 | 91 | 97 |
| 155 | 103 | 100 |
| 156 | 19 | 18 |
| 157 | 91 | 93 |
| 158 | 99 | 18 |
| 159 | 89 | 16 |
| 160 | 101 | 82 |
| 161 | 102 | 46 |
| 162 | 100 | 42 |
| 163 | 102 | 61 |
| 164 | 43 | 8 |
| 165 | 24 | 24 |
| 166 | 97 | 81 |
| 167 | 98 | 100 |
| 168 | 99 | 95 |
| 169 | 99 | 100 |
| 170 | 100 | 20 |
| 171 | 102 | 37 |
| 172 | 100 | 103 |
| 173 | 103 | 103 |
| 174 | 98 | 95 |
| 175 | 98 | 99 |
| 176 | 101 | 103 |
| 177 | 106 | 102 |
| 178 | 99 | 105 |
| 179 | 98 | 102 |
| 180 | 101 | 90 |
| 181 | 83 | 70 |
| 182 | 98 | 100 |
| 183 | 103 | 105 |
| 184 | 102 | 100 |
| 185 | 31 | 22 |
| 186 | 66 | 23 |
| 187 | 103 | 100 |
| 188 | 29 | 13 |
| 189 | 57 | 37 |
| 190 | 111 | 107 |
| 191 | 109 | 106 |
| 192 | 101 | 64 |
| 193 | 103 | 89 |
| 194 | 100 | 66 |
| 195 | 102 | 81 |
| 196 | 100 | 89 |
| 197 | 102 | 96 |
| 198 | 98 | 80 |
| 199 | 100 | 42 |
| 200 | 100 | 83 |
| 201 | 101 | 60 |
| 202 | 102 | 17 |
| 203 | 101 | 25 |
| 204 | 101 | 70 |
| 205 | 100 | 82 |
| 206 | 100 | 28 |
| 207 | 81 | 25 |
| 208 | 14 | 8 |
| 209 | 18 | −12 |

TABLE 10-continued

| Example No. | Human Orexin2 receptor inhibition (at 10 μM) | Human Orexin1 receptor inhibition (at 10 μM) |
| --- | --- | --- |
| 210 | 97 | 51 |
| 211 | 80 | 21 |
| 212 | 99 | 16 |
| 213 | 102 | 47 |
| 214 | 103 | 55 |
| 215 | 102 | 40 |
| 216 | 101 | 59 |
| 217 | 101 | 50 |
| 218 | 101 | 91 |
| 219 | 100 | 72 |
| 220 | 101 | 15 |
| 221 | 102 | 51 |
| 222 | 99 | 32 |
| 223 | 101 | 17 |
| 224 | 100 | 53 |
| 225 | 103 | 74 |
| 226 | 101 | 80 |
| 227 | 97 | 78 |
| 228 | 99 | 36 |
| 229 | 101 | 40 |
| 230 | 103 | 66 |
| 231 | 103 | 38 |
| 232 | 102 | 55 |
| 233 | 87 | 17 |

As is clear from Table 10, the compound of the present invention may have an orexin receptor antagonistic activity.

Experimental Example 2

Experimental Animals

Male SD rats were purchased from Charles River Laboratories Japan, Inc. They were used for an experiment after an acclimation period of at least one week after carrying them in the animal experimental facility. They were bred in the animal experimental facility with environment in which 12-hours light-dark cycle was performed, humidity and temperature were controlled, and free water drinking and feeding were allowed.

Effect of Compound of Example 102 on Sleep in Rat

Electrodes for brain wave measurement were implanted in rat cortex, muscle electrodes were implanted in rat cervical muscle, and a transmitter was implanted under rat back skin. Rats in which chronic electrodes were implanted were fully acclimated to a box for brain wave measurement, and then the brain wave measurement was performed. The brain wave data was obtained using Dataquest ART manufactured by Data Sciences International. For analysis, wakefulness, non-REM sleep and REM sleep were automatically determined using Sleep Sign which is a program for sleep analysis study by KISSEI COMTEC Co., Ltd. The compound of Example 102 was subcutaneously administered at a dose of 3 mg/kg immediately before beginning of dark period. The sum of non-REM sleep and REM sleep 1 hr after the administration was regarded as total sleep. All data were shown as the mean+standard error. For statistical analysis, variance analysis to crossover was performed (*p ?0.05). The results are shown in FIG. 1 and Table 11.

TABLE 11

| Drug treatment | Solvent | Ex. 102 |
| --- | --- | --- |
| Number of animals | 7 | 7 |
| Total sleep (min) | 11.76 | 33.51 |
| S.E.M | 2.65 | 3.88 |

As is clear from FIG. 1 and Table 11, the total sleep was significantly increased, compared with solvent control group (0.5% (w/v) methyl cellulose solution), by the subcutaneous administration of the compound (3 mg/kg) of Example 102.

Experimental Example 3

Experimental Animals

The male SD rats described in Experimental Example 2 were used.

Effects of Compounds of Examples 1 and 2 on Locomotor Activity Test Using Orexin-A-Induced Rats Guide cannula for cerebral ventricular administration was implanted in rat, and the rat was fully restored, and then used for locomotor activity measurement test. From the day before drug administration, the animals were acclimated to a locomotor activity measurement apparatus (Muromachi Kikai Co., Ltd.). Solvent (0.5% (w/v) methyl cellulose solution) and the compound (30 mg/kg) of Example 1 or the compound (30 mg/kg) of Example 2 were subcutaneously administered 30 min before administration of saline or Orexin-A (1 nmol). The locomotor activity was quantified for 30 min to 90 min after the cerebral ventricular administration of Orexin-A. A comparison with saline+solvent administration group was tested by Student's t-test (*p≤0.05). A comparison with Orexin-A+solvent administration group was tested by Dunnett's test (#p≤0.05). The results are shown in FIG. 2 and Table 12.

TABLE 12

| Drug treatment | Saline + Solvent | Orexin-A + Solvent | Orexin-A + Ex. 1 | Orexin-A + Ex. 2 |
| --- | --- | --- | --- | --- |
| Number of animals | 8 | 8 | 8 | 8 |
| Locomotor activity (Counts/90 min) | 3249 | 8105 | 3528 | 2638 |
| S.E.M | 873 | 799 | 1014 | 541 |

Figure 2:
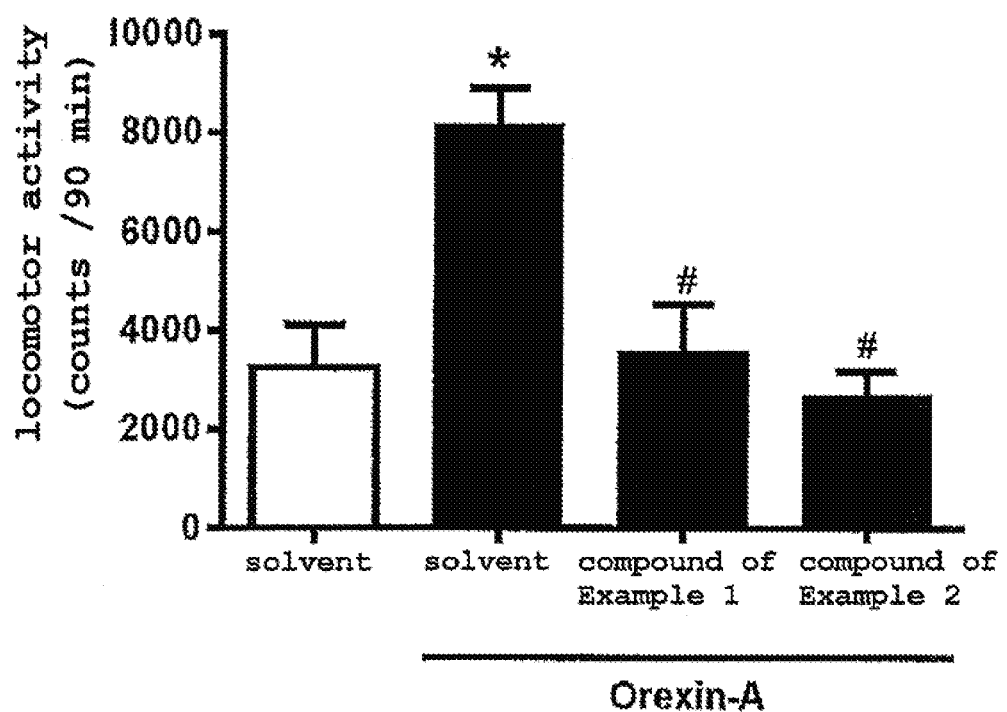
FIG. 2 shows effects of compounds of Example 1 and Example 2 in locomotor activity test using Orexin-A-induced rat in Experimental Example 3.

As is clear from FIG. 2 and Table 12, the locomotor activity increased by the cerebral ventricular administration of Orexin-A was significantly decreased, by the subcutaneous administration of the compound (30 mg/kg) of Example 1 or the compound (30 mg/kg) of Example 2.

Experimental Example 4 Measurement of Solubility n-Heptane was added to the compounds of Examples 1, 2 and 102 at 40 mg/mL, respectively, and the mixtures were continued to be stirred at room temperature in a suspended state. After 3 to 7 days, the mixtures were filtered, and the obtained crystals as a sample were subjected to powder X-ray diffraction measurement (measurement condition: mentioned above) and solubility measurement. The solubility measurement was performed by adding Britton-Robinson's Buffer (pH 3, warmed to 37° C.) at 5 mg/mL relative to the sample, and then shaking the mixture. When it was confirmed by visual check that the mixture after shaking at 37° C. for 2 hr became limpid, the solubility was defined as "5 mg/mL or more". When the mixture after shaking at 37° C. for 2 hr remain in a suspended state, additional Britton-Robinson's Buffer (pH 3, warmed to 37° C.) was added thereto, and the mixture was suitably stirred, and then the concentration in which the sample was completely dissolved was defined as solubility.

The solubilities of the compounds of Examples 1, 2 and 102 were all "5 mg/mL or more".

INDUSTRIAL APPLICABILITY

The compound of the present invention may have an orexin receptor antagonistic activity, and is expected to be useful as medicaments such as agents for the prophylaxis or treatment of sleep disorder, depression, anxiety disorder, panic disorder, schizophrenia, drug dependence, Alzheimer's disease and the like.

This application is based on patent application No. 2015-089714 filed on Apr. 24, 2015 in Japan, the contents of which are encompassed in full herein.

The invention claimed is:

1. A compound represented by the formula (I):

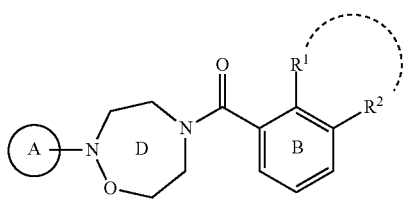

wherein
R$^1$ and R$^2$ are each independently a hydrogen atom or a substituent, or R$^1$ and R$^2$ are optionally bonded to each other to form, together with the adjacent carbon atoms, an optionally substituted ring,
Ring A is an optionally substituted aromatic ring,
Ring B is an optionally further substituted benzene ring, and
Ring D is an optionally further substituted 1,2,5-oxadiazepane ring,
or a salt thereof.

2. The compound or salt according to claim 1, wherein Ring A is a pyrimidine ring optionally substituted by 1 to 3 substituents selected from
 (a) a halogen atom,
 (b) a hydroxy group,
 (c) a cyano group,
 (d) a $C_{1-6}$ alkyl group optionally substituted by 1 to 3 halogen atoms,
 (e) a $C_{1-6}$ alkoxy group,
 (f) a $C_{3-10}$ cycloalkyl group optionally substituted by 1 to 3 $C_{1-6}$ alkyl groups, and
 (g) a $C_{6-14}$ aryl group optionally substituted by 1 to 3 halogen atoms.

3. The compound or salt according to claim 1, wherein Ring B is a benzene ring optionally further substituted by 1 to 3 substituents, in addition to R$^1$ and R$^2$, selected from
 (a) a halogen atom,
 (b) a cyano group,
 (c) a $C_{1-6}$ alkyl group optionally substituted by 1 to 3 halogen atoms,
 (d) a $C_{1-6}$ alkoxy group,
 (e) a $C_{3-10}$ cycloalkyl group, and
 (f) a 5- to 14-membered aromatic heterocyclic group.

4. The compound or salt according to claim 1, wherein R$^1$ is
 (1) a hydrogen atom,
 (2) a halogen atom,
 (3) a cyano group,
 (4) a $C_{1-6}$ alkyl group optionally substituted by 1 to 3 halogen atoms,
 (5) a $C_{1-6}$ alkoxy group,
 (6) a $C_{1-6}$ alkoxy-carbonyl group,
 (7) a $C_{3-10}$ cycloalkyl group,
 (8) a $C_{6-14}$ aryl group, or
 (9) a 5- to 14-membered aromatic heterocyclic group optionally substituted by 1 to 3 substituents selected from
  (i) a halogen atom, and
  (ii) a $C_{1-6}$ alkyl group;
R$^2$ is
 (1) a hydrogen atom,
 (2) a halogen atom,
 (3) a cyano group,
 (4) a $C_{1-6}$ alkyl group optionally substituted by 1 to 3 halogen atoms,
 (5) a $C_{1-6}$ alkoxy group,
 (6) a $C_{6-14}$ aryl group, or
 (7) a $C_{3-10}$ cycloalkyl group; or
R$^1$ and R$^2$ are optionally bonded to each other to form, together with the adjacent carbon atoms, benzene, a $C_{5-6}$ cycloalkene, a 5- or 6-membered monocyclic aromatic heterocycle, or a 5- or 6-membered monocyclic non-aromatic heterocycle, each of which is optionally substituted by 1 to 3 substituents selected from
 (a) a $C_{1-6}$ alkyl group, and
 (b) an oxo group;
Ring A is a benzene ring, a 5- or 6-membered monocyclic aromatic heterocycle or a 8- to 14-membered fused polycyclic aromatic heterocycle, each of which is optionally substituted by 1 to 3 substituents selected from
 (a) a halogen atom,
 (b) a hydroxy group,
 (c) a cyano group,
 (d) a $C_{1-6}$ alkyl group optionally substituted by 1 to 3 substituents selected from
  (i) a halogen atom, and
  (ii) a hydroxy group,
 (e) a $C_{1-6}$ alkoxy group,
 (f) a $C_{1-6}$ alkoxy-carbonyl group,
 (g) a $C_{3-10}$ cycloalkyl group optionally substituted by 1 to 3 $C_{1-6}$ alkyl groups,
 (h) a $C_{6-14}$ aryl group optionally substituted by 1 to 3 halogen atoms, and
 (i) a 5- to 14-membered aromatic heterocyclic group;
Ring B is a benzene ring optionally further substituted by 1 to 3 substituents, in addition to R$^1$ and R$^2$, selected from
 (a) a halogen atom,
 (b) a cyano group,
 (c) a $C_{1-6}$ alkyl group optionally substituted by 1 to 3 halogen atoms,
 (d) a $C_{1-6}$ alkoxy group,
 (e) a $C_{3-10}$ cycloalkyl group, and
 (f) a 5- to 14-membered aromatic heterocyclic group; and
Ring D is a 1,2,5-oxadiazepane ring optionally further substituted by 1 to 3 substituents selected from a $C_{1-6}$ alkyl group optionally substituted by 1 to 3 $C_{1-6}$ alkoxy groups.

5. The compound or salt according to claim 1, wherein R$^1$ is
 (1) a triazolyl group,
 (2) a thiazolyl group, or
 (3) a pyrimidinyl group;
R$^2$ is a hydrogen atom;
Ring A is a pyrimidine ring substituted by 1 to 3 substituents selected from (1) a $C_{1-6}$ alkyl group optionally substituted by 1 to 3 halogen atoms;

Ring B is a benzene ring optionally further substituted by 1 to 3 substituents, in addition to $R^1$ and $R^2$, selected from
  (a) a halogen atom, and
  (b) a $C_{1-6}$ alkyl group optionally substituted by 1 to 3 halogen atoms; and Ring D is a 1,2,5-oxadiazepane ring optionally further substituted by 1 to 3 $C_{1-6}$ alkyl groups.

6. The compound or salt according to claim 1, wherein $R^1$ is
(1) a triazolyl group, or
(2) a pyrimidinyl group;
$R^2$ is a hydrogen atom;
Ring A is a pyrimidine ring substituted by two $C_{1-6}$ alkyl groups;
Ring B is a benzene ring optionally further substituted by 1 or 2 substituents, in addition to $R^1$ and $R^2$, selected from
  (a) a halogen atom, and
  (b) a $C_{1-6}$ alkyl group; and Ring D is a 1,2,5-oxadiazepane ring optionally further substituted by one $C_{1-6}$ alkyl group.

7. ((7S)-2-(2,6-Dimethylpyrimidin-4-yl)-7-methyl-1,2,5-oxadiazepan-5-yl)(5-fluoro-2-(2H-1,2,3-triazol-2-yl)phenyl)methanone, or a salt thereof.

8. ((7S)-2-(2,6-Dimethylpyrimidin-4-yl)-7-methyl-1,2,5-oxadiazepan-5-yl)(2-(2H-1,2,3-triazol-2-yl)phenyl)methanone, or a salt thereof.

9. (5-Chloro-2-(2H-1,2,3-triazol-2-yl)phenyl)((7S)-2-(2,6-dimethylpyrimidin-4-yl)-7-methyl-1,2,5-oxadiazepan-5-yl)methanone, or a salt thereof.

10. A medicament comprising the compound or salt according to claim 1.

11. A method of antagonizing an orexin receptor in a mammal, which comprises administering an effective amount of the compound or salt according to claim 1 to the mammal.

12. A method for the treatment of sleep disorder, depression, anxiety disorder, panic disorder, schizophrenia, drug dependence or Alzheimer's disease in a mammal, which comprises administering an effective amount of the compound or salt according to claim 1 to the mammal.

* * * * *